US007649002B2

(12) United States Patent
Calabrese et al.

(10) Patent No.: US 7,649,002 B2
(45) Date of Patent: Jan. 19, 2010

(54) (3,5-DIMETHYLPIPERIDIN-1YL) (4-PHENYLPYRROLIDIN-3-YL)METHANONE DERIVATIVES AS MCR4 AGONISTS

(75) Inventors: Andrew Antony Calabrese, Sandwich (GB); David Sebastien Fradet, Sandwich (GB); David Hepworth, Sandwich (GB); Mark Lansdell, Sandwich (GB)

(73) Assignee: Pfizer Inc, New York, NY (US)

( * ) Notice: Subject to any disclaimer, the term of this patent is extended or adjusted under 35 U.S.C. 154(b) by 477 days.

(21) Appl. No.: 11/051,144

(22) Filed: Feb. 3, 2005

(65) Prior Publication Data

US 2005/0176772 A1 Aug. 11, 2005

Related U.S. Application Data

(60) Provisional application No. 60/543,950, filed on Feb. 12, 2004, provisional application No. 60/580,209, filed on Jun. 15, 2004, provisional application No. 60/634,916, filed on Dec. 10, 2004.

(30) Foreign Application Priority Data

| Feb. 4, 2004 | (GB) | ............................ 0402492.3 |
| Jun. 3, 2004 | (GB) | ............................ 0412417.8 |
| Nov. 19, 2004 | (GB) | ............................ 0425530.3 |

(51) Int. Cl.
*A61K 31/454* (2006.01)
*C07D 403/02* (2006.01)

(52) U.S. Cl. ................................ 514/326; 546/207
(58) Field of Classification Search ................. 514/326; 546/207
See application file for complete search history.

(56) References Cited

U.S. PATENT DOCUMENTS

| 3,752,814 | A | 8/1973 | Fluckiger et al. ............ 544/346 |
| 3,752,888 | A | 8/1973 | Fluckiger et al. ............ 424/250 |
| 4,929,629 | A | 5/1990 | Jeffery et al. ............... 514/646 |
| 5,274,143 | A | 12/1993 | Ramig et al. ................ 554/123 |
| 5,420,305 | A | 5/1995 | Ramig et al. ................ 549/292 |
| 5,521,186 | A | 5/1996 | Heeres et al. ............... 514/252 |
| 5,540,917 | A | 7/1996 | Isler et al. ................ 424/78.01 |
| 5,576,290 | A | 11/1996 | Hadley et al. ................ 514/11 |
| 5,576,322 | A | 11/1996 | Takase et al. ............... 514/260 |
| 5,624,941 | A | 4/1997 | Barth et al. ................. 514/326 |
| 5,643,874 | A | 7/1997 | Bremer et al. ................ 514/12 |
| 5,747,524 | A | 5/1998 | Cullinan et al. ............. 514/443 |
| 5,929,075 | A | 7/1999 | Heeres et al. ............... 514/252 |
| 6,051,555 | A | 4/2000 | Hadley et al. ................ 514/11 |
| 6,106,864 | A | 8/2000 | Dolan et al. ................. 424/488 |
| 6,265,431 | B1 | 7/2001 | Muller et al. ............... 514/408 |
| 6,303,593 | B1 * | 10/2001 | Bao et al. ................. 514/210.2 |
| 6,432,984 | B1 | 8/2002 | Barth et al. ................. 514/326 |
| 6,518,264 | B2 | 2/2003 | Achard et al. ............ 514/210.01 |
| 6,579,968 | B1 | 6/2003 | Blood et al. ................. 530/312 |
| 2002/0107185 | A1 | 8/2002 | Spencer ........................ 514/9 |
| 2002/0141985 | A1 | 10/2002 | Pittner et al. ............... 424/94.1 |
| 2003/0104980 | A1 | 6/2003 | Borsini et al. ................. 514/2 |
| 2004/0092520 | A1 | 5/2004 | Griffith et al. ............... 514/242 |
| 2004/0157839 | A1 | 8/2004 | Griffith et al. ............. 514/227.8 |
| 2004/0214838 | A1 | 10/2004 | Carpino et al. ........... 514/262.1 |
| 2004/0214855 | A1 | 10/2004 | Carpino et al. ............... 514/303 |

FOREIGN PATENT DOCUMENTS

| EP | 0526004 | 7/1992 |
| EP | 1258474 | 5/2002 |
| WO | WO 9519978 | 7/1995 |
| WO | WO 9621656 | 7/1996 |
| WO | WO 9849166 | 11/1998 |
| WO | WO 9902159 | 1/1999 |
| WO | WO 9954333 | 10/1999 |
| WO | WO 0002550 | 1/2000 |
| WO | WO 0027848 | 5/2000 |
| WO | WO 0028993 | 5/2000 |
| WO | WO 0035298 | 6/2000 |
| WO | WO 0127112 | 4/2001 |
| WO | WO 0127113 | 4/2001 |
| WO | WO 0202513 | 1/2002 |
| WO | WO 0203995 | 1/2002 |
| WO | WO 02068387 | 9/2002 |
| WO | WO 02068388 | 9/2002 |
| WO | WO 02074288 | 9/2002 |
| WO | WO 02076949 | 10/2002 |
| WO | WO 02079143 | 10/2002 |

(Continued)

OTHER PUBLICATIONS

Harris et al. "leptin responsiveness . . . " Physiology and Behavior v.75, p. 159-167 (2002).*

(Continued)

*Primary Examiner*—Celia Chang
(74) *Attorney, Agent, or Firm*—Gregg C. Benson; John A. Wichtowski

(57) ABSTRACT

The present invention relates to a class of melanocortin MCR4 agonists of general formula (I)

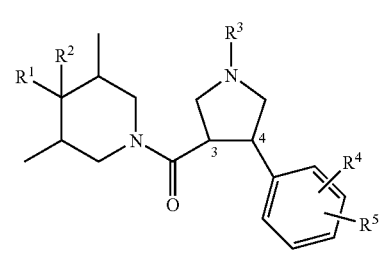

wherein $R^1$, $R^2$, $R^3$, $R^4$ and $R^5$ are as defined herein and especially to selective MCR4 agonist compounds, to their use in medicine, to compositions containing them, to processes for their preparation and to intermediates used in such processes.

42 Claims, 10 Drawing Sheets

FOREIGN PATENT DOCUMENTS

| WO | WO 03027637 | 4/2003 |
|---|---|---|
| WO | WO 03075660 | 9/2003 |
| WO | WO 2004012671 | 2/2004 |
| WO | WO 2004013120 | 2/2004 |
| WO | WO 2004048317 | 6/2004 |
| WO | WO 2004087159 | 10/2004 |
| WO | WO 2004092126 | 10/2004 |

OTHER PUBLICATIONS

Seddon "pseudopolymorph . . . " Crystal growth and design 496) 1087 (2004) (two pages from internet).*

U.S. Appl. No. 10/971,599, filed Oct. 22, 2004.

Ballard, et al., *The Journal of Urology*, "Effects Of Sildenafil On The Relasxation Of Human Corpus Cavemosum Tissue In Vitro And On The Activities Of Cyclic Nucleotide Phosphodiesterase Isozymes", vol. 159(6), pp. 2164-2171, (1998).

Benet, et al., *Comprehensive Therapy*, "Male Erectile Dysfunction Assessment And Treatment Options", vol. 20(12), pp. 699-673, (1994).

Bernabe, et al., *The American Physiological Society*, Intracavemous Pressure During Erection In Rats: An Integrative Approach Based On Telemetric Recording, pp. R441-R449, (1999).

Berman, et al., *Urology*, "Female Sexual Dysfunction: Incidence, Pathophysiology, Evaluation, And Treatment Options", vol. 54, pp. 385-391, (1999).

Carrier, et al., *Clinical Andrology*, "Erectile Dysfunction", vol. 23(4), pp. 773-781, (1994).

Cragnollni, et al., *Neuropeptides*, "The Role Of Melanocortin Receptors In Sexual Behavior In Female Rats", vol. 34(3&4), pp. 211-215, (2000).

Eardley, et al., *Pathophysiology of Erectile Dysfunction*, "Erectile Dysfunction-Current Investigation & Management", Chapter 3, pp. 21-32, (1998).

Feldman, et al., *The Journal of Urology*, "Impotence And Its Medical And Psychosocial Correlates: Results Of The Massachusetts Male Aging Study", vol. 151, pp. 54-61, (1994).

Goldstein, et al., *International Journal of Impotence Research*, "Vasculogenic Female Sexual Dysfunction: Vaginal Engorgement And Clitoral Erectile Insufficiency Syndromes", vol. 10, Suppl. 2, pp. S84-S90, (1998).

Gouarderes, et al., *Neuroscience*, "Quantitative Autoradiographic Distribution Of NPFF Neuropeptide FF Receptor In The Rat Brain And Comparison With $NPFF_2$ Receptor By Using $[^{125}I]YVP$ And $[^{125}I]EYE$ As Selective Radioligands", vol. 115(2), pp. 249-361, (2002).

Hadley, et al., *Annals of the New York Academy of Sciences*, "The Proopiomelanocortin System", vol. 885, pp. 1-21 (1999).

Leiblum, et al., *International Journal of Impotence Research*, Definition And Classification Of Female Sexual Disorders, vol. 10, Suppl 2, pp. S104-S106, (1998).

Lerner, et al., *The Journal of Urology*, "A Review Of Erectile Dysfunction: New Insights And More Questions", vol. 149, pp. 1246-1255, (1993).

Levin, et al., *Department of Biomedical Science*, "VIP, Vagina, Clitoral and Periurethral Glans—An Update On Human Female Genital Arousal".

Martin, et al., *European Journal of Pharmacology*, "Activation of melanocortin $MC_4$ receptors increases erectile activity in rates *ex copula*", vol. 454, pp. 71-79, (2002).

Melman, et al., *The Journal of Urology*, "The Epidemiology and Pathophysiology of Erectile Dysfunction", vol. 161. pp. 5-11. (1999).

Mollnoff, et al., *Annals of the New York Academy of Sciences*, "PT-141: A Melanocortin Agonist for the Treatment of Sexual Dysfunction", vol. 994, pp. 96-102, (2003).

Naylor, et al., *British Journal of Urology*, "Endogenous neurotransmitters mediating penile erection", vol. 81, pp. 424-431, (1998).

Park, et al., *International Journal of Impotence Research*, "Vasculogenic female sexual dysfunction: The hemodynamic basis for vaginal engorgement insufficiency and clitoral erectile insufficiency", vol. 9, pp. 27-37, (1997).

Sebhat, et al., *Journal of Medicinal Chemistry*, "Design and Pharmacology of N-[(3R)-1,2,3,4-Tetrahydroisoquinolinium-3-ylcarbonyl]-(1R)-1-(4-chlorobenzyl)- 2-[4-cyclohexyl-4-(1H-1,2,4-triazol- 1-ylmethyl)piperidin-1-yl]-2-oxoethylamine (1), a Potent, Selective, Melanocortin Subtype-4 Receptor Agonist", vol. 45(21), (2002).

Taub, et al., *Adult Urology*, "Relationship Between Contraction and Relaxation in Human and Rabbit Corpus Cavernosum", vol. 42(6), pp. 698-704, (1993).

Vergonl, et al., *European Journal of Pharmacology*, "Differential influence of a selective melanocortin MC4 receptor antagonist (HS014) on melanocortin-induced behaviorial effects in rats", vol. 362, pp. 95-101, (1998).

Van der Ploeg, et al., *PNAS*, "A role for the melanocodin 4 receptor in sexual function", vol. 99(17), pp. 11381-11386, (2002).

Wessells, et al., *International Journal of Impotence Research*, Melancortin receptor agonists, penile erection, and sexual motivation: human studies with Melanotan II, vol. 12, Suppl. 4, pp. S74-S79, (2000).

Wikberg, et al., *Pharmacological Research*, "New Aspects on the Melanocortins and Their Receptors", vol. 42(5), (2000).

Carpino, Expert Opinion on Therapeutic Patents, 2000, 10(6), pp. 819-831.

O'Rahilly, European Journal of Endocrinology, 2002, 147, pp. 435-441.

Van der Ploeg et al., PNAS, Aug. 20, 2002, vol. 99, No. 17, pp. 11381-11386.

Samama et al., Regulatory Peptides, 113, 2003, pp. 85-88.

* cited by examiner

ORTEP plot for the crystal structure of the compound of Example 5

ORTEP plot for the crystal structure of the compound of Preparation 16

ORTEP plot for the crystal structure of the compound of Preparation 22b

ORTEP plot for the asymmetric unit of the crystal structure of (3S,4R)-4-(2,4-difluorophenyl)-N-[(1R)-1-phenylethyl]pyrrolidine-3-carboxamide hydrochloride Simulated PXRD Pattern for Compound of Example 5

Simulated PXRD Pattern for Compound of Preparation 16

Simulated PXRD Pattern for Compound of Preparation 22b

Simulated PXRD Pattern for (3S,4R)-4-(2,4-difluorophenyl)-N-[(1R)-1-phenylethyl]pyrrolidine-3-carboxamide hydrochloride

(3,5-DIMETHYLPIPERIDIN-1-YL) (4-PHENYLPYRROLIDIN-3-YL)METHANONE DERIVATIVES AS MCR4 AGONISTS

This application claims priority from United Kingdom Application Number 0402492.3, filed Feb. 4, 2004, U.S. Application No. 60/543,950 filed Feb. 12, 2004, United Kingdom Application Number 0412417.8 filed Jun. 3, 2004, U.S. Application No. 60/580,209 filed Jun. 15, 2004, United Kingdom Application Number 0425530.3 filed Nov. 19, 2004, U.S. Application No. 60/634,916 filed Dec. 10, 2004.

The entire disclosure of the above parent applications are fully incorporated herein by reference thereto.

The present invention relates to a novel class of melanocortin MCR4 agonist compounds and especially to selective MCR4 agonist compounds, to their use in medicine, to compositions containing them, to processes for their preparation and to intermediates used in such processes. In particular the present invention relates to a class of MCR4 agonist compounds useful for the treatment of sexual dysfunctions and/or obesity.

Compounds of the present invention are useful in treating male and female sexual dysfunctions including hypoactive sexual desire disorder, sexual arousal disorder, orgasmic disorder and/or sexual pain disorder in females, male erectile dysfunction, as well as obesity (by reducing appetite, increasing metabolic rate, reducing fat intake or reducing carbohydrate craving) and diabetes mellitus (by enhancing glucose tolerance and/or decreasing insulin resistance). The compounds of the invention are useful in treating further diseases, disorders or conditions including, but not limited to, hypertension, hyperlipidemia, osteoarthritis, cancer, gall bladder disease, sleep apnea, depression, anxiety, compulsion, neuroses, insomnia/sleep disorder, substance abuse, pain, fever, inflammation, immune modulation, rheumatoid arthritis, skin tanning, acne and other skin disorders, neuroprotective and cognitive and memory enhancement including the treatment of Alzheimer's disease.

Compounds of the present invention are particularly suitable for treating female sexual dysfunction, male erectile dysfunction, obesity and diabetes.

Desirable properties for MCR4 agonist compounds of the present invention include: desirable MCR4 potencies as detailed hereinafter; selectivity for MCR4 versus MCR1, and/or MCR5, and/or MCR3 as detailed hereinafter; both desirable MC4R potency and selectivity for MCR4 versus, MCR1, and/or MCR5, and/or MCR3; good biopharmaceutical properties such as physical stability; solubility; appropriate metabolic stability.

GENERAL FORMULA

Figure 1:
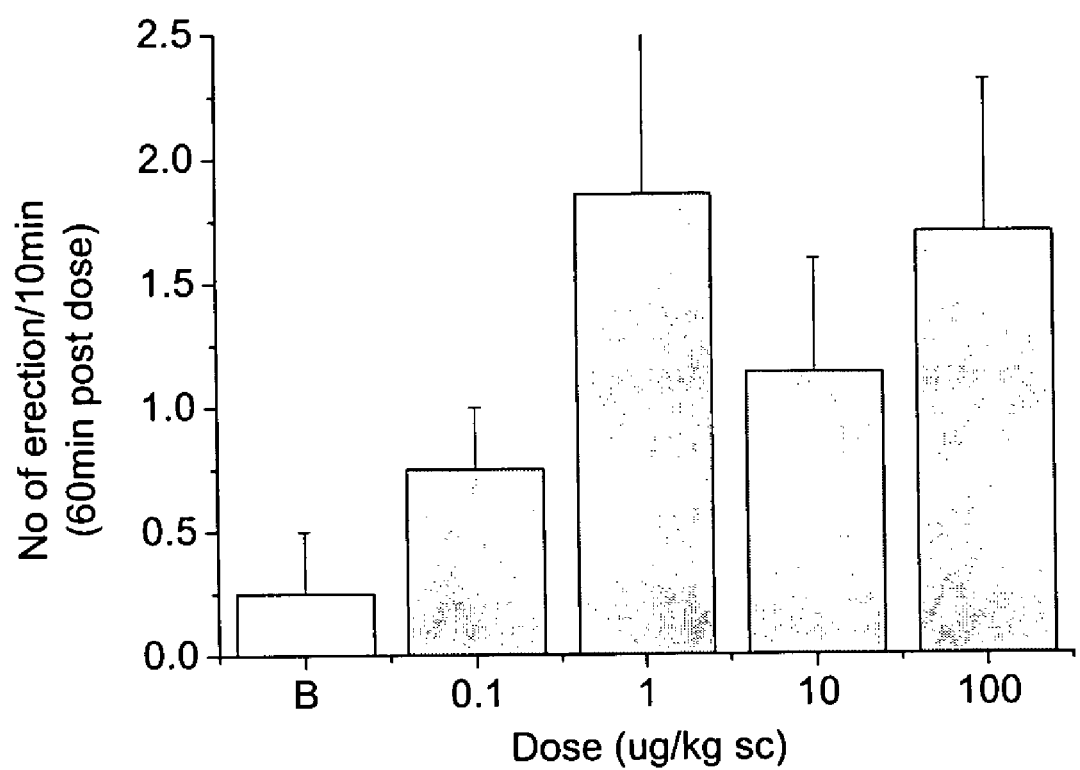
FIG. 1 depicts the number of erections observed over a 10 minute period starting 60 minutes post dosage for animals dosed with 1, 10 and 100 μg/kg subcutaneously with the compound of Example 1.

The present invention provides for compounds of formula (I)

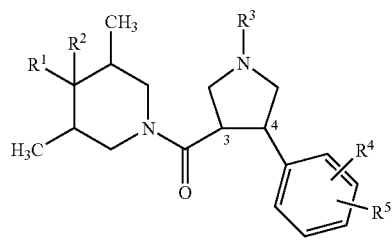

or a pharmaceutically acceptable salt, hydrate, solvate, isomer or prodrug thereof wherein $R^1$ is selected from: —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_1-C_2)$alkyl$(C_3-C_8)$cycloalkyl, aryl, —$(C_1-C_2)$alkylaryl, heterocyclic, or —$(C_1-C_2)$alkylheterocyclic groups wherein each of the foregoing $R^1$ groups is optionally substituted by one or more groups selected from: —$(C_1-C_4)$alkyl, —$(CH_2)_m(C_3-C_5)$cycloalkyl, halogen, —$(CH_2)_mOR^6$, CN, —C(O)OR$^6$, —$(CH_2)_mNR^7SO_2R^8$, CF$_3$, CH$_2$CF$_3$, OCF$_3$ or OCH$_2$CF$_3$ wherein m=0, 1 or 2;

$R^2$ is H, OH or OCH$_3$;

$R^3$ is selected from: H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_1-C_2)$alkyl$(C_3-C_8)$cycloalkyl, aryl, —$(C_1-C_2)$alkylaryl, heterocyclic, or —$(C_1-C_2)$alkylheterocyclic groups wherein each of latter ten $R^3$ groups is optionally substituted by one or more groups selected from: OH, —$(C_1-C_4)$alkyl, —$(CH_2)_n(C_3-C_5)$cycloalkyl, halogen, CN, —$(CH_2)_pOR^6$ or —$(CH_2)_pNR^7R^8$ wherein n=0, 1 or 2;

$R^4$ is selected from: H, —$(C_1-C_4)$alkyl, —$(C_2-C_4)$alkenyl, —$(C_2-C_4)$alkynyl, —$(CH_2)_p(C_3-C_5)$cycloalkyl, —$(CH_2)_p(C_5)$cyclo-alkenyl, halogen, —$(CH_2)_pOR^6$, —$(CH_2)_pNR^7R^8$, CN, —C(O)R$^6$, C(O)OR$^6$C(O)(O)NR$^7R^8$, —$(CH_2)_pNR^7SO_2R^8$, CF$_3$, CH$_2$CF$_3$, OCF$_3$ or OCH$_2$CF$_3$ groups wherein p=0, 1 or 2;

$R^5$ is selected from: —$(C_1-C_4)$alkyl, —$(C_2-C_4)$alkenyl, —$(C_2-C_4)$alkynyl, —$(CH_2)_p(C_3-C_5)$cycloalkyl, —$(CH_2)_p(C_5)$cyclo-alkenyl, halogen, —$(CH_2)_pOR^6$, —$(CH_2)_pNR^7R^8$, CN, —C(O)R$^6$, —C(O)OR$^6$, —C(O)NR$^7R^8$, —$(CH_2)_pNR^7SO_2R^8$, CF$_3$, CH$_2$CF$_3$, OCF$_3$ or OCH$_2$CF$_3$ groups wherein p=0, 1 or 2;

or $R^4$ and $R^5$ can together form a fused 5- to 7-membered saturated or unsaturated ring;

$R^6$, $R^7$ and $R^8$ are each independently selected from H, $CH_3$ or $CH_2CH_3$;

and wherein the heterocyclic groups of $R^1$ and $R^3$ are independently selected from 4- to 10-membered ring systems containing up to 4 heteroatoms independently selected from O, N or S.

Heterocyclic groups suitable for use herein are 4- to 10-membered mono or bicyclic heteroaryl rings containing one to three heteroatoms from the list N, S and O and combinations thereof and wherein said bicyclic heteroaryl rings are 9- or 10-membered ring systems which may be either two heteroaryl rings fused together or a heteroaryl ring fused to an aryl ring.

Suitable bicyclic heteroaryl groups for use herein include: include: benzimidazolyl, benzotriazolyl, benzothiazolyl, indazolyl, indolyl, imidazopyridinyl, imidazopyrimidinyl, pyrrolopyridinyl, quinolinyl, isoquinolinyl, quinazolinyl, naphthyridinyl and pyridopyrimidinyl groups.

Preferred for use herein are monocyclic 5- to 6-membered heteroaryl rings containing one or three heteroatoms from the list N and O and combinations thereof.

Suitable 5-membered ring monocyclic heteroaryl groups for use herein include: triazinyl, oxadiazinyl, oxazolyl, thiazolyl, thiadiazolyl, furyl, thienyl and pyrrolyl and imidazolyl groups.

Suitable 6-membered ring monocyclic heteroaryl groups for use herein include: pyridinyl, pyrimidinyl, pyridazinyl and pyrazinyl groups.

Preferred $R^1$ heterocyclic rings are monocyclic 5- to 6-membered heteroaryl rings containing one or two heteroatoms from the list N and O and combinations thereof. More preferred $R^1$ heterocyclic rings are monocyclic 5- to 6-membered heteroaryl rings containing one or 2 N heteroatoms. Highly preferred $R^1$ heterocyclic rings herein are monocyclic 6-membered heteroaryl rings containing one or two N heteroatoms such as pyridinyl and pyrimidinyl.

An especially preferred $R^1$ heteroaryl group herein is the pyridinyl group.

Preferred $R^3$ heterocyclic rings are monocyclic 5- to 6-membered heteroaryl rings containing one or two heteroatoms from the list N and O and combinations thereof such as tetrahydropyranyl, pyridinyl, pyridazinyl, pyrazinyl and pyrimidinyl groups. More preferred $R^3$ heterocyclic rings are monocyclic 5- to 6-membered heteroaryl rings containing one or two N heteroatoms. More preferred still as $R^3$ heterocyclic rings are monocyclic 6-membered heteroaryl rings containing one or two N heteroatoms such as pyridinyl, pyridazinyl, pyrazinyl and pyrimidinyl groups.

Particularly preferred $R^3$ 6-membered ring monocyclic heteroaryl groups for use herein are pyridin-2-yl, pyridin-3-yl, pyridazin-3-yl, pyrazinyl, pyrimidin-5-yl and pyrimidin-2-yl groups. Especially preferred $R^3$ 6-membered ring monocyclic heteroaryl groups for use herein include pyridin-2-yl, pyridin-3-yl and pyridazin-3-yl groups. Of these groups pyridazin-3-yl is most preferred.

Suitable fused ring systems formed by $R^4$ and $R^5$ together may be carbocyclic ring systems or heterocyclic ring systems containing up to two heteroatoms selected from O, N or S. Including the phenyl ring to which they are attached, preferred ring systems which $R^4$ and $R^5$ may form are: indane, 1,2,3,4-tetrahydronaphthalene, indolyl, indazolyl, naphthyl, quinolyl, benzothiazolyl, benzimidazolyl, benzo[1,3]dioxolane, 2,3-dihydrobenzo[1,4]dioxine, 2,3-dihydrobenzofuran, 2,3-dihydrobenzothiophene and 1,3-dihydroisobenzofuran.

In the above definitions, unless otherwise indicated, alkyl, alkenyl and alkynyl groups having three or more carbon atoms, and alkanoyl groups having four or more carbon atoms, may be straight chain or branched chain. For example, a $C_4$ alkyl substituent can be in the form of normal-butyl (n-butyl), iso-butyl (i-butyl), secondary-butyl (sec-butyl) or tertiary-butyl (t-butyl). For the avoidance of doubt where $R^1$ and/or $R^3$ is an optionally substituted alkyl group said alkyl group(s) may not be further substituted by a further (unsubstituted) alkyl group. Furthermore where $R^3$ is substituted with an alkenyl or an alkynyl group the carbon atom (of said unsaturated group), which is directly bonded to the N atom, may not itself be unsaturated.

The term halogen includes Cl, Br, F, and 1.

The term "aryl", when used herein, includes six- to ten-membered carbocyclic aromatic groups, such as phenyl and naphthyl.

The present invention additionally provides compounds of general formulae (IA) to (IF) as well as mixtures thereof as detailed hereinafter. For the avoidance of doubt, all references to compounds of general formula (I) hereinafter, such as for example, salts, polymorphs, pro-drugs or optical, geometric and tautomeric isomers thereof are intended to encompass compounds having general formulae (IA) to (IF) unless otherwise specifically provided.

The pharmaceutically acceptable salts of the compounds of the formula (I) include the acid addition and the base salts thereof.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of formula I may be prepared by one or more of three methods:
  (i) by reacting the compound of formula I with the desired acid or base;
  (ii) by removing an acid- or base-labile protecting group from a suitable precursor of the compound of formula I or by ring-opening a suitable cyclic precursor, for example, a lactone or lactam, using the desired acid or base; or
  (iii) by converting one salt of the compound of formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula I include references to salts, solvates, multi-component complexes and liquid crystals thereof and to solvates, multi-component complexes and liquid crystals of salts thereof.

The compounds of the invention include compounds of formula (I) as hereinbefore defined, polymorphs and crystal habits thereof, prodrugs, and isomers thereof (including optical, geometric and tautomeric isomers) as hereinafter defined and isotopically labelled compounds of formula (I).

As indicated, so-called 'prodrugs' of the compounds of formula (I) are also within the scope of the invention. Thus certain derivatives of compounds of formula (I), which may have little or no pharmacological activity themselves, can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T Higuchi and W Stella) and *Bioreversible Carriers in Drug Design*, Pergamon Press, 1987 (Ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H Bundgaard (Elsevier, 1985).

Some examples of prodrugs in accordance with the invention include (i) where the compound of formula I contains a carboxylic acid functionality (—COOH) or an ester thereof, for example, a compound wherein the hydrogen of the carboxylic acid functionality of the compound of formula (I) is replaced by —$(C_1$-$C_8)$alkyl;

(ii) where the compound of formula I contains an alcohol functionality (—OH), an ether thereof, for example, a compound wherein the hydrogen of the alcohol functionality of the compound of formula I is replaced by —$(C_1$-$C_6)$alkanoyloxymethyl, such as for example when $R^2$=OH, or when the $R^3$ group is substituted by an —OH group, a preferred prodrug herein is an ether; and (iii) where the compound of formula I contains a primary or secondary amino functionality (—$NH_2$ or —NHR where R≠H), such as for example where $R^3$=H, a preferred prodrug thereof is an amide thereof, for example, a compound wherein, as the case may be, one or both hydrogens of the amino functionality of the compound of formula I is/are replaced by —$(C_1$-$C_{10})$alkanoyl, preferably —$(C_1$-$C_6)$alkanoyl, more preferably methyl, ethyl or propylalkanoyl.

Particularly preferred pro-drugs herein are ethers, —$(C_1$-$C_4)$alkyl ethers and —$(C_1$-$C_4)$alkyl esters of the compounds of general formula (I), with esters being particularly preferred. Ester pro-drugs are described in detail in "Design of ester prodrugs to enhance oral absorption of poorly permeable compounds: Challenges to the discovery scientist", Current Drug Metabolism, (2003), 4(6), 461-485.

Further examples of replacement groups in accordance with the foregoing examples and examples of other prodrug types may be found in the aforementioned references.

Finally, certain compounds of formula (I) may themselves act as prodrugs of other compounds of formula (I).

Also included within the scope of the invention are metabolites of compounds of formula I, that is, compounds formed in vivo upon administration of the drug. Some examples of metabolites in accordance with the invention include (i) where the compound of formula I contains a methyl group, an hydroxymethyl derivative thereof (—$CH_3$→—$CH_2OH$):

(ii) where the compound of formula I contains an alkoxy group, an hydroxy derivative thereof (—OR→—OH);

(iii) where the compound of formula I contains a tertiary amino group, a secondary amino derivative thereof (—$NR^7R^8$→—$NHR^7$ or —$NHR^8$ where $R^8$ and $R^8$ are different groups);

(iv) where the compound of formula I contains a secondary amino group, a primary derivative thereof (—$NHR^7$→—$NH_2$);

(v) where the compound of formula I contains a phenyl moiety, a phenol derivative thereof (—Ph→—PhOH); and (vi) where the compound of formula I contains an amide group, a carboxylic acid derivative thereof (—$CONH_2$→—COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds that contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Specifically included within the scope of the present invention are stereoisomeric mixtures of compounds having formula (I), or a diastereomerically enriched or diastereomerically pure isomer of a compound of formula (I), or an enantiomerically enriched or enantiomerically pure isomer of a compound of formula (I).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2 to 20%, and may contain from 0 to 5% by volume of an alkylamine. Concentration of the eluate affords the enriched mixture. The absolute composition of the mobile phase will be dependant upon the chiral stationary phase (asymetric resin) selected. Preparation 2 as detailed hereinafter provides an example of such a separation technique.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

Thus the present invention additionally provides compounds of general formulae (IA), (IB), (IC), (ID), (IE), (IF), (IG) and (1H).

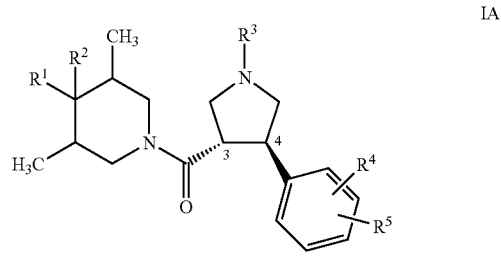

IA

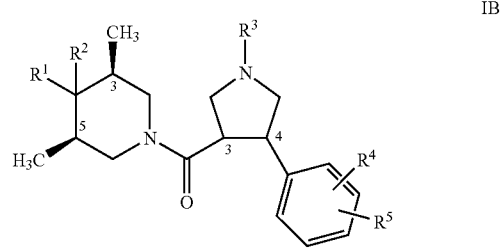

IB

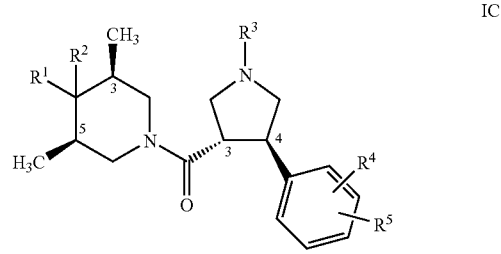

IC

-continued

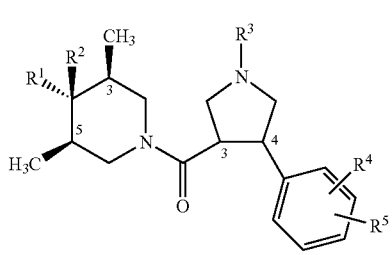
ID

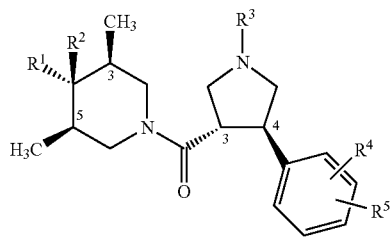
IE

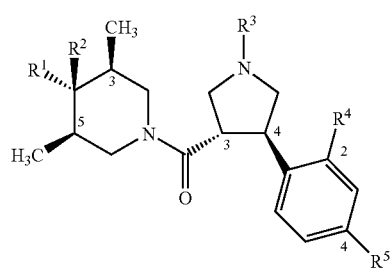
IF

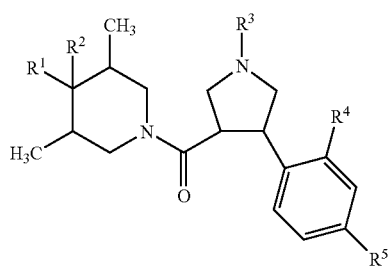
IG

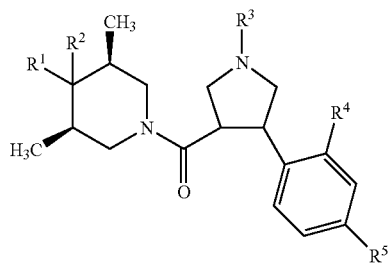
IH wherein $R^1$, $R^2$, $R^3$, $R^4$ and $R^5$ are as defined hereinbefore. Also included are compounds having the general formulae (IB) and (ID) wherein the stereochemistry of the groups at the 3 and 4 positions of the pyrrolidine ring are cis relative to each other.

Preferably the present invention provides compounds of general formula (IA), more preferably compounds of general formula (IC), more preferably still compounds of general formula (IE) and especially compounds of general formula (IF).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

According to a preferred embodiment the present invention provides a group of compounds having general formula (I), preferably formula (IA), more preferably formula (IC), more preferably still formula (IE) and especially formula (IF), wherein $R^1$ is selected from: —($C_1$-$C_6$)alkyl, —($C_3$-$C_8$)cycloalkyl, —($C_1$-$C_2$)alkyl($C_3$-$C_8$)cycloalkyl, phenyl, —($C_1$-$C_2$)alkylaryl, heterocyclic, or —($C_1$-$C_2$)alkylheterocyclic groups and wherein $R^1$ is optionally substituted by one or more groups selected from —($C_1$-$C_4$)alkyl, —$(CH_2)_m OR^6$, —$(CH_2)_m$($C_3$-$C_5$)cycloalkyl, halogen, $OCH_3$, $OCH_2CH_3$, CN, $CF_3$, $CH_2CF_3$, $OCF_3$ or $OCH_2CF_3$ wherein m=1 or 2 and wherein when $R^1$ is a heterocyclic, or a —($C_1$-$C_2$)alkylheterocyclic group said heterocyclic groups are independently selected from mono-cyclic 5- to 6-membered ring systems containing up to 3 heteroatoms independently selected from O, N or S and combinations thereof.

According to a more preferred embodiment the present invention provides a group of compounds having general formula (I), preferably formula (IA), more preferably formula (IC), more preferably still formula (IE) and especially formula (IF), wherein $R^1$ is selected from: —($C_1$-$C_6$)alkyl, —($C_3$-$C_8$)cycloalkyl, —($C_1$-$C_2$)alkyl($C_3$-$C_8$)cycloalkyl, phenyl, —($C_1$-$C_2$)alkylaryl, heterocyclic, or —($C_1$-$C_2$)alkylheterocyclic groups wherein each of the foregoing $R^1$ groups is optionally substituted by one or more groups selected from: —($C_1$-$C_4$)alkyl, halogen, —$(CH_2)_m OR^6$, CN, $CF_3$, $OCF_3$, wherein m=1 or 2;

$R^2$ is OH;

$R^3$ is selected from: H, —($C_1$-$C_6$)alkyl, —($C_3$-$C_8$)cycloalkyl, —($C_1$-$C_2$)alkyl($C_3$-$C_8$)cycloalkyl, aryl, —($C_1$-$C_2$)alkylaryl, heterocyclic, or —($C_1$-$C_2$)alkylheterocyclic groups wherein each of latter seven $R^3$ groups is optionally substituted by one or more groups selected from: OH, —$(C_1$-$C_4)$ alkyl, —$(CH_2)_n(C_3$-$C_5)$cycloalkyl, halogen, CN, —$(CH_2)_nOR^6$ or —$(CH_2)_pNR^7R^8$ wherein n=0, 1 or 2;

$R^4$ is selected from: H, —$(C_1$-$C_4)$alkyl, —$(CH_2)_p(C_3$-$C_5)$ cycloalkyl, halogen, —$(CH_2)_pOR^6$, $(CH_2)_pNR^7R^8$, CN, —$C(O)R^6$, —$C(O)OR^6$, —$C(O)NR^7R^8$, —$(CH_2)_pNR^7SO_2R^8$, $CF_3$, $CH_2CF_3$, $OCF_3$ or $OCH_2CF_3$ groups wherein p=0, 1 or 2;

$R^5$ is selected from: —$(C_1$-$C_4)$alkyl, —$(CH_2)_p(C_3$-$C_5)$cycloalkyl, halogen, —$(CH_2)_pOR^6$, —$(CH_2)_pNR^7R^8$, CN, —$C(O)R^6$, —$C(O)OR^6$, —$C(O)NR^7R^8$, —$(CH_2)_pNR^7SO_2R^8$, $CF_3$, $CH_2CF_3$, $OCF_3$ or $OCH_2CF_3$ groups wherein p=0, 1 or 2;

$R^6$, $R^7$ and $R^8$ are each independently selected from H, $CH_3$ or $CH_2CH_3$;

wherein the heterocyclic group of $R^3$ is selected from mono-cyclic 5- to 6-membered ring systems containing up to 2 heteroatoms independently selected from O or N and combinations thereof;

and wherein the heterocyclic group of $R^1$ is selected from mono-cyclic 5- to 6-membered ring systems containing 1 N heteroatom.

Preferred herein are the groups of compounds having general formula (I), preferably formula (IA), more preferably formula (IC), more preferably still formula (IE) and especially formula (IF), as defined hereinbefore wherein $R^3$ is H, —$(C_1$-$C_6)$alkyl, —$(C_3$-$C_8)$cycloalkyl, —$(C_1$-$C_2)$alkyl$(C_3$-$C_8)$cycloalkyl, —$(C_1$-$C_2)$alkylaryl or a heterocyclic group and wherein each of the latter five $R^3$ groups is optionally substituted by one or more groups selected from —OH, —$(C_1$-$C_4)$alkyl, —$(CH_2)_n(C_3$-$C_5)$cycloalkyl, halogen, —CN or —$(CH_2)_nOR^6$ wherein n=0 or 1 and wherein $R^6$ is H, $CH_3$ or $CH_2CH_3$ and wherein when $R^3$ is a heterocyclic group said heterocyclic group is selected from mono-cyclic 5- to 6-membered ring systems containing up to 2 heteroatoms independently selected from O or N and combinations thereof.

According to a further preferred embodiment the present invention provides a group of compounds of general formula (I), preferably formula (IA), more preferably formula (IC), more preferably still formula (IE) and especially formula (IF), wherein $R^1$ is selected from —$(C_1$-$C_6)$alkyl, —$(C_3$-$C_8)$ cycloalkyl, phenyl or heterocyclic groups and wherein each of the foregoing $R^1$ groups is optionally substituted by one or more groups selected from: —$(C_1$-$C_4)$alkyl, halogen, —$OR^6$ or —CN;

$R^2$ is OH;

$R^3$ is selected from H, —$(C_2$-$C_6)$alkyl, —$(C_3$-$C_8)$cycloalkyl, —$(C_1$-$C_2)$alkyl$(C_3$-$C_8)$cycloalkyl or heterocyclic groups and wherein each of latter four $R^3$ groups is optionally substituted by one or more groups selected from: —OH, —$(C_1$-$C_4)$alkyl, —$(CH_2)_r(C_3$-$C_5)$cycloalkyl, halogen, —CN, —$OR^6$ or —$(CH_2)_nNR^7R^8$ wherein n=0, 1 or 2;

$R^4$ is selected from: H, F or Cl;

$R^5$ is selected from: F or Cl;

$R^6$, $R^7$ and $R^8$ are each independently selected from H, $CH_3$ or $CH_2CH_3$;

wherein the heterocyclic group of $R^3$ is selected from mono-cyclic 5- to 6-membered ring systems containing up to 2 heteroatoms independently selected from O or N and combinations thereof;

and wherein the heterocyclic group of $R^1$ is selected from mono-cyclic 5- to 6-membered ring systems containing 1 N heteroatom.

Preferred herein are the groups of compounds having general formula (I), preferably formula (IA), more preferably formula (IC), more preferably still formula (IE) and especially formula (IF), as defined hereinbefore wherein the heterocyclic group of $R^1$ where present, is a monocyclic 6-membered ring systems containing up to 1 N heteroatom.

Preferred herein are the groups of compounds having general formula (I), preferably formula (IA), more preferably formula (IC), more preferably still formula (IE) and especially formula (IF), as defined hereinbefore wherein the heterocyclic group of $R^3$, where present, is a monocyclic 6-membered ring system containing up to 2 N heteroatoms.

Preferred $R^1$ groups for use herein are selected from —$(C_1$-$C_4)$alkyl, —$(C_3$-$C_6)$cycloalkyl, phenyl, pyridyl or pyrimidinyl wherein $R^1$ is optionally substituted by one or more groups selected from $CH_3$, $CH_2CH_3$, halogen, $OCH_3$, $OCH_2CH_3$, CN, $CF_3$ or $OCF_3$.

More preferred $R^1$ groups for use herein are selected from n-propyl, i-propyl, n-butyl, methoxymethyl, cyclopropyl, cyclohexyl, phenyl, 3-fluorophenyl, 4-fluorophenyl, 4-chlorophenyl, 4-methylphenyl, 4-methoxyphenyl, 2,6-difluorophenyl, 2,4-difluorophenyl, 3,4-difluorophenyl, pyridin-2-yl or pyridin-3-yl groups.

Highly preferred $R^1$ groups for use herein are selected from pyridin-2-yl, phenyl, 3-fluorophenyl, 4-fluorophenyl, 4-chlorophenyl, 4-methylphenyl, 4-methoxyphenyl, 2,6-difluorophenyl, 2,4-difluorophenyl or 3,4-difluorophenyl groups.

Preferred $R^3$ groups for use herein are selected from —H, —$(C_2$-$C_6)$alkyl, —$(C_3$-$C_8)$cycloalkyl, —$(C_1$-$C_2)$alkyl$(C_3$-$C_8)$cycloalkyl or heterocyclic and wherein each of the latter four $R^3$ groups is optionally substituted by one or more groups selected from —OH, —$(C_1$-$C_4)$alkyl or —$OR^6$ and wherein $R^6$ is —H, $CH_3$ or $CH_2CH_3$ and wherein when $R^3$ is a heterocyclic group said heterocyclic group is a monocyclic 6-membered ring system containing up to 2 N heteroatoms.

More preferred $R^3$ groups for use herein are selected from: hydrogen, ethyl, i-propyl, n-propyl, n-butyl, t-butyl, i-butyl, 2-methoxyethyl, cyclopentyl, cyclobutyl, cyclopentylmethyl, pyridin-2-yl, pyridin-3-yl, pyridazin-3-yl, pyrazinyl, pyrimidin-5-yl, pyrimidin-2-yl, pyrimidin-4-yl or tetrahydropyran-4-yl groups.

Preferred $R^4$ groups for use herein are selected from H, F or Cl and preferred $R^5$ groups for use herein are selected from F or Cl.

Preferred phenyl groups having $R^4$ and $R^5$ substituents for use herein are: a 2,4-substituted phenyl group wherein the $R^4$ and $R^5$ groups are each independently selected from F or Cl; or, a 4-mono-substituted phenyl group wherein $R^4$ is H and $R^5$ is F or Cl.

More preferred phenyl groups for use herein to which $R^4$ and $R^5$ are attached are 4-chlorophenyl or 2,4-difluorophenyl groups.

When $R^3$ is H, in a preferred group of compounds herein of general formula (IC), more preferably (IE) and especially (IF), $R^1$ is a phenyl, 3-fluorophenyl, 4-fluorophenyl, 2,6-difluorophenyl, 2,4-difluorophenyl, 3,4-difluorophenyl or pyridin-2-yl group; $R^2$ is OH; and $R^4$ is selected from: H or F and $R^5$ is selected from: F or Cl.

Preferred compounds herein wherein $R^3$ is H are the compounds of examples 12, 16, 24 and 48 or pharmaceutically acceptable salts, solvates or hydrates thereof.

When $R^3$ is a heterocyclic group as defined herein after, in a preferred group of compounds of general formula (IC), more preferably (IE) and especially (IF) herein, $R^1$ is a phenyl or pyridin-2-yl group; $R^3$ is —OH; $R^4$ is a heterocyclic group selected from: pyridin-2-yl, pyridin-3-yl, pyridazin-3-yl, pyrazinyl, pyrimidin-5-yl, pyrimidin-4-yl, pyrimidin-2-yl or tetrahyrdropyran-4-yl groups; and $R^4$ and $R^5$ are both F.

Preferred compounds herein wherein $R^3$ is a heterocyclic group selected from: pyridin-2-yl, pyridin-3-yl, pyridazin-3- yl, pyrazinyl, pyrimidin-5-yl, pyrimidin-4-yl, pyrimidin-2-yl or tetrahyrdropyran-4-yl groups are the compounds of examples numbers 31, 34, 35, 42 and 47 and pharmaceutically acceptable salts, solvates and hydrates thereof.

When $R^3$ is Et, i-Pr or t-Bu, in a preferred group of compounds herein of general formula (IC), more preferably (IE) and especially (IF), $R^1$ is phenyl, 4-fluorophenyl, 4-chlorophenyl, 3-fluorophenyl, 2,4-difluorophenyl, 3,4-difluorophenyl, pyridin-2-yl; $R^2$ is OH; and $R^4$ and $R^5$ are F.

Preferred compounds herein wherein $R^3$ is Et, i-Pr or t-Bu are the compounds of examples 1, 5, 6, 8, 9, 10, 13, 15, 22, 40, 50, 51, 52 and 53 and pharmaceutically acceptable salts, solvates and hydrates thereof.

Preferred compounds according to the present invention include:

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol;

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-isopropylpyrrolidin-3-yl]carbonyl}-3,5-dimethyl-4-phenylpiperidin-4-ol hydrochloride;

(3R,4R,5S)-1-{[(3S,4R)-1-tert-Butyl-4-(2,4-difluorophenyl)pyrrolidin-3-yl]carbonyl}-4-(3,4-difluorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-4-(2,4-difluorophenyl)-1-isopropylpyrrolidin-3-yl]carbonyl}-4-(4-fluorophenyl)-3,5-dimethylpiperidin-4-ol hydrochloride;

(3R,4R,5S)-1-{[(3S,4R)-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-chlorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(2,4-difluorophenyl)-3,5-dimethylpiperidin-4-ol hydrochloride;

(3R,4R,5S)-4-(2,4-difluorophenyl)-1-{[(3S,4R)-4-(2,4-difluorophenyl)pyrrolidin-3-yl]carbonyl}-3,5-dimethylpiperidin-4-ol hydrochloride;

(3R,4R,5S)-1-{[(3S,4R)-1-tert-Butyl-4-(2,4-difluorophenyl)pyrrolidin-3-yl]carbonyl}-3,5-dimethyl-4-pyridin-2-ylpiperidin-4-ol hydrochloride;

(3R,4R,5S)-1-{[(3S,4R)-4-(2,4-Difluorophenyl)pyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridin-2-ylpyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridin-3-ylpyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridazin-3-ylpyrrolidin-3-yl]carbonyl}-3,5-dimethyl-4-phenylpiperidin-4-ol hydrochloride;

(3R,4R,5S)-1-{[(3S,4R)-1-tert-Butyl-4-(2,4-difluorophenyl)pyrrolidin-3-yl]carbonyl}-3,5-dimethyl-4-propylpiperidin-4-ol hydrochloride;

(3R,4R,5S)-1-{[(3S,4R)-4-(2,4-Difluorophenyl)-1-pyrimidin-4-ylpyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridazin-3-ylpyrrolidin-3-yl]carbonyl}-3,5-dimethyl-4-pyridin-2-ylpiperidin-4-ol hydrochloride;

(3R,4R,5S)-1-{[(3S,4R)-4-(4-Chlorophenyl)pyrrolidin-3-yl]carbonyl}-3,5-dimethyl-4-phenylpiperidin-4-ol hydrochloride;

(3R,4R,5S)-4-(4-chlorophenyl)-1-{[(3S,4R)-4-(2,4-difluorophenyl)-1-isopropylpyrrolidin-3-yl]carbonyl}-3,5-dimethylpiperidin-4-ol hydrochloride;

(3R,4R,5S)-4-(3,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride;

(3R,4R,5S)-4-(2,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride; (3R,4R,5S)-1-{[(3S,4R)-4-(2,4-difluorophenyl)-1-ethylpyrrolidin-3-yl]carbonyl}-4-(3-fluorophenyl)-3,5-dimethylpiperidin-4-ol hydrochloride and pharmaceutically acceptable acid salts, solvates and hydrates thereof.

Preferred compounds according to the present invention are independently selected from the group consisting of:

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol;

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride;

(3R,4R,5S)-1-{[(3S,4R)-1-tert-Butyl-4-(2,4-difluorophenyl)pyrrolidin-3-yl]carbonyl}-4-(3,4-difluorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-chlorophenyl)-3,5-dimethylpiperidin-4-ol hydrochloride;

(3R,4R,5S)-4-(4-chlorophenyl)-1-{[(3S,4R)-4-(2,4-difluorophenyl)-1-isopropylpyrrolidin-3-yl]carbonyl}-3,5-dimethylpiperidin-4-ol hydrochloride and pharmaceutically acceptable acid salts, solvates and hydrates thereof.

Highly preferred herein are: (3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol also known as [1-tert-Butyl-4-(2,4-difluoro-phenyl)-pyrrolidin-3-yl]-(4-hydroxy-3,5-dimethyl-4-phenyl-piperidin-1-yl)-methanone (the compound of Example 1) and/or pharmaceutically acceptable acid salts thereof such as (3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride also known as [1-tert-Butyl-4-(2,4-difluoro-phenyl)-pyrrolidin-3-yl]-(4-hydroxy-3,5-dimethyl-4-phenyl-piperidin-1-yl)-methanone HCl salt (the compound of Example 5).

According to a yet further embodiment the present invention provides compounds of the general formula (I)

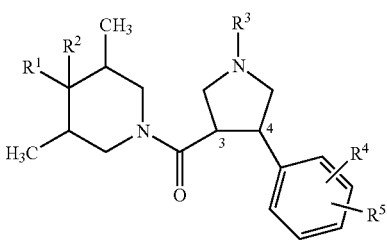

or a stereoisomeric mixture thereof, or a diastereomerically enriched or diastereomerically pure isomer thereof, or an enantiomerically enriched or enantiomerically pure isomer thereof, or a prodrug of such compound, mixture or isomer thereof, or a pharmaceutically acceptable salt of the compound, mixture, isomer or prodrug thereof wherein $R^1$ is selected from: $(C_1\text{-}C_6)$alkyl, $(C_2\text{-}C_6)$alkenyl, $(C_2\text{-}C_6)$alkynyl, $(C_3\text{-}C_8)$cycloalkyl, $(C_5\text{-}C_8)$cycloalkenyl, $(C_1\text{-}C_2)$alkyl$(C_3\text{-}C_8)$cycloalkyl, aryl, $(C_1\text{-}C_2)$alkylaryl, heterocyclic, or $(C_1\text{-}C_2)$alkylheterocyclic groups wherein each of the foregoing $R^1$ groups is optionally substituted by one or more groups selected from: $(C_1\text{-}C_4)$alkyl, $(CH_2)_m(C_3\text{-}C_5)$cycloalkyl, halogen, $(CH_2)_mOR^6$, $(CH_2)_mNR^7R^8$, CN, $C(O)R^6$, $C(O)OR^6$, $CON(R^7)_2$, $(CH_2)_mNR^7SO_2R^8$, $CF_3$, $CH_2CF_3$, $OCF_3$, $OCH_2CF_3$, SMe or SEt wherein m=0, 1 or 2;

$R^2$ is H, OH or OMe;

$R^3$ is selected from: H, $(C_1\text{-}C_6)$alkyl, $(C_2\text{-}C_6)$alkenyl, $(C_2\text{-}C_6)$alkynyl, $(C_3\text{-}C_8)$cycloalkyl, $(C_5\text{-}C_8)$cycloalkenyl, $(C_1\text{-}C_2)$alkyl$(C_3\text{-}C_8)$cycloalkyl, aryl, $(C_1\text{-}C_2)$alkylaryl, heterocyclic, or $(C_1\text{-}C_2)$alkylheterocyclic groups wherein each of latter ten $R^3$ groups is optionally substituted by one or more groups selected from: OH, $(C_1\text{-}C_4)$alkyl, $(CH_2)_r(C_3\text{-}C_5)$cycloalkyl, halogen, $(CH_2)_rOR^6$, $(CH_2)_rN(R^7)_2$, SMe or SEt wherein n=0, 1 or 2;

$R^4$ and $R^5$ are each independently selected from: $(C_1\text{-}C_4)$alkyl, $(C_2\text{-}C_4)$alkenyl, $(C_2\text{-}C_4)$alkynyl, $(CH_2)_p(C_3\text{-}C_5)$cycloalkyl, $(CH_2)_p(C_5)$cyclo-alkenyl, halogen, $(CH_2)_pOR^6$, $(CH_2)_pNR^7R^8$, CN, $C(O)R^6$, $C(O)OR^6$, $CON(R^7)_2$, $(CH_2)_pNR^7SO_2R^8$, $CF_3$, $CH_2CF_3$, $OCF_3$, $OCH_2CF_3$, SMe or SEt wherein p=0, 1 or 2 or $R^4$ and $R^5$ can together form a fused 5- to 7-membered saturated or unsaturated ring;

$R^6$, $R^7$ and $R^8$ are each independently selected from H, Me or Et;

wherein the $R^1$ and $R^3$ heterocyclic groups, where present, are optionally fused 4- to 10-membered ring systems containing up to 4 heteroatoms selected from O, N or S.

A preferred group of compounds according to this yet further embodiment are compounds wherein $R^1$ is selected from: $(C_1\text{-}C_6)$alkyl, $(C_3\text{-}C_8)$cycloalkyl, $(C_1\text{-}C_2)$alkyl$(C_3\text{-}C_8)$cycloalkyl, aryl, $(C_1\text{-}C_2)$alkylaryl, heterocyclic, or $(C_1\text{-}C_2)$alkylheterocyclic groups and wherein $R^1$ is optionally substituted by one or more groups selected from $(C_1\text{-}C_4)$alkyl, $(CH_2)_m(C_3\text{-}C_5)$cycloalkyl, halogen, OMe, OEt, CN, halogen, $CF_3$, $CH_2CF_3$, $OCF_3$, $OCH_2CF_3$, SMe or SEt wherein m=0, 1 or 2 and wherein said heterocyclic group is selected from: pyridinyl, pyrimidinyl, triazinyl, oxadiazinyl, oxazolyl, thiazolyl, thiadiazolyl, imidazolyl, benzimidazoloyl, benzothiazolyl, indazolyl, quinolyl or isoquinolyl; $R^2$ is H or OH; $R^3$ is H, $(C_1\text{-}C_6)$alkyl, $(C_3\text{-}C_8)$cycloalkyl, $(C_1\text{-}C_2)$alkyl$(C_3\text{-}C_8)$cycloalkyl, $(C_1\text{-}C_2)$alkylaryl, groups and wherein each of the latter four $R^3$ groups is optionally substituted by one or more groups selected from OH, $(C_1\text{-}C_4)$alkyl, $(CH_2)_m(C_3\text{-}C_5)$cycloalkyl, halogen, CN, $(CH_2)_nOR^6$, SMe or SEt wherein n=0 or 1; $R^4$ and $R^5$ are independently selected from $(C_1\text{-}C_4)$alkyl, cyclopropyl, halogen, $OR^6$, CN, $CF_3$, $CH_2CF_3$, $OCF_3$, $OCH_2CF_3$, SMe, SEt or $R^4$ and $R^5$ together form a fused 5 to 6 membered saturated or unsaturated ring; and wherein $R^6$ is as defined hereinbefore.

In a more preferred still group of compounds according to this yet further embodiment $R_1$ is a $(C_1\text{-}C_4)$alkyl, $(C_3\text{-}C_6)$ cycloalkyl, $(C_1\text{-}C_2)$alkyl$(C_3\text{-}C_5)$cycloalkyl, phenyl, pyridyl or pyrimidinyl group wherein $R^1$ is optionally substituted by one or more groups selected from Me, Et, halogen, OMe, OEt, CN, $CF_3$, $OCF_3$ and SMe; $R^2$ is OH; $R^3$ is a $(C_1\text{-}C_6)$alkyl group optionally substituted with one of the following groups OH, $OR^6$, $CF_3$; $R^4$ and $R^5$ are each independently $(C_1\text{-}C_4)$ alkyl, halogen, $OR^6$, CN, $CF_3$, $CH_2CF_3$, $OCF_3$, $OCH_2CF_3$; $R^6$ is H or Me.

In an especially preferred group of compounds according to this yet further embodiment $R^1$ is an n-butyl group, a cyclohexyl group, a phenyl group, or a 4-methyl phenyl group; $R^2$ is OH; $R^3$ is an ethyl group or a t-butyl group; and $R^4$ and $R^5$ are each independently F.

Highly preferred compounds according to this yet further embodiment are compounds of general formula IG whilst especially preferred compounds according to this yet further embodiment are compounds of general formula IH.

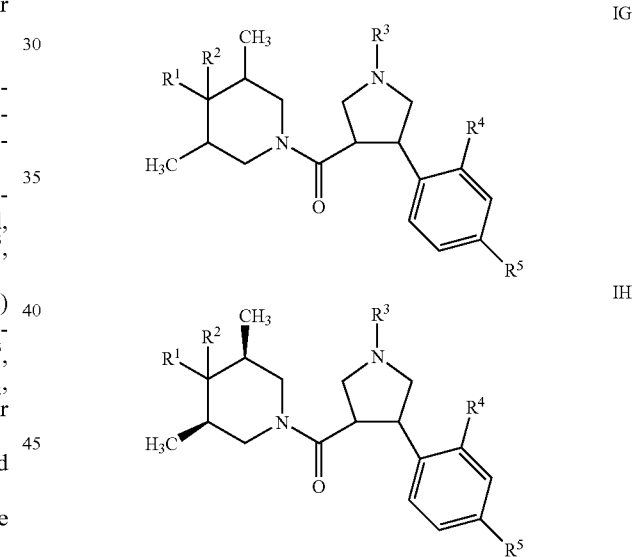

wherein $R^1$, $R^2$, $R^3$, $R^4$ and $R^5$ are as defined herein before.

More preferred compounds according to this yet further embodiment are compounds of formula (IG) or (IH), more preferably (IH) wherein the stereochemistry of the groups at the 3 and 4 positions of the pyrrolidine ring are trans relative to each other.

The routes below illustrate methods of synthesising compounds of formula (I).

Scheme 1 illustrates the preparation of compounds of formula (I) via peptide coupling of intermediates (II) and (III) if necessary adding a suitable base and/or additive (such as 1-hydroxybenzotriazole hydrate or 4-dimethylaminopyridine). Scheme 1a illustrates the preparation of compounds of formula (IA) via peptide coupling of intermediates (II) and (IIIA). Similarly, Schemes 1b to 1e illustrate the preparation of compounds of formulae (IC), (ID), (IE) and (IF) via peptide coupling of intermediates: (IIA) and (IIIA); (IIB) and (III); (IIB) and (IIIA); and (IIB) and (IIIB) respectively. Compounds of formulae (IB), (IG) and (IH) can be made in a similar fashion from the relevant intermediates.
Scheme 1
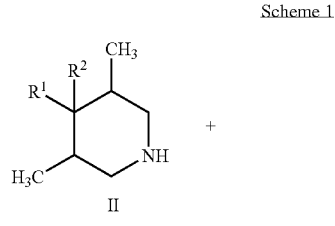
II
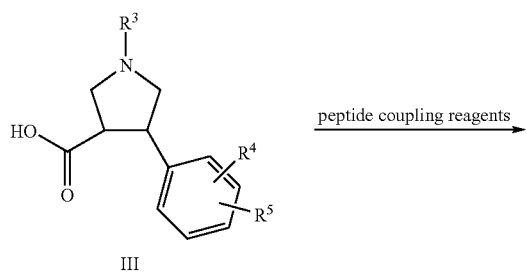
III
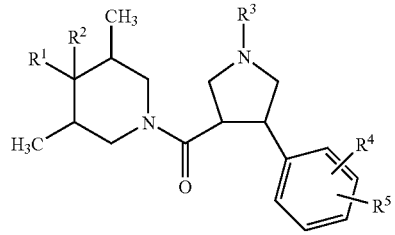
I
Scheme 1a
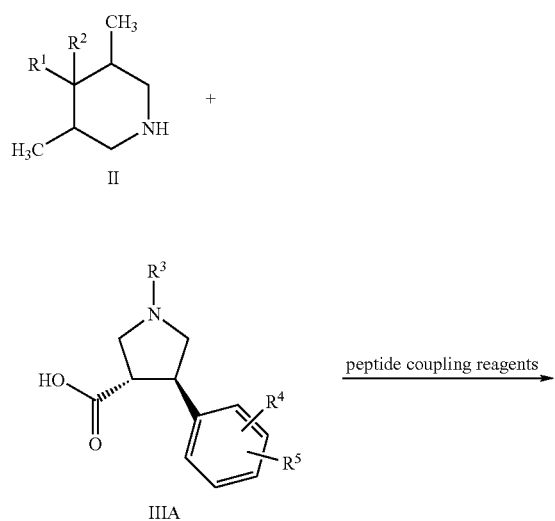
-continued
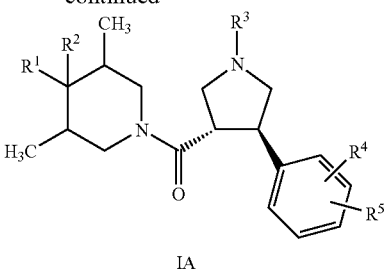
IA
Scheme 1b
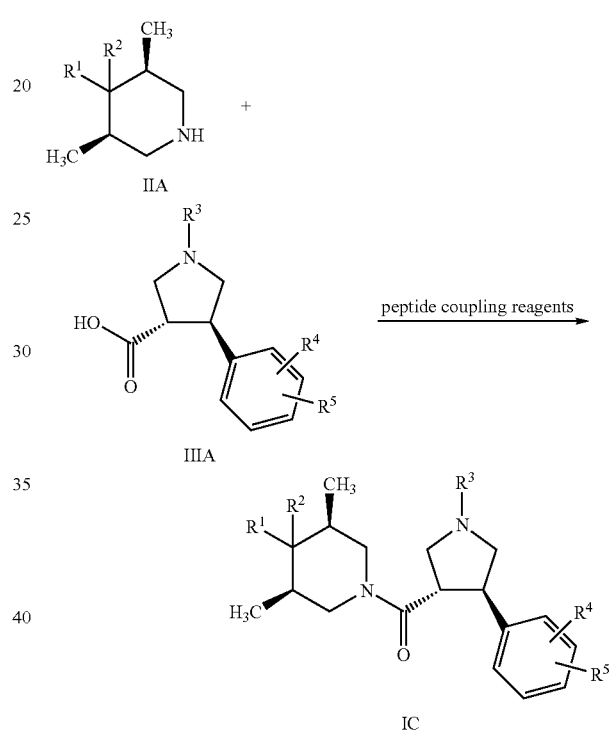
Scheme 1c
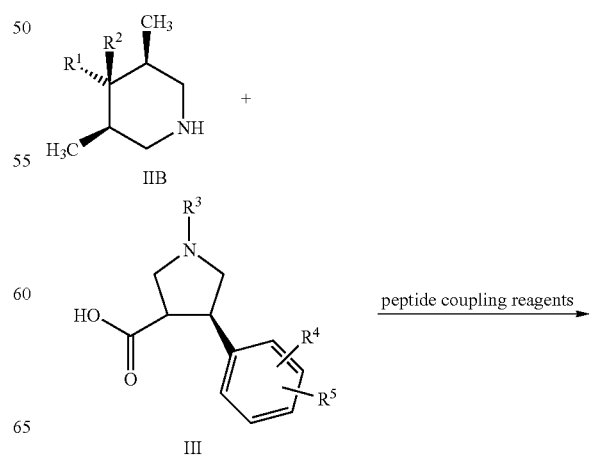

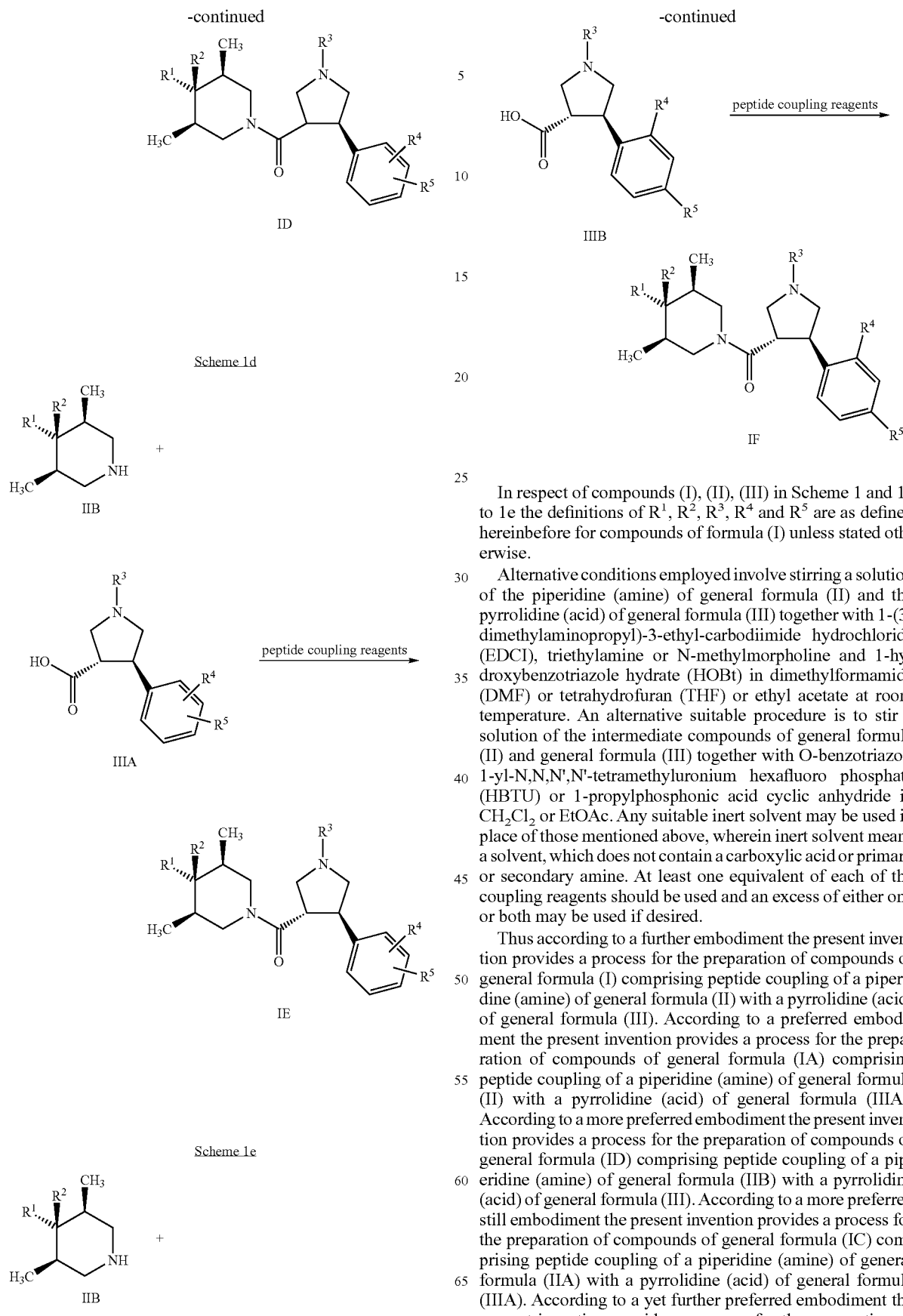

In respect of compounds (I), (II), (III) in Scheme 1 and 1a to 1e the definitions of $R^1$, $R^2$, $R^3$, $R^4$ and $R^5$ are as defined hereinbefore for compounds of formula (I) unless stated otherwise.

Alternative conditions employed involve stirring a solution of the piperidine (amine) of general formula (II) and the pyrrolidine (acid) of general formula (III) together with 1-(3-dimethylaminopropyl)-3-ethyl-carbodiimide hydrochloride (EDCI), triethylamine or N-methylmorpholine and 1-hydroxybenzotriazole hydrate (HOBt) in dimethylformamide (DMF) or tetrahydrofuran (THF) or ethyl acetate at room temperature. An alternative suitable procedure is to stir a solution of the intermediate compounds of general formula (II) and general formula (III) together with O-benzotriazol-1-yl-N,N,N',N'-tetramethyluronium hexafluoro phosphate (HBTU) or 1-propylphosphonic acid cyclic anhydride in $CH_2Cl_2$ or EtOAc. Any suitable inert solvent may be used in place of those mentioned above, wherein inert solvent means a solvent, which does not contain a carboxylic acid or primary or secondary amine. At least one equivalent of each of the coupling reagents should be used and an excess of either one or both may be used if desired.

Thus according to a further embodiment the present invention provides a process for the preparation of compounds of general formula (I) comprising peptide coupling of a piperidine (amine) of general formula (II) with a pyrrolidine (acid) of general formula (III). According to a preferred embodiment the present invention provides a process for the preparation of compounds of general formula (IA) comprising peptide coupling of a piperidine (amine) of general formula (II) with a pyrrolidine (acid) of general formula (IIIA). According to a more preferred embodiment the present invention provides a process for the preparation of compounds of general formula (ID) comprising peptide coupling of a piperidine (amine) of general formula (IIB) with a pyrrolidine (acid) of general formula (III). According to a more preferred still embodiment the present invention provides a process for the preparation of compounds of general formula (IC) comprising peptide coupling of a piperidine (amine) of general formula (IIA) with a pyrrolidine (acid) of general formula (IIIA). According to a yet further preferred embodiment the present invention provides a process for the preparation of compounds of general formula (IE) comprising peptide coupling of a piperidine (amine) of general formula (IIB) with a pyrrolidine (acid) of general formula (IIIA). According to an especially preferred embodiment the present invention provides a process for the preparation of compounds of general formula (IF) comprising peptide coupling of a piperidine (amine) of general formula (IIB) with a pyrrolidine (acid) of general formula (IIIB).

According to a yet further embodiment the present invention provides intermediate compounds of general formula (II), (IIA) and (IIB)

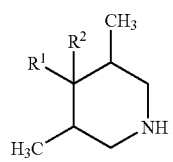
II

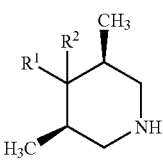
IIA

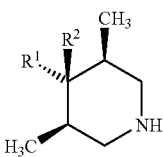
IIB wherein $R^1$ and $R^2$ are as defined hereinbefore. Preferred herein are intermediates of formula (II), more preferably formula (IIA) and especially formula (IIB) wherein $R^2$=OH and $R^1$=mono-substituted phenyl, or 2,6- or 3,4- or 2,4-di-substituted phenyl, or a pyridinyl group wherein the phenyl substituent groups are selected from F, Cl and $OCH_3$. A highly preferred group of intermediates herein are compounds of formula (II), more preferably formula (IIA) and especially formula (IIB) wherein $R^2$=—OH and $R^1$ is phenyl, 4-fluorophenyl, 3,4-difluorophenyl, 4-chlorophenyl, 3-fluorophenyl, 4-methylphenyl, 4-methoxyphenyl, 2,6-difluorophenyl, 2,4-difluorophenyl, 3,4-difluorophenyl or pyridine-2-yl.

Thus according to a preferred embodiment the present invention provides intermediates of general formula (IIB) wherein $R^2$=—OH and $R^1$ is phenyl, 4-fluorophenyl, 3,4-difluorophenyl, 3-fluorophenyl, 4-methylphenyl, 4-methoxyphenyl, 2,6-difluorophenyl, 2,4-difluorophenyl, 3,4-difluorophenyl or pyridine-2-yl.

According to a still further embodiment the present invention provides intermediate compounds of general formulae (III), (IIIA) and (IIIB)

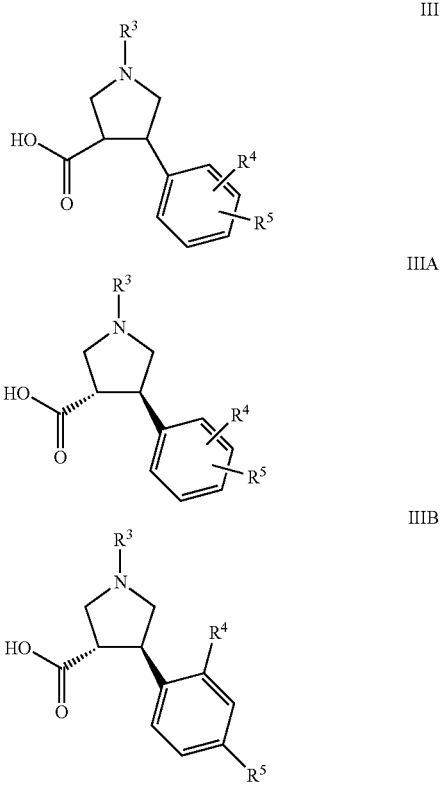

wherein $R^3$, $R^4$ and $R^5$ are as defined hereinbefore. Preferred herein are intermediates of formula (II), more preferably formula (IIA), most preferably formula (IIB) wherein $R^4$ is H or F or Cl and wherein $R^5$ is F or Cl and wherein $R^3$ is H or —$(C_2$-$C_4)$alkyl, —$(C_3$-$C_8)$cycloalkyl, $(C_1$-$C_2)$alkyl$(C_3$-$C_8)$cycloalkyl or heterocyclic. A preferred group of intermediates herein are compounds of formula (III), more preferably formula (IIIA) and especially formula (IIIB) wherein $R^3$ is —H, i-Pr, Et or a heterocyclic group selected from pyridine-2-yl, pyridine-3-yl, pyridazin-3-yl, pyrazinyl, pyrimidin-5-yl, pyrimidin-4-yl, pyrimidin-2-yl or tetrahydraopyran-4-yl groups.

Thus according to another embodiment the present invention provides a process for the preparation of compounds of general formula (I) more preferably general formula (IC), more preferably still general formula (IE) and especially general formula (IF) via peptide coupling of intermediates (II) and (III), preferably (IIA) and (IIIA), more preferably (IIB) and (IIIA), especially (IIB) and (IIIB) wherein: $R^2$ is —OH; $R^1$ is phenyl, 4-fluorophenyl, 3,4-difluorophenyl, 3-fluorophenyl, 4-methylphenyl, 4-methoxyphenyl, 2,6-difluorophenyl, 2,4-difluorophenyl, 3,4-difluorophenyl or pyridine-2-yl; $R^3$ is —H, t-Bu, i-Pr, Et or a heterocyclic group selected from pyridine-2-yl, pyridine-3-yl, pyridazin-3-yl, pyrazinyl, pyrimidin-5-yl, pyrimidin-4-yl, pyrimidin-2-yl or tetrahydraopyran-4-yl groups; $R^4$ is H, Cl or F and $R^5$ is Cl or F.

According to a preferred process herein compounds of general formula (IF) are prepared via peptide coupling of intermediates (IIA) and (IIIA) wherein: $R^2$ is —OH; $R^1$ is phenyl, 4-fluorophenyl, 3,4-difluorophenyl, 3-fluorophenyl, 4-methylphenyl, 4-methoxyphenyl, 2,6-difluorophenyl, 2,4-difluorophenyl, 3,4-difluorophenyl or pyridine-2-yl; $R^3$ is —H, t-Bu, i-Pr, Et or a heterocyclic group selected from pyridine-2-yl, pyridine-3-yl, pyridazin-3-yl, pyrazinyl, pyrimidin-5-yl, pyrimidin-4-yl, pyrimidin-2-yl or tetrahydraopyran-4-yl groups; $R^4$ is H, Cl or F and $R^5$ is Cl or F.

According to a more preferred process herein compounds of general formula (IF) are prepared via peptide coupling of intermediates (IIA) and (IIIA) wherein: $R^2$ is —OH; $R^1$ is phenyl, 4-fluorophenyl, 3,4-difluorophenyl, 3-fluorophenyl, 2,4-difluorophenyl or 3,4-difluorophenyl or pyridine-2-yl; $R^3$ is t-Bu, i-Pr or Et and $R^4$ and $R^5$ are both F.

Scheme 2 illustrates an alternative route for the preparation of compounds of general formula (I) having a range of $R^3$ groups via utility of a protecting group strategy. Compounds of general formulae (IA) to (IF) can also be prepared according to the route illustrated in Scheme 2 via utility of the appropriate intermediates (II), (IIA) or (IIB) with the appropriate protected amine of formula (IV), (IVA) or (IVB) as necessary.

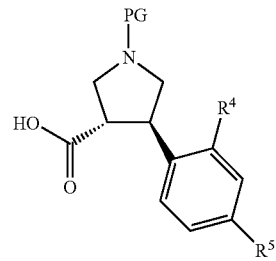
IVB

In scheme 2 the amine intermediates of general formulae (II) and protected pyrrolidine acid intermediates of general formula (IV) are coupled using standard peptide coupling Scheme 2

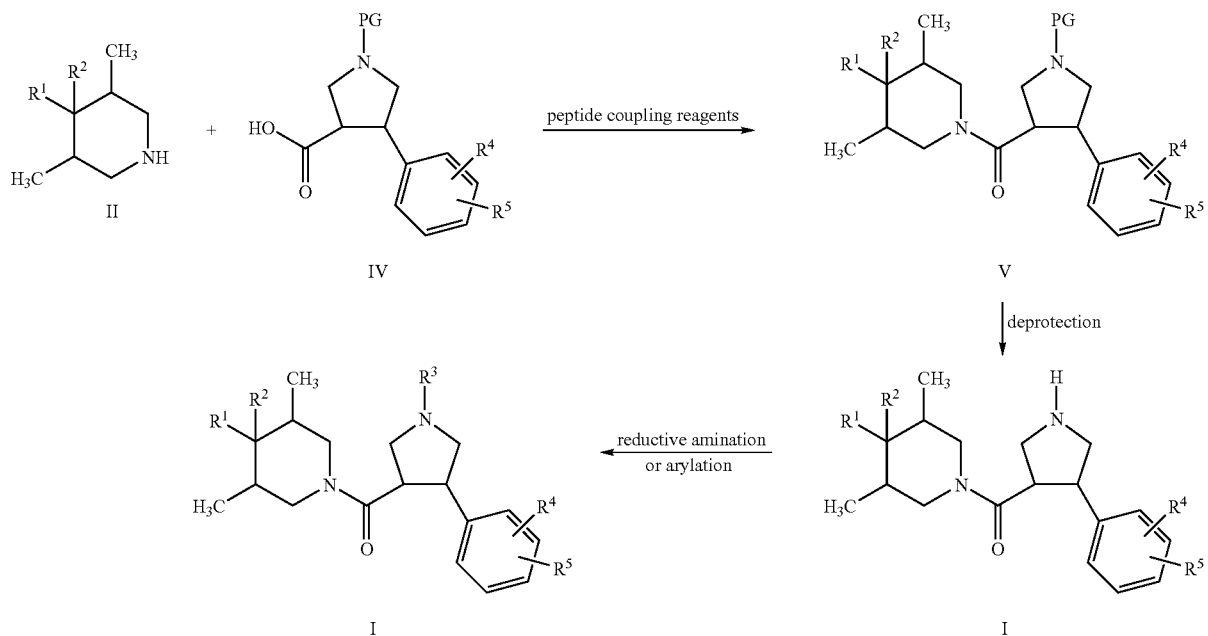

In respect of compounds (I), (II), (IV) and (V) in Scheme 2 or (IVA) or (IVB), as illustrated hereinafter, the definitions of $R^1$, $R^2$, $R^3$, $R^4$ and $R^5$ are as defined hereinbefore for compounds of formula (I) unless stated otherwise. PG is a nitrogen-protecting group.

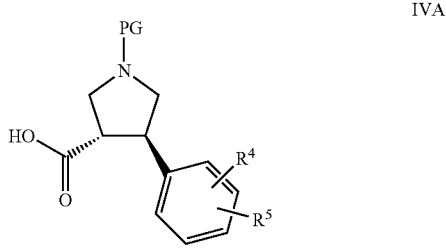
IVA methods as previously described in scheme 1 to provide a coupled and protected intermediate of general formula (V) from which the nitrogen protecting group can be removed using standard de-protection strategies to furnish a compound of general formula (I) in which $R^3$=H. Any suitable nitrogen protecting groups may be used (as described in "Protecting Groups in Organic Synthesis" $3^{rd}$ Edition T. W. Greene and P. G. Wuts, Wiley-Interscience, 1999). A common nitrogen protecting group (PG) suitable for use herein is tert-butoxy carbonyl, which is readily removed by treatment with an acid such as trifluoroacetic acid or hydrogen chloride in an organic solvent such as dichloromethane or 1,4-dioxane.

Alternative groups (to H) may be introduced at $R^3$ by using conventional alkylation techniques. Suitable methods for alkylation of secondary amines include:

(i) reaction with an aldehyde and a hydride reducing agent such as sodium triacetoxyborohydride, optionally in the presence of acetic acid in an inert solvent such as dichloromethane or acetonitrile (ii) reaction with an alkyl halide or suitably activated alcohol derivative (e.g. as a sulfonate ester) in the presence of a base (such as triethylamine) in an inert solvent;

Aryl and heteroaryl groups may be introduced as $R^3$ by displacement of a suitable leaving group from a heteroaromatic precursor. Suitable leaving groups include halogens. In certain cases transition metal catalysis (e.g. palladium, copper) or optionally in combination with a phosphine ligand such as 1,1'-binaphthalene-2,2'-diylbisdiphenylphosphine, may be required to achieve the required coupling products.

Scheme 3a illustrates the route for preparation of the acid pyrrolidine intermediates of general formula (III) from unsaturated ester intermediates of general formula (VI).

mula (VI), including esterification of a precursor cinnamic acid derivative (VII) using standard esterifcation methods, or Heck reaction of an aromatic halide (VIII) with a suitable acrylate ester such as t-butyl acrylate (IX) in the presence of palladium catalyst and a suitable base, such as triethylamine.

The resulting E-olefin intermediate of general formula (VI) will undergo an [3+2]-azomethine ylide cycloaddition by reaction with a compound of general formula (XI), to provide a pyrrolidine with almost exclusively the trans-stereochemistry. This reaction requires an inert solvent such as dichloromethane or toluene or tetrahydrofuran and activation by one or more of: (1) an acid catalyst, such as TFA; (2) a desilylation agent such as silver fluoride; (3) heating.

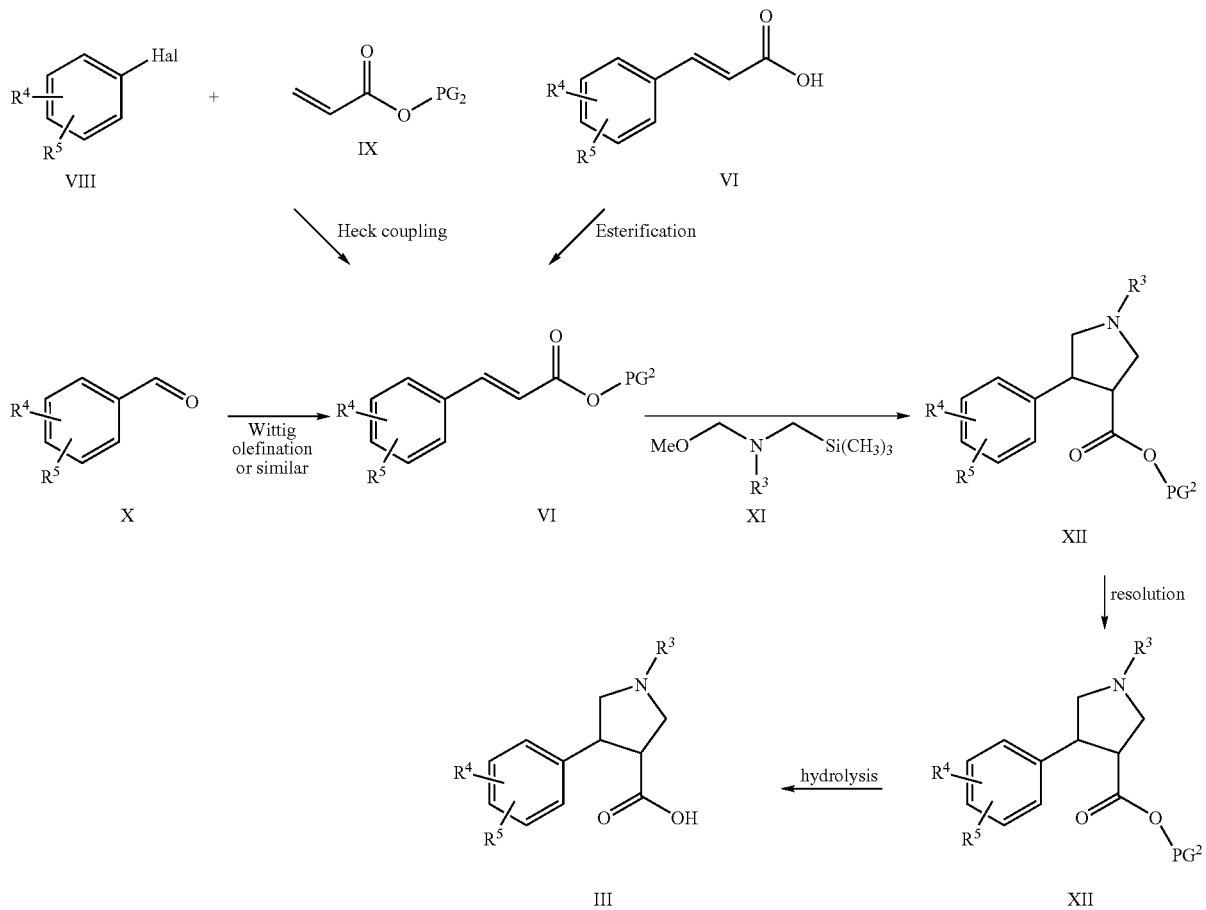

In respect of compounds (III), (VI), (VII), (VIII), (IX), (X), (XI), (XII), (XIII) in scheme 3a the definitions of $R^1$, $R^2$, $R^3$, $R^4$ and $R^5$ are as defined hereinbefore for compounds of formula (I) unless stated otherwise. $PG^2$ is a suitable carboxylic acid protecting group.

Compounds of general formula (VI) can be made by Wittig or similar olefination of an aldehyde intermediate of general formula (X) with a suitable ylide e.g. methyl (triphenylphosphoranylidene)acetate, or a phosphonate anion e.g. that is derived from deprotonation of trimethylphosphonoacetate, predominantly as the trans-isomer.

Many alternative methods exists in the literature for the production of unsaturated ester intermediates of general for- Alternatively, a pyrrolidine with almost exclusively cis-stereochemistry is provided by reaction a compound of general formula (XI) with an unsaturated ester or acid of Z-olefin configuration. Such Z-olefins may be prepared by means of Lindlar reduction of an alkyne or via the Still-Gennari olefination.

The compound of general formula (XII) obtained from the cycloaddition reaction is a racemate and may require resolution into its constituent enantiomers, which can be achieved by preparative HPLC using a chiral stationary phase. Alternatively the acid intermediate of general formula (III) can be resolved by standard methods (e.g. formation of diastereomeric derivatives by reaction with an enantiomerically pure reagent, separation of the resulting diastereomers by physical methods and cleaving to acid (III).

Intermediate compounds of general formula (XII) can be converted into compounds of general formula (III) by hydrolysis of the ester. Many methods are available to achieve this transformation (see Advanced Organic Chemistry: Reactions, Mechanisms, and Structure, Fourth Edition. March, Jerry, 1992, pp 378-383 published by Wiley, New York, N.Y. USA). In particular treatment of a compound of general formula (XII) with an aqueous alkali metal hydroxide solution, such as lithium hydroxide, sodium hydroxide or potassium hydroxide in a suitable organic solvent will provide the corresponding compounds of general formula (III). Preferably water-miscible organic co-solvents (such as 1,4-dioxane or tetrahydrofuran) are also utilised in such reactions. A preferred method herein for such ester hydrolysis involves treating the ester with potassium trimethylsilanolate in an inert solvent such as diethyl ether at room temperature. If required, the reaction may be heated to assist the hydrolysis. Ester hydrolysis may also be achieved using acid conditions e.g. by heating the ester in an aqueous acid such as hydrochloric acid. Certain esters are more conveniently hydrolysed in acidic conditions e.g. tert-butyl or benzhydryl esters. Such esters can be cleaved by treatment with anhydrous acids such as trifluoroacetic acid or hydrogen chloride in an inert organic solvent such as dichloromethane.

Scheme 3b illustrates an alternative route for the preparation of a single enantiomer of the acid pyrrolidine intermediate of general formula (III) from unsaturated ester intermediates of general formula (VI), using an oxazolidinone as a chiral auxiliary. The acid of formula (XVIII) may be obtained by hydrolysis of the unsaturated ester (VI) and an oxazolidinone may be employed as a chiral auxiliary (where R is preferably phenyl, tertiary butyl, or iso-propyl) to provide intermediate of formula (XVIII). Alternatively, the reaction of a compound of formula (VI) (when R=COt-Bu) with the lithium salt of an oxazolidinone, in a suitable solvent (e.g. THF), may also provide a compound of formula (XVIII).

The compound of formula (XVIII) will undergo an [3+2]-azomethine ylide cycloaddition by reaction with the compound of general formula (XI), to provide diastereomers (XX) and (XVIX) which can be separated by chromatography or crystallisation and hydrolysed to give a pyrrolidine of formula (III).

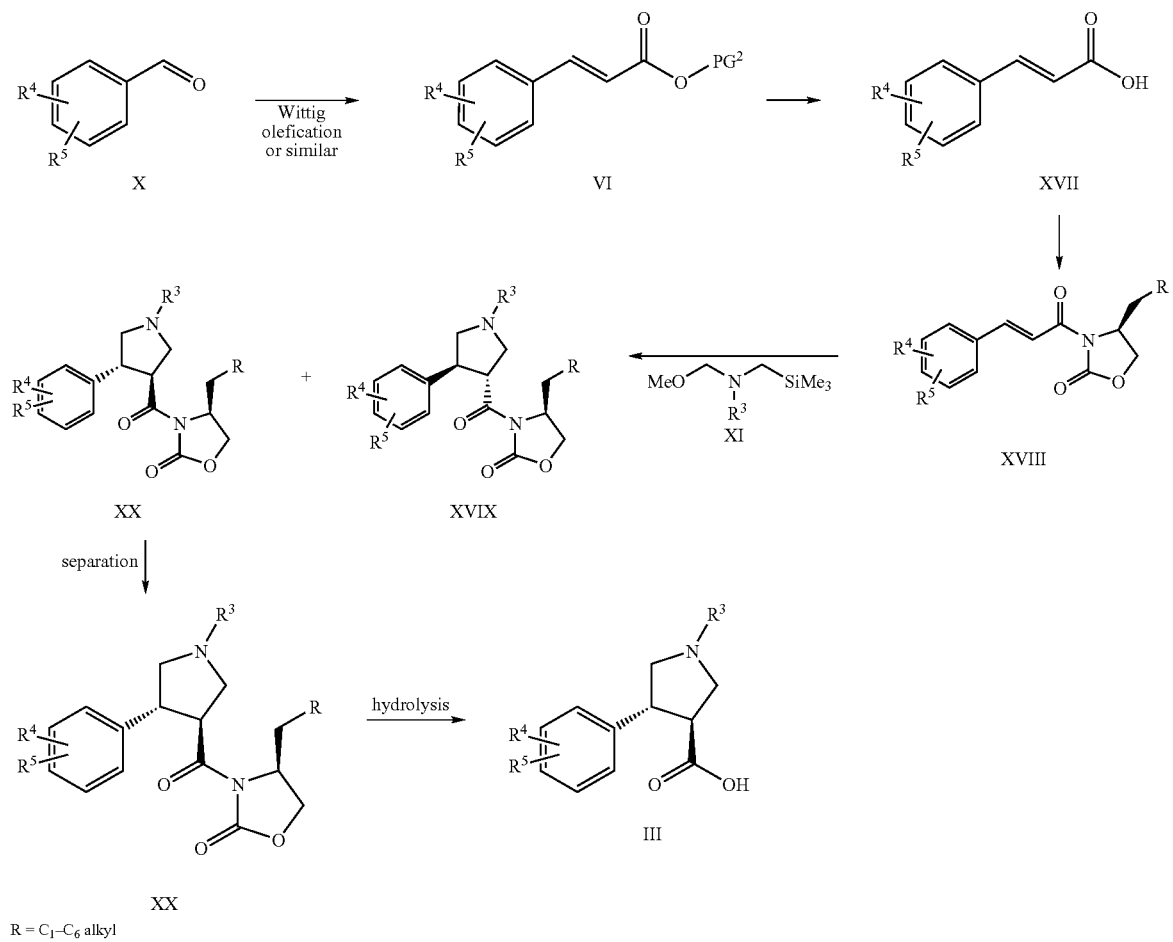

Scheme 3b $R = C_1$–$C_6$ alkyl

Scheme 4 illustrates that the synthesis of protected pyrrolidine acid intermediates of general formula (IV) can be achieved using a similar method to the process described hereinbefore for the intermediate of general formula (III) with the exception that the intermediate of general formula (XIIA) contains a nitrogen protecting group which may be removed subsequently in the synthetic scheme. Once the protecting group is removed, using any suitable conventional techniques, alternative $R^3$ groups may be introduced by the methods described in scheme 2.

Pyrrolidines of general formula IV bearing a nitrogen protecting group may also be obtained enantioselectively by employment of an oxazolidinone chiral auxiliary, in a similar manner to that described in Scheme 3b.

-continued

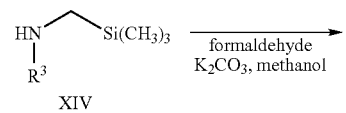

Scheme 4

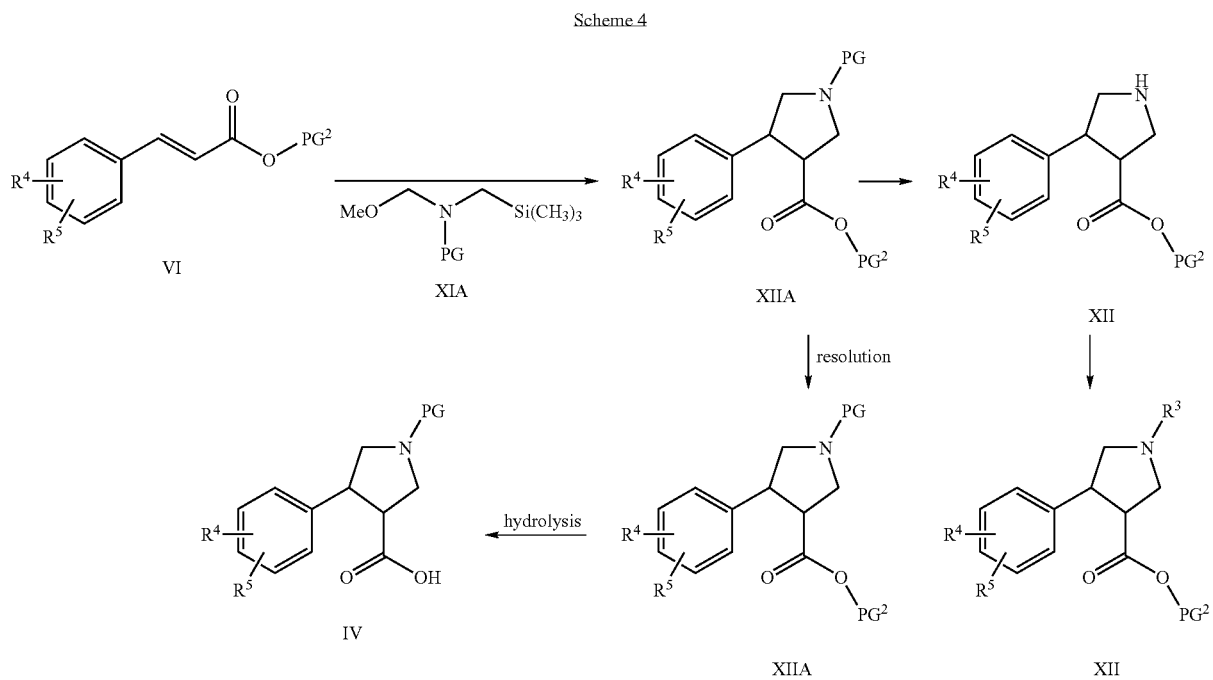

In respect of compounds (VI), (XIA), (XIIA), (XII) and (IV) in Scheme 4 the definitions of $R^1$, $R^2$, $R^3$, $R^4$ and $R^5$ are as defined hereinbefore for compounds of formula (I) unless stated otherwise. In formulae (XIA), (XIIA), and (IV), PG is selected from suitable nitrogen protecting groups. In formulae (VI), (XIIA), (VII) $PG^2$ is selected from suitable carboxylic acid protecting groups.

Synthesis of azomethine ylide precursor compounds of general formula (XI) can be achieved as illustrated in scheme 5. Thus, a primary amine of general formula (XIII) may be alkylated by treatment with chloromethyltrimethylsilane, optionally neat or in an inert solvent, heating the reaction if required. The resulting intermediates (XIV) can then be reacted with formaldehyde in methanol and in the presence of a suitable base such as potassium carbonate or tert-butylamine, to afford the intermediates (XI). To produce similar intermediates (XIA) containing a nitrogen protecting group a similar reaction sequence can be followed.

Scheme 5

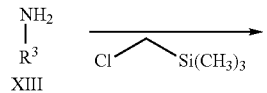

-continued

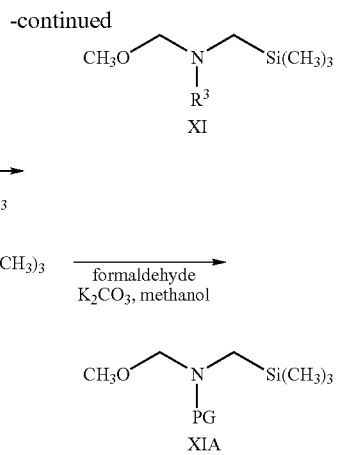

In respect of compounds (XIII), (XIIIA), (XIV), (XIVA), (XIA), and (XI) in Scheme 5 the definitions of $R^3$ are as defined hereinbefore for compounds of formula (I) unless stated otherwise. In formulae (XIIIA), (XIVA), (XIA), PG is selected from suitable nitrogen protecting groups.

As illustrated in Scheme 6, piperidine intermediates of general formula (II), where $R^2$=OH, can be prepared by addition of organometallic nucleophiles to ketones of general formula (XV) containing a suitable nitrogen protecting group to furnish intermediates of general formula (XVI). Such nucleophilic addition is generally carried out at low temperature in an anhydrous ethereal or non-polar solvent, using Grignard, organolithium or other suitable organometallic reagent. These organometallic reagents can be made by halogen-metal exchange using a suitable halide precursor, Y—Br or Y—I and n-butyl lithium or t-butyl lithium. Suitable protecting groups include Bn, which may be removed by hydrogenation or Boc, which may be removed by treatment with an acid such as TFA, or PMB which may be removed by treatment with DDQ, CAN or chloroethylchloroformate, to afford the desired piperidine intermediate of general formula (II). With certain protecting groups and under certain conditions the protecting group may be labile to treatment with the organometallic reagent, and so both transformations may be accomplished in one step. e.g. when PG=Boc the protecting group may sometimes be cleaved when intermediates of formula VII are treated with an organometallic reagent.

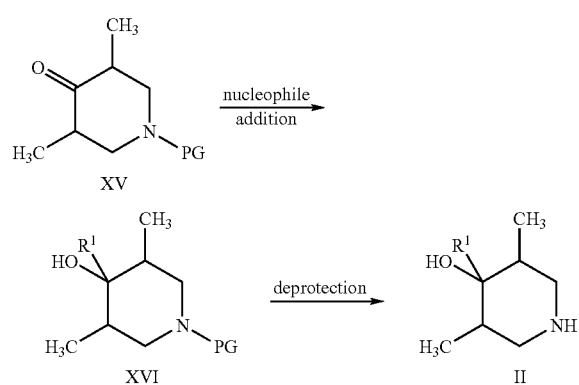

In respect of compounds (XV), (XVI), and (II) in scheme 6 the definitions of $R^1$ are as defined hereinbefore for compounds of formula (I) unless stated otherwise. In formulae (XV), (XVI), PG is selected from suitable nitrogen protecting groups.

As illustrated by Scheme 7 when (3R,5S)-1-benzyl-3,5-dimethyl-piperidin-4-one is used the stereochemistry of the addition is favoured such that the hydroxyl group in the product is cis to the two methyl groups. Controlled addition to carbonyl systems such as this have been described in the literature (Journal of Medicinal Chemistry (1964), 7(6), pp 726-8).

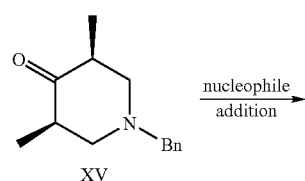

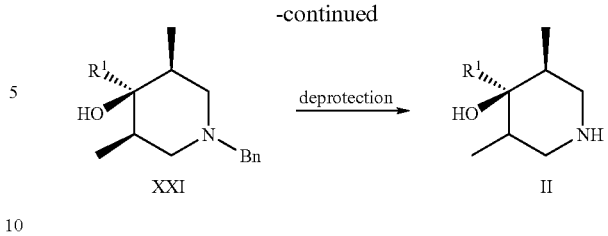

In respect of compounds (XV), (XXI), and (II) in Scheme 7 the definitions of $R^1$ are as defined hereinbefore for compounds of formula (I) unless stated otherwise. In formulae (XV), (XXI), PG is selected from suitable nitrogen protecting groups.

In addition, Scheme 8 illustrates that under forcing reduction conditions, such as hydrogenation at high pressure and or temperature, or strong acid plus triethylsilane, intermediate compounds of formula general formula (II), where $R^2$=OH may be converted into further intermediate compounds of general formula (II) where $R^2$=H. In certain cases protection of the piperidine nitrogen atom may be required to facilitate this transformation. Thus, intermediates of general formula (XVI) may be converted into further intermediate compounds of general formula (XXII) where $R^2$=H, and then subsequently deprotected to provide compounds of general formula (II) where $R^2$=H.

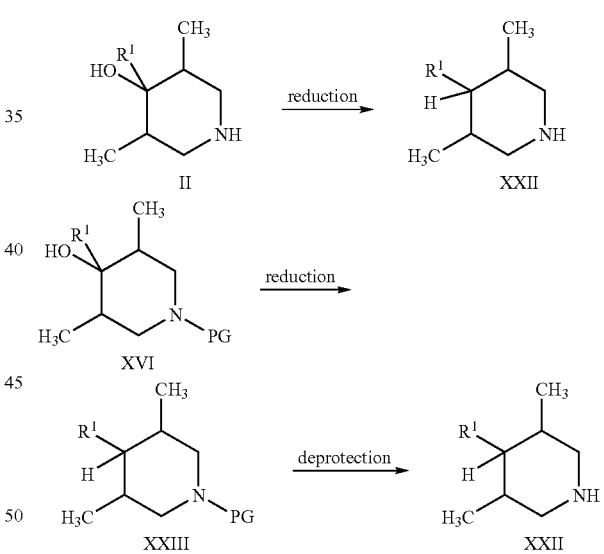

In respect of compounds (XVI), and (II) in Scheme 8 the definitions of $R^1$ are as defined hereinbefore for compounds of formula (I) unless stated otherwise. In formulae (II), and (XXIII), PG is selected from suitable nitrogen protecting groups.

In addition, scheme 9 illustrates that intermediate compounds of general formula (II), where $R^2$=OH may be converted into further intermediate compounds of general formula (II) where $R^2$=OMe. This transformation may be achieved by standard Williamson ether synthesis. That is, the alcohol group in compounds of formula general formula (II), where $R^2$=OH may be deprotonated with a strong base such as sodium hydride, in an anhydrous solvent, such as tetrahydrofuran or dimethylformamide, and the resulting anion reacted with iodomethane, heating the reaction if necessary. Protection of the piperidine nitrogen atom may be required to facilitate this transformation, thus intermediates of general formula (XVI) where $R^2$=OH may be converted into further intermediate compounds of general formula (XXV) where $R^2$=OMe, and then subsequently deprotected to provide compounds of general formula (II) where $R^2$=Ome, as illustrated in Scheme 9.

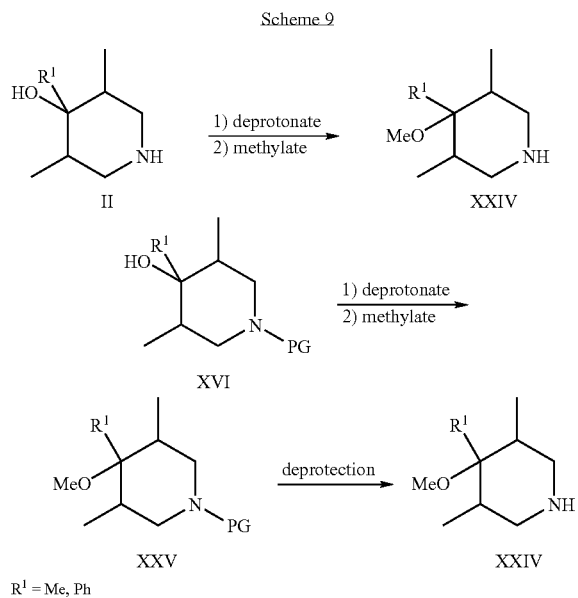

Scheme 9

In respect of compounds (XVI), and (II) in Scheme 9 the definitions of $R^1$ are as defined hereinbefore for compounds of formula (I) unless stated otherwise. In formulae (II), and (XVI), PG is selected from suitable nitrogen protecting groups.

The skilled man will appreciate that, in addition to protecting nitrogen groups, as discussed hereinbefore, at various times during the synthesis of the compounds of formula I, it may be necessary to protect further groups, such as for example, hydroxy groups with a suitable protecting group, then remove the protecting group. Methods for deprotection of any particular group will depend on the protecting group. For examples of protection/deprotection methodology see "Protective groups in Organic synthesis", T W Greene and P G M Wutz. For example, where a hydroxy group is protected as a methyl ether, deprotection conditions comprise refluxing in 48% aqueous HBr, or by stirring with borane tribromide in dichloromethane. Alternatively where a hydroxy group is protected as a benzyl ether, deprotection conditions comprise hydrogenation with a palladium catalyst under a hydrogen atmosphere.

According to a preferred embodiment the present invention provides processes for the preparation of compounds of general formula (I) using analogous methods to those provided for the preparation of the compounds of Example 1 via preparations 1 to 5 and 12 to 16 and more preferably Example 5 via preparations 1, 21, 22b, 4, 5 and 12 to 16 having the stereochemistry defined therein.

According to a further embodiment the present invention independently provides: the intermediate compound of preparation 1; and/or the intermediate compound of preparation 2; and/or the intermediate compound of preparation 3; and/or the intermediate compound of preparation 4; and/or the intermediate compound of preparation 5; and/or the intermediate compound of preparation 21; and/or the intermediate compound of preparation 22b; and/or the intermediate compound of preparation 12; and/or the intermediate compound of preparation 13; and/or the intermediate compound of preparation 14; and/or the intermediate compound of preparation 15; and/or the intermediate compound of preparation 16.

The general reaction mechanisms described hereinbefore for the preparation of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto.

MCR4 Activity

The compounds of the present invention have utility as MCR4 agonists in the treatment of various disease states.

Preferably said MCR4 agonists exhibit a functional potency at the MC4 receptor expressed as an $EC_{50}$, lower than about 100 nM, more preferably lower than 150 nM, yet more preferably lower than about 100 nM, more preferably still lower than about 50 nM and especially lower than about 10 nM wherein said $EC_{50}$ measurement of MCR4 functional potency can be carried out using Protocols C or E as described hereinafter. Compounds according to the present invention, including the compounds of Examples 12, 20, 16, 48, 1, 5, 6, 22, 13, 9, 10, 50, 14, 17, 19, 53, 40, 15, 52, 51, 8, 33, 31, 34, 35, 36, 42, 44 and 47, have been tested and found to demonstrate functional potencies of less than about 150 nM at the MC4 receptor. Thus according to a further embodiment the present invention provides compounds of formula I having a functional potency at the MC4R receptor of less than about 150 nM. A preferred group of compounds according to the present invention, including the compounds of Examples 1, 5, 6, 22, 13, 9, 17, 19, 53, 15, 52, 51, 8, 31, 34, 35, 42, 44 and 47 have been tested and found to demonstrate functional potencies of less than about 50 nM at the MC4 receptor. A further preferred group of compounds according to the present invention, including the compounds of Examples 1, 5, 9, 19, 8, 31, 34, 35, 42, and 47 have been tested and found to demonstrate functional potencies of less than about 10 nM at the MC4 receptor.

Preferred compounds herein exhibit functional potency at the MCR4 receptor as defined herein before and are selective for MCR4 over MCR1. Preferably said MCR4 agonists have a selectivity for MCR4 over MCR1 wherein said MCR4 receptor agonists are at least about 10-times, preferably at least about 20-times, more preferably at least about 30-times, even more preferably at least about 100-times, more preferably still at least about 300-times, even more preferably still at least about 500-times and especially at least about 1000-times more functionally selective for a MCR4 receptor as compared with the MCR1 receptor wherein said relative selectivity assessments are based on the measurement of MCR1 and MCR4 functional potencies which can be carried out using Protocols A and C, or E as described hereinafter. Compounds according to the present invention, including the compounds of Examples 1, 5, 6, 13, 10, 50, 14, 17, 33, 31 and 35, exhibit functional potency at the MCR4 receptor and have been tested and found to exhibit selectivity for MCR4 over MCR1 of greater than about 10-times. Thus according to a further embodiment the present invention provides compounds of formula I that exhibit functional potency at the MCR4 receptor and exhibit selectivity for MCR4 over MCR1 of greater than about 10-times. A preferred group of compounds according to the present invention, including the compounds of Examples 1, 5, 13, 14, 17, 31 and 35, exhibit functional potency at the MCR4 receptor have been tested and found to demonstrate exhibit selectivity for MCR4 over MCR1 of greater than about 30-times. A further preferred group of compounds according to the present invention, including the compounds of Examples 13, 14, 31 and 35, exhibit functional potency at the MCR4 receptor and have been tested and found to demonstrate exhibit selectivity for MCR4 over MCR1 of greater than about 100-times.

Preferably said MCR4 agonists have a selectivity for MCR4 over MCR3 wherein said MCR4 receptor agonists are at least about 10-times, preferably at least about 30-times, more preferably at least about 100-times, more preferably still at least about 300-times, even more preferably still at least about 500-times and especially at least about 1000-times more functionally selective for a MCR4 receptor as compared with the MCR3 receptor wherein said relative selectivity assessments are based on the measurement of MCR3 and MCR4 functional potencies which can be carried out using Protocols A and B, or E as described hereinafter. The compounds of Examples 1, 2 and 3 exhibit functional potency at the MCR4 receptor and have been tested and found to exhibit selectivity for MCR4 over MCR3 of greater than about 30-times.

Preferred compounds herein exhibit functional potency at the MCR4 receptor as defined herein before and are selective for MCR4 over MCR5. Preferably said MCR4 agonists have a selectivity for MCR4 over MCR5 wherein said MCR4 receptor agonists are at least about 10-times, preferably at least about 30-times, more preferably at least about 100-times, more preferably still at least about 300-times, even more preferably still at least about 500-times and especially about 1000-times more functionally selective for a MCR4 receptor as compared with the MCR5 receptor wherein said relative selectivity assessments are based on the measurement of MCR5 and MCR4 functional potencies which can be carried out using Protocols D and E as described hereinafter. Compounds according to the present invention, including the compounds of Examples 1, 5, 6, 22, 13, 9, 10, 50, 14, 17, 19, 53, 15, 52, 51, 33, 31, 35, 42 and 44, exhibit functional potency at the MCR4 receptor and have been tested and found to exhibit selectivity for MCR4 over MCR5 of greater than about 10-times. Thus according to a further embodiment the present invention provides compounds of formula I that exhibit functional potency at the MCR4 receptor and exhibit selectivity for MCR4 over MCR5 of greater than about 10-times. A preferred group of compounds according to the present invention, including the compounds of Examples 1, 5, 22, 13, 9, 50, 17, 19, 53, 15, 52, 31, 33, 35, 42 and 44, exhibit functional potency at the MCR4 receptor and have been tested and found to demonstrate exhibit selectivity for MCR4 over MCR5 of greater than about 100-times. A further preferred group of compounds according to the present invention, including the compounds of Examples 22, 13, 19, 15, 35, 42 and 44, exhibit functional potency at the MCR4 receptor and have been tested and found to demonstrate exhibit selectivity for MCR4 over MCR5 of greater than about 300-times.

Preferably said MCR4 agonists have a selectivity for MCR4 over MCR1 and MCR3 wherein said MCR4 receptors agonists are at least about 10-times, preferably at least about 30-times, more preferably at least about 100-times, more preferably still at least about 300-times, even more preferably still at least about 1000-times more functionally selective for a MCR4 receptor as compared with the MCR1 and MCR3 receptors.

Preferred compounds herein exhibit functional potency at the MCR4 receptor as defined herein before and are selective for MCR4 over MCR1 and MCR5. Preferably said MCR4 agonists have a selectivity for MCR4 over MCR1 and MCR5 wherein said MCR4 receptor agonists are at least about 10-times, preferably at least about 30-times, more preferably at least about 100-times, more preferably still at least about 300-times, even more preferably still at least about 500-times and especially at least about 1000-times more functionally selective for a MCR4 receptor as compared with the MCR1 and MCR5 receptors.

Compounds according to the present invention, including the compounds of Examples 1, 5, 6, 13, 10, 50, 14, 17, 33, 31 and 35, exhibit functional potency at the MCR4 receptor and have been tested and found to exhibit selectivity for the MCR4 receptor as compared with the MCR1 and MCR5 receptors of greater than about 10-times. Thus according to a further embodiment the present invention provides compounds of formula I that exhibit functional potency at the MCR4 receptor and exhibit selectivity for the MCR4 receptor as compared with the MCR1 and MCR5 receptors of greater than about 10-times. A preferred group of compounds according to the present invention, including the compounds of Examples 1, 5, 13, 31 and 35, exhibit functional potency at the MCR4 receptor and have been tested and found to demonstrate exhibit selectivity for the MCR4 receptor as compared with the MCR1 and MCR5 receptors of greater than about 100-times.

Preferably said MCR4 agonists have a selectivity for MCR4 over MCR3 and MCR5 wherein said MCR4 receptor agonists are at least about 10-times, preferably at least about 30-times, more preferably at least about 100-times, more preferably still at least about 300-times, most preferably at least about 1000-times more functionally selective for a MCR4 receptor as compared with the MCR3 and MCR5 receptors.

In addition to their role in treating sexual dysfunction the compounds of the present invention are likely to be efficacious in a number of additional indications as described hereinafter. The terms "treating", "treat", or "treatment" as used herein are intended to embrace both prevention and control i.e., prophylactic, and palliative treatment of the indicated conditions.

The compounds of the invention are useful in the treatment of diseases, disorders or conditions including, but not limited to, treating male and female sexual dysfunctions including hypoactive sexual desire disorder, sexual arousal disorder, orgasmic disorder and/or sexual pain disorder in females, male erectile dysfunction, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, fever, inflammation, immune modulation, rheumatoid arthritis, skin tanning, acne and other skin disorders, neuroprotective and cognitive and memory enhancement including the treatment of Alzheimer's disease.

Some compounds of formula I show highly specific activity toward the melanocortin-4 receptor making them especially useful in the treatment of male and female sexual dysfunctions, as well as obesity.

Compounds of present invention are useful in treating male and female sexual dysfunction, particularly male erectile dysfunction.

Female sexual dysfunction (FSD) includes female sexual arousal disorder (FSAD), desire disorders such as hypoactive sexual desire disorder (lack of interest in sex), and orgasmic disorders such as anorgasmia (unable to achieve orgasm).

Male sexual dysfunction includes male erectile dysfunction (MED) and ejaculatory disorders such as anorgasmia (unable to achieve orgasm) or desire disorders such as hypoactive sexual desire disorder (lack of interest in sex).

Compounds of the present invention are particularly useful in treating female sexual dysfunctions including hypoactive sexual desire disorder, sexual arousal disorder, orgasmic disorder, sexual pain disorder and male erectile dysfunction.

Compounds of the present invention are particularly suitable for treating female sexual dysfunctions, male erectile dysfunction, obesity and diabetes.

Male Erectile Dysfunction (MED)

Compounds of the present invention are useful in the treatment of male sexual dysfunction, particularly male erectile dysfunction. Male erectile dysfunction (MED), otherwise known as male erectile disorder, is defined as:

"the inability to achieve and/or maintain a penile erection for satisfactory sexual performance" (NIH Consensus Development Panel on Impotence, 1993)"

It has been estimated that the prevalence of erectile dysfunction (ED) of all degrees (minimal, moderate and complete impotence) is 52% in men 40 to 70 years old, with higher rates in those older than 70 (Melman et al 1999, J. Urology, 161, p 5-11). The condition has a significant negative impact on the quality of life of the individual and their partner, often resulting in increased anxiety and tension which can lead to depression and low self-esteem. Whereas two decades ago MED was primarily considered to be a psychological disorder (Benet et al 1994 Comp. Ther., 20: 669-673), it is now known that for the majority of individuals there is an underlying organic cause. As a result, much progress has been made in identifying the mechanism of normal penile erection and the pathophysiologies of MED.

Penile erection is a haemodynamic event dependent upon the balance of contraction and relaxation of the corpus cavernosal smooth muscle and vasculature of the penis (Lerner et al 1993, J. Urology, 149, 1256-1255). Corpus cavernosal smooth muscle is also referred to herein as corporal smooth muscle or in the plural sense corpus cavernosa. Relaxation of the corpus cavernosal smooth muscle leads to an increased blood flow into the trabecular spaces of the corpus cavernosa, causing them to expand against the surrounding tunica and compress the draining veins. This produces a vast elevation in blood pressure, which results in an erection (Naylor, 1998, J. Urology, 81, 424-431).

The changes that occur during the erectile process are complex and require a high degree of co-ordinated control involving the peripheral and central nervous systems, and the endocrine system (Naylor, 1998, J. Urology, 81, 424-431). Corporal smooth muscle contraction is modulated by sympathetic noradrenergic innervation via activation of postsynaptic $\alpha_1$ adrenoceptors. MED may be associated with an increase in the endogenous smooth muscle tone of the corpus cavernosum. However, the process of corporal smooth muscle relaxation is mediated partly by non-adrenergic, non-cholinergic (NANC) neurotransmission. There are a number of other NANC neurotransmitters found in the penis, other than NO, such as calcitonin gene related peptide (CGRP) and vasoactive intestinal peptide (VIP). The main relaxing factor responsible for mediating this relaxation is nitric oxide (NO), which is synthesised from L-arginine by nitric oxide synthase (NOS) (Taub et al 1993 Urology, 42, 698-704). It is thought that reducing corporal smooth muscle tone may aid NO to induce relaxation of the corpus cavernosum. During sexual arousal in the male, NO is released from neurones and the endothelium and binds to and activates soluble guanylate cyclase (sGC) located in the smooth muscle cells and endothelium, leading to an elevation in intracellular cyclic guanosine 3',5'-monophosphate (cGMP) levels. This rise in cGMP leads to a relaxation of the corpus cavernosum due to a reduction in the intracellular calcium concentration ($[Ca^{2+}]_i$), via unknown mechanisms thought to involve protein kinase G activation (possibly due to activation of Ca pumps and $Ca^{2+}$-activated $K^+$ channels).

Multiple potential sites have been identified within the central nervous system for the modulation of sexual behaviour. The key neurotransmitters are thought to be serotonin, norepinephrine, oxytocin, nitric oxide, dopamine and melanocortins e.g. alpha-melanocyte stimulating hormone. By mimicking the actions of one of these key neurotransmitters sexual function may be adjusted.

Melanocortins are peptides derived from pro-opiomelanocortins (POMC) that bind to and activate G-protein coupled receptors (GPCR's) of the melanocortin receptor family. Melanocortins regulate a diverse number of physiological processes including sexual function and sexual behaviour, food intake and metabolism.

There are five melanocortin receptors that have been cloned, MCR1, MCR2, MCR3, MCR4, MCR5, and are expressed in various tissues. MCR1 is specifically expressed in melanocytes and melanoma cells, MCR2 is the ACTH receptor and is expressed in adrenal tissue, MCR3 is predominately expressed in the brain and limbic system, MCR4 is widely expressed in the brain and spinal cord, and MCR5 is expressed in the brain and many peripheral tissues including skin, adipose tissue, skeletal muscle, and lymphoid tissue. MCR3 may be involved in the control of sexual function, food intake and thermogenesis. MCR4 activation has been shown to induce penile erection in rodents and MCR4 inactivation has been shown to cause obesity (reviewed in Hadley, 1999, Ann N Y Acad. Sci., 885:1-21, Wikberg et a 2000, Pharmacol Res., 42(5), 393-420).

Synthetic melanocortin receptor agonists have been found to initiate erections in men with psychogenic erectile dysfunction (Wessells et al, Int J Impot Res. 2000 October; 12 Suppl 4:S74-9.). Wessels et al describe the effects of Melanotan II (MT II), a non-selective melanocortin receptor agonist, in human subjects with erectile dysfunction (ED). MT II was administered to 20 men with psychogenic and organic ED using a double-blind placebo-controlled crossover design. Penile rigidity was monitored for 6 hours using RigiScan. Level of sexual desire and side effects were reported with a questionnaire. In the absence of sexual stimulation, Melanotan II led to penile erection in 17 of 20 men. Subjects experienced a mean of 41 minutes Rigiscan tip rigidity>80%. Increased sexual desire was reported after 13/19 (68%) doses of MT II vs. 4/21 (19%) of placebo (P<0.01). Nausea and yawning were frequently reported side effects due to MT II; at a dose of 0.025 mg/kg, 12.9% of subjects had severe nausea. Adverse reactions observed with MT-II may be the result of activation of MC-1R, MC-2R, MC-3R and/or MC 5R.

It is proposed herein that a selective MCR4 agonist can be administered orally (including buccal or sublingual administration) and will be effective in the treatment of female sexual dysfunction or male erectile dysfunction but will be devoid of significant adverse side effects such as those observed by Wessels et al i.e. a selective agent will be better tolerated.

Palatin's PT-141 is another synthetic peptide analogue of alpha-MSH. It is an agonist at melanocortin receptors including the MC3R and MC4R. Molinoff et al (Ann N.Y. Acad. Sci. (2003), 994, 96-102) describe how "administration of PT-141 to rats and nonhuman primates results in penile erections. Systemic administration of PT-141 to rats activates neurons in the hypothalamus as shown by an increase in c-Fos immunoreactivity. Neurons in the same region of the central nervous system take up pseudorabies virus injected into the corpus cavernosum of the rat penis. Administration of PT-141 (intranasally or subcutaneously) to normal men and to patients with erectile dysfunction resulted in a rapid dose-dependent increase in erectile activity."

Use of PT-141 for sexual dysfunction is described in U.S. Pat. No. 5,576,290, U.S. Pat. No. 6,579,968 and U.S. 2002/0107,182A1. In addition, peptides such as MT-II or PT-141 are metabolised extensively in the gut and as such are most effectively administered parenterally, such as by subcutaneous, intravenous, intranasal or intramuscular route, since it is not absorbed into the systemic circulation when given by the oral route.

Thus it would be desirable to develop MCR4 agonist compounds for the treatment of male and female sexual dysfunctions suitable for oral delivery (including buccal or sublingual administration) and either reduce or overcome undesirable side effects such as nausea.

It is proposed herein that selective MCR4 agonists according to the present invention will display oral bioavailability and as such will be capable of additionally being administered orally (including buccal or sublingual administration).

There have been a number of reports illustrating that selective MCR4 agonists increase erectile activity in rats (Martin et al, 2002, Eur J. Pharmacol., 454(1), 71-79; Van Der Ploeg et al, 2002, Proc. Natl. Acad. Sci. USA., 99(17), 11381-11386). An example of a MCR4 agonist used in these studies is N-[(3R)-1,2,3,4-tetrahydroisoquinolinium-3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine (1), which is a potent, selective, melanocortin subtype-4 receptor agonist (Sebhat et al, 2002, J. Med. Chem., 45(21), 4589-4593).

Cragnolini et al (Neuropeptides, 34(3-4), 211-5) have shown that alpha-MSH significantly increases lordosis sexual behaviour in female rats following injection into the ventromedial nucleus of the brain. Furthermore, they showed that HS014 (a putative MCR4 antagonist, Vergoni 1998, Eur. J. Pharmacol. 362(2-3), 95-101) dose dependently blocks the prosexual effect of alpha-MSH on lordosis in female rats. Methods of stimulating sexual response in females using various melanotropic peptides (similar to MT II) have been disclosed in U.S. Pat. No. 6,051,555.

In essence, MCR4 is an initiator of male and female sexual behaviour. Accordingly, the present invention provides for the use of a compound of formula (I) in the preparation of a medicament for the treatment of male and female sexual dysfunction and in particular male erectile dysfunction.

Patients with mild to severe MED should benefit from treatment with the compounds according to the present invention. However, early investigations suggest that the responder rate of patients with mild, moderate and severe MED may be greater with a selective MCR4 agonist/PDE5 inhibitor combination. Mild, moderate and severe MED will be terms known to the man skilled in the art, but guidance can be found in The Journal of Urology, vol. 151, 54-61 (January 1994).

Early investigations suggest the below mentioned MED patient groups should benefit from treatment with a selective MCR4 agonist and/or a PDE5i (or other combination set out hereinafter). These patient groups, which are described in more detail in Clinical Andrology vol. 23, no. 4, p 773-782 and chapter 3 of the book by 1. Eardley and K. Sethia "Erectile Dysfunction-Current Investigation and Management, published by Mosby-Wolfe, are as follows: psychogenic, organic, vascular, endocrinologic, neurogenic, arteriogenic, drug-induced sexual dysfunction (lactogenic) and sexual dysfunction related to cavernosal factors, particularly venogenic causes.

Accordingly the present invention provides for the use of a compound of formula (I) in the preparation of a medicament in combination with a PDE5 inhibitor for the treatment of male erectile dysfunction.

Suitable PDE5 inhibitors are described hereinafter.

Female Sexual Dysfunction (FSD)

The compounds of the present invention are useful in the treatment of female sexual dysfunction (FSD), particularly FSAD.

In accordance with the invention, FSD can be defined as the difficulty or inability of a woman to find satisfaction in sexual expression. FSD is a collective term for several diverse female sexual disorders (Leiblum, S. R. (1998)—Definition and classification of female sexual disorders. *Int. J. Impotence Res.,* 10, S104-S106; Berman, J. R., Berman, L. & Goldstein, I. (1999)—Female sexual dysfunction: Incidence, pathophysiology, evaluations and treatment options. *Urology,* 54, 385-391.). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998)—Definition and classification of female sexual disorders. Int. *J. Impotence Res.,* 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Hypoactive sexual desire disorder is present if a woman has no or little desire to be sexual, and has no or few sexual thoughts or fantasies. This type of FSD can be caused by low testosterone levels due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants e.g. selective serotonin re-uptake inhibitors (SSRIs) or antihypertensive agents.

Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

As previously discussed, MCR4 is thought to be an initiator of sexual behaviour. The clitoris is considered to be a homologue of the penis (Levin, R. J. (1991), *Exp. Clin. Endocrinol.*, 98, 61-69); the same mechanism that provides an erectile response in the male produces an increase in genital blood flow in the female with an associated effect upon FSD. In addition there are changes in proceptivity and receptivity (lordosis).

Thus, in accordance with a preferred aspect of the invention, there is provided use of a compound of formula (I) in the preparation of a medicament for the treatment or prophylaxis of female sexual dysfunction, more particularly hypoactive sexual desire disorder, sexual arousal disorder, orgasmic disorder and sexual pain disorder.

Preferably the compounds of formula (I) are useful in the treatment or prophylaxis of sexual arousal disorder, orgasmic disorder, and hypoactive sexual desire disorder, and most preferably in the treatment or prophylaxis of sexual arousal disorder.

In a preferred embodiment the compounds of formula (I) are useful in the treatment of a subject with female sexual arousal disorder and concomitant hypoactive sexual desire disorder.

The Diagnostic and Statistical Manual (DSM) IV of the American Psychiatric Association defines Female Sexual Arousal Disorder (FSAD) as being:

" . . . a persistent or recurrent inability to attain or to maintain until completion of the sexual activity adequate lubrication-swelling response of sexual excitement. The disturbance must cause marked distress or interpersonal difficulty . . . ".

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, per- and post-menopausal (±hormone replacement therapy (HRT)) women. It is associated with concomitant disorders such as depression, cardiovascular diseases, diabetes and urogenital (UG) disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

It has recently been hypothesised that there is a vascular basis for at least a proportion of patients with symptoms of FSAD (Goldstein et al., Int. J. Impot. Res., 10, S84-S90, 1998) with animal data supporting this view (Park et al., Int. J. Impot. Res., 9, 27-37, 1997).

R. J. Levin teaches us that because " . . . male and female genitalia develop embryologically from the common tissue anlagen, [that] male and female genital structures are argued to be homologues of one another. Thus the clitoris is the penile homologue and the labia homologues of the scrotal sac . . . " (Levin, R. J. (1991), *Exp. Clin; Endocrinol.*, 98, 61-69).

Drug candidates for treating FSAD, which are under investigation for efficacy, are primarily erectile dysfunction therapies that promote circulation to male genitalia.

The compounds of the present invention are advantageous by providing a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the present invention provides a means to restore, or potentiate, the normal sexual arousal response.

Thus, in accordance with a preferred aspect of the invention, there is provided use of a compound of formula (I) in the preparation of a medicament for the treatment or prophylaxis of female sexual arousal disorder.

By female genitalia herein we mean: "The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands" (Gray's Anatomy, C. D. Clemente, 13$^{th}$ American Edition).

The compounds of the invention find application in the following sub-populations of patients with FSD: the young, the elderly, pre-menopausal, peri-menopausal, post-menopausal women with or without hormone replacement therapy.

The compounds of the invention find application in patients with FSD arising from:— i) Vasculogenic etiologies e.g. cardiovascular or atherosclerotic diseases, hypercholesterolemia, cigarette smoking, diabetes, hypertension, radiation and perineal trauma, traumatic injury to the iliohypogastric pudendal vascular system;

ii) Neurogenic etiologies such as spinal cord injuries or diseases of the central nervous system including multiple sclerosis, diabetes, Parkinsonism, cerebrovascular accidents, peripheral neuropathies, trauma or radical pelvic surgery;

iii) Hormonal/endocrine etiologies such as dysfunction of the hypothalamic/pituitary/gonadal axis, or dysfunction of the ovaries, dysfunction of the pancreas, surgical or medical castration, androgen deficiency, high circulating levels of prolactin e.g. hyperprolactinemia, natural menopause, premature ovarian failure, hyper and hypothyroidism;

iv) Psychogenic etiologies such as depression, obsessive compulsive disorder, anxiety disorder, postnatal depression/ "Baby Blues", emotional and relational issues, performance anxiety, marital discord, dysfunctional attitudes, sexual phobias, religious inhibition or a traumatic past experiences; and/or v) Drug-induced sexual dysfunction resulting from therapy with selective serotonin reuptake inhibitors (SSRis) and other antidepressant therapies (tricyclics and major tranquilizers), anti-hypertensive therapies, sympatholytic drugs, chronic oral contraceptive pill therapy.

The compounds of the present invention may be delivered in combination with an auxiliary active agent for the treatment of sexual dysfunction, obesity or diabetes. Suitable auxiliary active agents for use in the combinations of the present invention include:

1) Compounds which modulate the action of naturetic factors in particular atrial naturetic factor (also known as atrial naturetic peptide), B type and C type naturetic factors such as inhibitors or neutral endopeptidase and in particular the compounds described and claimed in WO 02/02513, WO 02/03995, WO 02/079143 and EP-A-1258474, and especially the compound of Example 22 of WO 02/079143 (2S)-2{[1-{3-4(-chlorophenyl)propyl]amino}carbonyl)-cyclopentyl]methyl}-4-methoxybutanoic acid;

2) Compounds which inhibit angiotensin-converting enzyme such as enapril, and combined inhibitors of angiotensin-converting enzyme and neutral endopeptidase such as omapatrilat;

3) Substrates for NO-synthase, such as L-arginine;

4) Cholesterol lowering agents such as statins (e.g. atorvastatin/Lipitor-trade mark) and fibrates;

5) Estrogen receptor modulators and/or estrogen agonists and/or estrogen antagonists, preferably raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof the preparation of which is detailed in WO 96/21656;

6) A PDE inhibitor, more particularly a PDE 2, 3, 4, 5, 7 or 8 inhibitor, preferably PDE2 or PDE5 inhibitor and most preferably a PDE5 inhibitor (see hereinafter), said inhibitors preferably having an IC50 against the respective enzyme of less than 100 nM (with the proviso that PDE 3 and 4 inhibitors are only administered topically or by injection to the penis);

7) Vasoactive intestinal protein (VIP), VIP mimetic, VIP analogue, more particularly mediated by one or more of the VIP receptor subtypes VPAC1, VPAC or PACAP (pituitary adenylate cyclase activating peptide), one or more of a VIP receptor agonist or a VIP analogue (e.g. Ro-125-1553) or a VIP fragment, one or more of a α-adrenoceptor antagonist with VIP combination (e.g. Invicorp, Aviptadil);

8) A serotonin receptor agonist, antagonist or modulator, more particularly agonists, antagonists or modulators for 5HT1A (including VML 670 [WO02/074288] and flibanserin [U.S. 2003/0104980]), 5HT2A, 5HT2C, 5HT3 and/or 5HT6 receptors, including those described in WO-09902159, WO-00002550 and/or WO-00028993;

9) A testosterone replacement agent (including dehydroandrostendione), testosterone (e.g. Tostrelle, LibiGel), dihydrotestosterone or a testosterone implant;

10) Selective androgen receptor modulators e.g. LGD-2226;

11) Estrogen, estrogen and medroxyprogesterone or medroxyprogesterone acetate (MPA) (i.e. as a combination), or estrogen and methyl testosterone hormone replacement therapy agent (e.g. HRT especially Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone);

12) A modulator of transporters for noradrenaline, dopamine and/or serotonin, such as bupropion, GW-320659;

13) An agonist or modulator for oxytocin/vasopressin receptors, preferably a selective oxytocin agonist or modulator; and 14) An agonist or modulator for dopamine receptors, preferably a D3 or D4 selective agonist or modulator e.g. apomorphine.

Preferred herein are combinations of the compounds of the present invention and one or more additional therapeutic agents selected from: PDE5 inhibitors; NEP inhibitors; D3 or D4 selective agonists or modulators; estrogen receptor modulators and/or estrogen agonists and/or estrogen antagonists; testosterone replacement agents, testosterone or a testosterone implant; estrogen, estrogen and medroxyprogesterone or medroxyprogesterone acetate (MPA), or estrogen and methyl testosterone hormone replacement therapy agent.

Preferred combinations for the treatment of MED are combinations of the compounds of the present invention and one or more PDE5 inhibitors and/or NEP inhibitors.

Preferred combinations for the treatment of FSD are combinations of the compounds of the present invention and PDE5 inhibitors, and/or NEP inhibitors, and/or D3 or Dr4 selective agonists or modulators, and/or estrogen receptor modulators, estrogen agonists, estrogen antagonists, and/or testosterone replacement agents, testosterone, testosterone implant, and/or estrogen, estrogen and medroxyprogesterone or medroxyprogesterone acetate (MPA), estrogen and methyl testosterone hormone replacement therapy agent.

Particularly preferred PDE5 inhibitors for such combined products for the treatment of MED or FSD are sildenafil, tadalafil, vardenafil and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one.

Particularly preferred NEP inhibitors for such combined products for the treatment of MED or FSD are the compounds exemplified in WO 02/079143.

Preferred combined products herein for the treatment of MED or FSD are: a combination of sildenafil, tadalafil, vardenafil or 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one with the compound of Example 1 herein; and/or a combination of any of the compounds exemplified in WO 02/079143 with the compound of Example 1 herein.

By cross reference herein to compounds contained in patents and patent applications which can be used in accordance with invention, we mean the therapeutically active compounds as defined in the claims (in particular of claim 1) and the specific examples (all of which is incorporated herein by reference).

If a combination of active agents is administered, then they may be administered simultaneously, separately or sequentially.

Auxiliary Agents—PDE5 Inhibitors

Particularly preferred herein as auxiliary active agents are PDE5 inhibitors.

The suitability of any particular cGMP PDE5 inhibitor can be readily determined by evaluation of its potency and selectivity using literature methods followed by evaluation of its toxicity, absorption, metabolism, pharmacokinetics, etc in accordance with standard pharmaceutical practice.

IC50 values for the cGMP PDE5 inhibitors may be determined using the PDE5 assay (see herein below).

Preferably the cGMP PDE5 inhibitors used in the pharmaceutical combinations according to the present invention are selective for the PDE5 enzyme. Preferably (when used orally) they are selective over PDE3, more preferably over PDE3 and PDE4. Preferably (when oral), the cGMP PDE5 inhibitors of the invention have a selectivity ratio greater than 100 more preferably greater than 300, over PDE3 and more preferably over PDE3 and PDE4.

Selectivity ratios may readily be determined by the skilled person. $IC_{50}$ values for the PDE3 and PDE4 enzyme may be determined using established literature methodology, see S A Ballard et al., Journal of Urology, 1998, vol. 159, pages 2164-2171 and as detailed herein after.

Suitable cGMP PDE5 inhibitors for the use according to the present invention include:
(i) 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]

pyrimidin-5-yl)-4-ethoxyphenyl]sulphonyl]-4-methylpiperazine (see EP-A-0463756);
(ii) 5-(2-ethoxy-5-morpholinoacetylphenyl)-1-methyl-3-n-propyl-1,6-dihydro-7H-pyrazolo[4,3-d]pyrimidin-7-one (see EP-A-0526004);
(iii) 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166);
(iv) 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);
(v) (+)-3-ethyl-5-[5-(4-ethylpiperazin-1-ylsulphonyl)-2-(2-methoxy-1 (R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333);
(vi) 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8);
(vii) 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);
(viii) 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO01/27113, Example 66);
(ix) 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO01/27112, Example 124);
(x) 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);
(xi) (6R,12aR)-2,3,6,7,12,12a-hexahydro-2-methyl-6-(3,4-methylenedioxyphenyl)-pyrazino[2',1':6,1]pyrido[3,4-b]indole-1,4-dione (tadalafil, IC-351, Cialis®), i.e. the compound of examples 78 and 95 of published international application WO95/19978, as well as the compound of examples 1, 3, 7 and 8;
(xii) 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433;
(xiii) the pyrazolo[4,3-d]pyrimidin-4-ones disclosed in WO00/27848, in particular N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide [DA-8159 (Example 68 of WO00/27848)];
(xiv) the compound of example 11 of published international application WO93/07124;
(xv) 4-(4-chlorobenzyl)amino-6,7,8-trimethoxyquinazoline; and
(xvi) 7,8-dihydro-8-oxo-6-[2-propoxyphenyl]-1H-imidazo[4,5-g]quinazoline;
(xvii) 1-[3-[1-[(4-fluorophenyl)methyl]-7,8-dihydro-8-oxo-1H-imidazo[4,5-g]quinazolin-6-yl]-4-propoxyphenyl]carboxamide;
(xviii) 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; and
(xix) 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine; and pharmaceutically acceptable salts and solvates thereof.

The suitability of any particular PDE5 inhibitor can be readily determined by evaluation of its potency and selectivity using literature methods followed by evaluation of its toxicity, absorption, metabolism, pharmacokinetics, etc in accordance with standard pharmaceutical practice.

Preferably, the PDE5 inhibitors have an $IC_{50}$ at less than 100 nanomolar, more preferably, at less than 50 nanomolar, more preferably still at less than 10 nanomolar.

Preferably the PDE5 inhibitors used in the pharmaceutical combinations according to the present invention are selective for the PDE5 enzyme. Preferably they have a selectivity of PDE5 over PDE3 of greater than 100 more preferably greater than 300. More preferably the PDE5 inhibitor has a selectivity over both PDE3 and PDE4 of greater than 100, more preferably greater than 300. Selectivity ratios may be readily determined by the skilled person from the relevant $IC_{50}$ values. $IC_{50}$ values for the PDE3 and PDE4 enzyme may be determined using established literature methodology, such as the method described in S A Ballard et al, Journal of Urology, 1998, vol. 159, pages 2164-2171. $IC_{50}$ values for the PDE5 enzyme may be determined using established literature methodology and as described in WO 01/27113.

Pro Sexual In Vivo Data

MCR4 in vivo data for the compound of Example 1 was assessed by selective activation of melanocortin MCR4 receptors using the methodology assessing spontaneous penile erection in the conscious rat.

Erectile responses were recorded by measuring intracavernosal pressure using a surgically implanted telemetric device (TA11PA-C40, 8 mm catheter, modified 3 mm tip, available from Data Sciences International Inc.). An increase in intracavernosal pressure is indicative of penile erection, as an increase in intracavernosal pressure is an essential hemodynamic event during the initiation and maintenance of penile erection. The specific details of the surgical procedures, data acquisition and analysis used herein to measure increases in intracavernosal pressure can be found in detail in Bernabe J., Rampin O., Sachs B. D., Giuliano F., "Intracavernous pressure during erection in rats: an integrative approach based on telemetric recording", Am. J. Physiol. 1999 February; 276 (2 Pt 2):R441-9.

The test animals (rats) (during the dark cycle) were habituated for 18 hours before baseline assessment of erectile function. Prior to administration of the test agent the baseline erectile activity (B) was assessed for the vehicle for 10 minutes using telemetric recording of intracavernosal pressure. Following subcutaneous administration of the compound of Example 1 (in the same vehicle), penile erections were assessed (using telemetric recording of intracavernosal pressure) over 10 minute periods, at intervals of 30, 60, and 90 minutes post dosage.

The compound of Example 1 produced a dose dependent increase in the number of penile erections when dosed at a level of 1-100 kg/kg subcutaneously (s.c.). (see FIGS. 1 and 2). Baseline/vehicle treated animals showed minimal erectile activity (see FIG. 1).

FIG. 1 illustrates the results of preliminary studies and compares the number of erections observed over a 10 minute period starting at 60 minutes post dosage for animals dosed with 1, 10 and 100 μg/kg s.c. of the compound of Example 1 with the baseline erectile activity (B). The data in FIG. 1 illustrates that at all doses tested the compound of Example 1 increases the erectile activity versus baseline erectile activity (B). Further FIG. 1 illustrates that the compound of Example 1 dose dependently increased the number of spontaneous erection in the conscious rat. The maximum effective dose observed in this preliminary study was 1 μg/kg s.c.

Figure 2:
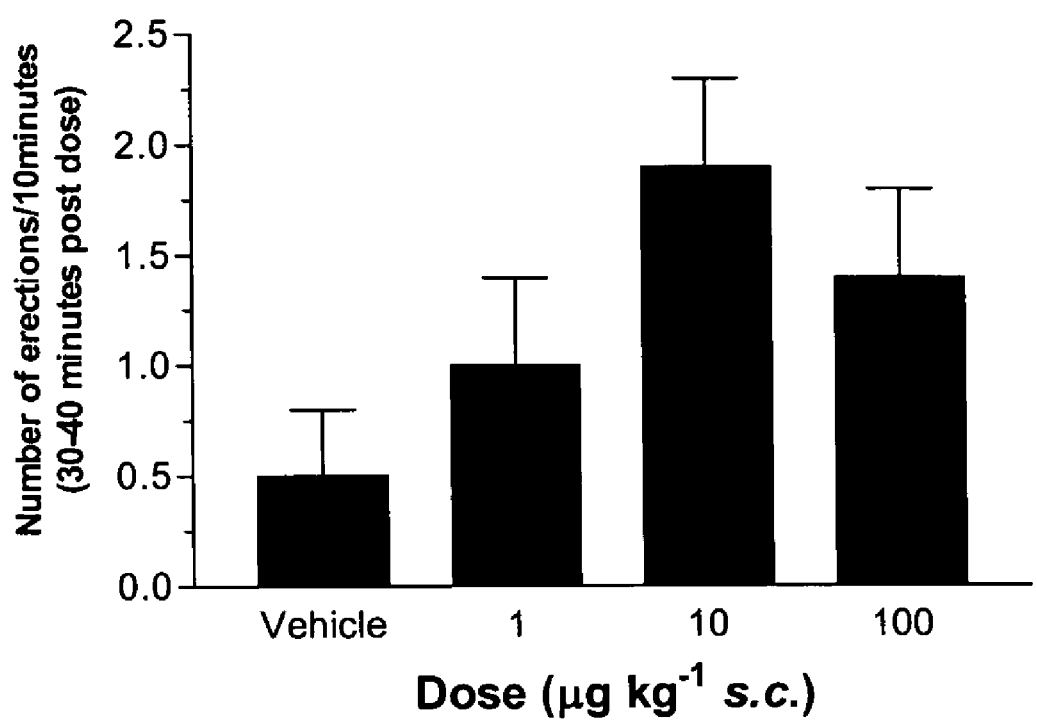
FIG. 2 depicts the number of erections observed over a 10 minute period starting 60 minutes post dosage for animals dosed with 1, 10 and 100 μg/kg subcutaneously with the compound of Example 1 and with baseline vehicle.

FIG. 2 illustrates the results from an additional, more detailed, study and compares the number of erections observed over a 10 minute period starting at 30 minutes post dosage for animals dosed with 1, 10 and 100 μg/kg s.c. of the compound of Example 1 with the baseline erectile activity (treatment vehicle). The data in FIG. 2 illustrates that at all doses tested the compound of Example 1 increases the erectile activity versus baseline erectile activity (treatment vehicle). Further FIG. 2 illustrates that the compound of Example 1 dose dependently increased the number of spontaneous erection in the conscious rat. The maximum effective dose observed in this additional, more detailed, study was 10 μg/kg s.c.

For the compound of Example 1, in the preliminary study the maximum effective dose observed in this preliminary study was 1 μg/kg s.c. and in the additional, more detailed, study the maximum effective dose observed was 10 μg/kg s.c. The number of erections observed was not significantly different between these two studies and at these dose levels. The same conclusion, that compound of Example 1 dose dependently increased the number of spontaneous erection in the conscious rat, can be independently drawn from both of these studies. It is proposed herein that the difference observed between the preliminary and more detailed study with regards to the dose at which the maximum effect was observed is a reflection of the anticipated biological variation associated with this type of animal model.

The data illustrated by FIGS. 1 and 2 strongly suggests that MCR4 receptors are involved in the induction and maintenance of penile erection and it is proposed herein that selective MCR4 agonists according to the present invention may provide an opportunity for treating male erectile dysfunction.

Assay

Stimulation of adenylate cyclase following receptor activation is a widely used measure of functional activity for a number of receptor systems. The functional assay to measure cyclic AMP (cAMP) utilises human embryonic kidney (HEK) cells that stably express the human melanocortin MCR1, MCR3 or MCR4 receptor. Activation of MCR1, MCR3 or MCR4 receptors stimulates adenylate cyclase, generating cAMP, which is measured using AlphaScreen™ (PerkinElmer assay kits.

The AlphaScreen™ cAMP assay kit consists of 'donor beads', 'acceptor beads', and biotinylated cAMP which links the different beads together. Excitation of this linked complex at 680 nM in the Fusion™-α microplate analyser results in light emission between 520-620 nM.

The cAMP generated in the assay competes with the biotinylated cAMP for binding sites on the acceptor beads, preventing linking of 'donor' and 'acceptor' beads and hence reducing the light emission.

(i) MCR1. MCR3 and MCR4 Standard Functional Assay Methodology [Assay Protocol A, B AND C Respectively]

Assay Concept

Determination of activity against the human MCR1, MCR3 and MCR4 receptor subtypes was carried out for compounds according to the present invention using three immortalised human embryonic kidney (HEK) cell lines that had been biologically engineered to express the human melanocortin MCR1, MCR3 or MCR4 receptor subtypes. These cell lines were engineered using protocols akin to those outlined by Gouarderes et al (Gouarderes, C., (2002) Neuroscience, 115(2); 349-361).

Such-compound-induced activation of these MCR1, MCR3 or MCR4 receptors lead to the stimulation of the cellular enzyme adenylate cyclase, which in turn lead to the cellular generation, and intra-cellular accumulation, of cyclic adenosine monophosphate (cAMP). The magnitude of these increases in intracellular cAMP was found to be proportional to the degree to which the test compound activated the MCR1, MCR3 or MCR4 receptors present in these cell lines. Intracellular levels of cAMP were quantified using the commercially available AlphaScreen™ assay kits from PerkinElmer. A detailed assay protocol and an explanation of the concept underlying this kit is available through the PerkinElmer website (www.perkinelmer.com). The protocol listed below provides a summary this information.

The quantity of intracellular cAMP produced by compound-induced activation of the MCR1, MCR3 and MCR4 receptors in these three cell lines was measured using a Fusion™-α microplate analyser set to stimulate at a wavelength of 680 nM and to measure the energy emitted at wave lengths between 520-620 nM. Compound-induced increases in MCR1, MCR3 or MCR4 receptor activation were subsequently quantified as a decrease in the quantity of light emitted at wavelengths between 520-620 nM. Data analysis was subsequently performed using a curve-fitting program and the apparent potency of the test compound (expressed as an $EC_{50}$ and defined as the effective compound concentration that elicited 50% of the maximum compound-induced response) extrapolated from the fitted curve.

Materials

From PerkinElmer: AlphaScreen™ cAMP assay kit, Cat No 6760600M, Fusion™-α microplate analyser (set to stimulate at a wavelength of 680 nM and to record light emitted at wave lengths between 520-620 nM).

From Invitrogen: Phosphate buffered saline (PBS) (w/o $Ca^{2+}$ and $Mg^{2+}$), Cat No 14190-094; Dulbecco's modified Eagle media (DMEM) high glucose, Cat No 21969-035; Hank's balanced salt solution (HBSS), Cat No 14065-049; Geneticin, Cat No 10131-027.

From Sigma: Bovine serum albumin (BSA), Cat No A7030; L-Glutamine, Cat No g7513; (N-(2-Hydroxyethyl) piperazine-N'-(2-ethanesulfonic acid) (HEPES), Cat No H0887; Cell dissociation solution fluid, Cat No 5914; Dimethyl sulphoxide (DMSO), Cat No D8418; Cyclic adenosine monophosphate (cAMP), Cat No A9501; 3-Isobutyl-1-methylxanthine (IBMX), Cat No 15879; Magnesium chloride ($MgCl_2$) 1M solution, Cat No M1028; Trypan blue, Cat No T-8154, Cell-counting chamber (Bright-line 35,962-9).

From PAA laboratories GmbH: Foetal calf serum (FCS), Cat No A15-043.

From Gilson: pipettes ranging from 10 μl to 1000 μl.

From Hereaus; Hera Cell $CO_2$ cell incubator.

From Medical Air Technology; BioMat2 class II microbiological safety cabinet

From Bachem: α-Melanocyte Stimulating Hormone α-MSH, Cat No H1075, used as a positive control.

Buffers

Stimulation buffer (as per AlphaScreen™ protocol): HBSS supplemented with 0.5 mM IBMX, 5 mM HEPES, 0.1% (w/v) BSA and 10 mM $MgCl_2$.

Lysis buffer (as per AlphaScreen™ protocol): 5 mM HEPES solution supplemented with 0.1% (w/v) BSA and 0.3% (v/v) Tween-20.

Detection mix (as per AlphaScreen™ protocol): Lysis buffer supplemented with the biotinylated cAMP (10 nM) and Donor beads (10 µg/ml) as supplied in the AlphaScreenT cAMP assay kit.

Consumables

From Fisher: Non-binding surface 384-well assay plates, Cat No DPS-172-020Q.

From Costar: Sterile pipettes from 2 to 50 ml volumes; Sterile tips from P10 up to P1000; Sterile reservoirs, Cat No. 4878; T225 flasks vent cap, Cat No. 3001.

Compound Preparation

For the MCR1, MCR3 and MCR4 standard functional assay methodologies compounds were initially dissolved in DMSO to give a compound concentration of 4 mM and then further diluted for the assay in stimulation buffer to give actual concentrations 2-fold greater than that desired as the final assay concentration.

Day-to-Day Cell Culture

The three HEK cell lines, as detailed hereinbefore, expressing the human MCR1, MCR3 or MCR4 receptor subtypes were grown in T225 vent cap flasks containing 50 ml of growth medium (DMEM supplemented with 10% (v/v) FCS, 2 mM L-Glutamine, 25 mM HEPES and 1.0 mg/ml Geneticin) and maintained in a cell incubator at a temperature of 37° C. and in an environment containing 5% $CO_2$. Cells were harvested when they reached 80-90% confluency by first removing the existing growth medium and then washing with PBS that had been pre-warmed to a temperature of 37° C. This PBS was then removed and 5 ml of cell dissociation fluid added to the flask. The flasks were incubated for 5 minutes in a cell incubator set at a temperature of 37° C. and in an environment containing 5% $CO_2$ to detach the cells. Cells were dislodged from the bottom of the flask by administering a sharp tap to the flask. When cells were detached, growth media pre-warmed to a temperature of 37° C. was added, the cells re-suspended and mixed gently to achieve a single cell suspension by pipetting. This cell suspension was then counted using a cell counting chamber and either used for experimentation, or transferred into a new T225 flask to perpetuate the cell culture.

Assay Procedure

The assay procedure used was essentially as described in the AlphaScreen™ kit methodology (www.perkinelmer.com), however, to ease liquid handling all assay volumes were doubled.

Firstly, 10 µl of the test compound solutions were transferred to the non-binding surface 384-well assay plate.

Secondly, assay cells were harvested as described above.
 (i) For the MCR1 standard functional assay methodology a suspension of cells at $3 \times 10^5$ cells/ml in stimulation buffer (supplemented with 10 µL/ml of the anti-cAMP acceptor bead solution supplied in the AlphaScreen™ cAMP assay kit) was prepared;
 (ii) For the MCR3 standard functional assay methodology a suspension of cells at $5 \times 10^4$ cells/ml in stimulation buffer (supplemented with 10 µl/ml of the anti-cAMP acceptor bead solution supplied in the AlphaScreen™ cAMP assay kit) was prepared; and
 (iii) For the MCR4 standard functional assay methodology a suspension of cells at $1 \times 10^5$ cells/ml in stimulation buffer (supplemented with 10 µl/ml of the anti-cAMP acceptor bead solution supplied in the AlphaScreen™ cAMP assay kit) was prepared.

Subsequently, 10 µl of the cell suspensions were transferred to each well of non-binding surface 384-well assay plate. The assay plates were then incubated in the dark at room temperature for 30 minutes.

Thirdly, the assay reaction was terminated by the addition of 30 µl per well of detection mix. The plates were incubated overnight in the dark at room temperature before transfer to the Fusion™-α microplate analyser for quantification.

(ii) MCR5 Standard Functional Assay Methodology and MCR4 Improved Functional Assay Methodology [Assay Protocol D and E Respectively]

Assay Concept

Determination of compound activity against the human MCR5 receptor subtype was carried out using an immortalised Chinese hamster ovary cell line (CHO-K1) that had been engineered to stably express both the recombinant human MCR5 receptor and a β-lactamase gene reporter (CHO-K1-MC5R-CRE-β-lactamase). Similarly, using an improved assay methodology the activity of compounds were also determined against the human MCR4 receptor subtype using an immortalised CHO-K1 cell line that had been engineered to stably express both the recombinant human MCR4 receptor and a β-lactamase gene reporter (CHO-K1-MC4R-CRE-β-lactamase). These cell lines were engineered using protocols akin to those outlined by Zaccolo et al (Zaccolo, M., (2000) Nature, 2(1); 25-29).

Compound-induced activation of the MCR5 or MCR4 receptors in these two cell lines stimulated the production, and intracellular accumulation, of the enzyme β-lactamase. The quantity of β-lactamase enzyme produced was directly proportional to the degree to which the test compound activated the MCR5 or MCR4 receptors present on these cells and was quantified using the P-lactamase gene reporter analysis kit that is commercially available from Invitrogen Life Technologies. An in-depth description of this technology and assay protocols are available from the Invitrogen web site (www.invitrogen.com). The protocol listed below provides a summary of that assay methodology.

The quantity of β-lactamase enzyme produced by compound-induced activation of the MCR5 or MCR4 receptors expressed in these cell lines was quantified using a LjI Biosystems Analyst™ HT 96.384 plate reader set to excite at a wave length of 405 nm, and measure the energy emitted at wave lengths of 450 nm and 530 nm. Cellular responses were quantified by dividing the measured energy emitted at a wavelength of 450 nm by the measured energy emitted at a wavelength of 530 nm. Data analysis was subsequently performed using a curve-fitting program and the apparent potency of the test compound (expressed as an $EC_{50}$ and defined as the effective compound concentration that elicited 50% of the maximum compound-induced response) extrapolated from the fitted curve.

Materials

From Invitrogen: Dulbecco's modified Eagle media (DMEM) with Glutamax-1, Cat No 32430-027; Non-essential amino acids, Cat No 1140-0.35; Geneticin (G418), Cat No 10131-027; Cell dissociation buffer (enzyme-free PBS-based), Cat No 13151-014; Phosphate buffered saline (PBS) (w/o $Ca^{2+}$ and $Mg^{2+}$), Cat No 14190-094; CCF4-AM, Cat No K1028; Pluronic F127s solution (Solution B), Cat No K1026N; 24% PEG and 18% TR40 solution (Solution C), Cat No K1026N; Zeocin, Cat No R250-05.

From Sigma: Foetal calf serum (FCS), Cat No F7524; Sodium pyruvate, Cat No S8636; N-(2-Hydroxyethyl)piperazine-N'-(2-ethanesulfonic acid) (HEPES), Cat No H0887; Dimethyl sulphoxide (DMSO), Cat No D-8418; Cyclohexamide, Cat No C-7698; Trypan blue solution, Cat No T-4424; Probenecid, Cat No P8761; Bovine serum albumin (BSA), Cat No A2153; Pluronic F-127, Cat No 9003-11-6.

From Gilson: pipettes ranging from 10 µl to 1000 µl.

From Hereaus; Hera Cell $CO_2$ cell incubator.

From Medical Air Technology; BioMat2 Class II Microbiological safety cabinet

From LjI Biosystems; Analystm HT 96.384 plate reader set to excite at a wavelength of 405 nm, and measure the energy emitted at wavelengths of 450 nm and 530 nm.

From Bachem: α-Melanocyte Stimulating Hormone α-MSH, Cat No H1075, used as a positive control compound.

Buffers

CCF4-AM was dissolved in 100% DMSO to give a final solution concentration of 1 mM. This solution was termed Solution A.

Probenecid was dissolved in 200 mM NaOH to give a final solution concentration of 200 mM. This solution was termed Solution D.

Composition of the β-lactamase assay dye solution: for 1072 µL of assay dye solution combine: 12 µL of Solution A, 60 µL of Solution B, 925 µL of Solution C and 75 µL of Solution D.

Consumables

From Greiner: 384-well black µclear bottom Microplate assay plates, Cat No. 781091.

From Costar: Sterile Pipettes from 2 up to 50 ml volume, Sterile tips from P10 up to P1000; Sterile reservoirs, Cat No. 4878; T225 flasks vent cap, Cat No. 3001.

Compound Preparation

For the MCR5 standard functional assay methodology all test compounds were initially dissolved in DMSO to give a compound concentration of 4 mM and then further diluted for the assay in PBS, containing 1.25% v/v DMSO and 0.1% w/v BSA, to give actual concentrations 5-fold greater than that desired as the final assay concentration.

For the MCR4 improved functional assay methodology all test compounds were initially dissolved in DMSO to give a compound concentration of 4 mM and then further diluted for the assay in PBS, containing 2.5% v/v DMSO and 0.05% w/v pluronic F-127, to give actual concentrations 5-fold greater than that desired as the final assay concentration.

Day-to-Day Cell Culture

Cells were grown in T225 vent cap flasks containing 50 ml of growth medium and maintained in a cell incubator at a temperature of 37° C. and in an environment containing 5% $CO_2$. The composition of the growth medium for the CHO-K1-MC5R-CRE-β-lactamase was 90% v/v DMEM supplemented with; Glutamax-1, 25 mM HEPES, 10% v/v foetal calf serum (FCS), 1 mM sodium pyruvate, 0.1 mM non essential amino acids and 800 µg/ml genetic in. For the CHO-K1-MC4R-CRE-β-lactamase this growth media was further supplemented with 2001 g/ml Zeocin. Cells were harvested when they reached 80-90% confluency by first removing the existing growth medium and then washing with PBS that had been pre-warmed to a temperature of 37° C. This PBS was then removed and 5 ml of cell dissociation fluid added to the flask. These cells were incubated for 5 minutes in a cell incubator set at a temperature of 37° C. and in an environment containing 5% $CO_2$ to detach the cells. When cells were detached, pre-warmed growth media was added, the cells re-suspended and mixed gently to achieve a single cell suspension by pipetting. This cell suspension was then used for experimentation, or transferred into a new T225 flask to perpetuate the cell culture.

Assay Procedure

On the first day of the assay cells were harvested as described above. For the MCR5 standard functional assay methodology a suspension of cells at $3.33 \times 10^5$ cells/ml in modified growth medium, containing 1% instead of 10% FCS, was prepared and 30 µl of this cell suspension added into each well of a Greiner: 384-well black, µclear bottom Microplate assay plate.

For the MCR4 improved functional assay methodology a suspension of cells at $2 \times 10^5$ cells/ml in modified growth medium, containing 5% instead of 10% FCS, was prepared and 40 µl of this cell suspension added into each well of a Greiner 384-well black µclear bottom Microplate assay plate.

For each assay the cell plates were then retuned to a cell incubator maintained at a temperature of 37° C. and in an environment containing 5% $CO_2$ overnight before performing the assay on the second assay day.

On the second day of the assay for the MCR5 standard functional assay methodology the cell plate was removed from the cell incubator and 10 µL of a 5 µM cyclohexamine solution (made up in PBS with 5% v/v DMSO) was added to each well of the assay plate. For the MCR4 improved functional assay methodology the solution of cyclohexamide was not added. Subsequently, 10 µL of the test compound solution was transferred to the assay plate. The assay plate was then transferred to a cell incubator, set at 37° C. and in an environment containing 5% $CO_2$, and left for 4 hours for the MCR4 improved assay methodology, or 5 hours for the MCR5 standard assay methodology. After this incubation period the plate was removed from the incubator, 10 µL of the µ-lactamase assay dye solution was added to each well and then the plate returned to the cell incubator. Following a further incubation period of 60 minutes for the MCR4 improved assay methodology or 90 minutes for the MCR5 standard assay methodology the plates were removed from the incubator and transferred to the LjI Biosystems Analyst™ HT 96.384 plate reader for quantification.

Obesity

The compounds of this invention may also be used in conjunction with pharmaceutical agents for the treatment of diseases, conditions and/or disorders related to obesity. Therefore, compositions (or medicaments) for use in treating obesity that include compounds of the present invention in combination with anti-obesity agents are also provided. Suitable anti-obesity agents include cannabinoid 1 (CB-1) receptor antagonists (such as rimonabant), apolipoprotein-B secretion/microsomal triglyceride transfer protein (apo-B/MTP) inhibitors (in particular, gut-selective MTP inhibitors, such as edipatapide or dirlotapide), 11β-hydroxy steroid dehydrogenase-1 (11β-HSD type 1) inhibitors, peptide $YY_{3-36}$ and analogs thereof, cholecystokinin-A (CCK-A) agonists, monoamine reuptake inhibitors (such as sibutramine), sympathomimetic agents, $\beta_3$ adrenergic receptor agonists, dopamine receptor agonists (such as bromocriptine), melanocyte-stimulating hormone receptor analogs, 5HT2c receptor agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists (in particular, NPY-5 receptor antagonists), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

Especially preferred are anti-obesity agents selected from the group consisting of CB-1 antagonists, gut-selective MTP inhibitors, orlistat, sibutramine, bromocriptine, ephedrine, leptin, peptide $YY_{3-36}$ and analogs thereof, and pseudoephedrine. Preferably, compounds of the present invention and combination therapies for the treatment of obesity and related conditions are administered in conjunction with exercise and a sensible diet.

Preferred CB-1 antagonists include Rimonabant (SR141716A also known under the tradename Acomplia™ available from Sanofi-Synthelabo) described in U.S. Pat. No. 5,624,941; and compounds described in U.S. Pat. Nos. 5,747,524, 6,432,984 and 6,518,264; U.S. Patent Publication Nos. U.S. 2004/0092520, U.S. 2004/0157839, U.S. 2004/0214855, and U.S. 2004/0214838; U.S. patent application Ser. No. 10/971,599 filed on Oct. 22, 2004; and PCT Patent Publication Nos. WO 02/076949, WO 03/075660, WO04/048317, WO04/013120, and WO 04/012671.

Preferred gut-slective MTP inhibitors include dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431.

Other representative anti-obesity agents for use in the combinations, pharmaceutical compositions, and methods of the invention can be prepared using methods known to one of ordinary skill in the art, for example; sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and $PYY_{3-36}$ (including analogs) can be prepared as described in U.S. Publication No. 2002/0141985 and WO 03/027637.

Food Intake

The following screen can be used to evaluate the efficacy of test compounds for inhibiting food intake in Sprague-Dawley rats after an overnight fast.

Male Sprague-Dawley rats can be obtained from Charles River Laboratories, Inc. (Wilmington, Mass.). The rats are individually housed and fed powdered chow. They are maintained on a 12-hour light/dark cycle and receive food and water ad libitum. The animals are acclimated to the vivarium for a period of one week before testing is conducted. Testing is completed during the light portion of the cycle.

To conduct the food intake efficacy screen, rats are transferred to individual test cages without food the afternoon prior to testing, and the rats are fasted overnight. After the overnight fast, rats are dosed the following morning with vehicle or test compounds. A known antagonist is dosed (3 mg/kg) as a positive control, and a control group receives vehicle alone (no compound). The test compounds are dosed at ranges between 0.1 and 100 mg/kg depending upon the compound. The standard vehicle is 0.5% (w/v) methylcellulose in water and the standard route of administration is oral. However, different vehicles and routes of administration can be used to accommodate various compounds when required. Food is provided to the rats 30 minutes after dosing and the Oxymax automated food intake system (Columbus Instruments, Columbus, Ohio) is started. Individual rat food intake is recorded continuously at 10-minute intervals for a period of two hours. When required, food intake is recorded manually using an electronic scale; food is weighed every 30 minutes after food is provided up to four hours after food is provided. Compound efficacy is determined by comparing the food intake pattern of compound-treated rats to vehicle and the standard positive control.

Administration and Dose Ranges

The compounds of formula (I) should be assessed for their biopharmaceutical properties, such as for example, solubility, solution stability (across a range of pHs), likely dose level and permeability, in order to select the most appropriate dosage forms and routes of administration considered appropriate for the treatment of the desired indication. Preliminary biopharmaceutical assessments have indicated that some compounds according to the present invention may be especially suited for administration via the oral route (including buccal and sublingual) or the intranasal route. For example the oral sublingual or the intranasal route may be suitable for the compound of Examples 1 and 5, with the oral sublingual route being preferred. Other compounds may be more suited for any form of oral administration, such as for example the compound of Example 9.

Thus according to a further embodiment the present invention provides a pharmaceutical composition comprising a compound of general formula I as defined hereinbefore, preferably the compound of Examples 1 and 5, formulated for sublingual delivery.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Any suitable route of administration may be employed for providing a mammal, especially a human with an effective dosage of a compound of the present invention. For example, oral (including buccal and sublingual administration), rectal, topical, parental, ocular, pulmonary, nasal, and the like may be employed. Dosage forms include tablets, troches, dispersions, suspensions, solutions, capsules, creams, ointments, aerosols, and the like. Preferably compounds of formula (I) are administered orally or intranasally.

The effective dosage of active ingredient employed may vary depending on the particular compound employed, the mode of administration, the condition being treated and the severity of the condition being treated. Such dosage may be ascertained readily by a person skilled in the art.

For the treatment of sexual dysfunction compounds of the present invention are given in a dose range of from about 0.001 milligram (mg) to about 1000 mg, preferably from about 0.001 mg to about 500 mg, more preferably from about 0.001 mg to about 100 mg, even more preferably from about 0.001 mg to about 50 mg and especially from about 0.002 mg to about 25 mg per kilogram of body weight, preferably as a single dose orally or as a nasal spray. For example, oral administration may require a total daily dose of from about 0.1 mg up to about 1000 mg, while an intravenous dose may only require from about 0.001 mg up to about 100 mg. The total daily dose may be administered in single or divided doses and may, at the physician's discretion, fall outside of the typical range given herein.

When treating obesity, in conjunction with diabetes and/or hyperglycemia, or alone, generally satisfactory results are obtained when the compounds of the present invention are administered at a daily dosage of from about 0.0001 mg to about 1000 mg, preferably about 0.001 mg to about 500 mg, more preferably about 0.005 mg to about 100 mg and especially about 0.005 mg to about 50 mg per kilogram of animal body weight, preferably given in a single dose or in divided doses two to six times a day, or in sustained release form. In the case of a 70 kg adult human, the total daily dose will generally be from about 0.7 mg up to about 3500 mg. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 mg up to about 100 mg per kilogram of animal body weight, preferably given in a single dose or in divided doses two to six times a day, or in sustained release form. In the case of a 70 kg adult human, the total daily dose will generally be from about 0.07 mg up to about 350 mg. This dosage regimen may be adjusted to provide the optimal therapeutic response.

These dosages are based on an average human subject having a weight of about 65 kg to 70 kg. The physician will readily be able to determine doses for subjects whose weight falls outside this range, such as infants and the elderly.

Oral Administration

The compounds of the invention may be administered orally. Oral administration may involve swallowing, so that the compound enters the gastrointestinal tract, and/or buccal, lingual or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula I may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-Line*, 25(2), 1-14 by Verma et al (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose, blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (I). The overall daily dose will typically be in the range 0.001 mg to 40 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For the avoidance of doubt, references herein to "treatment" include references to curative, palliative and prophylactic treatment.

The invention is illustrated by the following non-limiting examples in which the following abbreviations and definitions are used:

ABBREVIATIONS

APCI atmospheric pressure chemical ionisation mass spectrum
$[\alpha]_D$ specific rotation at 587 nm.
Arbocel® filter agent
δ chemical shift
d Doublet
dd double doublet
GC-MS gas chromatography mass spectrometry
HPLC high performance liquid chromatography
HRMS high resolution mass spectrum
LC-MS liquid chromatography mass spectrometry
LRMS low resolution mass spectrum
m Multiplet
min Minutes
m/z mass spectrum peak
NMR nuclear magnetic resonance
psi pounds per square inch
q Quartet
s Singlet
t Triplet For synthetic convenience whilst in many instances compounds have been initially isolated in their free-base form, these have often been converted to their corresponding hydrochloride salts for analytical identification purposes. For the avoidance of doubt both the free-base and HCl salt forms are considered provided herein.

X-Ray Crystal Data

Crystalline material for four compounds was obtained as follows: (1) the compound of Example 5 was dissolved in 90:5:5 i-PrOH/MeCN/AcOH at reflux, and the solution was then allowed to cool to room temperature to furnish crystalline material which can be isolated for further analysis; (2) the compound of Preparation 16 was dissolved in 95:5 MeCN/THF at reflux, and the solution was then allowed to cool to room temperature to furnish crystalline material which can be isolated for further analysis; (3) the compound of Preparation 22b was dissolved in hot EtOAc and pentane was then added to the point of cloudiness and the solution was then allowed to cool to room temperature to furnish crystalline material which can be isolated for further analysis; and (4) for (3S, 4R)-4-(2,4-difluorophenyl)-N-[(1R)-1-phenylethyl]pyrrolidine-3-carboxamide hydrochloride, crystalline material was obtained from EtOH/i-Pr$_2$O via vapor diffusion methodology.

The stereochemistry of crystalline material obtained for these four compounds was determined using X-ray crystallography. Representations of the 3D structures of these compounds are illustrated in FIGS. 3, 4, 5, and 6 hereinafter.

Figure 3:
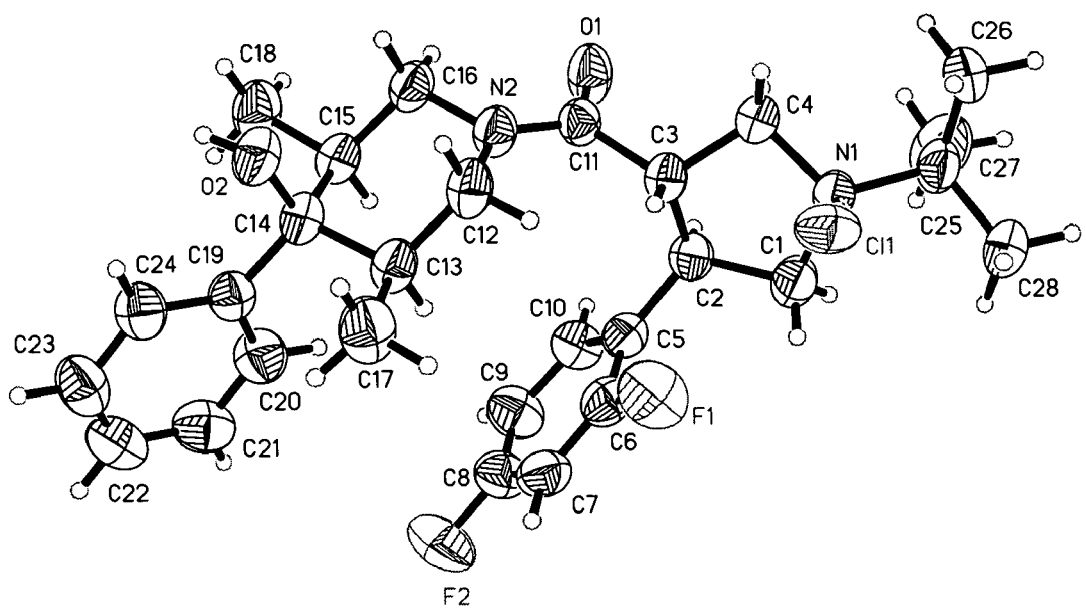
FIG. 3 depicts the ORTEP plot for the crystal structure of the compound of Example 5.

FIG. 3 illustrates an ORTEP plot with thermal ellipsoids drawn at the 50% confidence level for the asymmetric unit of the crystal structure of the compound of Example 5.

Figure 4:
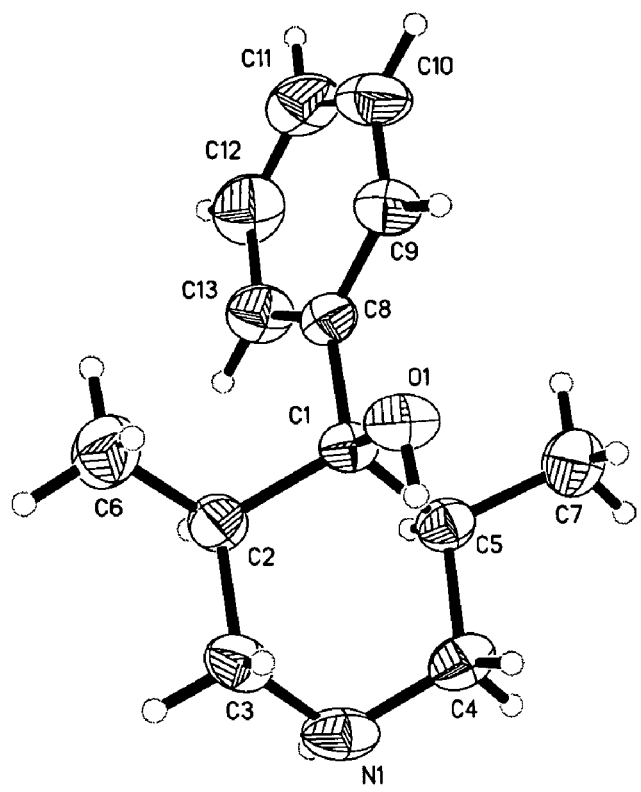
FIG. 4 depicts the ORTEP plot for the crystal structure of the compound of Preparation 16.

FIG. 4 illustrates an ORTEP plot with thermal ellipsoids drawn at the 50% confidence level for the asymmetric unit of the crystal structure of the compound of Preparation 16.

Figure 5:
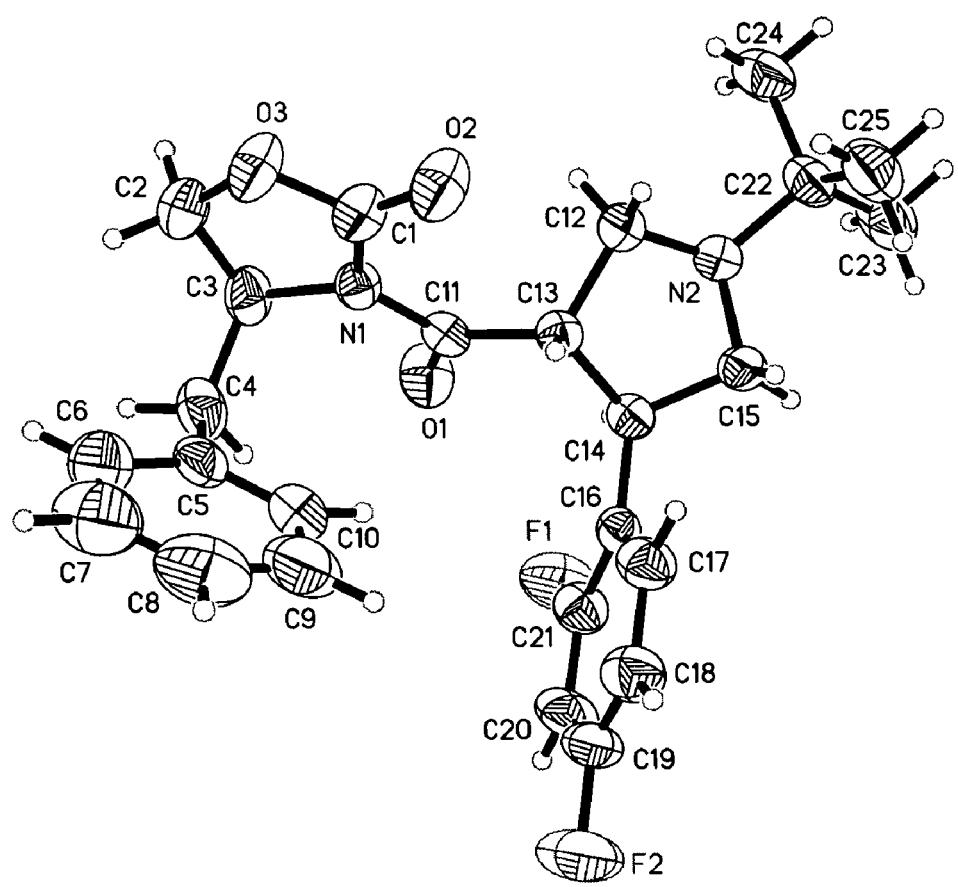
FIG. 5 depicts the ORTEP plot for the crystal structure of the compound of Preparation 22b.

FIG. 5 illustrates an ORTEP plot with thermal ellipsoids drawn at the 50% confidence level for the asymmetric unit of the crystal structure of the compound of Preparation 22b.

Figure 6:
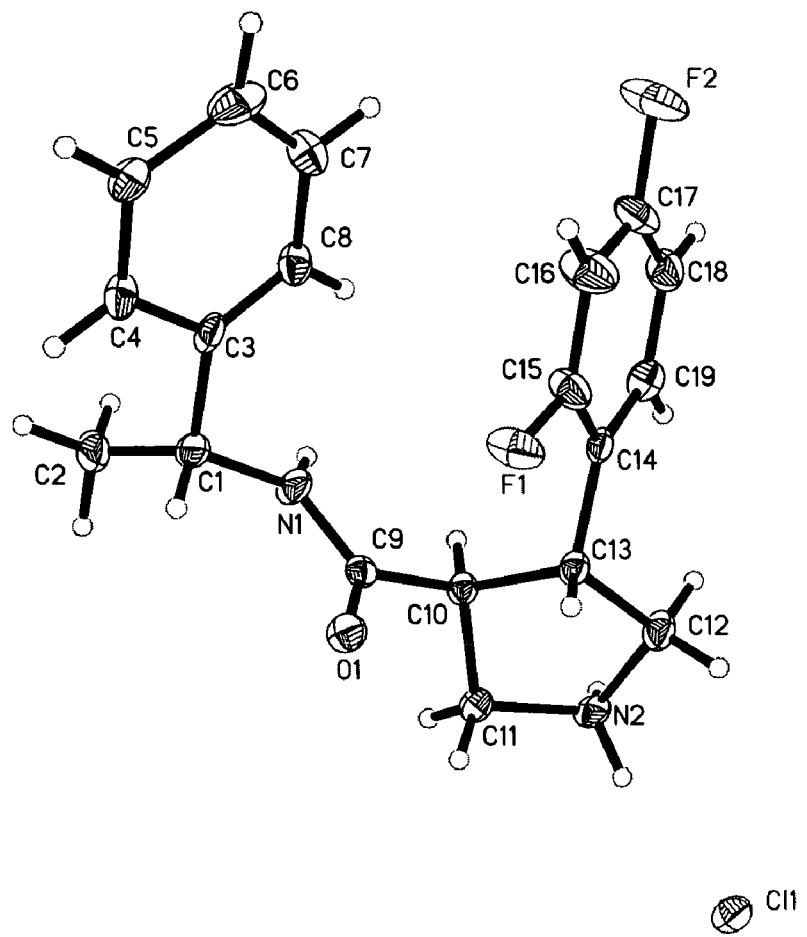
FIG. 6 depicts the ORTEP plot for the asymmetric unit of the crystal structure of (3S,4R)-4-(2,4-difluorophenyl)-N-[(1R)-1-phenylethyl]pyrrolidine-3-carboxamide hydrochloride.

FIG. 6 illustrates an ORTEP plot with thermal ellipsoids drawn at the 50% confidence level for the asymmetric unit of the crystal structure of (3S,4R)-4-(2,4-difluorophenyl)-N-[(1R)-1-phenylethyl]pyrrolidine-3-carboxamide hydrochloride. The disorder of the difluorophenyl ring and the phenyl ring have been omitted for clarity.

The X-ray crystal data for the compound of Example 5 (where $R^1$=phenyl, $R^2$=OH, $R^3$=Bu$^t$ and $R^4$ and $R^5$=F) illustrates: the relative cis relationship of the methyl substituents on the piperidine ring; the cis-arrangement of $R^2$ to the methyl substituents on the piperidine ring; the relative trans arrangement for the groups at the C3 and C4 positions of the pyrrolidine ring; and the absolute configuration at C3 and C4 of the pyrrolidine ring.

The X-ray crystal data for the intermediate compound of Preparation 16 (where $R^1$=phenyl and $R^2$=OH) illustrates: the relative cis relationship of the methyl substituents on the piperidine ring and the cis-arrangement of $R^2$ to the methyl substituents on the piperidine ring. The compound of Preparation 16 is a direct precursor for the compound of Example 5. The X-ray data confirms that there was no stereochemical interconversion at the piperidine ring in the subsequent reaction of the compound of Preparation 16 and the compound of Preparation 1 to furnish the compound of Example 5.

The X-ray crystal data for the intermediate compound of Preparation 22b (where $R^3$=Bu$^t$ and $R^4$ and $R^5$=F) illustrates: the relative trans arrangement for the groups at the C3 and C4 positions of the pyrrolidine ring; and (by virtue of the known absolute configuration of the benzyloxazolidinone moiety) the absolute configuration at C3 and C4. The intermediate compound of Preparation 22b is hydrolysed to provide the intermediate compound of Preparation 1 which is a direct precursor for the final compound of Example 5. The X-ray data confirms that there was no stereochemical interconversion at the pyrrolidine ring in the synthetic process from the conversion of the intermediate of Preparation 22b to the intermediate of Preparation 16 and its subsequent reaction with the intermediate of Preparation 1 to furnish the final compound of Example 5.

The relative and absolute configuration of the compound of Preparation 53 was determined by its conversion to (3S,4R)-4-(2,4-difluorophenyl)-N-[(1R)-1-phenylethyl]pyrrolidine-3-carboxamide hydrochloride. This conversion was achieved by:

(i) reaction of the compound of Preparation 53 with (R)-(+)-α-methylbenzylamine in the presence of 1-[3-(dimethylamino)propyl]-3-ethylcarbodiimide hydrochloride and 1-hydroxybenzotriazole in tetrahydrofuran at room temperature to form tert-butyl (3R,4S)-3-(2,4-difluorophenyl)-4-({[(1R)-1-phenylethyl]amino}carbonyl) pyrrolidine-1-carboxylate;

(ii) Boc-deprotection by treatment of a solution of tert-butyl (3R,4S)-3-(2,4-difluorophenyl)-4-({[(1R)-1-phenylethyl]amino}carbonyl)pyrrolidine-1-carboxylate in dichloromethane with a solution of 4M hydrogen chloride in dioxane at room temperature to form (3S,4R)-4-(2,4-difluorophenyl)-N-[(1R)-1-phenylethyl]pyrrolidine-3-carboxamide hydrochloride. X-Ray crystal data for (3S,4R)-4-(2,4-difluorophenyl)-N-[(1R)-1-phenylethyl]pyrrolidine-3-carbox-amide hydrochloride demonstrated both the relative trans relationship of the substituents at C3 and C4 of the pyrrolidine ring, and also the absolute configuration at C3 and C4 of the pyrrolidine ring. Representation of the 3D structure of this is illustrated in FIG. 6 hereinafter.

The stereochemistries illustrated for the remaining compounds in the Examples and Preparations have been assigned on the basis of the stereochemical precedents established in the synthesis of the compounds of Example 5, Preparation 22b, Preparation 16, and Preparation 53 as described hereinbefore. The exception to this is the compound of Example 7 which has a cis-arrangement at the 3- and 4-positions of the pyrrolidine ring.

X-ray diffraction data for the single crystals of the compounds of Example 5 and Preparations 16 and 22b were recorded at room temperature using a Bruker AXS SMART-APEX CCD area-detector diffractometer (Mo Kαx radiation). Intensities were intergrated from several series of exposures using the methodology described in SMART v5.622 (control) and SAINT v6.02 (integration) software, Bruker AXS Inc., Madison, Wis. 1994. Each exposure covered 0.3° in ω, with an exposure time of 60 s (Example 5), 10 s (Preparation 16) or 120 s (Preparation 22b) and the total data sets were: more than a sphere (Example 5); hemisphere (Preparations 16 and 22b). The data sets were corrected for absorption using the multiscans method, as described in SADABS, program for scaling and correction of area detector data, G. M. Sheldrick, University of Göttingen, 1997 (based on the method of R. H. Blessing, *Acta Cryst.* 1995, A51, 33-38).

X-ray diffraction data for the crystal of (3S,4R)-4-(2,4-difluorophenyl)-N-[(1R)-1-phenylethyl]pyrrolidine-3-carboxamide hydrochloride were recorded at 100 K using a Bruker AXS SMART-APEX CCD area-detector diffractometer (Mo Kα radiation) fitted with an Oxford Cryosystems Series 700 Liquid Nitrogen Cryostream. Intensities were intergrated from several series of exposures (as described herein before). Each exposure covered 0.3° in ω, with an exposure time of 60 s and the total data set was more than a sphere. The data set was corrected for absorption using the multiscans method (as detailed herein before).

The crystal structures were successfully solved by direct methods using SHELXS-97, (as described in SHELXS-97, Program for crystal structure solution. G. M. Sheldrick, University of Göttingen, Germany, 1997, release 97-2) in: Space Group P2$_1$ (Example 5); Space Group Pna2$_1$ (Preparation 16); Space Group P2$_1$2$_1$2$_1$ (Preparation 22b and (3S,4R)-4-(2,4-difluorophenyl)-N-[(1R)-1-phenylethyl]-pyrrolidine-3-carboxamide hydrochloride) and all of the non-hydrogen atoms in the asymmetric units were located from the resultant electron density maps. From these maps and subsequent structure refinements it was found that: there was one cation and one chloride ion in the asymmetric unit for the compound of Example 5 (as illustrated in FIG. 3); there was one molecule of the compound of Preparation 16 in the asymmetric unit (as illustrated in FIG. 4); there was one molecule of the compound of Preparation 22b in the asymmetric unit (as illustrated in FIG. 5); and that there was one (3S,4R)-4-(2,4-difluorophenyl)-N-[(1R)-1-phenylethyl]pyrrolidine-3-carboxamide hydrochloride cation and one chloride anion in the asymmetric unit (as illustrated in FIG. 6).

For all four crystals assessed the co-ordinates of the non-hydrogen atoms were refined against the diffraction data by the method of least-squares using SHELXL-97 (as described in SHELXL-97, Program for crystal structure refinement. G. M. Sheldrick, University of Göttingen, Germany, 1997, release 97-2) each with anisotropic displacement parameters.

For the crystal of Example 5 the positions of the hydroxyl and N—H+ hydrogen atoms were located from a Fourier difference map and their coordinates were refined with constraints placed on the respective O—H and N—H bond distances and angles such that the groups retained an idealised geometry. The remaining hydrogen atoms were placed in calculated positions and refined with a riding model and all hydrogen atoms were refined isotropic displacement parameters. The absolute configuration of the cation stereochemistry for the compound of Example 5 was determined directly from the X-ray diffraction data by the method of Flack. (as detailed in H. D. Flack, Acta Cryst. 1983, A39, 876-881). The final refined Flack parameter was 0.00 (5) for the enantiomer depicted in FIG. 3.

For the crystal of Preparation 16 the positions of the amine and hydroxyl hydrogen atoms were located from a Fourier difference map and their coordinates were refined with restraints placed on the respective N—H and O—H bond distances and angles such that the group retained an idealised geometry. The remaining hydrogen atoms were placed in calculated positions and refined with a riding model and all hydrogen atoms were refined with isotropic displacement parameters.

For the crystal of Preparation 22b the hydrogen atoms were placed in calculated positions and refined with a riding model and all with isotropic displacement parameters. The absolute stereochemistry of the compound of Preparation 22b could not be determined directly from the diffraction data. However this crystal structure did establish that the configuration could only be one of a pair of enantiomers (either that shown in FIG. 5 or it's mirror image with all chiral centres inverted). If it is assumed that the configuration of the centre at C4 of the oxazolidnone ring was the same as in the starting material i.e. 'S', by inference the other two centres can be assigned as in FIG. 5.

For the crystal of (3S,4R)-4-(2,4-difluorophenyl)-N-[(1R)-1-phenylethyl]-pyrrolidine-3-carboxamide hydrochloride large thermal ellipsoids associated with both phenyl rings strongly suggested that the two groups were disordered. The diflurophenyl ring was modelled over two orientations related by a two-fold rotation about the C14 . . . C17 axis with a relative occupancy of 80:20. The unsubstituted phenyl ring was finally modelled over two overlapping orientations with equal occupancies. The hydrogen atoms were placed in calculated positions and refined with a riding model and all with isotropic displacement parameters. The position of the amide and amine N—H hydrogen atoms, were located from a Fourier difference map refined with isotropic displacement parameters. The remaining hydrogen atoms were placed in calculated positions and refined with a riding model and all with isotropic displacement parameters. The absolute configuration of the (3S,4R)-4-(2,4-difluorophenyl)-N-[(1R)-1-phenylethyl]pyrrolidine-3-carboxamide hydrochloride cation stereochemistry was determined directly from the X-ray diffraction data by the method of Flack (as detailed hereinbefore). The final refined Flack parameter was −0.01 (7) for the diastereomer depicted in FIG. 6.

The final refined R-factor % [For data I>2σI] are: for Example 5 is 4.15%; Preparation 16 is 4.07%; Preparation 22b is 4.62%; and for (3S,4R)-4-(2,4-difluorophenyl)-N-[(1R)-1-phenylethyl]pyrrolidine-3-carboxamide hydrochloride is 5.00%.

Simulated Powder X-Ray Diffraction Data (i) Compound of Example 5

2-theta Angles, d spacings and relative intensities were calculated from the single crystal structure of the compound of Example 5 using the "Reflex Powder Diffraction" module of Accelrys Materials Studio™ [version 3.0]. Pertinent simulation parameters were in each case: Wavelength=1.540562 Å (Cu Kα); Polarisation Factor=0.5; Pseudo-Voigt Profile (U=0.01, V=−0.001, W=0.002).

The single crystal structure data derived via the methodology described hereinbefore was used in these calculations. Table 1 tabulates the most intense peaks of the Simulated Powder Pattern of Example 5 from the Single Crystal Data Collection (as illustrated in FIG. 7).

TABLE 1

| Angle (°2-theta) | Intensity (%) |
| --- | --- |
| 8.6 | 17.4 |
| 10.9 | 42.3 |
| 11.3 | 86 |
| 11.7 | 53.6 |
| 13.9 | 100 |
| 16.1 | 61.5 |
| 18.2 | 13.6 |
| 18.9 | 51.4 |
| 19.7 | 72.5 |
| 20.3 | 32.2 |
| 23.5 | 33.5 |
| 24.1 | 22.2 |
| 24.7 | 12 |
| 25.3 | 29.5 |
| 25.8 | 11.8 |
| 28.1 | 10.3 |

Figure 7:
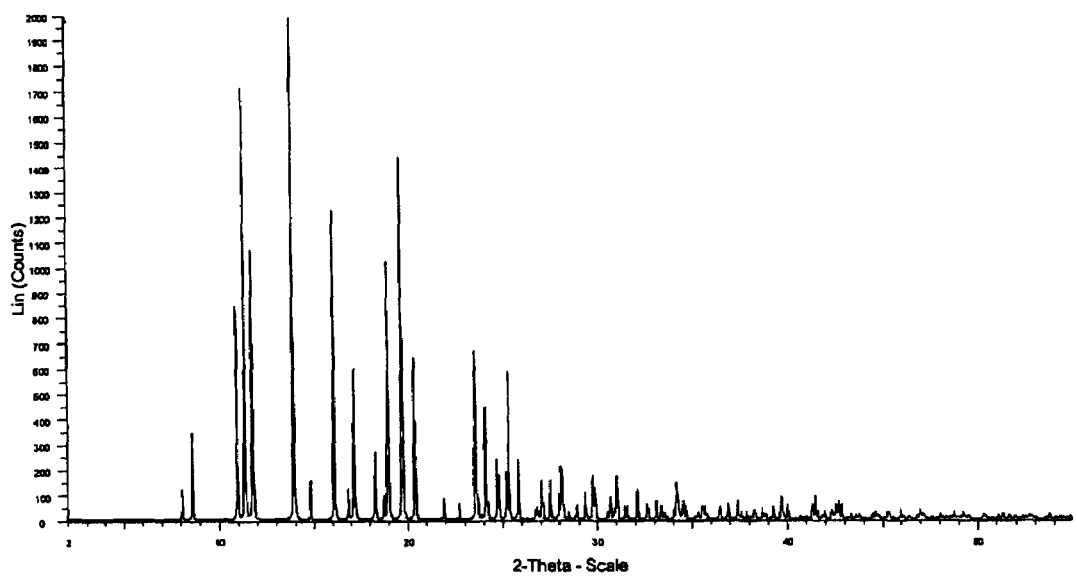
FIG. 7 depicts the simulated PXRD pattern for the compound of Example 5.

Thus according to a further aspect the present invention provides the compound of Example 5 having the simulated PXRD pattern illustrated in FIG. 7 with most intense peaks as illustrated in Table 1 when said simulated PXRD pattern is generated via the method outlined hereinbefore.

(ii) Compound of Preparation 16

2-theta Angles, d spacings and relative intensities were calculated from the single crystal structure of Preparation 16 using the "Reflex Powder Diffraction" module of Accelrys Materials Studio™ [version 3.0]. Pertinent simulation parameters were in each case: Wavelength=1.540562 Å(Cu Kα); Polarisation Factor=0.5; Pseudo-Voigt Profile (U=0.01, V=−0.001, W=0.002).

The single crystal structure data derived via the methodology described hereinbefore was used in these calculations. Table 2 tabulates the most intense peaks of the Simulated Powder Pattern of Preparation 16 from the Single Crystal Data Collection (as illustrated in FIG. 8).

TABLE 2

| Angle (°2-theta) | Intensity (%) |
|---|---|
| 9.2 | 65.5 |
| 11.6 | 14.4 |
| 14.3 | 100 |
| 15.5 | 41.6 |
| 16.6 | 78.9 |
| 18.1 | 85.7 |
| 20.8 | 13.5 |
| 22.6 | 16 |
| 24.6 | 17.1 |
| 25.7 | 12.5 |
| 26.4 | 14.9 |
| 27.2 | 15.5 |

Figure 8:
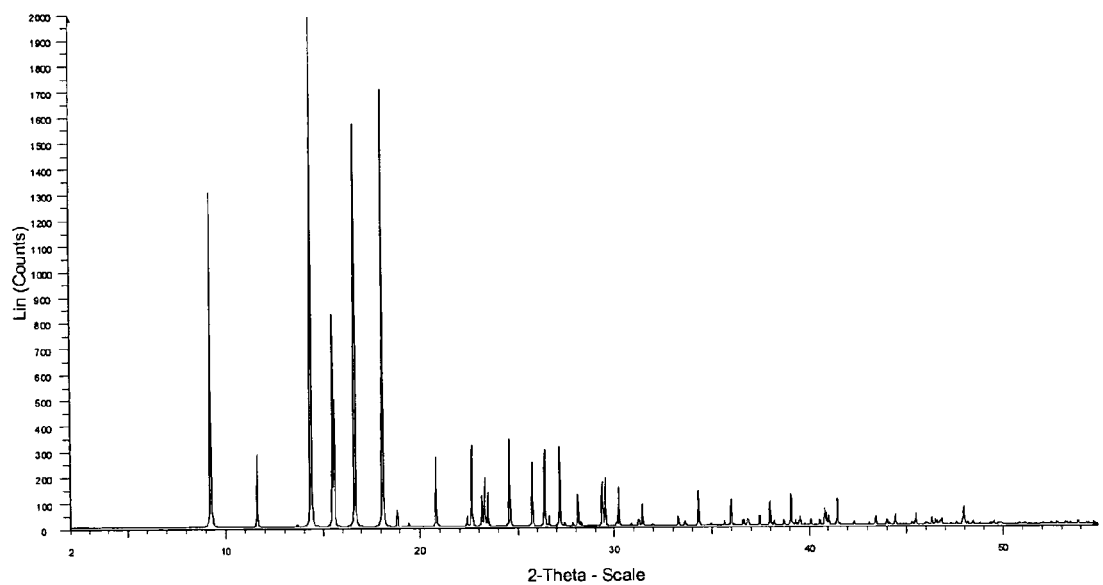
FIG. 8 depicts the simulated PXRD pattern for the compound of Preparation 16.

Thus according to a further aspect the present invention provides the compound of Preparation 16 having the simulated PXRD pattern illustrated in FIG. 8 with most intense peaks as illustrated in Table 2 when said simulated PXRD pattern is generated via the method outlined hereinbefore.

(iii) Compound of Preparation 22b 2-theta Angles, d spacings and relative intensities were calculated from the single crystal structure of Preparation 22b using the "Reflex Powder Diffraction" module of Accelrys Materials Studio™ [version 3.0]. Pertinent simulation parameters were in each case: Wavelength=1.540562 Å(Cu Kα); Polarisation Factor=0.5; Pseudo-Voigt Profile (U=0.01, V=−0.001, W=0.002).

Figure 9:
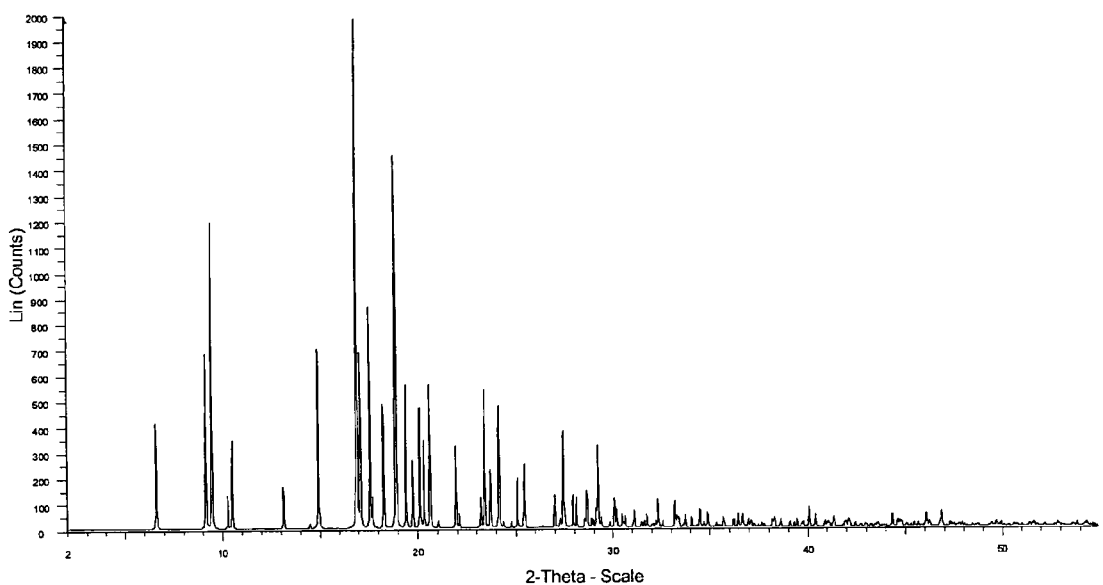
FIG. 9 depicts the simulated PXRD pattern for the compound of Preparation 22b.

The single crystal structure data derived via the methodology described hereinbefore was used in these calculations. Table 3 tabulates the most intense peaks of the Simulated Powder Pattern of Preparation 22b from the Single Crystal Data Collection (as illustrated in FIG. 9).

TABLE 3

| Angle (°2-theta) | Intensity (%) |
|---|---|
| 6.5 | 20.7 |
| 9.1 | 34.3 |
| 9.4 | 60.1 |
| 10.5 | 17.4 |
| 14.9 | 35.2 |
| 16.9 | 100 |
| 17.1 | 19.8 |
| 17.5 | 43.6 |
| 18.3 | 24.5 |
| 18.9 | 73.1 |
| 19.4 | 28.3 |
| 19.7 | 13.3 |
| 20.1 | 23.7 |
| 20.3 | 17.3 |
| 20.6 | 28.2 |
| 21.9 | 16.2 |
| 23.4 | 27.3 |
| 23.7 | 11.3 |
| 24.1 | 24.1 |
| 25.4 | 12.5 |

TABLE 3-continued

| Angle (°2-theta) | Intensity (%) |
|---|---|
| 27.4 | 19.2 |
| 29.2 | 16.2 |

Thus according to a further aspect the present invention provides the compound of Preparation 22b having the simulated PXRD pattern illustrated in FIG. 9 with most intense peaks as illustrated in Table 2 when said simulated PXRD pattern is generated via the method outlined hereinbefore.

(iv) (3S,4R)-4-(2,4-difluorophenyl)-N-[(1R)-1-phenylethyl]pyrrolidine-3-carboxamide hydrochloride 2-theta Angles, d spacings and relative intensities were calculated from the single crystal structure of (3S,4R)-4-(2, 4-difluorophenyl)-N-[(1R)-1-phenylethyl]pyrrolidine-3-carboxamide hydrochloride using the "Reflex Powder Diffraction" module of Accelrys Materials Studio™[version 3.0]. Pertinent simulation parameters were in each case: Wavelength=1.540562 ™ (Cu Kα); Polarisation Factor=0.5; Pseudo-Voigt Profile (U=0.01, V=−0.001, W=0.002).

Figure 10:
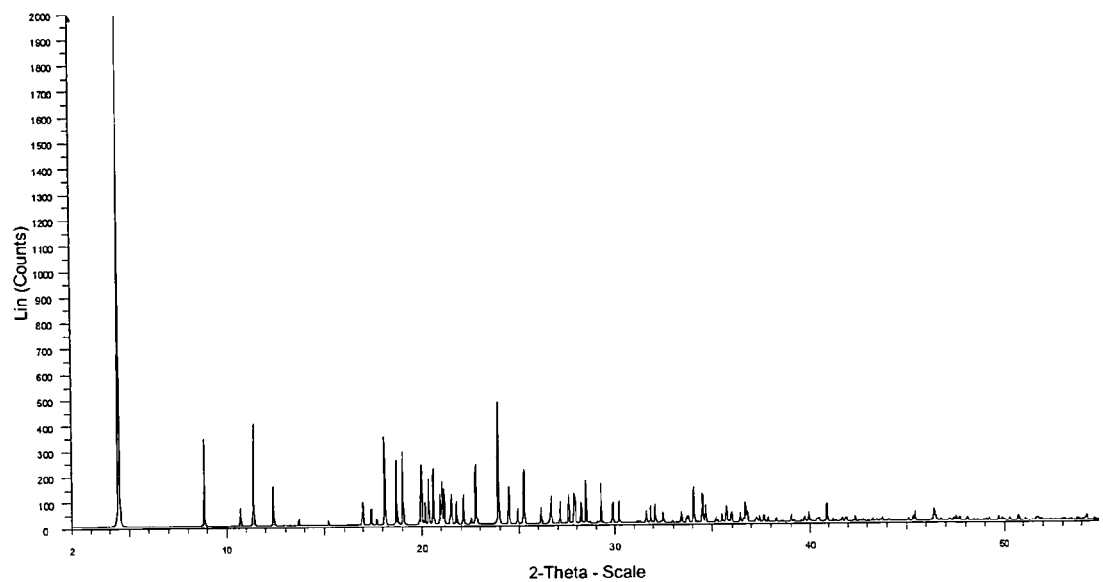
FIG. 10 depicts the simulated PXRD pattern for (3S,4R)-4-(2,4-difluorophenyl)-N-[(1R)-1-phenylethyl]pyrrolidine-3-carboxamide hydrochloride.

The single crystal structure data derived via the methodology described hereinbefore was used in these calculations. Table 4 tabulates the most intense peaks of the Simulated Powder Pattern of (3S,4R)-4-(2,4-difluorophenyl)-N-[(1R)-1-phenylethyl]pyrrolidine-3-carboxamide hydrochloride from the Single Crystal Data Collection (as illustrated in FIG. 10).

TABLE 4

| Angle (°2-theta) | Intensity (%) |
|---|---|
| 4.4 | 100 |
| 8.8 | 17.1 |
| 11.4 | 20.1 |
| 18.1 | 17.4 |
| 18.7 | 12.7 |
| 19.0 | 14.6 |
| 20.0 | 11.7 |
| 20.6 | 11.2 |
| 22.8 | 11.8 |
| 23.9 | 24 |
| 25.2 | 10.8 |

Example 1

(3R,4R,5S)-1-{[(3S,4R)-1-tert-Butyl-4-(24-difluorophenyl)pyrrolidin-3-yl]carbonyl}-3,5-dimethyl-4-phenylpiperidin-4-ol

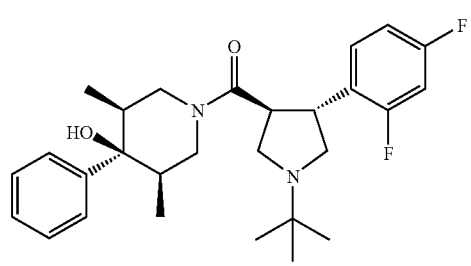

To a stirred suspension of (3S,4R)-1-tert-butyl-4-(2,4-difluorophenyl)pyrrolidine-3-carboxylic acid hydrochloride salt from preparation 1, (57 mg, 0.2 mmol) in dichloromethane (1 mL) at room temperature under dry nitrogen was added O-benzotriazol-1-yl-N,N,N',N' tetramethyluronium hexafluorophosphate (76 mg, 0.2 mmol), followed by N-methylmorpholine (132 mL, 0.4 mmol), and then (3R,4s,5S)-3,5-dimethyl-4-phenylpiperidin-4-ol, from preparation 16 (45 mg, 0.2 mmol) all in single portions. The resulting mixture was stirred at room temperature under dry nitrogen for 18 hours, quenched by the addition of water (10 mL) then extracted with dichloromethane (2×10 mL). The combined organic layers were dried (magnesium sulfate), filtered, and concentrated in vacuo. The residue was purified by flash column chromatography on silica gel eluting with 10% methanol in dichloromethane to afford the title compound as a white foam (72 mg, 77%). LRMS (APCI) 471 (100%) [MH$^+$], 298 (40%), 220 (20%); HRMS $C_{28}H_{37}F_2O_2$ [MH$^+$] requires 471.2818 found 471.2815.

Example 2

(3R,4R,5S)-4-Cyclohexyl-1-{[(3S*,4R*)4-(2,4-difluorophenyl)-1-ethylpyrrolidin-3-yl]carbonyl}-3,5-dimethylpiperidin-4-ol

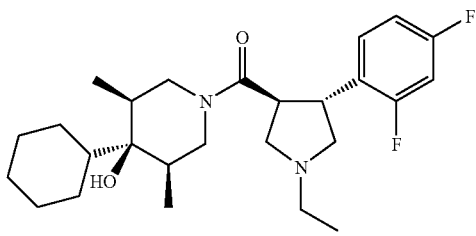

To a stirred suspension of (3S*,4R*)-4-(2,4-difluorophenyl)-1-ethylpyrrolidine-3-carboxylic acid hydrochloride salt, from preparation 17 (161 mg, 0.6 mmol) in N,N-dimethylformamide (10 mL) at room temperature under dry nitrogen was added triethylamine (0.2 mL, 1.4 mmol), then 1-hydroxybenzotriazole hydrate (77 mg, 0.6 mmol), 1-(3-dimethylaminopropyl)-3-ethylcarbodiimide hydrochloride (109 mg, 0.6 mmol), and (3R,4s,5S)-4-cyclohexyl-3,5-dimethylpiperidin-4-ol (from preparation 7) (100 mg, 0.5 mmol) all in single portions. The resulting mixture was stirred at 30° C. under dry nitrogen for 25 hours. The reaction was quenched by the addition of 2M sodium hydroxide solution (75 mL) then extracted with diethyl ether (80 mL). The organic layer was washed with brine (50 mL) separated, dried over magnesium sulfate, filtered, and concentrated in vacuo to afford the title compound as a clear oil (209 mg, 99%). LRMS (APCI) 449 (100%) [MH$^+$], 298 (40%), 220 (20%); HRMS $C_{26}H_{39}F_2O_2$ [MH$^+$] requires 449.2974 found 449.2970.

Example 3

(3R,4R,5S)-4-Butyl-1-{[(3S,4R)-1-tert-butyl-4-(2,4-difluorophenyl)pyrrolidin-3-yl]carbonyl}-3,5-dimethylpiperidin-4-ol

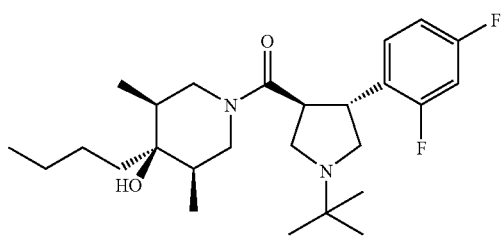

To a stirred suspension of (3S,4R)-1-tert-butyl-4-(2,4-difluorophenyl)pyrrolidine-3-carboxylic acid hydrochloride salt from preparation 1, (71 mg, 0.3 mmol) in N,N-dimethylformamide (10 mL) at room temperature under dry nitrogen was added O-benzotriazoyl-1-yl-N,N,N',N'-tetramethyluronium hexafluorophosphate (95 mg, 0.3 mmol), N-methylmorpholine (83 µL, 0.8 mmol), and then (3R,4s,5S)-4-butyl-3,5-dimethylpiperidin-4-ol (from preparation 9) (50 mg, 0.3 mmol) all in single portions. The resulting mixture was stirred at room temperature under dry nitrogen for 2.5 days then quenched by the addition of water (5 mL) and extracted with diethyl ether (10 mL). The organic layer was separated, dried (magnesium sulfate), filtered, and concentrated in vacuo. The residue was purified by HPLC using a Phenomenex Luna C18(2) column 150×15 mm (10 micron particle size, 100 Å porosity), using a 2 solvent eluent of acetonitrile:water:trifluoroacetic acid (5:95:0.1) [solvent A] and acetonitrile [solvent B].

A solvent gradient was run at a flow-rate of 20 ml/min as follows: Time 0 min—5% B; 0.6 min—5% B; 9.5 min—95% B; 10.5 min—95% B. This afforded the title compound, retention time 6.05 min, as an oil (18 mg, 13%). LRMS (APCI) 451 (100%) [MH$^+$]; HRMS $C_{26}H_{40}F_2O_2$ requires 451.3131 found 451.3114.

Example 4

(3R,4R,5S)-1-{[(3S,4R)-1-tert-Butyl-4-(24-difluorophenyl)pyrrolidin-3-yl]carbonyl}-3,5-dimethyl-4-(4-methylphenyl)piperidin-4-ol

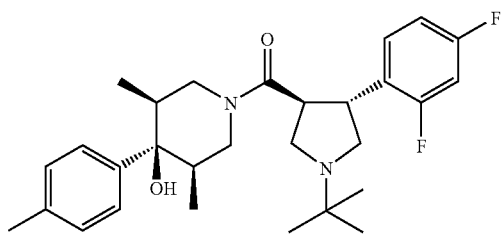

To a stirred suspension of (3S,4R)-1-tert-butyl-4-(2,4-difluorophenyl)pyrrolidine-3-carboxylic acid hydrochloride salt from preparation 1, (172 mg, 0.6 mmol) in N,N-dimethylformamide (10 mL) at room temperature under dry nitrogen was added O-benzotriazol-1-yl-N,N,N',N' tetramethyluronium hexafluorophosphate (231 mg, 0.6 mmol), N-methylmorpholine (201 µL, 1.8 mmol), and then (3R,4s,5S)-3,5-dimethyl-4-(4-methylphenyl)piperidin-4-ol (from preparation 10) (136 mg, 0.6 mmol) all in single portions. The resulting mixture was stirred at room temperature under dry nitrogen for 2.5 days, quenched by the addition of water (5 mL) then extracted with diethyl ether (10 mL). The organic layer was separated and then dried (magnesium sulfate), filtered, and concentrated in vacuo. The residue was purified by HPLC using a Phenomenex Luna C18(1) column 150×15 mm (10 micron particle size, 100 Å porosity), using a 2 solvent eluent acetonitrile:water:trifluoroacetic acid (5:95:0.1) [solvent A] and acetonitrile [solvent B]. A solvent gradient was run at a flow-rate of 20 ml/min as follows: Time 0 min—5% B; 0.6 min—5% B; 9.5 min—95% B; 10.5 min—95% B. This afforded the title compound, retention time 6.15 min, as an oil (24 mg, 9%). LRMS (APCI) 485 (100%) [MH⁺]; HRMS $C_{29}H_{39}F_2O_2$ requires 485.2974 found 485.2959.

Example 5

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride

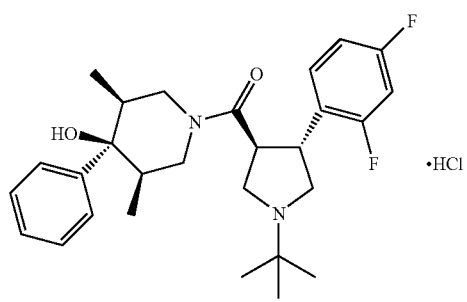

(3S,4R)-1-tert-Butyl-4-(2,4-difluorophenyl)pyrrolidine-3-carboxylic acid from Preparation 1 (26.0 g, 92 mmol) and (3R,4s,5S)-3,5-dimethyl-4-phenylpiperidin-4-ol from Preparation 16 (17.4 g, 85 mmol) were suspended in dichloromethane (1000 mL). Triethylamine (14.2 mL, 102 mmol) was added and the mixture was cooled to 0° C. with stirring under nitrogen. 1-Propylphosphonic acid cyclic anhydride (50% in ethyl acetate) (54.5 mL, 92 mmol) was added dropwise, maintaining the temperature below 5° C. The mixture was then allowed to warm to room temperature with continuous stirring. After stirring for 1 hour at room temperature, acetic acid (5 mL) was added to remove the last traces of the (3R,4s,5S)-3,5-dimethyl-4-phenylpiperidin-4-ol. The reaction mixture was stirred for a further hour at room temperature. A 10% potassium carbonate solution (500 mL) was added and the mixture was stirred vigorously at room temperature for 2 hours. The organic layer was separated and then stirred with 10% potassium carbonate solution (500 mL) for 1 hour. The dichloromethane layer was then separated, washed with water (3×300 mL), dried over sodium sulfate, and filtered. A solution of 4M hydrogen chloride in dioxane (50 mL) was then added to the dichloromethane solution. The solvent was then evaporated to give the crude hydrochloride as a white powder. Acetone (500 ml) was added to the crude hydrochloride and the mixture boiled for 30 minutes and then allowed to cool to room temperature. The hydrochloride salt was filtered off and washed with acetone (5×100 mL). Recrystallisation of the product from isopropyl alcohol gave analytically pure hydrochloride (39.5 g).

MS (APCI⁺) 471 (M+H)

¹H NMR (400 MHz, CD₃OD) δ (Rotamers), 0.35 (d, 2H), 0.50 (m, 3.60H), 0.95 (m, 0.6H), 1.22 (s, 9H), 1.65 (m, 0.75H), 1.97 (m, 0.48H), 2.70 (m, 1.02H), 2.87 (m, 0.54H), 3.2 (m, 0.66H), 3.70 (m, 0.8H), 3.20-3.40 (m, H), 3.57 (m, 0.66H), 3.65 (m, 0.24H), 3.80 (m, 1.5H), 4.30 (m, 1H), 7.05 (m, 0.5H), 7.20 (m, 1.5H), 7.25 (m, 3.5H), 7.45 (m, 0.5H), 7.60 (m, 1H).

[α]²⁵_D=–51.9 (c=0.3, MeOH).

Example 6

(3R,4R,5S)-1-{[(3S,4R)-4-(2,4-Difluorophenyl)-1-isopropylpyrrolidin-3-yl]carbonyl}-3,5-dimethyl-4-phenylpiperidin-4-ol hydrochloride

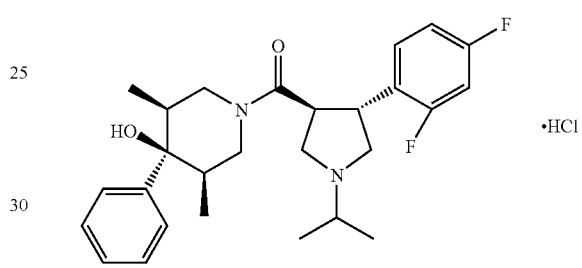

To a stirred solution of (3S,4R)-4-(2,4-difluorophenyl)-1-isopropylpyrrolidine-3-carboxylic acid, from preparation 33 (160 mg, 0.58 mmol) and (3R,4s,5S)-3,5-dimethyl-4-phenylpiperidin-4-ol, from preparation 16 (100 mg, 0.48 mmol) in ethyl acetate (2 mL) was added triethylamine (140 µL, 0.97 mmol) and 1-propylphosphonic acid cyclic anhydride (50% in ethyl acetate) (290 µL, 0.48 mmol) at 0° C. The reaction mixture was stirred for 30 minutes, then warmed to room temperature and the solvent was removed in vacuo. The residue was partitioned between dichloromethane (20 mL) and a saturated solution of potassium carbonate (2×20 mL). The phases were separated and the organic phase was washed with brine (10 mL), dried over magnesium sulfate, filtered and concentrated in vacuo. Purification of the residue by column chromatography using dichloromethane:methanol:0.88 ammonia (99:1:0.1-98:2:0.2-97:3:0.3) as eluent gave 170 mg of product as a colourless oil. The oil was dissolved in 1,4-dioxane (3 mL) and 4M hydrogen chloride in dioxane (6 mL) was slowly added. The solvent was then removed in vacuo. Recrystallisation from acetone afforded the desired product, 110.8 mg.

¹H NMR (400 MHz, CD₃OD) (Rotamers) □ 0.27-0.56 (m, 6H), 1.45 (m, 7H), 1.69-2.02 (m, 1H), 2.75 (m, 2H), 3.14 (m, 2H), 3.40 (m, 1H), 3.61 (m, 1H), 3.77 (m, 1H), 3.92 (m, 2H), 4.01-4.17 (m, 1H), 4.32 (dd, 1H), 7.05-7.24 (m, 4H), 7.34 (m, 3H), 7.62-7.72 (m, 1H).

LRMS (APCI) 457 [MH⁺].

[α]²⁵_D=–53.5 (c=0.26, MeOH).

Example 7

(3R,4s,5S)-1-{[(3R*,4R*)1-tert-Butyl-4-(24-difluorophenyl)pyrrolidin-3-yl]carbonyl}-3,5-dimethyl-4-phenylpiperidin-4-ol

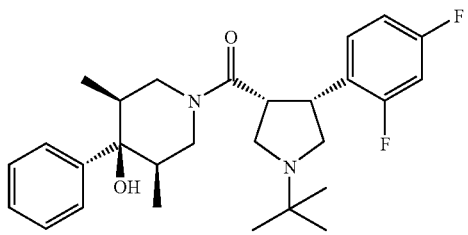

To a cooled solution of (R*,R*)-1-tert-butyl-4-(2,4-difluorophenyl)pyrrolidine-3-carboxylic acid, from preparation 36 (500 mg, 1.76 mmol) in dichloromethane (20 mL) was added a catalytic amount of N,N-dimethylformamide followed by oxalyl chloride (309 µL, 3.53 mmol). The reaction mixture was stirred for 2 hours and the solvent was then removed in vacuo. The residual white powder obtained was azeotroped with dichloromethane (2×10 mL). The white powder was redissolved in dichloromethane (10 mL) and added dropwise to a solution of (3R,4s,5S)-3,5-dimethyl-4-phenylpiperidin-4-ol [prepared as in preparation 16] (362 mg, 1.76 mmol) and triethylamine (246 µL, 1.76 mmol) in dichloromethane (10 mL) over 10 minutes at room temperature. The resulting mixture was stirred for 24 hours, diluted with dichloromethane (10 mL) and partitioned with saturated sodium hydrogen carbonate solution (2×30 mL). The phases were separated and the organic phase was washed with brine (30 mL), dried over magnesium sulfate, filtered and concentrated in vacuo to give the crude residue. Purification by column chromatography on silica gel using dichloromethane:methanol:0.88 ammonia (99:1:0.1-98:2:0.2) gave the desired product as a white foam, 497 mg.

¹H NMR (400 MHz, CD₃OD) (Rotamers) □ 0.43-0.55 (m, 6H), 0.75-0.79 (m, 1H), 1.25 (s, 9H), 1.87-1.97 (m, 1H), 2.16-2.66 (m, 2H), 3.09 (t, 2H), 3.18-3.30 (m, 2H), 3.41-3.61 (m, 2H), 3.80-4.17 (m, 3H), 6.91-7.09 (m, 3H), 7.28-7.35 (m, 3H), 7.47 (q, 1H).

LCMS (APCI)=471 [MH⁺].

Example 8

(3R,4R,5S)-1-{[(3S,4R)-1-tert-Butyl-4-(2,4-difluorophenyl)pyrrolidin-3-yl]carbonyl}-4-(3,4-difluorophenyl)-3,5-dimethylpiperidin-4-ol hydrochloride

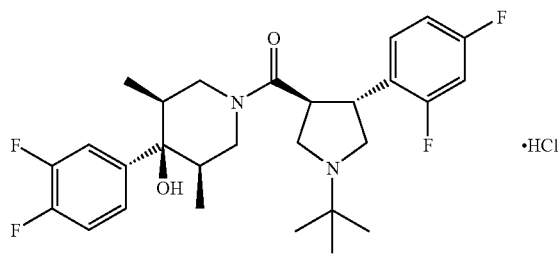

A solution of (3S,4R)-1-tert-butyl-4-(2,4-difluorophenyl)pyrrolidine-3-carboxylic acid from Preparation 1 (159 mg, 0.49 mmol), (3R,4s,5S)-4-(3,4-difluorophenyl)-3,5-dimethylpiperidin-4-ol (100 mg, 0.41 mmol) from Preparation 39, 1-propylphosphonic acid cyclic anhydride (50% in ethyl acetate) (244 µL, 0.41 mmol) and triethylamine (120 µL, 0.41 mmol) in dichloromethane (2.5 mL) was stirred for 3 days at room temperature. The reaction was then diluted with dichloromethane (20 mL) and partitioned with 10% potassium carbonate solution (20 mL). The phases were separated and the organic phase was washed with brine, dried over magnesium sulfate, filtered and concentrated in vacuo. Purification by column chromatography on silica gel using dichloromethane:methanol:0.88 ammonia (99:1:0.1-96:4:0.4) as eluent gave the free base as a colourless oil 117 mg. The oil was dissolved in dichloromethane (1 mL) and treated with 2M hydrogen chloride in diethylether (3 mL). The solvent was then removed in vacuo and the residue was azeotroped with diethyl ether to afford the title compound as a white solid, 108 mg.

¹H NMR (400 MHz, CD₃OD) (Rotamers) □ 0.30-0.56 (m, 6H), 1.48 (s, 9H), 1.62-1.94 (m, 1H), 2.64-2.75 (m, 1H), 3.12 (t, 2H), 3.40-3.54 (m, 2H), 3.70-3.96 (m, 2H), 4.00 (m, 1H), 4.2 (dd, 1H), 7.02-7.21 (m, 4H), 7.52 (m, 1H), 7.65 (m, 1H).

LRMS (APCI) 507 [MH⁺].

[α]²⁵_D=-34.89 (c=0.23, MeOH).

Example 9

(3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol hydrochloride

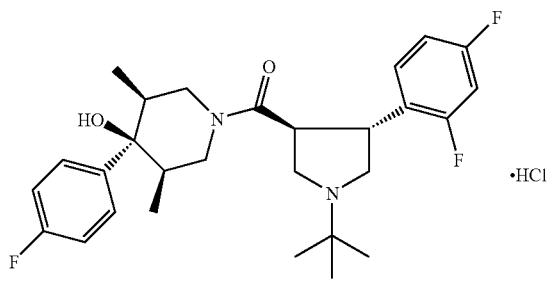

1-Propylphosphonic acid cyclic anhydride (50% wt solution in ethyl acetate) (0.67 mL, 2.0 mmol) was added dropwise to a mixture of (3R,4s,5S)-4-(4-fluorophenyl)-3,5-dimethylpiperidin-4-ol from Preparation 41 (267 mg, 1.2 mmol), (3S,4R)-1-tert-butyl-4-(2,4-difluorophenyl)pyrrolidine-3-carboxylic acid from Preparation 1 (450 mg, 1.4 mmol), and triethylamine (0.48 mL, 3.6 mmol) in dichloromethane (25 mL) at 0° C. under nitrogen. On completion of addition the resulting homogenous solution was stirred for 6 hours at room temperature. The solution was washed with 10% aqueous potassium carbonate solution (3×20 mL) then dried over sodium sulfate and filtered. The solvent was removed in vacuo and the crude product was purified by column chromatography (Reverse phase C-18, 40 g Redisep® cartridge) utilising an ISCO Companion® autopurification system. Mobile phase gradient over 20 minutes: MeCN/H₂O/TFA (5%/95%/0.1%) 95%:MeCN(100%) 5% eluting to; MeCN/H₂O/TFA(5%/95%/0.1%) 5%:MeCN(100%) 95%. The purified product was then dissolved in 1,4 dioxane (100 mL) and a 4M solution of hydrogen chloride in dioxane (20 mL) was added. The solution was then evaporated to dryness, redissolved in a solution of 4M hydrogen chloride in dioxane (100 mL) and evaporated to dryness once more. The residue was then dried in vacuo at 50° C. to give the product hydrochloride (391 mg) as a white amorphous solid.

$^1$H NMR (CD$_3$OD 400 MHz): (Rotamers), 0.31-0.57 (3×d, 6H), 0.83-2.08 (3×m, 2H), 1.55 (s, 9H), 1.60-2.07 (3×m, 2H), 2.68-3.20 (2×m, 2H), 3.20-4.12 (m, 5H), 4.29 (m, 1H), 6.95-7.19 (m, 5H), 7.38-7.85 (m, 2H)

LRMS (APCI)=489 [MH$^+$]

$[\alpha]^{25}_D$=−42.7 (c=0.31, MeOH)

Example 10

(3R,4R,5S)-1-{[(3S,4R)-4-(2,4-difluorophenyl)-1-isopropylpyrrolidin-3-yl]carbonyl}-4-(4-fluorophenyl)-3,5-dimethylpiperidin-4-ol hydrochloride

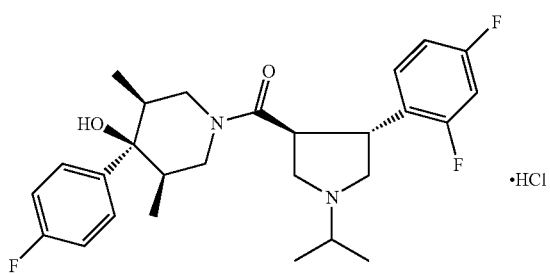

The title compound was prepared from the compounds of Preparations 33 and 41 by a similar method to that described for Example 9.

$^1$H NMR (400 MHz, CD$_3$OD) δ (Rotamers), 0.31-0.57 (m, 6H), 0.83-2.08 (m, 2H), 1.42 (m, 6H), 1.64-2.35 (m, 2H), 2.65 (m, 1H), 3.11-4.18 (m, 7H), 4.35 (m, 1H), 6.95-7.19 (m, 5H), 7.38-7.85 (m, 2H) LRMS (APCI) 475 [MH$^+$]

$[\alpha]^{25}_D$=−39.6 (c=0.3, MeOH)

Example 11

(3R,4R,5S)-1-{[(3S,4R)-4-(2,4-difluorophenyl)-1-methylpyrrolidin-3-yl]carbonyl}-4-(4-fluorophenyl)-3,5-dimethylpiperidin-4-ol hydrochloride

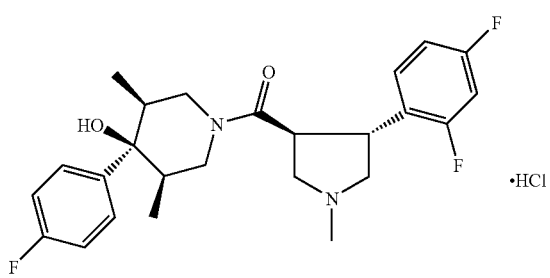

The title compound was prepared from the compounds of Preparations 62 and 41 by a similar method to that described for Example 9.

$^1$H NMR (400 MHz, CD$_3$OD) δ (Rotamers), 0.23-0.60 (m, 6H) 1.03-1.98 (m, 2H), 2.65 (m, 1H), 3.11-4.18 (m, 11H), 4.35 (m, 1H), 6.95-7.19 (m, 5H), 7.38-7.85 (m, 2H)

LRMS (APCI) 448 [MH$^+$]

$[\alpha]^{25}_D$=+49.7 (c=0.3, MeOH)

Example 12

(3R,4R,5S)-1-{[(3S,4R)-4-(2,4-difluorophenyl)pyrrolidin-3-yl]carbonyl}-4-(4-fluorophenyl)-3,5-dimethylpiperidin-4-ol hydrochloride

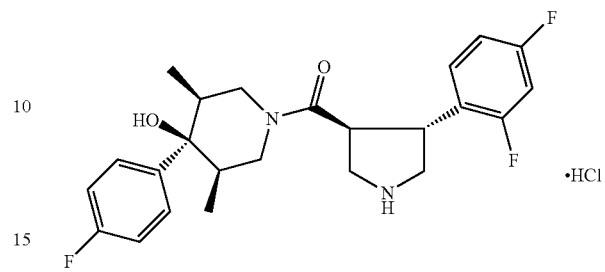

1-Propylphosphonic acid cyclic anhydride (50% wt solution in ethyl acetate) (0.67 mL, 2.0 mmol) was added dropwise to a mixture of (3R,4s,5S)-4-(4-fluorophenyl)-3,5-dimethylpiperidin-4-ol from Preparation 41 (265 mg, 1.2 mmol), (3S,4R)-1-(tert-butoxycarbonyl)-4-(2,4-difluorophenyl)pyrrolidine-3-carboxylic acid from Preparation 53 (0.75 mg, 1.4 mol) and triethylamine (0.48 mL, 3.6 mmol) in dichloromethane (25 mL) at 0° C. under nitrogen. On completion of addition the resulting homogenous solution was stirred for 6 hours at room temperature. The solution was washed with 10% aqueous potassium carbonate solution (3×20 mL), 3% aqueous citric acid (3×50 mL), then dried over sodium sulfate and filtered. The solvent was then removed in vacuo, and the residue was purified by column chromatography on silica eluting with ethyl acetate:pentane (1:9 to 4:6 gradient) to give the Boc-protected product as white solid (529 mg). A portion of this product (300 mg, 5.6 mmol) was dissolved in 1,4 dioxane (20 mL) and a solution of 4M hydrogen chloride in dioxane (80 mL) was then added. The solution was stirred for a further 8 hours and then the solvent was removed in vacuo. The residue was then dried in vacuo at 50° C. to give the title compound (311 mg) as a white solid.

$^1$H NMR (400 MHz, CD$_3$OD) δ (Rotamers), 0.36-0.66 (m, 6H) 0.81-1.97 (m, 2H), 2.70 (m, 1H), 3.19-4.05 (m, 8H), 4.31 (m, 1H), 6.85-7.31 (m, 6H), 7.28-7.80 (m, 2H)

LRMS (APCI) 433 [MH$^+$]

$[\alpha]^{25}_D$=−62.2 (c=0.3, MeOH)

Example 13

(3R,4R,5S)-1-{[(3S,4R)-1-tert-butyl-4-(2,4-difluorophenyl)pyrrolidin-3-yl]carbonyl}-4-(4-chlorophenyl)-3,5-dimethylpiperidin-4-ol hydrochloride

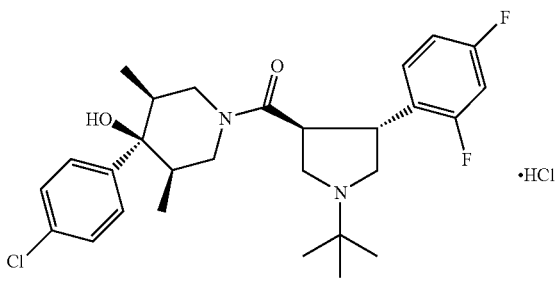

The title compound was prepared from the compounds of Preparations 1 and 43 by a similar method to that described for Example 9.

$^1$H NMR (400 MHz, CD$_3$OD) δ (Rotamers), 0.31-0.57 (m, 6H), 0.79-1.99 (m, 2H), 1.45 (s, 9H), 1.60-2.07 (m 2H), 2.68-3.20 (m, 2H), 3.20-4.12 (m, 5H), 4.29 (m, 1H), 7.05-7.29 (m, 5H), 7.40-7.75 (m, 2H)

LRMS (APCI) 505 [MH$^+$]

[α]$^{25}_D$=−37.6 (c=0.3, MeOH)

Example 14

(3R,4R,5S)-1-{[(3S,4R)-4-(2,4-difluorophenyl)-1-ethylpyrrolidin-3-yl]carbonyl}-4-(4-methoxyphenyl)-3,5-dimethylpiperidin-4-ol hydrochloride

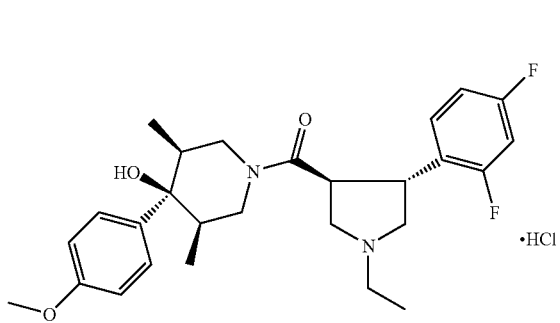

The title compound was prepared from the compounds of Preparations 48 and 75 by a similar method to that described for Example 9.

$^1$H NMR (400 MHz, CD$_3$OD) δ (Rotamers), 0.20-0.57 (m, 6H) 1.05 (t, 3H), 1.81 (q, 2H), 0.79-1.99 (m, 4H), 1.60-2.07 (m, 3H), 2.68-3.20 (m, 2H), 3.20-4.12 (m, 5H), 4.29 (m, 1H), 6.81-7.29 (m, 5H), 7.60-7.74 (m, 2H)

LRMS (APCI) 472 [MH$^+$]

[α]$^{25}_D$=−42.7 (c=0.3, MeOH)

Example 15

(3R,4R,5S)-1-{[(3S,4R)-1-tert-butyl-4-(2,4-difluorophenyl)pyrrolidin-3-yl]carbonyl}-4-(2,4-difluorophenyl)-3,5-dimethylpiperidin-4-ol hydrochloride

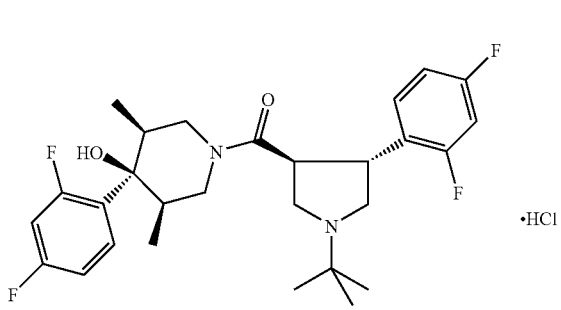

The title compound was prepared from the compounds of Preparation 1 and 49 by a similar method to that described for Example 9.

$^1$H NMR (400 MHz, CD$_3$OD) δ (Rotamers), 0.31-0.55 (m, 6H) 0.83-1.95 (m, 2H), 1.50 (s, 9H), 1.57-2.01 (m, 2H), 2.68-3.20 (m, 2H), 3.12-4.17 (m, 5H), 4.29 (m, 1H), 7.04-7.28 (m, 4H), 7.55-7.72 (m, 2H)

LRMS (APCI) 507 [MH$^+$]

[α]$^{25}_D$=−79.7 (c=0.3, MeOH)

Example 16

(3R,4R,5S)-4-(2,4-difluorophenyl)-1-{[(3S,4R)-4-(2,4-difluorophenyl)pyrrolidin-3-yl]carbonyl}-3,5-dimethylpiperidin-4-ol hydrochloride

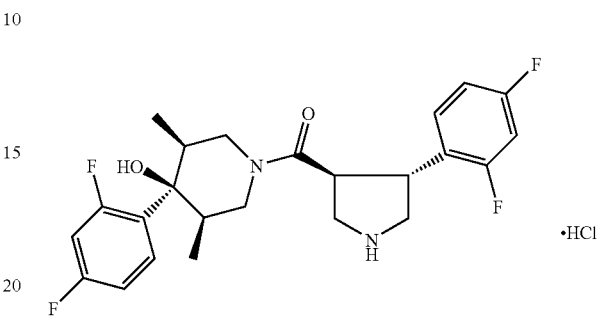

The title compound was prepare from the compounds of Preparations 49 and 53 by a similar method to that described for Example 12.

$^1$H NMR (400 MHz, CD$_3$OD) δ (Rotamers), 0.36-0.66 (m, 6H), 0.81-1.97 (m, 2H), 2.70 (m, 1H), 3.19-4.05 (m, 8H), 4.31 (m, 1H), 7.05-7.35 (m, 4H), 7.45-7.65 (m, 2H)

LRMS (APCI) 451 [MH$^+$]

[α]$^{25}_D$=−42.7 (c=0.3, MeOH)

Example 17

(3R,4R,5S)-1-[{(3S,4R)-1-tert-butyl-4-(2,4-difluorophenyl)pyrrolidin-3-yl]carbonyl}-4-(2,6-difluorophenyl)-3,5-dimethylpiperidin-4-ol hydrochloride

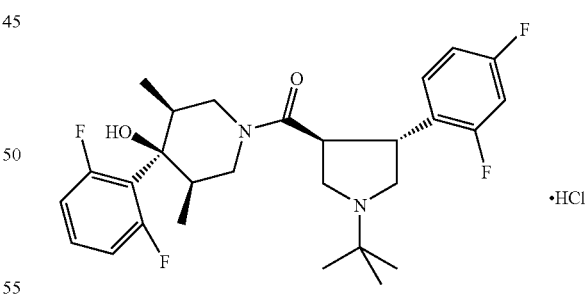

The title compound was prepared from the compounds of Preparations 1 and 44 by a similar method to that described for Example 9.

$^1$H NMR (400 MHz, CD$_3$OD) δ (Rotamers), 0.31-0.59 (m, 6H), 0.83-2.08 (m, 2H), 1.55 (s, 9H), 1.60-2.07 (m, 2H), 2.68-3.20 (m, 2H), 3.20-4.12 (m, 5H), 4.29 (m, 1H), 7.05-7.15 (m, 4H), 7.45-7.65 (m, 2H)

LRMS (APCI) 507 [MH$^+$]

[α]$^{25}_D$=−77.7 (c=0.3, MeOH)

Example 18

(3R,4R,5S)-4-(2,6-difluorophenyl)-1-{[(3S,4R)-4-(2,4-difluorophenyl)pyrrolidin-3-yl]carbonyl}-3,5-dimethylpiperidin-4-ol hydrochloride

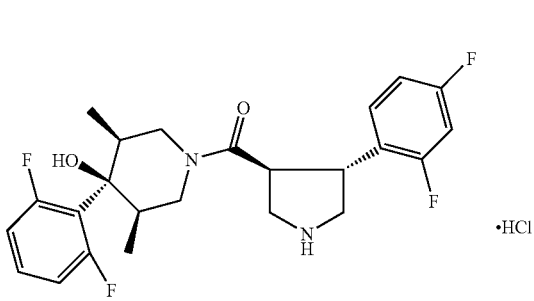

The title compound was prepared from the compounds of Preparations 44 and 53 by a similar method to that used for Example 12.

$^1$H NMR (400 MHz, CD$_3$OD) δ (Rotamers), 0.36-0.57 (m, 6H), 0.81-1.97 (m, 2H), 2.70 (m, 1H), δ 3.15-4.05 (m, 8H), 4.31 (m, 1H), 7.05-7.35 (m, 4H), 7.50-7.63 (m, 2H).

LRMS (APCI) 451 [MH$^+$]

$[α]^{25}_D$=−22.7 (c=0.3, MeOH)

Example 19

(3R,4R,5S)-1-{[(3S,4R)-1-tert-butyl-4-(2,4-difluorophenyl)pyrrolidin-3-yl]carbonyl}-4-(3-fluorophenyl)-3,5-dimethylpiperidin-4-ol hydrochloride

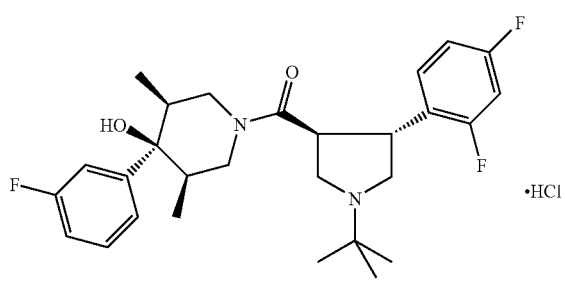

The title compound was prepared from the compounds of Preparations 1 and 46 by a similar method to that described for Example 9.

$^1$H NMR (400 MHz, CD$_3$OD) δ (Rotamers), 0.31-0.54 (m, 6H), 0.83-2.08 (m, 2H), 1.55 (s, 9H), 1.58-2.09 (m, 2H), 2.68-3.20 (m, 2H), 3.25-4.15 (m, 5H), 4.29 (m, 1H), 6.95-7.19 (m, 4H), 7.33 (m, 1H), 7.38-7.85 (m, 2H))

LRMS (APCI) 489 [MH$^+$]

$[α]^{25}_D$=−81.3 (c=03 E

Example 20

(3R,4R,5S)-1-{[(3S,4R)-4-(2,4-difluorophenyl)pyrrolidin-3-yl]carbonyl}-4-(3-fluorophenyl)-3,5-dimethylpiperidin-4-ol hydrochloride

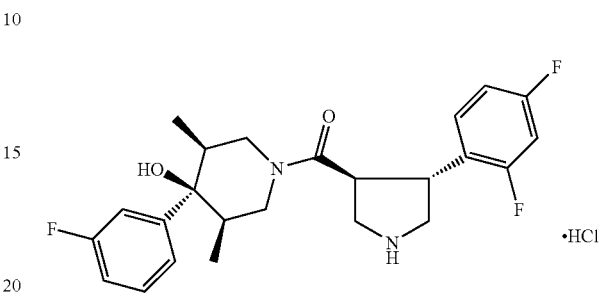

The title compound was prepared from the compounds of Preparations 46 and 53 by a similar method to that described for Example 12.

$^1$H NMR (CD$_3$OD, 400 MHz) (Rotamers), 0.36-0.60, (m, 6H) 0.81-2.01 (m, 2H), 2.70 (m, 1H), 3.19-4.05 (m, 8H), 4.31 (m, 1H), 6.95-7.15 (m, 4H), 7.32 (m, 1H), 7.28-7.80 (m, 2H)

LRMS (APCI) 433 [MH$^+$]

$[α]^{25}_D$=−72.7 (c=0.3, MeOH)

Example 21

(3R,4R,5S)-4-(4-chlorophenyl)-1-{[(3S,4R)-4-(2,4-difluorophenyl)-1-methylpyrrolidin-3-yl]carbonyl}-3,5-dimethylpiperidin-4-ol hydrochloride

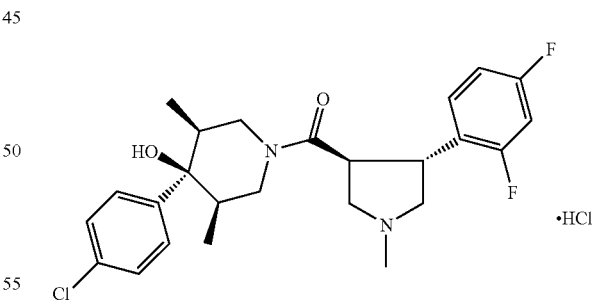

The title compound was prepared from the compounds of Preparations 43 and 62 by a similar method to that described for Example 9.

$^1$H NMR (CD$_3$OD, 400 MHz) (Rotamers), 0.20-0.62 (m, 6H) 1.03-1.98 (m, 2H), 2.67 (m, 1H), 3.09-4.16 (m, 10H), 4.31 (m, 1H), 6.95-7.19 (m, 5H), 7.38-7.85 (m, 2H)

LRMS (APCI) 463 [MH$^+$]

$[α]^{25}_D$=−39.3 (c=0.3, MeOH)

Example 22

(3R,4R,5S)-1-[(3S,4R)-1-tert-Butyl-4-(2,4-difluorophenyl)pyrrolidin-3-yl]carbonyl-3,5-dimethyl-4-pyridin-2-ylpiperidin-4-ol hydrochloride

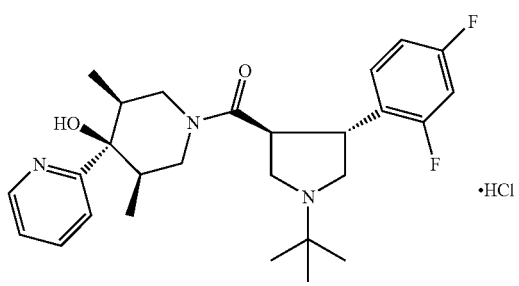

A solution of (3R,4s,5S)-3,5-dimethyl-4-pyridin-2-ylpiperidin-4-ol, from preparation 74 (260 mg, 1.26 mmol), (3R,4S)-1-tert-butyl-4-(2,4-difluorophenyl)pyrrolidine-3-carboxylic acid, from preparation 1 (267 mg, 0.94 mmol), 1-(3-dimethylaminopropyl)-3-ethylcarbodiimide hydrochloride (181 mg, 0.95 mmol) and 1-hydroxybenzotriazole hydrate (9 mg, 0.07 mmol) in tetrahydrofuran (5 mL) was stirred for 18 hours at room temperature. The solvent was removed in vacuo and the residue partitioned between water (5 mL) and ethyl acetate (5 mL). The phases were separated and the aqueous phase was extracted with ethyl acetate (2×5 mL). The combined organic extracts were dried over magnesium sulfate, filtered and concentrated in vacuo to give the crude residue. Purification by column chromatography on silica gel eluting with dichloromethane:methanol (100:0-99:1-97:3-94:6-92:8) and then dichloromethane:methanol:0.88 ammonia (95:5:0.5) afforded the desired product as colourless oil, 11 mg. This was converted to the hydrochloride salt by treatment with 4M hydrogen chloride in dioxane followed by evaporation of solvent.

$^1$H NMR (400 MHz, CD$_3$OD) (Rotamers) δ 0.32-0.64 (m, 6H), 0.69-2.42 (m, 5H), 2.60-3.22 (m, 5H), 3.47-4.17 (m, 10H), 4.46 (m, 1H), 7.00-7.26 (m, 2H), 7.97 (m, 1H), 7.53-8.66 (m, 3H), 8.71 (d, 1H)

LRMS (APCI) 472 [MH$^+$]

$[\alpha]_D^{25}$=−42.46 (c=0.35, MeOH)

Example 23

(3R,4R,5S)-1-{[(3S,4R)-4-(2,4-difluorophenyl)pyrrolidin-3-yl]carbonyl}-3,5-dimethyl-4-pyridin-2-ylpiperidin-4-ol hydrochloride

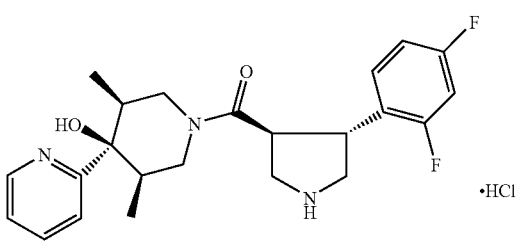

To a stirred solution of tert-butyl (3R,4R,5S)-3-(2,4-difluorophenyl)-4-{[(3R,4R,5S)-4-hydroxy-3,5-dimethyl-4-pyridin-2-ylpiperidin-1-yl]carbonyl}pyrrolidine-1-carboxylate, from preparation 54 (250 mg, 0.48 mmol) in dichloromethane (2 mL) was added 4M hydrochloric acid solution in dioxane (3.9 mL) at room temperature. The reaction mixture was stirred for 27 hours and the solvent was removed in vacuo to give a white solid which was triturated with diethyl ether to give the desired product in quantitative yield.

$^1$H NMR (400 MHz, CD$_3$OD) (Rotamers) δ 0.36-0.66 (m, 6H), 1.08-2.41 (m, 2H), 2.66-3.23 (m, 2H), 3.45-4.10 (m, 7H), 4.47 (m, 1H), 7.01-7.24 (m, 2H), 7.53-7.72 (2×q, 1H), 7.74-8.22 (m, 2H), 8.63 (m, 1H), 8.72 (d, 1H)

LRMS (APCI) 472 [MH$^+$]

$[\alpha]_D^{25}$=−44.00 (c=0.37, MeOH)

Example 24

(3R,4R,5S)-1-{[(3S,4R)-4-(2,4-Difluorophenyl)pyrrolidin-3-yl]carbonyl}-3,5-dimethyl-4-phenylpiperidin-4-ol hydrochloride

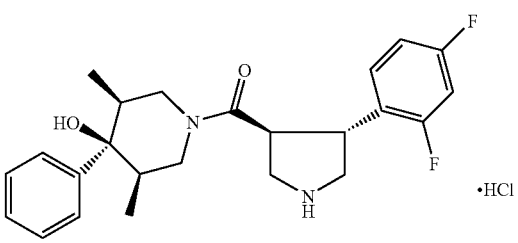

The title compound was prepared from the compound of Preparation 55 by a similar method to that described for Example 23.

$^1$H NMR (400 MHz, CD$_3$OD) (Rotamers) δ 0.27-0.56 (m, 6H), 0.77-2.06 (m, 2H), 2.68-3.19 (m, 2H), 3.40-4.08 (m, 7H), 4.30 (m, 1H), 6.98-7.39 (m, 7H), 7.46-7.64 (2×q, 1H)

LRMS (APCI) 415 [MH$^+$]

$[\alpha]_D^{25}$=−51.81 (c=0.47, MeOH)

Example 25

(3R,4R,5S)-1-{[(3S,4R)-1-Butyl-4-(2,4-difluorophenyl)pyrrolidin-3-yl]carbonyl}-3,5-dimethyl-4-phenylpiperidin-4-ol hydrochloride

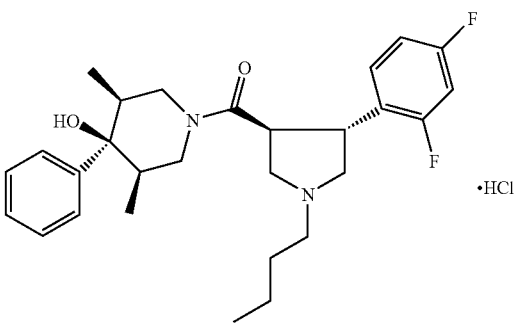

To a stirred solution of (3R,4R,5S)-1-{[(3S,4R)-4-(2,4-difluorophenyl)pyrrolidin-3-yl]carbonyl}-3,5-dimethyl-4-phenylpiperidin-4-ol hydrochloride, from Example 24 (135 mg, 0.3 mmol) in dichloromethane (2 mL) was added triethylamine (85 μL, 0.61 mmol) at room temperature. The reaction mixture was stirred for 10 minutes and butyraldehyde (54 μL, 0.61 mmol) was added and the solution was stirred for a further 20 minutes. Sodium triacetoxyborohydride (95 mg, 0.45 mmol) was then added and the reaction mixture was stirred for 24 hours at room temperature. The reaction mixture was diluted with dichloromethane (3×2 mL) and saturated sodium hydrogen carbonate solution (6 mL) was added. The phases were separated and the aqueous phase was extracted with dichloromethane (3×2 mL). The combined organic fractions were dried over magnesium sulfate and concentrated in vacuo to give the crude residue. Purification by column chromatography on silica gel using dichloromethane:methanol (100:0-97:3) as eluent afforded the pure product, 45 mg. This was converted to the hydrochloride salt by dissolution in dichloromethane, treatment with 2M hydrogen chloride in diethylether and then evaporation of solvent.

$^1$H NMR (400 MHz, CD$_3$OD) (Rotamers) δ 0.20-0.58 (m, 6H), 0.65-2.06 (m, 2H), 1.02 (t, 3H), 1.47 (m, 2H), 1.77 (m, 2H), 2.67-3.20 (m, 2H), 3.32-4.22 (m, 9H), 4.32 (m, 1H), 7.00-7.40 (m, 7H), 7.54-7.74 (m, 1H)

LRMS (APCI$^+$)=471 [MH$^+$]

$[\alpha]_D^{25}$=−60.39 (c=0.32, MeOH)

Example 26

(3R,4R,5S)-1-{[(3S,4R)-4-(2,4-Difluorophenyl)-1-isobutylpyrrolidin-3-yl]carbonyl}-3,5-dimethyl-4-phenylpiperidin-4-ol hydrochloride

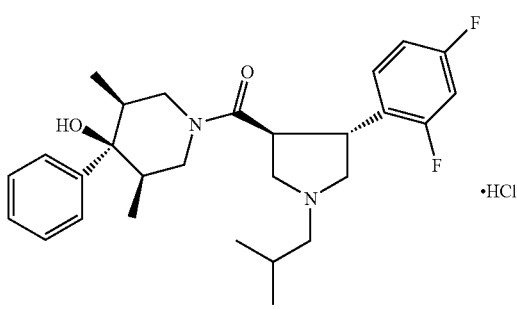

The title compound was prepared from the compound of Example 24 and isobutyraldehyde by a similar method to that described for Example 25.

$^1$H NMR (400 MHz, CD$_3$OD) (Rotamers) δ 0.19-0.79 (m, 6H), 1.10 (t, 6H), 0.93-2.07 (m, 2H), 2.16 (m, 1H), 2.68-4.22 (m, 11H), 4.32 (m, 1H), 6.60-7.43 (m, 7H), 7.56-7.76 (m, 1H)

LRMS (APCI) 471 [MH$^+$]

$[\alpha]_D^{25}$=−71.94 (c=0.31, MeOH)

Example 27

(3R,4R,5S)-1-{[(3S,4R)-4-(2,4-difluorophenyl)-1-propylpyrrolidin-3-yl]carbonyl}-3,5-dimethyl-4-phenylpiperidin-4-ol hydrochloride

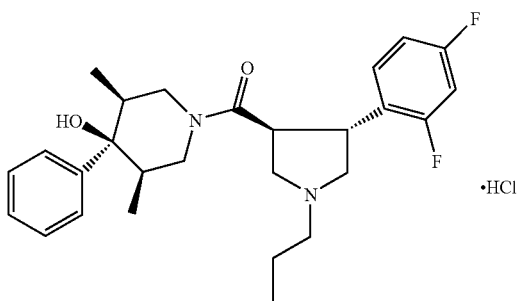

To a solution of (3R,4R,5S)-1-{[(3S,4R)-4-(2,4-difluorophenyl)pyrrolidin-3-yl]carbonyl}-3,5-dimethyl-4-phenylpiperidin-4-ol hydrochloride, from example 24 (250 mg, 0.55 mmol) in acetonitrile (3 mL) was added triethylamine (115 µL, 0.83 mmol), potassium carbonate (151 mg, 1.11 mmol) and 1-bromopropane (55 µL, 0.61 mmol) at room temperature. The reaction mixture was heated to 40° C. for 90 minutes. The mixture was cooled down and the solvent removed in vacuo. The residue was partitioned between water (40 mL) and ethyl acetate (40 mL). The phases were separated and the organic layer was dried over magnesium sulfate, filtered and concentrated in vacuo to give the crude residue. Purification by column chromatography on silica gel using dichloromethane:methanol (100:0-99:1-98:2-97:3-96:4) afforded the desired product as a colourless oil, 193 mg (70%). This was converted to the hydrochloride salt by treatment with 4M hydrochloride in dioxane followed by evaporation of solvent to give a white solid.

$^1$H NMR (400 MHz, CD$_3$OD) (Rotamers) δ 0.20-0.57 (m, 6H), 1.05 (t, 3H), 1.81 (q, 2H), 0.83-2.04 (m, 2H), 2.69-3.18 (2×m, 2H), 3.20-4.18 (m, 9H), 4.31 (m, 1H), 6.94-7.38 (m, 7H), 7.51-7.70 (m, 1H)

LRMS (APCI) 457 [MH$^+$]

$[\alpha]_D^{25}$=−62.57 (c=0.33, MeOH)

Example 28

(3R,4R,5S)-1-{[(3S,4R)-4-(2,4-Difluorophenyl)-1-methylpyrrolidin-3-yl]carbonyl}-3,5-dimethyl-4-pyridin-3-ylpiperidin-4-ol trifluoroacetate

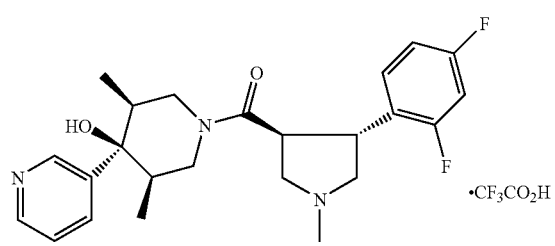

To a solution of (3R,4R)-4-(2,4-difluorophenyl)-1-methylpyrrolidine-3-carboxylic acid, from preparation 62 (323 mg, 1.16 mmol), (3R,4s,5S)-3,5-dimethyl-4-pyridin-3-ylpiperidin-4-ol, from preparation 51 (200 mg, 0.96 mmol) in ethyl acetate (5 mL) was added triethylamine (400 µL, 2.88 mmol) followed by 1-propylphosphonic acid cyclic anhydride (50% in ethyl acetate) (570 µL, 0.96 mmol) at room temperature. The reaction mixture was stirred for 24 hours, treated with saturated potassium carbonate solution (10 mL) and diluted with ethyl acetate (5 mL). The phases were separated and the organic layer was washed with saturated potassium carbonate solution (2×30 mL), brine (1×30 mL) and dried over magnesium sulfate. The solvent was removed in vacuo to give the crude residue. Purification by chromatography on reverse phase silica gel using acetonitrile:water:trifluoroacetic acid (5:95:0.1-100:0:0) as eluent gave a colourless oil, which was azeotroped with toluene, then triturated with diethyl ether and finally evaporated to dryness to give a white solid 44 mg.

$^1$H NMR (400 MHz, CD$_3$OD) (Rotamers) δ 0.23-0.60 (m, 6H), 1.03-2.13 (m, 2H), 3.06 (s, 3H), 2.67-3.18 (m, 2H), 3.30-4.15 (m, 7H), 4.38 (m, 1H), 7.10 (m, 2H), 7.48-7.67 (m, 1H), 7.89 (m, 1H), 8.05-8.81 (m, 3H)

LRMS (APCI) 430 [MH$^+$]

Example 29

(3R,4R,5S)-1-{[(3S,4R)-4-(2,4-difluorophenyl)-1-Pyrimidin-2-ylpyrrolidin-3-yl]carbonyl}-3.5-dimethyl-4-phenylpiperidin-4-ol hydrochloride

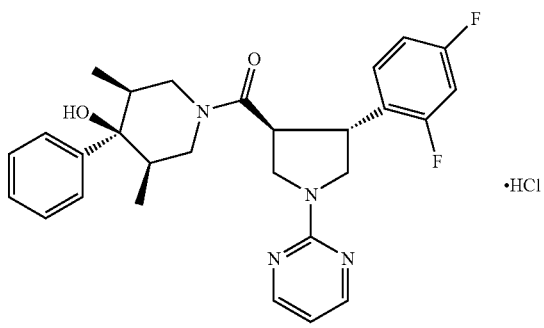

A solution of (3R,4R,5S)-1-{[(3S,4R)-4-(2,4-difluorophenyl)pyrrolidin-3-yl]carbonyl}-3,5-dimethyl-4-phenylpiperidin-4-ol hydrochloride, from example 24 (250 mg, 0.55 mmol), 2-bromopyrimidine (123 mg, 0.79 mmol) and triethylamine (230 µL, 1.65 mmol) in ethanol (5 mL) were heated under reflux for 24 hours. The solvent was removed in vacuo and the residue was partitioned between ethyl acetate (5 mL) and water (5 mL). The phases were separated and the organic phase was dried over magnesium sulfate, filtered and concentrated in vacuo to give the crude residue. Purification by column chromatography on silica gel using dichloromethane:methanol (100:0-99:1-98:2-97:3) gave the desired product as a white foam, 220 mg (74%). This was converted to the hydrochloride salt by treatment with 4M hydrogen chloride in dioxane followed by evaporation of solvent.

$^1$H NMR (400 MHz, CD$_3$OD) (Rotamers) δ 0.36-0.60 (m, 6H), 0.76-2.10 (m, 2H), 2.70-3.25 (m, 2H), 3.63-4.37 (m, 9H), 6.98-7.44 (m, 8H), 7.46-7.68 (m, 1H), 8.64 (d, 2H)

LRMS (ESI+)=493 [MH$^+$]

$[\alpha]_D^{25}$=−52.10 (c=0.44, MeOH)

Example 30

(3R,4R,5S)-1-{[(3S,4R)-1-Cyclobutyl-4-(2,4-difluorophenyl)pyrrolidin-3-yl]carbonyl}-3,5-dimethyl-4-phenylpiperidin-4-ol hydrochloride

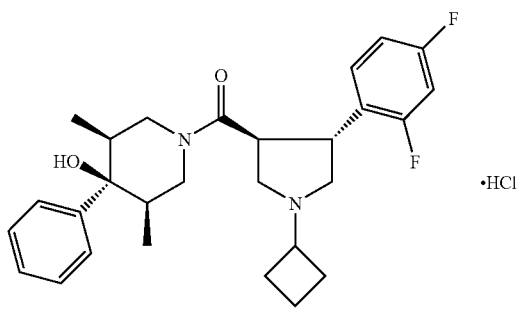

The title compound was prepared from the compound of Example 24 and cyclobutanone by a similar method to that described for Example 25, except that ethanol was used as the solvent.

$^1$H NMR (400 MHz, CD$_3$OD) (Rotamers) δ 0.15-0.51 (3×m, 6H), 0.58-2.01 (m, 4H), 2.15-3.13 (m, 6H), 3.25-4.17 (m, 8H), 4.25 (m, 1H), 6.93-7.35 (m, 7H), 7.47-7.66 (m, 1H)

LRMS (APCI) 469 [MH$^+$]

$[\alpha]_D^{25}$=−61.50 (c=0.45, MeOH)

Example 31

(3R,4R,5S)-1-{[(3S,4R)-4-(2,4-difluorophenyl)-1-pyridin-2-ylpyrrolidin-3-yl]carbonyl}-3,5-dimethyl-4-phenylpiperidin-4-ol hydrochloride

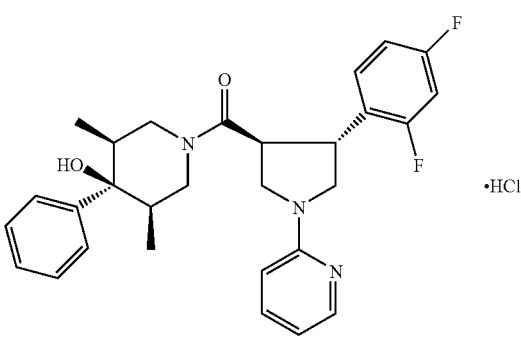

To a solution of (3R,4R,5S)-1-{[(3S,4R)-4-(2,4-difluorophenyl)pyrrolidin-3-yl]carbonyl}-3,5-dimethyl-4-phenylpiperidin-4-ol hydrochloride from Example 24 (200 mg, 0.44 mmol) in toluene (4 mL) was added sodium 2-methylpropan-2-olate (97 mg, 1.31 mmol) and the reaction was stirred for 10 minutes at room temperature. 2-Bromopyridine (63 µL, 0.66 mmol) was added followed by tris(dibenzylideneacetone)dipalladium(0) (40 mg, 0.04 mmol), (+/−) 1,1'-binaphthalene-2,2'-diylbis(diphenylphosphine) (55 mg, 0.09 mmol) and the reaction mixture was heated under reflux for 24 hours. The solvent was removed in vacuo and the residue partitioned between ethyl acetate (4 mL) and water (4 mL). The phases were separated and the organic phase was dried over magnesium sulfate, filtered and concentrated in vacuo to give the crude residue. Purification by column chromatography on silica gel using dichloromethane:methanol (100:0-96:4) as eluent afforded the desired product as foam, 160 mg (67%). This was converted to the hydrochloride salt by treatment with 4M hydrogen chloride in dioxane followed by evaporation of solvent.

$^1$H NMR (400 MHz, CD$_3$OD) (Rotamers) δ 0.38-0.62 (m, 6H), 0.87-2.14 (m, 2H), 2.70-3.24 (m, 2H), 3.51-4.20 (m, 7H), 4.33 (m, 1H), 6.58-6.68 (m, 2H), 6.93-7.62 (m, 9H), 8.02 (m, 1H)

LRMS (APCI) 492 [MH$^+$]

$[\alpha]_D^{25}$=−44.46 (c=0.37, MeOH)

Example 32

(3R,4R,5S)-1-{[(3S,4R)-4-(2,4-difluorophenyl)-1-(2-methoxyethyl)pyrrolidin-3-yl]carbonyl}-3,5-dimethyl-4-phenylpiperidin-4-ol hydrochloride

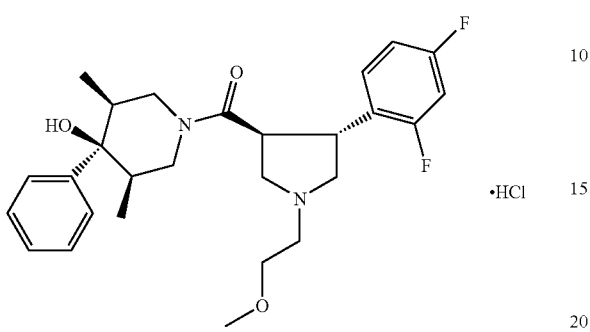

The title compound was prepared from the compound of Example 24 and 1-bromo-2-methoxyethane by a similar method to that used for Example 27.

$^1$H NMR (400 MHz, CD$_3$OD) (Rotamers) δ 0.20-0.58 (m, 6H), 0.77-2.05 (m, 2H), 2.68-3.19 (m, 2H), 3.43 (s, 3H), 3.30-4.20 (m, 11H), 4.31 (m, 1H), 6.98-7.38 (m, 7H), 7.50-7.71 (m, 1H)

LRMS (APCI) 473 [MH$^+$]

$[\alpha]_D^{25}$=−62.03 (c=0.32, MeOH)

Example 33

(3R,4R,5S)-1-{[(3S,4R)-4-(2,4-Difluorophenyl)-1-pyrazin-2-ylpyrrolidin-3-yl]carbonyl}-3,5-dimethyl-4-phenylpiperidin-4-ol hydrochloride

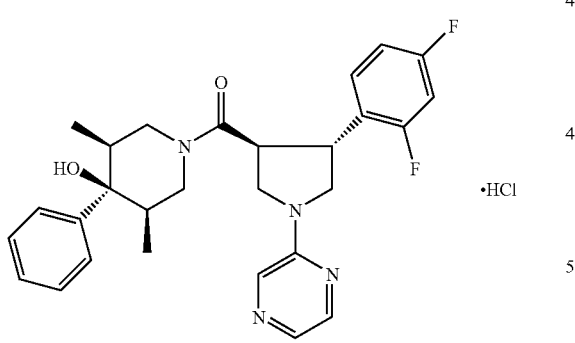

A solution of (3R,4R,5S)-1-{[(3S,4R)-4-(2,4-difluorophenyl)pyrrolidin-3-yl]carbonyl}-3,5-dimethyl-4-phenylpiperidin-4-ol hydrochloride from Example 24 (200 mg, 0.44 mmol), 2-chloropyrazine (75 mg, 0.84 mmol) and triethylamine (122 μL, 0.88 mmol) in N,N-dimethylformamide (4 mL) was heated at 100° C. for 24 hours. The solvent was removed in vacuo and the crude residue was partitioned between water (4 mL) and ethyl acetate (4 mL). The phases were separated and the organic phase was dried over magnesium sulfate, filtered and concentrated in vacuo to give the crude residue. Purification by column chromatography on silica gel using ethyl acetate:pentane (10:90-100:0) as eluent afforded the desired product as a foam, 121 mg (55%). This was converted to the hydrochloride salt by treatment with 4M hydrogen chloride in dioxane followed by evaporation of solvent.

$^1$H NMR (400 MHz, CD$_3$OD) (Rotamers) δ 0.37-0.60 (m, 6H), 0.82-2.10 (m, 2H), 2.70-3.26 (m, 2H), 3.64-4.21 (m, 7H), 4.34 (m, 1H), 6.94-7.43 (m, 7H), 7.43-7.64 (m, 1H), 7.90 (d, 1H), 8.26 (m, 2H)

LRMS (APCI) 493 [MH$^+$]

$[\alpha]_D^{25}$=−46.98 (c=0.31, MeOH)

Example 34

(3R,4R,5S)-1-{[(3S,4R)-4-(2,4-Difluorophenyl)-1-pyridin-3-ylpyrrolidin-3-yl]carbonyl}-3,5-dimethyl-4-phenylpiperidin-4-ol hydrochloride

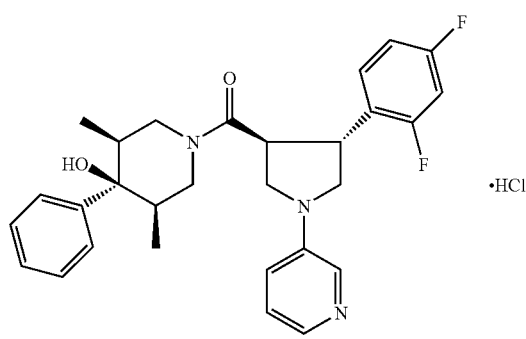

The title compound was prepared from the compound of Example 24 and 3-bromopyridine by a similar method to that described for Example 31.

$^1$H NMR (400 MHz, CD$_3$OD) (Rotamers) δ 0.36-0.57 (m, 6H), 0.83-2.08 (m, 2H), 2.69-3.24 (m, 2H), 3.56-4.23 (m, 7H), 4.33 (m, 1H), 6.94-7.62 (m, 8H), 7.70-7.83 (m, 2H), 7.98-8.10 (m, 2H)

LRMS (APCI) 492 [MH$^+$]

$[\alpha]_D^{25}$=−33.26 (c=0.36, MeOH).

Example 35

(3R,4R,5S)-1-{[(3S,4R)-4-(2,4-difluorophenyl)-1-pyridazin-3-ylpyrrolidin-3-yl]carbonyl}-3,5-dimethyl-4-phenylpiperidin-4-ol hydrochloride

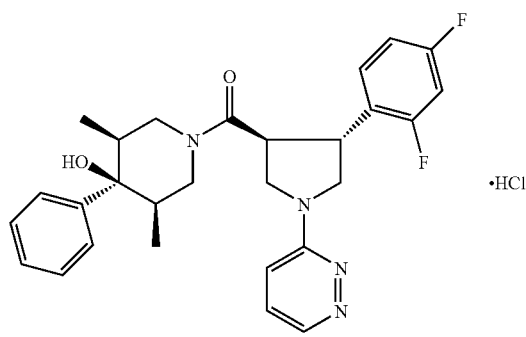

The title compound was prepared from the compound of Example 24 and 3-chloropyridazine (*J. Med. Chem.* 30 (2), 239, 1987) by a similar method to that described for Example 31.

¹H NMR (400 MHz, CD₃OD) (Rotamers) δ 0.35-0.58 (m, 6H), 0.73-2.08 (m, 2H), 2.68-3.24 (m, 2H), 3.60-4.27 (m, 7H), 4.30 (m, 1H), 6.97-8.11 (m, 10H), 8.50-9.30 (2×d, 1H)
LRMS (APCI) 493 [MH⁺]
$[\alpha]_D^{25}$=−36.61 (c=0.31, MeOH)

Example 36

(3R,4R,5S)-1-{[(3S,4R)-4-(2,4-Difluorophenyl)-1-pyrimidin-5-ylpyrrolidin-3-yl]carbonyl}-3,5-dimethyl-4-phenylpiperidin-4-ol hydrochloride

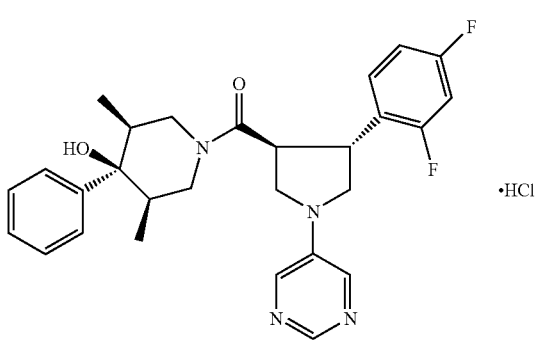

The title compound was prepared from the compound of Example 24 and 5-bromopyrimidine by a similar method to that described for Example 31.

¹H NMR (400 MHz, CD₃OD) (Rotamers) δ 0.37-0.60 (m, 6H), 0.85-2.12 (m, 2H), 2.70-3.26 (m, 2H), 3.60-4.22 (m, 7H), 4.35 (m, 1H), 6.93-7.43 (m, 7H), 7.43-7.64 (m, 1H), 8.52 (m, 2H), 8.71-9.26 (m, 1H)
LRMS (APCI) 493 [MH⁺]
$[\alpha]_D^{25}$=−37.45 (c=0.25, MeOH)

Example 37

(3R,4R,5S)-1-{[(3S,4R)-1-tert-Butyl-4-(2,4-difluorophenyl)pyrrolidin-3-yl]carbonyl}-4-isopropyl-3,5-dimethylpiperidin-4-ol hydrochloride

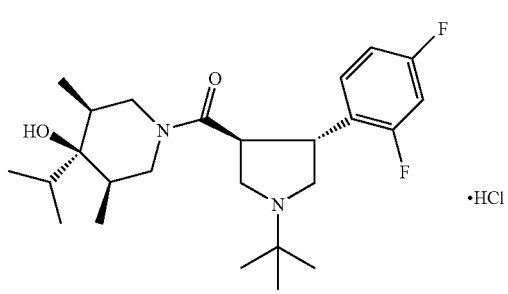

The title compound was prepared from the compounds of Preparations 1 and 57 by a similar method to that described for Example 8.

¹H NMR (400 MHz, CD₃OD) (Rotamers) δ 0.37-0.97 (m, 12H), 1.46 (s, 9H), 1.33-2.07 (m, 3H), 2.55-3.05 (m, 2H), 3.07-4.06 (m, 8H), 7.05 (m, 2H), 7.60 (m, 1H)
LRMS (APCI) 437 [MH⁺]
$[\alpha]_D^{25}$=−26.07 (c=0.60, MeOH)

Example 38

(3R,4R,5S)-1-{[(3S,4R)-1—(Cyclopropylmethyl)-4-(2,4-difluorophenyl)pyrrolidin-3-yl]carbonyl}-3,5-dimethyl-4-phenylpiperidin-4-ol hydrochloride

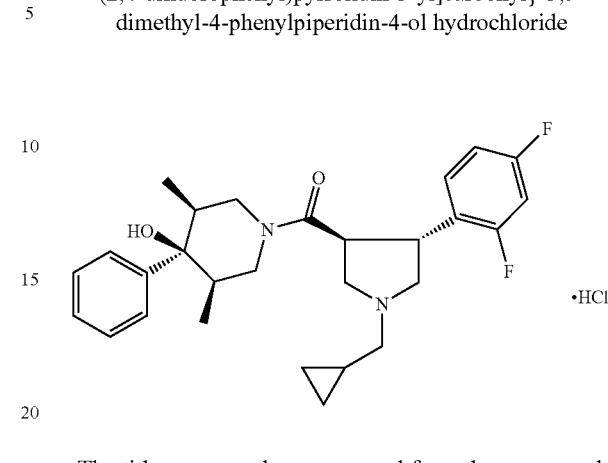

The title compound was prepared from the compound of Example 24 and (bromomethyl)cyclopropane by a similar method to that described for Example 27.

¹H NMR (400 MHz, CD₃OD) (Rotamers) δ 0.20-0.80 (m, 10H), 1.19 (m, 1H), 0.83-2.02 (m, 2H), 2.68-3.18 (m, 2H), 3.19-4.18 (m, 9H), 4.31 (m, 1H), 7.00-7.38 (m, 7H), 7.52-7.71 (m, 1H)
LRMS (APCI⁺)=469 [MH⁺]
$[\alpha]_D^{25}$=−66.40 (c=0.28, MeOH)

Example 39

(3R,4R,5S)-1-{[(3S,4R)-4-(2,4-Difluorophenyl)-1-(tetrahydro-2H-pyran-4-yl)pyrrolidin-3-yl]carbonyl}-3,5-dimethyl-4-phenylpiperidin-4-ol hydrochloride

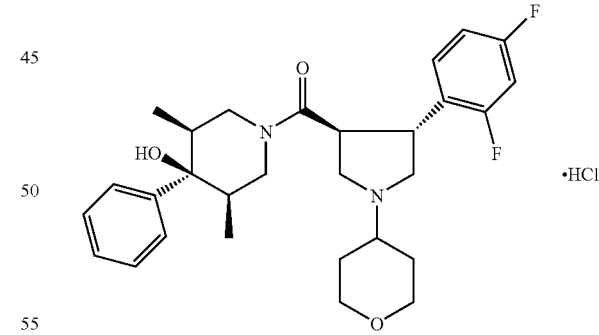

The title compound was prepared from the compound of Example 24 and tetrahydro-4H-pyran-4-one by a similar method to that described for Example 25, except that ethanol was used as the solvent.

¹H NMR (400 MHz, CD₃OD) (Rotamers) δ 0.18-0.55 (m, 6H), 0.78-2.20 (m, 6H), 2.67-3.18 (m, 2H), 3.30-4.18 (m, 12H), 4.30 (m, 1H), 7.00-7.35 (m, 7H), 7.53-7.71 (m, 1H)
LRMS (APCI) 499 [MH⁺]
$[\alpha]_D^{25}$=−51.40 (c=0.37, MeOH)

Example 40

(3R,4R,5S)-1-{[(3S,4R)-1-tert-Butyl-4-(24-difluorophenyl)pyrrolidin-3-yl]carbonyl}-3,5-dimethyl-4-propylpiperidin-4-ol hydrochloride

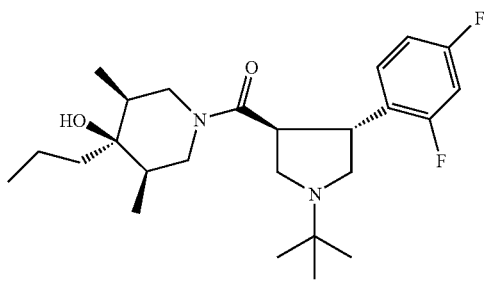

The title compound was prepared from the compounds of Preparations 1 and 59 by a similar method to that described for Example 8.

$^1$H NMR (400 MHz, CD$_3$OD) (Rotamers) δ 1.45 (s, 9H), 0.19-1.66 (m, 15H), 2.49-304 (m, 2H), δ 3.17-4.05 (m, 7H), 4.11 (m, 1H), 7.05 (m, 2H), 7.59 (m, 1H).

LRMS (APCI) 437 [MH$^+$]

$[α]_D^{25}$=−28.03 (c=0.38, MeOH)

Example 41

(3R,4R,5S)-1-{[(3S,4R)-1-Cyclopropyl-4-(2,4-difluorophenyl)pyrrolidin-3-yl]carbonyl}-3,5-dimethyl-4-phenylpiperidin-4-ol hydrochloride

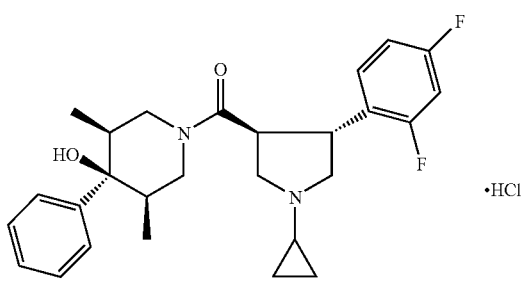

A 1M sodium hydroxide solution (15 mL) was added to (3R,4R,5S)-1-{[(3S,4R)-4-(2,4-difluorophenyl)pyrrolidin-3-yl]carbonyl}-3,5-dimethyl-4-phenylpiperidin-4-ol hydrochloride, from Example 24 (200 mg, 0.48 mmol). The suspension was stirred and extracted with ethyl acetate (2×30 mL). The combined organic layers were dried over magnesium sulfate, filtered and concentrated in vacuo. The residual oil was dissolved in methanol (5 mL) and acetic acid (275 μL, 4.8 mmol), [(1-ethoxycyclopropyl)oxy](trimethyl)silane (580 μL, 2.88 mmol) and sodium triacetoxyborohydride (90 mg, 0.96 mmol) were added at room temperature. The reaction mixture was heated under reflux for 2 hours, cooled to room temperature and methanol (5 mL) was added. The mixture was filtered and the filtrate was concentrated in vacuo. The solid recovered was partitioned between 1M sodium hydroxide solution (10 mL) and ethyl acetate (10 mL). The phases were separated and the aqueous phase was extracted with ethyl acetate (2×5 mL). The combined organic extracts were dried over magnesium sulfate, filtered and concentrated in vacuo to give the crude residue. Purification by column chromatography on silica gel using dichloromethane:methanol (100:0-97:3) as eluent afforded the desired product as a colourless oil 131 mg. This was converted to the hydrochloride salt by treatment with 4M hydrogen chloride in dioxane followed by evaporation of solvent to give a white solid.

$^1$H NMR (400 MHz, CD$_3$OD) (Rotamers) δ 0.20-0.55 (m, 6H), 1.03 (m, 4H), 0.76-2.05 (m, 2H), 2.67-3.18 (m, 2H), 3.29-4.24 (m, 8H), 4.30 (m, 1H), 6.99-7.37 (m, 7H), 7.54-7.71 (m, 1H)

LRMS (ESI+)=455 [MH$^+$]

$[α]_D^{25}$=−64.04 (c=0.26, MeOH)

Example 42

(3R,4R,5S)-1-{[(3S,4R)-4-(2,4-difluorophenyl)-1-pyrimidin-4-ylpyrrolidin-3-yl]carbonyl}-3,5-dimethyl-4-phenylpiperidin-4-ol hydrochloride

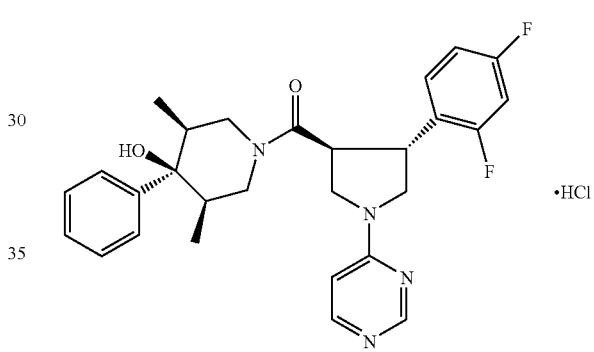

A solution of (3R,4R,5S)-1-{[(3S,4R)-4-(2,4-difluorophenyl)pyrrolidin-3-yl]carbonyl}-3,5-dimethyl-4-phenylpiperidin-4-ol hydrochloride, from Example 24 (200 mg, 0.44 mmol), 4-chloropyrimidine (Biorg. Chem. 30 (3), 188, 2002) (140 mg, 0.88 mmol) and triethylamine (250 μL, 1.80 mmol) in N,N-dimethylformamide (3 mL) was heated at 80° C. for 3 hours. The reaction mixture was cooled to room temperature and the solvent removed in vacuo. The crude residue was partitioned between ethyl acetate (5 mL) and water (5 mL). The phases were separated and the organic phase was washed with 1M sodium hydroxide solution (2×20 mL) and brine (1×20 mL), dried over magnesium sulfate, filtered and concentrated in vacuo to give the desired compound as a yellow foam, 192 mg (81%). This was converted to the hydrochloride salt by treatment with 4M hydrogen chloride in dioxane followed by evaporation of solvent to give a yellow oil. The oil was triturated with diethyl ether to produce solidified product which was then isolated by filtration.

$^1$H NMR (400 MHz, CD$_3$OD) (Rotamers) δ 0.32-0.58 (m, 6H), 0.75-2.08 (m, 2H), 2.67-3.23 (m, 2H), 3.60-4.47 (m, 9H), 6.84-7.40 (m, 8H), 8.19 (t, 1H), 8.71 (m, 1H)

LRMS (ESI+)=493 [MH$^+$]

$[α]_D^{25}$=−54.71 (c=0.35, MeOH)

Example 43

(3R,4R,5S)-1-{[(3S,4R)-1-tert-Butyl-4-(2,4-difluorophenyl)pyrrolidin-3-yl]carbonyl}-4-cyclopropyl-3,5-dimethylpiperidin-4-ol hydrochloride

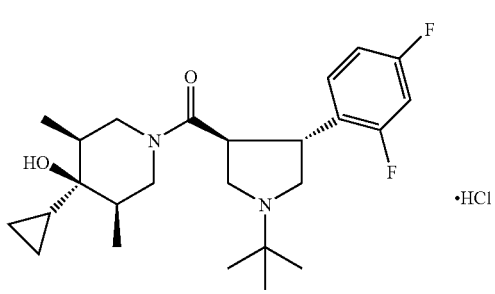

The title compound was prepared from the compounds of Preparations 1 and 61 by a similar method to that described for Example 8.

¹H NMR (400 MHz, CD₃OD) (Rotamers) δ 0.19-0.53 (m, 4H), 0.65-0.99 (m, 6H), 1.27-1.74 (m, 2H), 1.47 (s, 9H), 2.50-3.01 (m, 2H), 3.15-4.04 (m, 8H), 4.12 (m, 1H), 7.08 (m, 2H), 7.49-7.64 (m, 1H)

LRMS (ESI+)=435 [MH⁺]

$[\alpha]_D^{25}$=−21.74 (c=0.33, MeOH)

Example 44

(3R,4R,5S)-1-{[(3S,4R)-4-(2,4-difluorophenyl)-1-pyrimidin-4-ylpyrrolidin-3-yl]carbonyl}-3,5-dimethyl-4-pyridin-2-ylpiperidin-4-ol hydrochloride

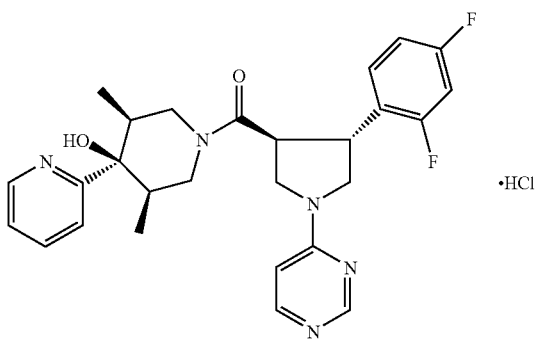

The title compound was prepared from the compounds of Example 23 and 4-chloropyrimidine (*Biorg. Chem.* 30 (3), 188, 2002) by a similar method to that described for Example 42.

¹H NMR (400 MHz, CD₃OD) Rotamers δ0.45-0.65 (m, 6H), 1.07-2.50 (m, 2H), 2.66-3.28 (m, 2H), 3.79-4.52 (m, 8H), 6.90-8.26 (m, 7H), 7.96 (m, 1H), 8.56 (m, 1H), 8.73 (m, 2H)

LRMS (APCI+)=494 [MH⁺]

$[\alpha]_D^{25}$=−30.35 (c=0.30, MeOH)

Example 45

(3R,4R,5S)-4-(3,4-Difluorophenyl)-1-{[(3S,4R)-4-(2,4-difluorophenyl)pyrrolidin-3-yl]carbonyl}-3,5-dimethylpiperidin-4-ol hydrochloride

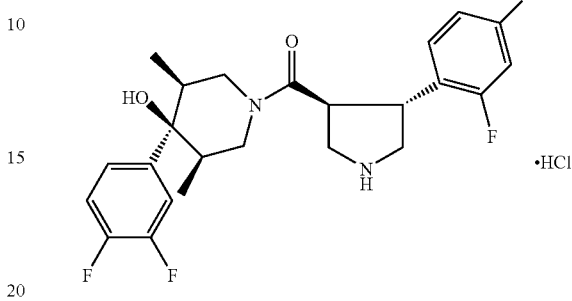

To a solution of tert-butyl (3R,4S)₃-(2,4-difluorophenyl)-4-{[(3R,4R,5S)-4-(3,4-difluorophenyl)-4-hydroxy-3,5-dimethylpiperidin-1-yl]carbonyl}pyrrolidine-1-carboxylate, from Preparation 63 (176 mg, 0.32 mmol) in dichloromethane (2 mL) was added a solution of 4M hydrogen chloride in dioxane (2 mL) at room temperature. The reaction mixture was stirred overnight at room temperature. The solvent was then evaporated and the residual solid was triturated with diethyl ether (10 mL), filtered and dried in a vacuum oven to give the title compound as a white solid, 116 mg.

¹H NMR (400 MHz, CD₃OD) (Rotamers) □ 0.31-0.76 (m, 7H), 1.81-2.00 (m, 1H), 2.65-2.81 (m, 1.5H), 3.14 (t, 0.5H), 3.48 (m, 2H), 3.66-3.81 (m, 3H), 3.89 (m, 1H), 4.03 (m, 1H), 4.34 (d, 1H), 7.04-7.27 (m, 4H), 7.46-7.60 (m, 2H).

LRMS (APCI) 451 [MH⁺]

$[\alpha]^{25}_D$=−65 (c=0.17, MeOH).

Example 46

(3R,4R,5S)-1-{[(3S,4R)-4-(2,4-difluorophenyl)pyrrolidin-3-yl]carbonyl}-3,5-dimethyl-4-[4-(trifluoromethyl)phenyl]piperidin-4-ol hydrochloride

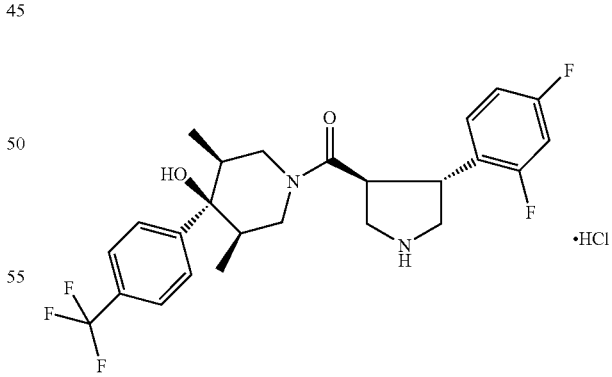

The title compound was prepared from the compound of Preparation 66 by a similar method to that described for Example 45.

¹H-NMR (400 MHz, CD₃OD): (rotamers) □□0.31-0.56 (4×d, 7H), 0.83-2.06 (4×bm, 2H), 2.69-2.90 (m, 1.5H), 3.16 (t, 0.5H), 3.50 (m, 2H), 3.56-3.82 (m, 3H), 3.91 (m, 1H), 4.05 (m, 1H), 4.34 (d, 1H), 7.02-7.23 (m, 3H), 7.51-7.69 (m, 3H).

LRMS (APCI)=483 [MH+]

[α]$^{25}_D$=−55.67 (c=0.26, MeOH).

Example 47

(3R,4R,5S)-1-{[(3S,4R)-4-(2,4-Difluorophenyl)-1-pyridazin-3-ylpyrrolidin-3-yl]carbonyl}-3,5-dimethyl-4-pyridin-2-ylpiperidin-4-ol hydrochloride

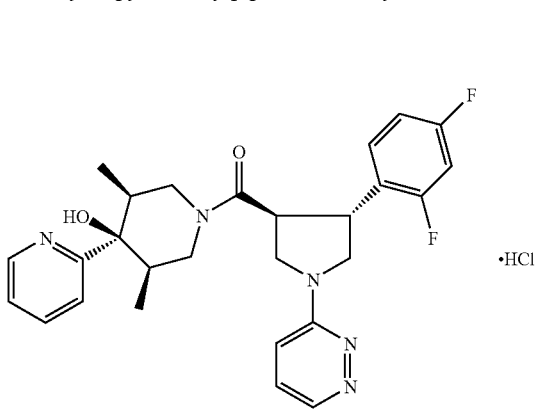

The title compound was prepared from the compound of Example 23 and 3-chloropyridazine (*J. Med. Chem.* 30 (2), 239, 1987) by a similar method to that described for Example 31.

$^1$H NMR (400 MHz, CD$_3$OD) (Rotamers) δ 0.46-0.66 (m, 6H), 1.02-2.49 (m, 2H), 2.65-3.28 (3×m, 2H), 3.78-4.27 (m, 7H), 4.48 (m, 1H), 6.98-7.22 (m, 2H), 7.49-8.29 (m, 5H), 8.55 (d, 1H), 8.65 (t, 1H), 8.73 (d, 1H)

LRMS (APCI) 494 [MH+]

[α]$_D^{25}$=−21.45 (c=0.27, MeOH)

Example 48

(3R,4R,5S)-1-{[(3S,4R)-4-(4-Chlorophenyl)pyrrolidin-3-yl]carbonyl}-3,5-dimethyl-4-phenylpiperidin-4-ol hydrochloride

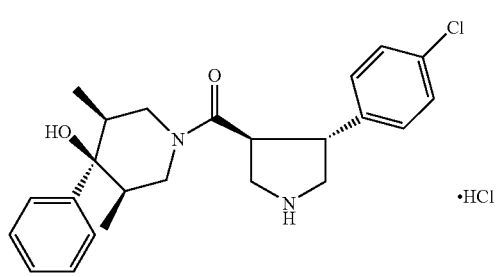

The title compound was prepared from the compound of Preparation 69 by a similar procedure to that described for Example 45.

$^1$H NMR (400 MHz, CD$_3$OD) (Rotamers) δ 0.14-0.46 (m, 6H), 0.42-1.93 (m, 2H), 2.57-3.03 (m, 2H), 3.25-3.72 (m, 6H), 3.76-3.91 (m, 1H), 4.20 (m, 1H), 7.07-7.42 (m, 9H).

LRMS (APCI) 413 [MH+]

[α]$_D^{25}$=−122.15 (c=0.36, MeOH)

Example 49

4-((3R,4R,5S)-1-{[(3S,4R)-1-tert-butyl-4-(2,4-difluorophenyl)pyrrolidin-3-yl]carbonyl}-4-hydroxy-3,5-dimethylpiperidin-4-yl)benzonitrile

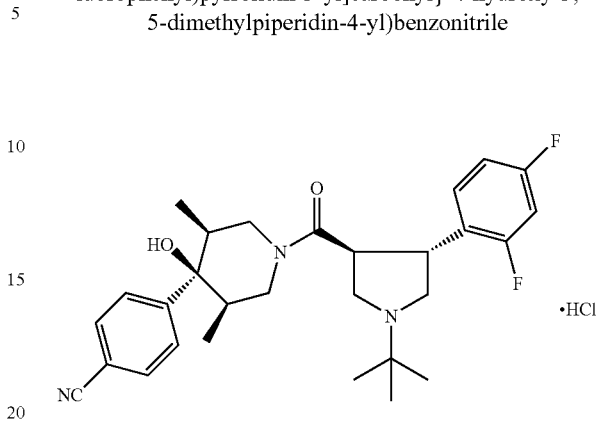

The title compound was prepared from the compounds of Preparations 1 and 72 by a method similar to that described for Example 9.

$^1$H NMR (400 MHz, CD$_3$OD) δ (Rotamers), 0.31-0.59 (m, 6H), 0.83-2.08 (m, 2H), 1.55 (s, 9H), 1.60-2.07 (m, 2H), 2.68-3.20 (m, 2H), 3.20-4.12 (m, 5H), 4.29 (m, 1H), 7.05-7.15 (m, 3H), 7.62-7.73 (m, 2H), 8.10-8.20 (m, 2H)

LRMS (APCI)=496 [MH+]

[α]$^{25}_D$=−97.7 (c=0.30, MeOH)

Example 50

(3R,4R,5S)-4-(4-chlorophenyl)-1-{[(3S,4R)-4-(2,4-difluorophenyl)-1-isopropylpyrrolidin-3-yl]carbonyl}-3,5-dimethylpiperidin-4-ol hydrochloride

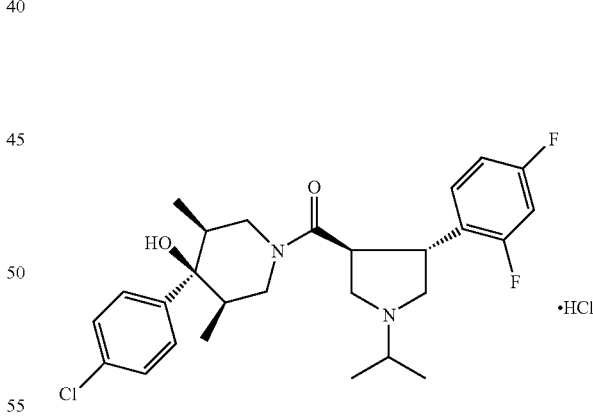

The title compound was prepared from the compounds of Preparations 33 and 43 by a similar method to that described for Example 9.

$^1$H NMR(CD$_3$OD, 400 MHz): (Rotamers), 0.30-0.54 (3×d, 6H) 0.81-2.18 (3×m, 2H), 1.37 (m, 6H), 1.55-2.28 (3×m, 2H), 2.65 (m, 1H), 3.11-4.18 (m, 7H), 4.31 (m, 1H), 6.80-7.05 (m, 5H), 7.30-7.65 (m, 2H)

LRMS (APCI)=492 [MH+]

[α]$_D^{25}$=−43.8 (c=0.35, MeOH)

Example 51

(3R,4R,5S)-4-(3,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride

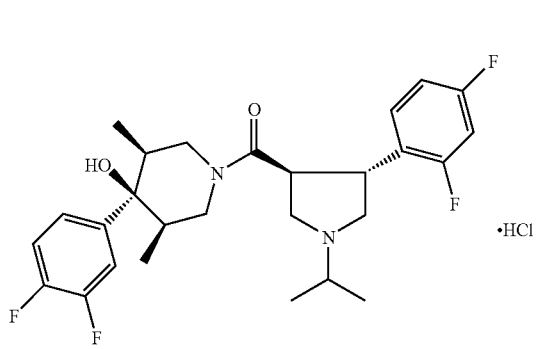

The title compound was prepared from the compounds of Preparations 39 and 33 by a similar method to that described for Example 8.

$^1$H-NMR (400 MHz, CD$_3$OD): (rotamers) □=0.30-0.59 (4×d, 6H), 1.36-1.41 (m, 6H), 1.66-1.98 (m, 1H), 2.66-2.81 (m, 2H), 3.12 (t, 1H), 3.38-3.49 (m, 3H), 3.61-3.70 (m, 1H), 3.71-3.83 (m, 2H), 3.90-4.05 (m, 2H), 4.35 (dd, 1H), 7.02-7.31 (m, 5H), 7.57-7.68 (m, 1H).

LRMS (APCI)=493 [MH$^+$].

$[\alpha]^{25}_D$=−49.77 (c=0.21, MeOH).

Example 52

(3R,4R,5S)-4-(2,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride

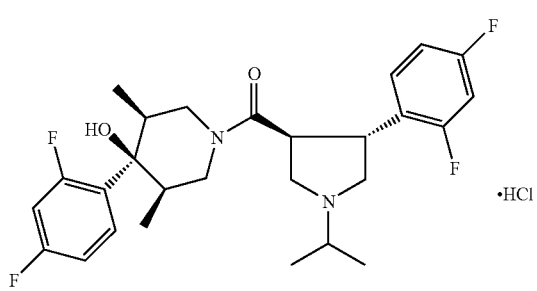

The title compound was prepared from the compounds of Preparations 33 and 49 by a similar method to that described for Example 9.

$^1$H NMR(CD$_3$OD, 400 MHz): (Rotamers), 0.34-0.52 (3×d, 6H) 0.79-1.20 (3×m, 2H), 1.39 (m, 6H), 1.49-2.30 (3×m, 2H), 2.65 (m, 1H), 3.19-4.21 (m, 7H), 4.35 (m, 1H), 6.80-7.18 (m, 4H), 7.28-7.75 (m, 2H)

LRMS (APCI)=493 [MH$^+$]

$[\alpha]_D^{25}$=−49.8 (c=0.33, MeOH)

Example 53

(3R,4R,5S)-1-{[(3S,4R)-4-(2,4-difluorophenyl)-1-ethylpyrrolidin-3-yl]carbonyl}-4-(3-fluorophenyl)-3,5-dimethylpiperidin-4-ol hydrochloride

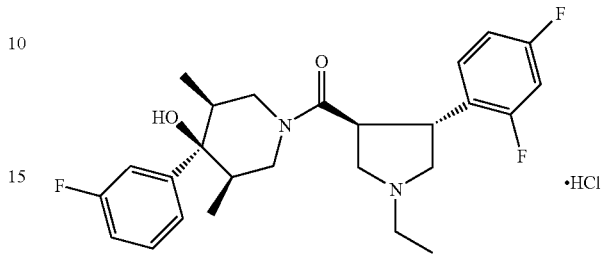

The title compound was prepared from the compounds of Preparations 46 and 75 by a similar method to that described for Example 9.

$^1$H NMR(CD$_3$OD, 400 MHz): (Rotamers), 0.28-0.56 (3×d, 6H) 0.85-1.98 (3×m, 2H), 1.47 (m, 4H), 1.55-2.05 (3×m, 2H), 2.55 (m, 1H), 3.11-4.20 (m, 7H), 4.31 (m, 1H), 6.85-7.20 (m, 5H), 7.35 (m, 1H), 7.55-7.95 (m, 1H)

LRMS (APCI)=461 [MH$^+$]

$[\alpha]^{25}_D$=−57.3 (c=0.35, MeOH)

Preparation 1

(3S,4R)-1-tert-Butyl-4-(2,4-difluorophenyl)pyrrolidine-3-carboxylic acid hydrochloride

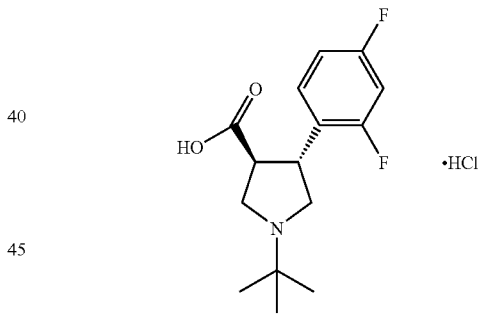

To a stirred solution of methyl (3S,4R)-1-tert-butyl-4-(2,4-difluorophenyl) pyrrolidine-3-carboxylate, from preparation 2 (6.1 g, 20.5 mmol) in diethyl ether (60 mL) at room temperature under dry nitrogen was added potassium trimethylsilanolate (3.5 g, 24.6 mmol) in a single portion. The resulting mixture was stirred at room temperature under dry nitrogen for 24 hours. 4M Hydrogen chloride in dioxane (60 mL) was then added and the resulting mixture was stirred under dry nitrogen at room temperature for 30 minutes, then concentrated in vacuo to afford the hydrochloride salt of the title compound as a white solid containing potassium chloride (8.4 g, ca. 100%).

$^1$H NMR (400 MHz, CDCl$_3$) 8H 1.40 (9H, s), 3.45 (2H, m), 3.90 (4H, m), 7.00 (2H, m), 7.60 (1H, m);

LRMS (APCI) 284 (100%) [MH$^+$].

Alternative Method (Isolation as Zwitterion)

A solution of lithium hydroxide (0.93 g, 39 mmol) in water (15 mL) was added dropwise to a stirred suspension of (4S)-

4-benzyl-3-{[(3S,4R)-1-tert-butyl-4-(2,4-difluorophenyl)pyrrolidin-3-yl]carbonyl}-1,3-oxazolidin-2-one, from preparation 22b (8.63 g, 19.5 mmol) in tetrahydrofuran (50 mL). The resulting reaction mixture was then stirred at room temperature for 1.5 hours, diluted with water (50 mL) and extracted with ethyl acetate (4×150 mL). The aqueous layer was separated, treated with 2M aqueous hydrogen chloride solution (19.5 mL), concentrated to dryness and azeotroped with toluene (5×50 mL). The residual white solid was triturated in dichloromethane (40 mL) and insoluble lithium chloride was removed by filtration. The filtrate was then evaporated to afford the product as a white foam, 5.05 g MS m/z (APCI$^+$): 284 [MH$^+$]; $^1$H NMR (CD$_3$OD, 400 MHz) δ 1.44 (s, 9H), 3.36 (m, 2H), 3.64 (t, 1H), 3.25 (dd, 1H), 3.88 (m, 3H), 6.98 (t, 2H), 7.55 (q, 1H).

Preparation 2

Methyl (3S,4R)-1-tert-butyl-4-(2,4-difluorophenyl)pyrrolidine-3-carboxylate

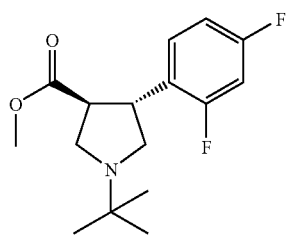

To a stirred solution of methyl (2E)-3-(2,4-difluorophenyl)acrylate from preparation 3 (10 g, 50.5 mmol) and N-(methoxymethyl)-2-methyl-N-[(trimethylsilyl)methyl]propan-2-amine (preparation 4) (10.3 g, 50.5 mmol) in dichloromethane (200 mL) at room temperature under dry nitrogen was added trifluoroacetic acid (0.39 mL, 5.1 mmol). The resulting mixture was stirred at room temperature under dry nitrogen for 17 hours. To the reaction mixture was then added a further portion of N-(methoxymethyl)-2-methyl-N-[(trimethylsilyl)methyl]propan-2-amine (from preparation 4) (3.9 g, 19.2 mmol) and trifluoroacetic acid (0.39 mL, 5.1 mmol). The resulting mixture was stirred at room temperature under dry nitrogen for 18 hours, then quenched by the addition of saturated sodium bicarbonate solution (200 mL) and extracted with ethyl acetate (3×75 mL). The combined organic layers were dried (magnesium sulfate), filtered, and concentrated in vacuo. The residue was purified by an automated flash column chromatography system (CombiFlash® Separation System Sg 100c by Isco) using a pre-packed column (Redisep™ Disposable Columns for Flash Chromatography by Isco, 40 g column) eluting with 5% ethyl acetate in pentane increasing polarity with a linear gradient up to 100% ethyl acetate over the course of 1 hour. The residue was then subjected to chiral HPLC (eluting with 95:5 hexane:isopropyl alcohol at 80 mL/min at ambient temperature on a Chirapak AD500*80 mm column) to afford the desired enantiomer of the title compound, which we designate here Enantiomer 1, and which was obtained as the faster running enantiomer (retention time 8 minutes) as a clear oil (6.1 g, 80%) with enantiomeric excess of >99% as determined by chiral HPLC with reference to a racemic standard. The undesired enantiomer was obtained as the slower eluting component (Enantiomer 2, retention time 8.7 min) $^1$H NMR (400 MHz, CDCl$_3$) δ$_H$ 1.10 (9H, s), 2.80 (1H, m), 3.00 (1H, m), 3.15 (3H, m), 3.60 (3H, s), 3.80 (1H, m), 6.80 (2H, m), 7.40 (1H, m); LRMS (APCI) 298 (100%) [MH$^+$].

Preparation 3

Methyl (2E)-3-(2,4-difluorophenyl)acrylate

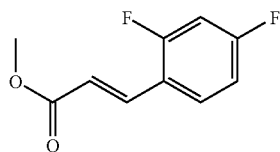

To a solution of 2,4-difluorocinnamic acid (20 g, 135 mmol) in N,N-dimethylformamide (500 mL) at room temperature under dry nitrogen was added potassium carbonate (90 g, 675 mmol) then iodomethane (21 mL, 337.5 mmol). The resulting mixture was stirred at room temperature under dry nitrogen for 7 hours before being quenched by the addition of water (1 L) and extracted with diethyl ether (3×200 mL). The combined organic extracts were dried over magnesium sulfate, filtered, and concentrated in vacuo. The residue was purified by an automated flash column chromatography system (CombiFlash® Separation System Sg 100c by Isco) using a pre-packed column (Redisep™ Disposable Columns for Flash Chromatography by Isco, 120 g column) eluting with 2% ethyl acetate in pentane increasing polarity in a linear gradient to 10% ethyl acetate in pentane over 1 hour to afford the title compound as a white solid (20.5 g, 77%). $^1$H NMR (400 MHz, CDCl$_3$) δ$_H$ 3.80 (3H, s), 6.50 (1H, d), 6.85 (1H, m), 7.50 (1H, m), 7.75 (1H, d); LRMS (APCI) 216 [MNH$_4^+$], 199 [MH$^+$].

Preparation 4

N-(Methoxymethyl)-2-methyl-N-[(trimethylsilyl)methyl]propan-2-amine

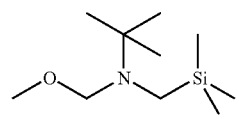

2-Methyl-N-[(trimethylsilyl)methyl]propan-2-amine (from preparation 5) (4.31 g, 27 mmol) was added to an ice-cooled mixture of methanol (1.29 mL, 31.8 mmol) and aqueous formaldehyde (37% w/v 2.49 mL, 33 mmol) over 45 minutes. The heterogeneous mixture was stirred at 0° C. for 2 hours and then solid potassium carbonate (325 mesh) (1.08 g, 13 mmol) was added and the mixture stirred for 30 minutes at 0° C. The layers were separated and the aqueous phase extracted with ethyl acetate (3×20 mL). The combined organic layers were dried over sodium sulfate, filtered, and evaporated under reduced pressure to give an 80:20 mixture of the title compound and unreacted tert-butyl[(trimethylsilyl)methyl]amine as a colourless oil (5.09 g). The mixture was used directly without further purification in preparation 2.

$^1$H NMR (400 MHz, CD$_3$OD) δ$_H$ 0.04 (s, 9H), 1.11 (s, 9H), 2.27 (s, 2H), 3.34 (s, 3H), 4.17 (s, 2H).

Preparation 5

2-Methyl-N-[(trimethylsilyl)methyl]propan-2-amine

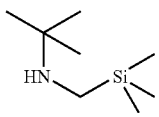

A procedure is given in *J. Org. Chem.* 53(1), 194, 1988 for the preparation of this intermediate. Alternative procedures are given below:

A solution of chloromethyltrimethyl silane (50 g, 408 mmol) and tert-butylamine (130 mL) under dry nitrogen was heated at 200° C. in a sealed tube for 18 hours before being quenched by the addition of 2M sodium hydroxide solution (700 mL). The resulting mixture was extracted with diethyl ether (3×100 mL) and the combined organic layers were distilled under dry nitrogen at 1 atmosphere to afford the title compound as a clear oil (62 g, 96%). $^1$H NMR (400 MHz, CDCl$_3$) δ$_H$ 0.05 (9H, s), 1.05 (9H, s), 1.95 (2H, s).

Alternative Preparation:

Chloromethyltrimethylsilane (100 mL, 730 mmol) and tert-butylamine (250 mL, 2400 mmol) were placed in a sealed bomb and heated with vigorous stirring for 18 hours. On cooling to room temperature, the slurry of the hydrochloride salts produced and residual excess tert-butylamine were poured into 4M sodium hydroxide solution (500 mL) and stirred vigorously for 1 hour. The aqueous layer was separated and the organic layer was stirred vigorously with water (3×500 mL) (the excess tert-butylamine is very water soluble, the product tert-butyl-trimethylsilanylmethyl-amine is only sparingly soluble). The residual organic layer was dried over sodium sulfate to give essentially pure tert-butyl-trimethylsilanylmethylamine (105.4 g), which was used directly in preparation 23 without further purification.

$^1$H NMR (400 MHz, CD$_3$OD) 0.05 (s, 9H), 1.05 (s, 9H), 1.95 (s, 2H)$^-$.

Preparation 6

(3R,4s,5S)-1-Benzyl-4-cyclohexyl-3,5-dimethylpiperidin-4-ol

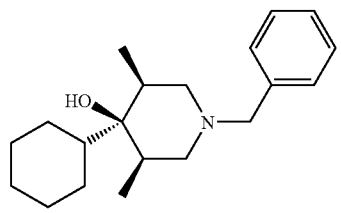

(3R,5S)-1-Benzyl-3,5-dimethylpiperidin-4-one [prepared according to preparation 14; also described in *J. Med. Chem.* 7, 726, 1964] (36 g, 166 mmol) was dissolved in anhydrous tetrahydrofuran (331 mL) in a flame-dried flask under an atmosphere of dry nitrogen. The solution was cooled to −78° C. and cyclohexylmagnesium chloride (2M solution in tetrahydrofuran) (2.42 mL, 4.84 mmol) was added dropwise over 2 hours. The reaction mixture was allowed to reach room temperature slowly over 18 hours. The reaction was quenched by the cautious addition of water (1 L) and diluted with ethyl acetate (1 L). The organic layer was separated and washed with water (2×1 L), then brine. After drying over anhydrous sodium sulfate, and filtration, the solution was evaporated to a yellow oily residue (ca. 50 g). This material was purified by flash chromatography on silica gel in two batches eluting with 10% acetone in hexane. This afforded the desired N-benzyl piperidinol intermediate containing ca. 8% of residual 1-benzyl-3,5-dimethyl-piperidin-4-one, as estimated by $^1$H NMR.

Preparation 7

(3R,4s,5S)-4-Cyclohexyl-3,5-dimethylpiperidin-4-ol

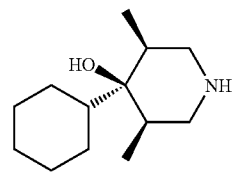

To a solution of (3R,4s,5S)-1-benzyl-4-cyclohexyl-3,5-dimethylpiperidin-4-ol, from preparation 6 (23 g, 76 mmol) in methanol (762 mL) was added ammonium formate (24.07 g, 381 mmol) and palladium hydroxide (35%, 40.25 g) followed by 5M hydrogen chloride in methanol (20 mL). The reaction flask was fitted with a condenser and heated in an oil bath at 60° C. for 2 hours. The mixture was then filtered through Celite®, washing the filter cake with ethyl acetate. The filtrate was concentrated in vacuo and then basified with 5M sodium hydroxide solution and extracted with ethyl acetate (ca. 600 mL). The organic layer was washed four times with 5M sodium hydroxide solution and (the resulting organic layer) dried over anhydrous sodium sulfate. After filtration, evaporation of the aqueous layer afforded the title compound as a white powder (11 g, 68%). LC-MS 212 [MH$^+$]; $^1$H NMR (400 MHz, CDCl$_3$) δ 0.84 (6H, d), 0.83-0.85 [1H, m (obscured)], 1.16 (6H, m), 1.63-1.83 (6H, m), 2.62-2.29 (4H, m).

The relative stereochemistry of the product was established by X-ray crystallography, and is in accord with the stereochemistry reported in the literature for (3R,4s,5S)-3,5-dimethyl-4-phenylpiperidin-4-ol [*J. Med. Chem.* 1964, 7, 726]

Preparation 8

(3R,4s,5S)-1-Benzyl-4-butyl-3,5-dimethylpiperidin-4-ol

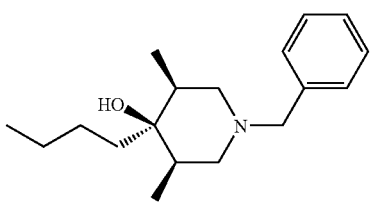

(3R,5S)-1-Benzyl-3,5-dimethylpiperidin-4-one [prepared according to preparation 14; also described in *J. Med. Chem.* 1964, 7, 726] (500 mg, 2.3 mmol) was dissolved in anhydrous tetrahydrofuran (15 mL) and placed in a flame-dried round bottomed flask under an atmosphere of nitrogen. The solution was cooled to −78° C. and n-butylmagnesium chloride (2M solution in tetrahydrofuran) (2.42 mL, 4.84 mmol) was added dropwise via syringe, and the solution was then allowed to reach room temperature. The reaction mixture was re-cooled to 0° C. and quenched by the addition of water and diluted with ethyl acetate. The organic layer was separated and washed twice with water before being dried over anhydrous sodium sulfate and evaporated. The resulting residue was purified by flash chromatography on silica gel eluting with 15% acetone in dichloromethane increasing solvent polarity in a gradient up to 30% acetone in dichloromethane, to afford the title compound (300 mg, 47%). $^1$H NMR (400 MHz, CD$_2$Cl$_2$) δ 0.78 (6H, d), 0.91 (3H, t), 1.00-1.20 (2H, m), 1.26-1.33 (2H, m), 1.47-1.52 (2H, m), 1.80-1.85 (2H, m), 1.98-2.03 (2H, m), 2.48-2.51 (2H, m), 3.43 (2H, s), 7.21-7.30 (5H, m).

Preparation 9

(3R,4s,5S)-4-Butyl-3,5-dimethylpiperidin-4-ol

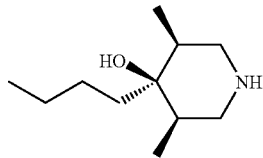

(3R,4s,5S)-1-Benzyl-4-butyl-3,5-dimethylpiperidin-4-ol (from preparation 8) (300 mg, 1.1 mmol) was dissolved in methanol (10 mL). Palladium hydroxide on carbon (525 mg) was added followed by ammonium formate (237 mg, 5.5 mmol) and 2M hydrochloric acid solution (10.1 mL, 2.2 mmol). The reaction mixture was heated to 60° C. overnight before being cooled to room temperature. The mixture was then filtered through Celite® washing the cake with methanol (500 mL). The filtrate was evaporated and the residue diluted with water, the pH adjusted to ca. 12 by the addition of saturated sodium carbonate solution and extracted with ethyl acetate. The organic layer was washed with water then dried over sodium sulfate and evaporated to provide the title compound (75 mg, 37%).

$^1$H NMR (400 MHz, CD$_2$Cl$_2$) δ 0.77 (6H, d), 0.79-0.81 (2H, m), 0.91 (3H, t), 1.11-1.96 (8H, m), 2.57-2.64 (2H, m).

Preparation 10

(3R,4s,5S)-3,5-Dimethyl-4-(4-methylphenyl)piperidin-4-ol

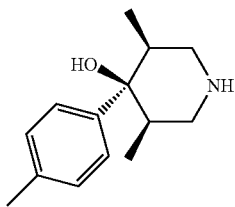

To a solution of 4-bromotoluene (0.80 mL, 6.5 mmol) in cyclohexane (2 mL) at 0° C. under dry nitrogen was added n-butyllithium (2.5 M in hexanes) (2.5 mL, 6.25 mmol). The resulting mixture was stirred at 0° C. under dry nitrogen for 2 hours. tert-Butyl (3R,5S)-3,5-dimethyl-4-oxopiperidine-1-carboxylate (from Preparation 11) (300 mg, 1.3 mmol) in toluene (4.5 mL) was then added and the resulting mixture was stirred at 0° C. under dry nitrogen for 2.5 hours, then quenched at 0° C. with water (10 mL). 2M Hydrochloric acid solution (10 mL) was added, the mixture was extracted with ethyl acetate (20 mL) and the organic layer discarded. The aqueous layer was basified to pH 11 with 2M sodium hydroxide solution and extracted with ethyl acetate (2×15 mL). The combined organic layers (from the extraction of the basic aqueous phase only) were dried over magnesium sulfate, filtered and concentrated in vacuo to afford the title compound as a white solid (136 mg, 47%).

$^1$H NMR (400 MHz, CDCl$_3$) δ$_H$ 0.55 (6H, m), 2.00 (3H, m), 2.35 (3H, s), 5.80 (5H, m), 7.10 (4H, m);

LRMS (APCI) 220 (100%) [MH$^+$]; HRMS C$_{14}$H$_{22}$O [MH$^+$] requires 220.1695 found 220.1693.

Preparation 11 tert-Butyl (3R,5S)-3,5-dimethyl-4-oxopiperidine-1-carboxylate

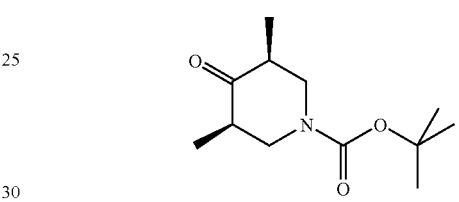

(3R,5S)-1-Benzyl-3,5-dimethyl-piperidin-4-one (from preparation 14) was dissolved in ethanol (200 mL) and di-tert-butyl dicarbonate (5.08 g, 23 mmol) was added, followed by palladium hydroxide on carbon (20% on carbon, 200 mg) and the reaction mixture placed under 40 atmosphere pressure of hydrogen and stirred overnight at room temperature. The reaction mixture was then filtered through a pad of Celite® and Arbocel® and concentrated in vacuo to afford a yellow oil which crystallised on standing to afford the title compound (5.2 g, 90%) of sufficient purity to use directly in the next stage (preparation 10). $^1$H NMR (400 MHz, CDCl$_3$) δ 1.03 (6H, d), 1.49 and 1.52 [9H, 2×s (Rotamers)], 2.48-2.76 (4H, m), 4.24-4.53 (2H, m).

Preparation 12

Dimethyl 2,4-dimethyl-3-oxopentanedioate

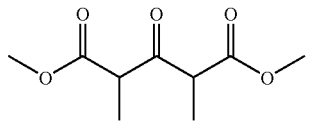

Potassium carbonate (325 mesh) (298.8 g, 2160 mmol) was added to a solution of dimethyl 3-oxopentanedioate (150.62 g, 865 mmol) in tetrahydrofuran (1.33 L). The suspension was heated to 45° C. Iodomethane (107.7 mL, 1.73 mol) was added slowly at such a rate as to keep the temperature below 60° C. The slurry was stirred between 50-60° C. for 1 hour before being cooled to 20° C. and then filtered. The filter cake was washed with tetrahydrofuran (500 mL) and the combined filtrates were concentrated to dryness in vacuo. The crude dimethyl 2,4-dimethyl-3-oxopentanedioate (179 g)

was obtained as a light-yellow viscous oil quantitatively. The ¹H NMR indicated that the material was an enol and keto tautomeric mixture and it was used in preparation 13 without further purification.

MS (APCI⁻): 201 (M+H); ¹H NMR (400 MHz, CDOD) 1.25 (s, 6H), 3.65 (s, 6H).

Preparation 13

Dimethyl 1-benzyl-3,5-dimethyl-4-oxopiperidine-3,5-dicarboxylate

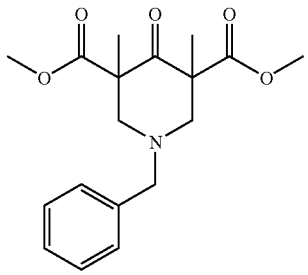

1M Hydrochloric acid solution (69 mL, 68.8 mmol) was added to a cooled (9° C.) solution of dimethyl 2,4-dimethyl-3-oxopentanedioate [from preparation 12] (69.69, 344 mmol) and benzylamine (37.6 mL, 344 mmol) in methanol (1.8 L). Formaldehyde, 37% solution in water (56.8 mL, 760 mmol) was added and the solution was stirred for 3 days at room temperature and then concentrated to dryness. The crude dimethyl 1-benzyl-3,5-dimethyl-4-oxopiperidine-3,5-dicarboxylate (125.7 g) was obtained as a light brown oil. GC-MS indicated that the material was 91% pure and it was used in preparation 14 without further purification.

GC-MS: 333 (M+); ¹H NMR (400 MHz, CDCl₃) δ 7.27-7.38 (m, 5H), 3.64 (s, 6H), 3.62 (s, 2H), 3.48 (d, 2H), 2.21 (d, 2H), 1.26 (s, 6H).

Preparation 14

(3R,5S)-1-Benzyl-3,5-dimethylpiperidin-4-one

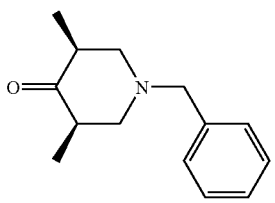

A mixture of the crude dimethyl 1-benzyl-3,5-dimethyl-4-oxopiperidine-3,5-dicarboxylate (786.0 g, ca. 2.3 mol) and 1M hydrochloric acid solution (11.5 L) was refluxed for 24 hours. The reaction mixture was cooled to 10° C. and 25% wt. aqueous sodium hydroxide solution (1.92 kg) was added slowly. The mixture was extracted with dichloromethane (4×4 L), and the combined organic extracts concentrated to dryness to give the crude (3R,5S)-1-benzyl-3,5-dimethylpiperidin-4-one (475 g) as a light brown oil. The ¹H NMR indicated that it was a 6:1 desired: undesired diastereomeric mixture.

205 g of the above crude was purified over silica gel (4.7 kg) eluting with hexane/ethyl acetate (20:1 to 7:1) to afford 94.8 g of the pure (3R,5S)-1-benzyl-3,5-dimethyl-piperidin-4-one (>19:1 diastereomeric ratio) and 44.8 g of the less pure material (~8:1 diastereomeric ratio). Both of the materials were colourless oils.

Analytical data for (3R,5S)-1-benzyl-3,5-dimethylpiperidin-4-one: GC-MS: 217 (M+); ¹H NMR (400 MHz, CDCl₃) δ 7.27-7.38 (m, 5H), 3.60 (s, 2H), 3.15 (m, 2H), 2.70 (m, 2H), 2.04 (t, J=11.6 Hz, 2H) 0.93 (d, J=6.6 Hz, 6H).

Alternative Method:

A mixture of crude 1-benzyl-3,5-dimethyl-4-oxo-piperidine dicarboxylic acid methyl ester, from preparation 13 (786.0 g, ca 2300 mmol) and 1M aqueous hydrochloric acid (11.5 L) was refluxed for 24 hours. The reaction mixture was cooled to 10° C. and 25% wt. aqueous sodium hydroxide (1.92 kg) was added slowly. The mixture was extracted with dichloromethane (4×4 L). The combined organic extracts were concentrated to dryness to give 1-benzyl-3,5-dimethyl-piperidin-4-one (475 g) as a light brown oil. The ¹H NMR indicated a 6:1 cis:trans diastereomeric mixture. A portion of the crude diastereomeric mixture (15 g) was purified using an automated chromatographic purification system employing a normal phase Redisep silica cartridge column (330 g), solvent flow rate 100 mL/min, with elution of cyclohexane/ethyl acetate 2-3% ethyl acetate linear gradient over 25 minutes, 3-14% ethyl acetate linear gradient over 10 minutes, completing elution with 14% ethyl acetate. This produced pure (3R,5S)-1-benzyl-3,5-dimethylpiperidin-4-one (10.2 g, 99%+by LC-MS).

LC-MS (ESI⁺): 218 (M+H);

Alternatively, the crude cis/trans mixture could be enriched in the desired cis-component prior to purification by the following procedure:

The crude cis:trans mixture of 1-benzyl-3,5-dimethylpiperidin-4-one (typically 6:1 cis:trans) (45 g) was added to a 5% solution of sodium methoxide in methanol (500 mL) and stirred at room temperature for 6 hours. Saturated aqueous ammonium chloride (30 mL) was added and the mixture stirred for a further 30 minutes at room temperature. The mixture was evaporated to dryness and then redissolved in dichloromethane (500 mL). The insoluble solids were filtered off and the solvent was then evaporated to give an enriched mixture 96:4 cis:trans by ¹H NMR (quantitative mass recovery). Longer reaction times did not give any further enrichment. If required, pure cis-product could then be obtained by chromatographic purification as described above.

Preparation 15

(3R,4s,5S)-1-Benzyl-3,5-dimethyl-4-phenylpiperidin-4-ol

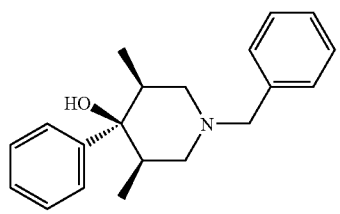

(3R,5S)-1-Benzyl-3,5-dimethylpiperidin-4-one (prepared as in preparation 14; also reported in *J. Med. Chem.* 7, 726, 1964) (5 g, 23 mmol) was dissolved in anhydrous tetrahydrofuran (77 mL) in a flame-dried flask under an atmosphere of dry nitrogen. The solution was cooled to −78° C. and phenyllithium (2M solution in cyclohexane-ether) (34.6 mL, 69 mmol) was added dropwise. The reaction mixture was allowed to reach room temperature slowly overnight and then quenched by the cautious addition of water (50 mL). The resulting mixture was diluted with ethyl acetate and the organic layer was separated and then washed three times with water and once with brine. The organic layer was then dried (sodium sulfate), filtered and evaporated. The resulting residue was purified by flash chromatography on silica gel eluting with 10% to 50% ethyl acetate in hexanes (1 L) to afford (3R,4s,5S)-1-benzyl-3,5-dimethyl-4-phenylpiperidin-4-ol of >90% purity.

LRMS: 296 (MH$^+$); $^1$H NMR (400 MHz, CD$_2$Cl$_2$) δ 0.52 (6H, d), 2.09-2.24 (4H, m), 2.67-2.71 (2H, m), 3.54 (2H, s), 7.22-7.38.

Alternative Method:

Phenyllithium in diisopropyl ether (2M, 34.5 mL, 690 mmol) was added dropwise to a stirred solution of (3R,5S)-1-benzyl-3,5-dimethylpiperidin-4-one, from preparation 14 (10.0 g, 46 mmol) in anhydrous diethyl ether (150 mL) at −78° C. The mixture was stirred for a further 30 minutes at −78° C., before saturated aqueous ammonium chloride solution (10 mL) was added and the mixture was allowed to warm to room temperature. The organic layer was separated, washed with water (3×200 mL) and dried over sodium sulfate, and then filtered. The solvent was then evaporated to give the crude (3R,4s,5S)-1-benzyl-3,5-dimethyl-4-phenylpiperidin-4-ol (12.8 g) as a white solid. The crude compound was >95% pure by $^1$H NMR and used directly in preparation 21.

LC-MS (ESI$^+$): 296 (M+H); $^{11}$H NMR (400 MHz, CD$_3$OD) δ 0.51 (d, 6H), 2.18 (m, 2H), 2.30 (m, 2H), 2.42 (m, 2H), 3.6 (s, 2H), 7.15 (m, 1H), 7.35 (m, 9H).

Preparation 16

(3R,4s,5S)-3,5-Dimethyl-4-phenylpiperidin-4-ol

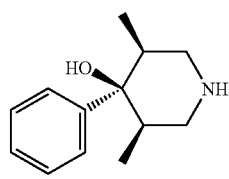

(3R,4s,5S)-1-Benzyl-3,5-dimethyl-4-phenylpiperidin-4-ol from preparation 15 was dissolved in methanol (156 mL) and ammonium formate (4.9 g, 78 mmol) then palladium hydroxide on carbon (8 g) followed by 2M hydrochloric acid solution in diethyl ether (11 mL, 22 mmol) were added. A water condenser was fitted to the flask and the reaction was heated to 60° C. overnight. After cooling to room temperature the reaction mixture was filtered through Celite® washing the cake with an additional 1 L of methanol. The combined filtrates were evaporated and the residue dissolved in a minimal amount of water, which was made basic (to pH 11) by the addition of saturated sodium carbonate solution. The resulting mixture was extracted twice with ethyl acetate and the combined organic layers washed with water, dried over sodium sulfate, filtered and concentrated to afford the title compound (3.23 g, 68%).

$^1$H NMR (400 MHz, CD$_2$Cl$_2$) δ 0.52 (6H, d), 2.03-2.10 (2H, m), 2.71-2.77 (2H, m), 2.83-2.88 (2H, dd), 7.22-7.38 (5H, m).

Alternative Method:

(3R,4s,5S)-1-Benzyl-3,5-dimethyl-4-phenylpiperidin-4-ol, from preparation 15 (15 g, 51 mmol) was dissolved in methanol, and Pd(OH)$_2$/(C) 20% wt water (1.5 g) was added. The mixture was hydrogenated at 50° C./50 psi for 18 hours. The mixture was then filtered through Arbocel filtration agent, and the methanol was evaporated to give crude (3R,4s,5S)-3,5-dimethyl-4-phenylpiperidin-4-ol as a white solid. Recrystallisation of the crude material from acetonitrile gave analytically pure (3R,4s,5S)-3,5-dimethyl-4-phenylpiperidin-4-ol as white needles (9.6 g).

Preparation 17

(3S*,4R*)-4-(2,4-difluorophenyl)-1-ethylpyrrolidine-3-carboxylic acid hydrochloride

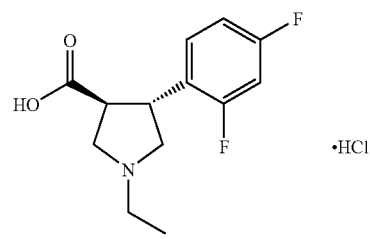

To a stirred solution of methyl (3S,4R)-4-(2,4-difluorophenyl)-1-ethylpyrrolidine-3-carboxylate, from preparation 18 (5.9 g, 22 mmol) in diethyl ether (59 mL) at room temperature under dry nitrogen was added potassium trimethylsilanolate (2.36 g, 26 mmol) in a single portion. The resulting mixture was stirred at room temperature under N$_2$ for 3 hours. A solution of 4M hydrogen chloride in dioxane (20 mL) was then added and the resulting mixture was stirred under dry nitrogen at room temperature for 18 hours, and then concentrated in vacuo to afford the title compound as a white solid containing potassium chloride residues (7.0 g).

$^1$H NMR (400 MHz, CDCl$_3$) δ$_H$ 1.25 (3H, m), 3.25 (5H, m), 3.8 (2H, m), 4.10 (1H, m), 7.20 (2H, m), 7.80 (1H, m); LRMS (APCI) 256 (100%) [MH$^+$]; HRMS C$_{13}$H$_{15}$F$_2$O$_2$ [MH$^+$] requires 256.1144 found 256.1142.

Preparation 18

Methyl (3S*,4R*)-4-(2,4-difluorophenyl)-1-ethylpyrrolidine-3-carboxylate

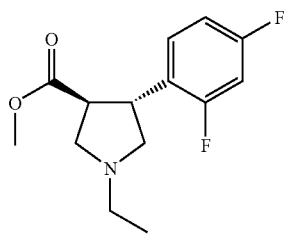

To a stirred solution of methyl (3S,4R)-4-(2,4-difluorophenyl)pyrrolidine-3-carboxylate, from preparation 19 (10.5 g, 43 mmol) in tetrahydrofuran (215 mL) at room temperature under dry nitrogen was added iodoethane (3.8 mL, 48 mmol) and N,N-diisopropylethylamine (8.3 mL, 48 mmol) in single portions. The resulting mixture was stirred at room temperature under dry nitrogen for 72 hours, then quenched by the addition of water (200 mL) and extracted with ethyl acetate (2×250 mL). The combined organic layers were dried (magnesium sulfate), filtered, and concentrated in vacuo. The residue was purified by flash column chromatography eluting with a 2:1 pentane:ethyl acetate mixture increasing polarity to 1:1. This afforded the title compound as a clear oil (7.9 g, 68%).

$^1$H NMR (400 MHz, CDCl$_3$) δH 1.15 (3H, m), 2.45 (1H, m), 2.55 (1H, m), 2.65 (1H, m), 2.95 (3H, m), 3.15 (1H, m), 3.65 (3H, s), 3.85 (1H, m), 6.80 (2H, m), 7.40 (1H, m); LRMS (APCI) 270 (100%) [MH$^+$].

Preparation 19

Methyl (3S*,4R*)-4-(2,4-difluorophenyl)pyrrolidine-3-carboxylate

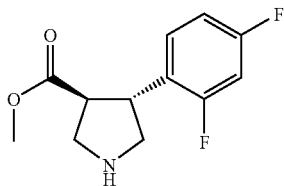

To a suspension of methyl (3S,4R)-1-benzyl-4-(2,4-difluorophenyl)pyrrolidine-3-carboxylate, from preparation 20 (15 g, 45 mmol) in ethanol (225 mL) at room temperature under dry nitrogen was added 10% palladium on carbon (Degussa type) (1.5 g), and the reaction mixture placed under 50 psi pressure of hydrogen, and heated to 40° C. overnight. After cooling to room temperature, the reaction mixture was filtered through Celite® and concentrated in vacuo to afford the title compound as an orange oil (10.8 g, 98%).

$^1$H NMR (400 MHz, CDCl$_3$) δ$_H$ 2.85 (1H, m), 3.15 (1H, m), 3.30 (2H, m), 3.45 (1H, m), 3.65 (4H, m), 6.80 (2H, m), 7.20 (1H, m); LRMS (APCI) 242 (100%) [MH$^+$]; HRMS C$_{12}$H$_{14}$F$_2$O$_2$ [MH$^+$] requires 242.0987 found 242.0986.

Preparation 20

Methyl (3S*,4R*)-1-benzyl-4-(2,4-difluorophenyl)pyrrolidine-3-carboxylate

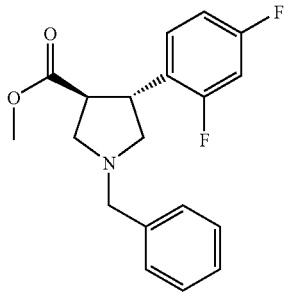

A solution of trifluoroacetic acid (2.42 mL, 31.5 mmol) in dichloromethane (5 mL) was added at 0-5° C. to a stirred solution of N-benzyl-N-(methoxymethyl)trimethylsilylamine (45.1 g, 190 mmol) and methyl (2E)-3-(2,4-difluorophenyl)acrylate (from preparation 3) (25.1 g, 126 mmol) in dichloromethane (100 mL). After stirring overnight at room temperature, the organic solution was washed with saturated sodium bicarbonate solution and then brine. The resulting organic solution was dried over anhydrous sodium sulfate, filtered and then evaporated. The residue was purified by flash chromatography on silica gel eluting with toluene:tetrahydrofuran mixture (11:1) to afford the title compound (31.6 mL, 71%) as a colourless oil.

$^1$H NMR (400 MHz, CDCl$_3$) δH 2.80 (1H, m), 3.05 (3H, m), (3.25 (1H, m), 3.62 (3H, s), 3.85 (1H, m), 4.20 (2H, s), 6.55 (5H, m), 6.80 (2H, m), 7.40 (1H, m); LRMS (APCI) 332 (100%) [MH$^+$].

Preparation 21

(4S)-4-Benzyl-3-[(2E)-3-(2,4-difluorophenyl)prop-2-enoyl]-1,3-oxazolidin-2-one

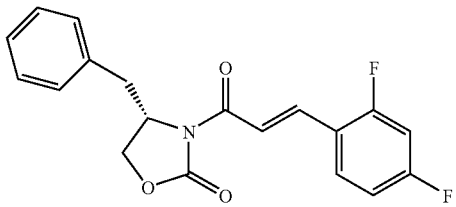

Oxalyl chloride (19 mL, 216 mmol) in dichloromethane (50 mL) was added dropwise to an ice-cooled stirred suspension of 2,4-difluorocinnamic acid (20.0 g, 108 mmol) in dichloromethane (400 mL) and N,N-dimethylformamide (0.4 mL) over 0.5 hours (waste gases from the reaction were scrubbed with a solution of concentrated sodium hydroxide). Once addition was complete, the reaction mixture was allowed to warm up to room temperature and was stirred at room temperature under nitrogen for 18 hours. The reaction mixture was then concentrated and azeotroped with dichloromethane (2×50 mL). The resulting acid chloride was redissolved in dichloromethane (50 mL) and this solution was added dropwise under nitrogen to a vigorously stirred suspension of lithium chloride (23.0 g, 540 mmol), triethylamine (76 mL, 540 mol) and (S)-(–)-4-benzyl-2-oxazolidinone (18.3 g, 103 mmol) in dichloromethane (400 mL) over 30 minutes. Once addition was complete, the reaction mixture was stirred at room temperature under nitrogen for 2.5 hours. The reaction mixture was diluted with dichloromethane (200 mL) and treated with a solution of 5% citric acid solution (500 mL). The organic layer was then separated and dried over magnesium sulfate. Filtration and evaporation of the dichloromethane gave the crude product as an orange oil. The crude material was redissolved in dichloromethane (100 mL) and the resulting solution was passed through a plug of silica, eluting with dichloromethane. The filtrate (1 L) was finally concentrated to afford 30.8 g of the product as a white solid.

MS m/z (APCI$^+$): 344 [MH$^+$]; $^1$H NMR (CDCl$_3$, 400 MHz) δ 2.85 (dd, 1H), 3.36 (dd, 1H), 4.22 (m, 2H), 4.80 (m, 1H), 6.90 (m, 2H), 7.68 (m, 5H), 7.68 (dd, 1H), 7.91 (d, 1H), 8.01 (dd, 1H).

Preparation 22a (4S)-4-Benzyl-3-{[(3R,4S)-1-tert-butyl-4-(2,4-difluorophenyl)pyrrolidin-3-yl]carbonyl}-1,3-oxazolidin-2-one and Preparation 22b (4S)-4-Benzyl-3-{[(3S,4R)-1-tert-butyl-4-(2,4-difluorophenyl)pyrrolidin-3-yl]carbonyl}-1,3-oxazolidin-2-one

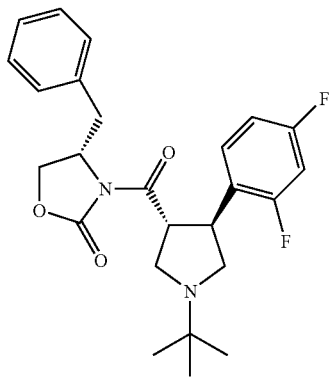

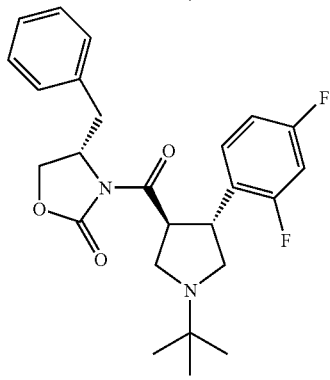

A stirred solution of (S)-4-benzyl-3-[3-(2,4-difluoro-phenyl)-acryloyl]-oxazolidin-2-one, from preparation 21 (1.70 g, 4.95 mmol) and N-(methoxymethyl)-2-methyl-N-[(trimethylsilyl)methyl]propan-2-amine, from preparation 4 (1.60 g, 5.94 mmol) in dichloromethane (15 mL) was treated with trifluoroacetic acid (0.075 mL, 1 mmol). The resulting mixture was stirred at room temperature under nitrogen for 4.5 hours. The reaction mixture was diluted with dichloromethane (50 mL) and treated with saturated aqueous sodium hydrogen carbonate solution (50 mL). The organic layer was separated and the aqueous layer was extracted with dichloromethane (50 mL). The organic fractions were combined and dried over magnesium sulfate. Filtration and evaporation of the dichloromethane gave the crude mixture of diastereoisomers.

Separation by column chromatography on silica gel with pentane:ethyl acetate 80/20 to 10/90 v/v, gradient elution, afforded firstly 0.74 g (1.67 mmol) of (4S)-4-benzyl-3-{[(3R,4S)-1-tert-butyl-4-(2,4-difluorophenyl)pyrrolidin-3-yl]carbonyl}-1,3-oxazolidin-2-one as a colourless oil, and then 0.82 g (1.85 mmol) of (4S)-4-benzyl-3-{[(3S,4R)-1-tert-butyl-4-(2,4-difluorophenyl)pyrrolidin-3-yl]carbonyl}-1,3-oxazolidin-2-one as a white solid.

(4S)-4-benzyl-3-{[(3R,4S)-1-tert-butyl-4-(2,4-difluorophenyl)pyrrolidin-3-yl]carbonyl}-1,3-oxazolidin-2-one—MS m/z (APCI$^+$): 443 [MH$^+$]; $^1$H NMR (CDCl$_3$, 400 MHz) δ 1.12 (s, 9H), 2.77 (dd, 1H), 2.85 (m, 1H), 3.25 (dd, 1H), 3.17-3.47 (m, 1H), 4.15 (m, 3H), 4.65 (m, 1H), 6.74 (t, 1H), 6.82 (t, 1H), 7.17-7.42 (m, 6H).

(4S)-4-benzyl-3-{[(3S,4R)-1-tert-butyl-4-(2,4-difluorophenyl)pyrrolidin-3-yl]carbonyl}-1,3-oxazolidin-2-one—MS m/z (APCI$^+$): 443 [MH$^+$]; $^1$H NMR (CDCl$_3$, 400 MHz) 1.12 (s, 9H), 2.72 (dd, 1H), 2.83 (m, 2H), 3.20 (m, 2H), 3.36 (t, 1H), 4.14 (m, 3H), 4.29 (m, 1H), 4.67 (m, 1H), 6.77 (t, 1H), 6.85 (t, 1H), 7.08 (m, 2H), 7.24 (m, 3H), 7.43 (m, 1H).

The full relative and absolute stereochemistry of (4S)-4-benzyl-3-{[(3S,4R)-1-tert-butyl-4-(2,4-difluorophenyl)pyrrolidin-3-yl]carbonyl}-1,3-oxazolidin-2-one was determined by X-ray analysis of crystals obtained from ethyl acetate/pentane.

Preparation 23

(4S)-4-Benzyl-3-[(2E)-3-(4-chlorophenyl)prop-2-enoyl]-1,3-oxazolidin-2-one

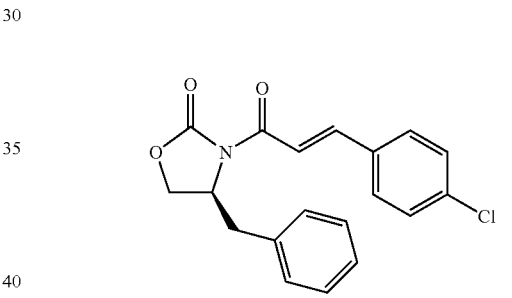

A solution of oxalyl chloride (10.82 mL, 124 mmol) in dichloromethane (50 mL) was added dropwise to a cooled solution of (2E)-3-(4-chlorophenyl)acrylic acid (11.33 g, 62.0 mmol) in dichloromethane (110 mL) and N,N-dimethylformamide (0.4 μL, 0.01 mmol). After stirring the reaction mixture for 24 hours, the solution was added dropwise to a cooled solution of (4S)-4-benzyl-1,3-oxazolidin-2-one (9.49 g, 53.6 mmol), triethylamine (39.2 mL, 282 mmol) and lithium chloride (11.95 g, 282 mmol) in dichloromethane (110 mL). The reaction mixture was slowly warmed to room temperature, stirred for 2 hours and then water (50 mL) was added. The mixture was diluted with dichloromethane (100 mL) and 5% citric acid solution (2×150 mL) was added. The phases were separated and the organic phase was dried over magnesium sulfate, filtered and concentrated in vacuo. Purification by column chromatography on silica gel using dichloromethane as eluent afforded the desired product as a white solid, 14.6 g (74%).

$^1$H NMR (400 MHz, CDCl$_3$) δ 2.86 (dd, 1H), 3.37 (dd, 1H), 4.23 (m, 2H), 4.81 (m, 1H), 7.21-7.41 (m, 7H), 7.57 (d, 2H), 7.87 (2×d, 2H)

LRMS (APCI) 342 [MH$^+$]

Preparation 24

(4S)-4-Benzyl-3-{[(3S,4R)-1-benzyl-4-(4-chlorophenyl)pyrrolidin-3-yl]carbonyl}-1,3-oxazolidin-2-one

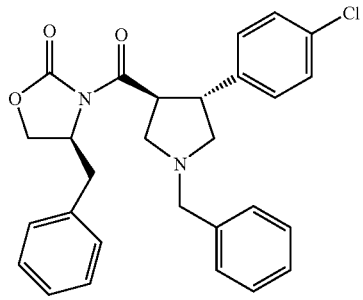

To a cooled solution of (4S)-4-benzyl-3-[(2E)-3-(4-chlorophenyl)prop-2-enoyl]-1,3-oxazolidin-2-one, from preparation 23 (5 g, 14.62 mmol) and N-benzyl-1-methoxy-N-[(trimethylsilyl)methyl]methanamine (5.24 mL, 20.47 mmol) in dichloromethane (50 mL) was added trifluoroacetic acid (60 L, 0.73 mmol). The reaction mixture was stirred at 0° C. for 20 minutes and then warmed to room temperature and stirred for 24 hours. Sodium hydrogen carbonate solution (80 mL) was added and the reaction mixture was stirred for 10 minutes. The phases were separated and the organic phase was dried over magnesium sulfate and the solvent was removed in vacuo to give a yellow oil. Purification by column chromatography on silica gel using ethyl acetate:pentane (10:50-50:50) as eluent afforded the desired product (which is the second-eluting diastereomer) as a white crystalline solid, 733 mg (11%).

$^1$H NMR (400 MHz, CDCl$_3$) δ 2.63-2.82 (m, 3H), 3.09-3.25 (m, 3H), 3.67 (dd, 2H), 3.98-4.28 (m, 4H), 4.65 (m, 1H), 7.03 (m, 2H), 7.17-7.39 (m, 12H)

LRMS (APCI) 475 [MH$^+$]

Preparation 25

Methyl (3S,4R)-1-benzyl-4-(4-chlorophenyl)pyrrolidine-3-carboxylate

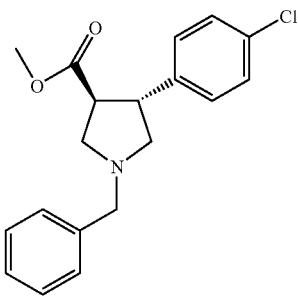

To a stirred solution of (4S)-4-benzyl-3-{[(3S,4R)-1-benzyl-4-(4-chlorophenyl)pyrrolidin-3-yl]carbonyl}-1,3-oxazolidin-2-one, from preparation 24 (2.51 g, 5.28 mmol) and dimethyl carbonate (2.22 g, 26.4 mmol) in dichloromethane (40 mL) was added sodium methoxide (1.42 g, 26.4 mmol) at room temperature. The reaction mixture was stirred for 24 hours and diluted with dichloromethane (50 mL). The phases were separated and the organic phase was washed with water (2×40 mL), dried over magnesium sulfate and concentrated in vacuo. The crude residue was purified by column chromatography on silica gel using ethyl acetate:pentane (5:95-20:80) as eluent to afford the desired product as a colourless oil, 1.61 g (79%).

$^1$H NMR (400 MHz, CDCl$_3$) δ 2.67-3.17 (m, 5H), 3.65 (s, 3H), 3.53-3.75 (m, 3H), 7.20-7.40 (m, 9H)

LRMS (APCI) 330 [MH$^+$]

Preparation 26

Methyl (3S,4R)-4-(4-chlorophenyl)pyrrolidine-3-carboxylate hydrochloride

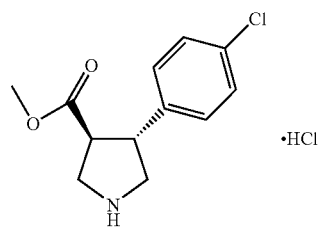

To a solution of methyl (3S,4R)-1-benzyl-4-(4-chlorophenyl)pyrrolidine-3-carboxylate, from preparation 25 (0.93 g, 2.8 mmol) in dichloromethane (9 mL) cooled with an ice-bath was added 1-chloroethyl chloroformate (0.46 mL). The reaction mixture was allowed to warm to room temperature and stirred for 48 hours. The reaction mixture was then cooled to 0° C. and triethylamine (0.43 mL, 3.1 mmol) was added followed by additional 1-chloroethylchloroformate (0.31 mL, 2.8 mmol). The ice-bath was removed and the reaction mixture was stirred at room temperature for 1.5 hours before being diluted with dichloromethane, washed with water (20 mL), 5% aqueous citric acid (20 mL) and then dried over magnesium sulfate and filtered. The solvent was removed in vacuo and the residual oil was refluxed in methanol (20 mL) for 1 hour. The solvent was then removed in vacuo and the residue was triturated with diethyl ether and filtered to give the desired product as a white solid, 0.874 g.

$^1$H NMR (400 MHz, CD$_3$OD) δ 3.64 (s, 3H), 3.31-3.83 (m, 6H), 7.36 (s, 4H)

LRMS (APCI) 240 [MH$^+$]

Preparation 27 tert-Butyl (2E)-3-(2,4-difluorophenyl)prop-2-enoyl carbonate

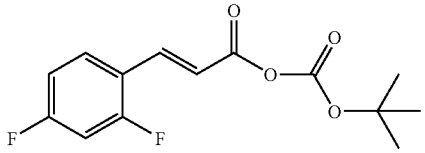

To a stirred solution of (2E)-3-(2,4-difluorophenyl)acrylic acid (42.0 g, 230 mmol) in anhydrous tetrahydrofuran (400 mL) was added triethylamine (37.5 mL, 270 mmol) and the reaction mixture was cooled to −70° C. Trimethyl acetyl chloride (30 mL, 250 mmol) was added dropwise over 20 minutes and the solution was allowed to warm to room temperature over 1 hour. Thin layer chromatography analysis indicated that the desired product had formed and this was used directly in the following step.

Preparation 28

(4S)-4-Benzyl-3-[(2E)-3-(2,4-difluorophenyl)prop-2-enoyl]-1,3-oxazolidin-2-one

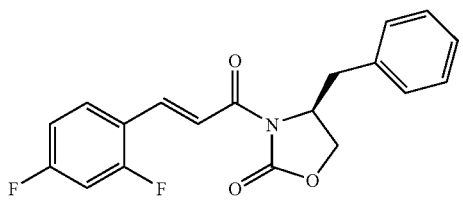

n-Butyllithium (2.5M in hexanes) (100 mL, 250 mmol) was added dropwise to a stirred solution of (S)-(−)-4-benzyl-2-oxazolidinone (43.55 g, 250 mmol) in anhydrous tetrahydrofuran (350 mL) at 0° C. The resulting solution was cooled to −78° C. for 30 minutes and added dropwise to a stirring solution of tert-butyl (2E)-3-(2,4-difluorophenyl)prop-2-enoyl carbonate, from preparation 27 via cannula at −78° C. The resulting suspension was allowed to warm to 0° C. and saturated ammonium chloride solution (75 mL) was added, followed by water (50 mL). The phases were separated and the aqueous layer was extracted with ethyl acetate (2×300 mL). The combined organic extracts were dried over magnesium sulfate, filtered and concentrated in vacuo to give a slurry. Cyclohexane (178.5 mL) and tert-butyl methyl ether (126 mL) were added to the slurry and the mixture was stirred for 2 hours at room temperature. The resulting white solid was collected via filtration and dried in a vacuum oven at 40° C. to give the desired product, 45.48 g (61%).

$^1$H NMR (400 MHz, CDCl$_3$) ☐2.82 (dd, 1H), 3.34 (dd, 1H), 4.20 (m, 2H), 4.77 (m, 1H), 6.84 (m, 1H), 6.91 (t, 1H), 7.20-7.33 (m, 3H), 7.65 (m, 2H), 7.96 (m, 3H).

Preparation 29

(4S)-4-Benzyl-3-{[(3S,4R)-1-benzyl-4-(2,4-difluorophenyl)pyrrolidin-3-yl]carbonyl}-1,3-oxazolidin-2-one

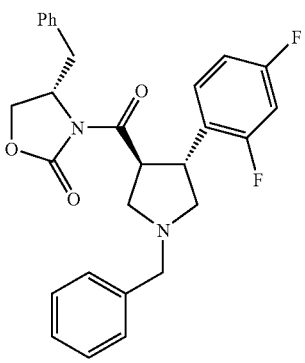

To a stirred solution of (4S)-4-benzyl-3-[(2E)-3-(2,4-difluorophenyl)prop-2-enoyl]-1,3-oxazolidin-2-one, from preparation 28 (46.83 g, 140 mmol) in dichloromethane (300 mL) was added N-methoxymethyl-N-(trimethylsilylmethyl)benzylamine (50.2 mL, 210 mmol) at room temperature. The solution was cooled to −12° C. and a solution of trifluoroacetic acid (1.05 mL) in dichloromethane (10 mL) was added dropwise. The reaction mixture was warmed to room temperature and stirred for 24 hours and saturated sodium hydrogen carbonate solution (180 mL) was added. The phases were separated and the aqueous phase was extracted with dichloromethane (180 mL). The organic extracts were combined, dried over magnesium sulfate, filtered and concentrated in vacuo to afford the crude residue. Purification of the residue by column chromatography using toluene:methyl tert-butyl ether (12:1) followed by dichloromethane:methyl tert-butyl ether (19:1) as the eluent afforded the title compound (which is the second eluting diastereomer), 63.0 g (49%).

$^1$H NMR (400 MHz, CDCl$_3$) ☐2.75 (m, 3H), 3.12 (t, 1H), 3.24 (m, 2H), 3.70 (q, 2H) 4.13 (m, 2H), 4.27 (q, 1H), 4.33 (m, 1H), 4.67 (m, 1H), 6.57 (m, 1H), 6.84 (t, 1H), 7.13 (m, 2H), 7.16 (m, 1H), 7.24-7.41 (m, 8H).

Preparation 30

Methyl (3S,4R)-1-benzyl-4-(2,4-difluorophenyl)pyrrolidine-3-carboxylate

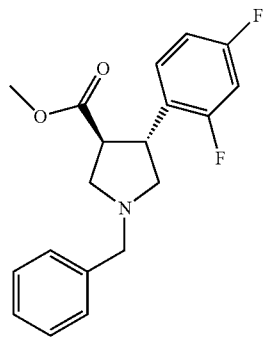

Samarium triflate (6.32 g, 10 mmol) was added to a stirred solution of (4R)-4-benzyl-3-{[(3S,4R)-1-benzyl-4-(2,4-difluorophenyl)pyrrolidin-3-yl]carbonyl}-1,3-oxazolidin-2-one, from preparation 29 (63 g, 130 mmol) in methanol (350 mL) at room temperature. The reaction mixture was stirred for 24 hours and the solvent was removed in vacuo. Dichloromethane (290 mL) was added followed by saturated sodium hydrogen carbonate solution (140 mL) and the mixture stirred for 15 minutes. The resulting precipitate was filtered and washed with dichloromethane (250 mL) and water (25 mL). The phases were separated and the aqueous layer was extracted with dichloromethane (2×40 mL). The organic extracts were combined, dried over magnesium sulfate, filtered and concentrated in vacuo to give the crude residue. The residue was suspended in warm cyclohexane (300 mL) and shaken till formation of a solid occurred. The mixture was allowed to stand at room temperature for 24 hours. The solid was filtered and washed with cold cyclohexane (150 mL). The filtrate was concentrated in vacuo to afford the desired compound, 38 g (87%).

$^1$H NMR (400 MHz, CDCl$_3$) ☐2.67 (t, 1H), 2.86 (m, 1H), 2.93 (t, 1H), 3.04 (m, 2H), 3.64 (s, 3H), 3.65 (t, 1H), 3.84 (m, 1H), 6.72 (m, 1H), 6.80 (t, 1H), 7.23 (m, 2H), 7.29-7.38 (m, 5H).

$[\alpha]^{25}_D$=−38 (c=0.5, MeOH)

Preparation 31

Methyl (3S,4R)-4-(2,4-difluorophenyl)pyrrolidine-3-carboxylate

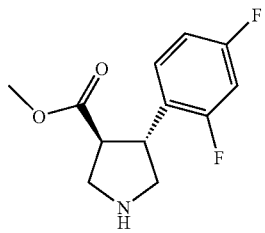

Palladium hydroxide (20% on carbon, 1 g) was added to a solution of methyl (3S,4R)-1-benzyl-4-(2,4-difluorophenyl)pyrrolidine-3-carboxylate, from preparation 30 (10 g, 30 mmol) in ethanol (50 mL) at room temperature. The reaction mixture was hydrogenated at 50 psi for 24 hours and then filtered through Arbocel® washing with ethanol (50 mL). The solvent was removed in vacuo to give the desired compound as a colourless oil, 7.19 g (98%).

$^1$H NMR (400 MHz, CD$_3$OD) ☐ 2.60 (s, 1H), 2.91 (t, 1H), 3.08 (q, 1H), 3.31-3.44 (m, 1H), 3.50 (t, 1H), 3.63 (m, 1H), 3.66 (s, 3H), 6.76 (m, 1H), 6.84 (m, 1H), 7.20 (m, 1H).

LRMS (EI) 242 [MH$^+$].

Preparation 32

Methyl (3S,4R)-4-(2,4-difluorophenyl)-1-isopropylpyrrolidine-3-carboxylate

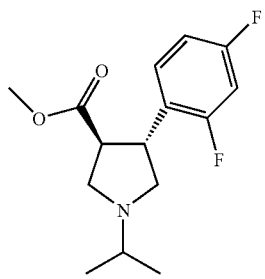

Sodium triacetoxyborohydride (1.32 g, 6.22 mmol) and acetic acid (235 µL, 4.14 mmol) were added to a solution of acetone (304 µL, 4.14 mmol) and methyl (3S,4R)-4-(2,4-difluorophenyl)pyrrolidine-3-carboxylate, from preparation 31 (1 g, 4.14 mmol) in dichloromethane (20 mL) at room temperature. The resulting mixture was stirred for 2 hours and diluted with dichloromethane (10 mL). Aqueous sodium hydrogen carbonate solution was added (2×20 mL) followed by brine (20 mL). The phases were separated, the organic phase was dried over magnesium sulfate, filtered and the solvent was removed in vacuo to give the crude residue. Purification of the residue by column chromatography using dichloromethane:methanol (99:1-98:2) as eluent afforded the desired product, 1.01 g (86%).

$^1$H NMR (400 MHz, CDCl$_3$) ☐ 1.10-1.13 (m, 6H), 2.48 (m, 1H), 2.72 (t, 1H), 3.00 (q, 1H), 3.05-3.12 (m, 3H), 3.65 (s, 3H), 3.83 (q, 1H), 6.73 (m, 1H), 6.82 (t, 1H), 7.37 (q, 1H).

LRMS (APCI) 284 [MH$^+$].

Preparation 33

(3S,4R)-4-(2,4-Difluorophenyl)-1-isopropylpyrrolidine-3-carboxylic acid

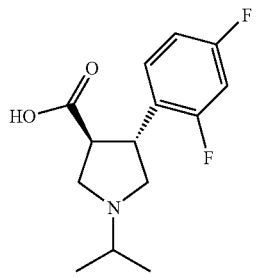

Lithium hydroxide (171 mg, 7.14 mmol) was added to a solution of methyl (3S,4R)-4-(2,4-difluorophenyl)-1-isopropylpyrrolidine-3-carboxylate, from preparation 32 (1.01 g, 3.59 mmol) in tetrahydrofuran (10 mL) at room temperature. The reaction mixture was stirred for 3 hours and the solvent was removed in vacuo. The residue was dissolved in water (20 mL) and washed with ethyl acetate (2×20 mL). The phases were separated and the aqueous phase was acidified with 2M aqueous hydrochloric acid solution (3.59 mL) and extracted with ethyl acetate (20 mL). The organic extracts were combined, dried over magnesium sulfate and concentrated in vacuo to afford the desired product as a foam, 686 mg (71%).

$^1$H NMR (400 MHz, CD$_3$OD) ☐ 1.42 (m, 6H), 3.31 (m, 3H), 3.32 (m, 1H), 3.57 (m, 2H), 3.91 (m, 1H), 7.03 (t, 2H), 7.55 (m, 1H).

LRMS (EI) 270 [MH$^+$].

Preparation 34

Methyl (2Z)-3-(2,4-difluorophenyl)acrylate

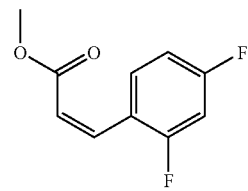

To a solution of 18-crown-6 (30 g, 110 mmol), bis(2,2,2-trifluororethyl) (methoxycarbonylmethyl)phosphonate (6 mL, 28 mmol) in tetrahydrofuran at −78° C. was added potassium hexamethyldisilazide (0.5M in toluene) (50 mL, 25 mmol) followed by 2,4-difluorobenzaldehyde (4 g, 28 mmol). The reaction mixture was stirred at this temperature for 8 hours and slowly warmed to room temperature over 24 hours. The reaction mixture was then poured into a saturated solution of ammonium chloride (200 mL). The phases were separated, the organic phase was dried over magnesium sulfate, filtered and concentrated in vacuo to give the crude residue. Purification of the residue by column chromatography using pentane:ethyl acetate (99:1-98:2) as eluent afforded the desired product as a colourless oil, 5.1 g (91%).

$^1$H NMR (400 MHz, CDCl$_3$) ☐3.70 (s, 3H), 6.05 (d, 1H), 6.80 (m, 1H), 6.86 (m, 1H), 6.97 (d, 1H), 7.69 (q, 1H).

LRMS (APCI) 199 [MH$^+$]

Preparation 35

(2Z)-3-(2,4-Difluorophenyl)acrylic acid

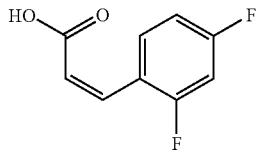

A solution of methyl (2Z)-3-(2,4-difluorophenyl)acrylate, from preparation 34 (1.3 g, 6.56 mmol) and 1M lithium hydroxide (314 mg, 13.1 mmol) in tetrahydrofuran (51 mL) was stirred at room temperature for 24 hours. The solvent was removed in vacuo and the residue was dissolved in water (10 mL) and ethyl acetate (20 mL) was added. The phases were separated and the aqueous phase was acidified to pH 2 using 2M hydrochloric acid solution (3 mL). The aqueous phase was extracted with diethyl ether (2×30 mL). These organic extracts were combined, dried over magnesium sulfate, filtered and concentrated in vacuo to give the desired product as a white solid, 1.03 g (86%).

$^1$H NMR (400 MHz, CD$_3$OD): □6.09 (d, 1H), 6.93 (m, 2H), 6.97 (d, 1H), 7.66 (q, 1H).

Preparation 36

(3R*,4R*)-1-tert-Butyl-4-(2,4-difluorophenyl)pyrrolidine-3-carboxylic acid

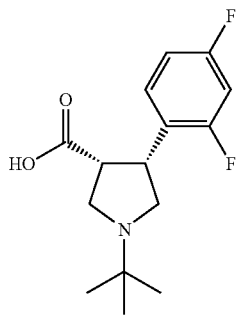

To a stirred solution of (2Z)-3-(2,4-difluorophenyl)acrylic acid, from preparation 35 (400 mg, 2.17 mmol) and trifluoroacetic acid (17 μL, 0.2 mmol) in dichloromethane (1 mL) was added N-(methoxymethyl)-2-methyl-N-[(trimethylsilyl)methyl]propan-2-amine, from preparation 23 (882 mg, 4.35 mmol) over 30 minutes at 0° C. The reaction mixture was warmed to room temperature and stirred for 24 hours. The solvent was removed in vacuo and the white residue formed was triturated with diethyl ether (5 mL) and the solid filtered off to give the desired product, 400 mg (65%).

$^1$H NMR (400 MHz, CD$_3$OD) □1.46 (s, 9H), 3.31 (s, 1H), 3.59 (m, 1H), 3.69 (m, 1H), 3.78 (d, 1H), 3.89 (t, 1H), 3.97 (m, 1H), 6.93 (m, 2H), 7.41 (m, 1H).

LCMS (APCI)=284 [MH$^+$].

Preparation 37

Methyl (3S,4R)-4-(2,4-difluorophenyl)-1-methylpyrrolidine-3-carboxylate

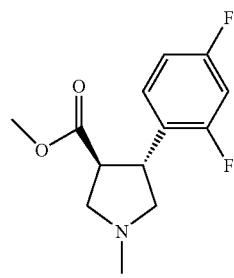

To a solution of methyl (3S,4R)-4-(2,4-difluorophenyl)pyrrolidine-3-carboxylate, from preparation 31 (500 mg, 2.07 mmol) and formaldehyde (155 μL, 2.07 mmol) in dichloromethane (20 mL) was added acetic acid (188 μL, 2.07 mmol) followed by sodium triacetoxyborohydride (659 mg, 3.11 mmol) at room temperature. The reaction mixture was stirred for 2 hours, diluted with dichloromethane (10 mL) and partitioned with saturated sodium hydrogen carbonate solution (40 mL). The phases were separated and the organic phase was washed with brine (20 mL), dried over magnesium sulfate, filtered and concentrated in vacuo to give the desired product as a colourless oil, 288 mg (54%).

$^1$H NMR (400 MHz, CDCl$_3$) δ 2.41 (s, 3H), 2.68 (t, 1H), 3.00 (m, 2H), 3.01 (q, 1H), 3.11 (m, 1H), 3.65 (s, 3H), 3.88 (m, 1H), 6.78 (m, 1H), 6.82 (t, 1H), 7.37 (m, 1H).

LRMS: m/z APCI$^+$256 [MH$^+$].

Preparation 38 tert-Butyl (3R,4S)-3-(2,4-difluorophenyl)-4-{[(3R,4R,5S)-4-(4-fluorophenyl)-4-hydroxy-3,5-dimethylpiperidin-1-yl]carbonyl}pyrrolidine-1-carboxylate

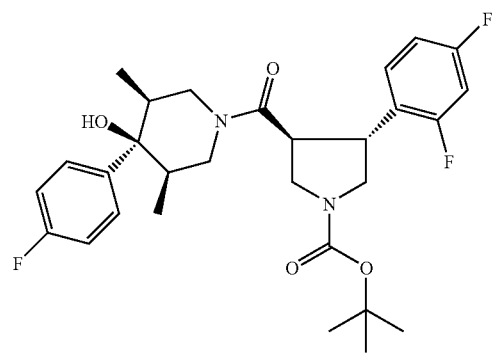

(3R,4s,5S)-4-(4-Fluorophenyl)-3,5-dimethylpiperidin-4-ol, from preparation 41 (265 mg, 1.2 mmol), (3S,4R)-1-(tert-butoxycarbonyl)-4-(2,4-difluorophenyl)pyrrolidine-3-carboxylic acid, from preparation 53 (0.75 mg, 1.4 mmol) and triethylamine (0.48 mL, 3.6 mmol) were added to dichloromethane (25 mL). The stirred suspension was cooled under nitrogen and 1-propylphosphonic acid cyclic anhydride (50% in ethyl acetate) (0.67 mL, 2 mmol) was added dropwise. On completion of addition the resulting homogenous solution was stirred for a further 6 hours at room temperature. The solution was washed with 10% aqueous potassium carbonate solution (3×20 mL), citric acid 3% (3×50 mL), then dried over sodium sulfate and filtered. The dichloromethane was then removed in vacuo and the crude compound was purified by column chromatography (silica) gradient eluting with ethyl acetate:pentane (10:90) to ethyl acetate:pentane (40:80) to give the desired product as a white solid (529 mg).

$^1$H NMR (CD$_3$OD, 10 mg/mL, 400 MHz) (Rotamers), 0.21-0.58 (m, 6H), 1.46 (s, 9H), 0.81-1.97 (m, 2H), 2.68 (m, 1H), 4.35 (m, 1H), 2.93-3.91 (m, 7H), 4.31 (m, 1H), 6.90-7.29 (m, 5H), 7.38-7.85 (m, 2H)

$[\alpha]^{25}_D = -82.7$ (c=0.3, MeOH)

Preparation 39

(3R,4s,5S)-4-(3,4-Difluorophenyl)-3,5-dimethylpiperidin-4-ol

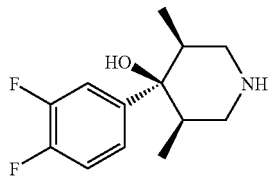

A solution of 3,4-difluorobromobenzene (4.45 g, 21 mmol) in diethylether (25 mL) was cooled to −78° C. under nitrogen. n-Butyllithium (2.5M in hexanes) (8.10 mL, 20 mmol) was added dropwise with stirring, maintaining the temperature below −65° C. The mixture was stirred at −78° C. for 4 hours. (3R,5S)-1-Benzyl-3,5-dimethylpiperidin-4-one, from preparation 14 (5.90 g, 20 mmol) in diethylether (25 mL) was then added dropwise, maintaining the temperature below −65° C. The mixture was stirred at −78° C. for 1 hour then allowed to warm to room temperature. Saturated ammonium chloride solution (40 mL) was added and the mixture stirred for 30 minutes. The ether layer was separated, washed with water (3×50 mL), dried over sodium sulfate, filtered and then evaporated to dryness. The crude product was dissolved in methanol (100 mL) and the solution was hydrogenated at 50 psi and 50° C. over 20% palladium on carbon for 18 hours. The mixture was filtered through Celite® and the filtrate was evaporated to dryness. Recrystallisation of the crude product from acetonitrile afforded the desired product as a solid, 1.58 g (24%).

$^1$H NMR (400 MHz, CD$_3$OD) δ 0.60 (d, 6H), 2.21 (m, 2H), 3.10 (m, 4H), 7.38 (d, 2H), 7.05-7.20 (m, 1H), 7.25 (m, 1H), 7.30-7.50 (m, 1H)

LRMS: m/z APCI$^+$ 242 [MH$^+$]

Preparation 40

(3R,4s,5S)-1-Benzyl-4-(4-fluorophenyl)-3,5-dimethylpiperidin-4-ol

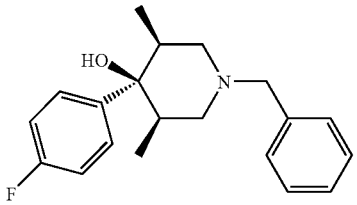

A solution of 4-fluorobromobenzene (4.51 g, 0.024 mol) in diethylether (20 mL) was cooled to −78° C. under nitrogen. n-Butyllithium (8.40 mL, 21 mmol) (2.5M in hexanes) was added dropwise with stirring, maintaining the temperature below −65° C. The mixture was stirred at −78° C. for 1 hour then allowed to warm to room temperature. The resultant solution of 4-fluorophenyllithium was then added dropwise to a solution of (3R,5S)-1-benzyl-3,5-dimethylpiperidin-4-one [from preparation 14] (6 g, 19 mmol) in diethylether (20 mL) at −78° C., maintaining the temperature below −65° C. The mixture was stirred at −78° C. for 1 hour then allowed to warm to room temperature. Saturated ammonium chloride solution (40 mL) was added and the mixture stirred for 30 minutes. The organic phase was separated, washed with water (3×50 mL), dried over sodium sulfate, filtered and then evaporated to dryness. The crude product was used without further purification.

$^1$H NMR (400 MHz, CD$_3$OD) δ 0.51 (d, 6H), 2.18 (m, 2H), 2.39 (m, 2H), 2.71 (m, 1H), 3.58 (s, 1H), 3.65 (s, 2H), 7.12 (m, 2H), 7.35 (m, 7H)

LRMS (APCI) 314 [MH$^+$]

Preparation 41

(3R,4s,5S)-4-(4-Fluorophenyl)-3,5-dimethylpiperidin-4-ol

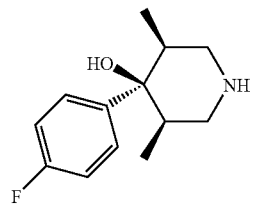

A solution of (3R,4s,5S)-1-benzyl-4-(4-fluorophenyl)-3,5-dimethylpiperidin-4-ol, from preparation 40 (5.0 g, 16 mmol) in methanol (100 mL) was hydrogenated at 50 psi and 50° C. over 20% palladium on carbon (1.1 g) for 18 hours. The mixture was then filtered through Celite® and the filtrate was evaporated to dryness. Recrystallisation of the crude product from acetonitrile afforded the desired product as a solid, (3.81 g)

$^1$H NMR (400 MHz, CD$_3$OD) δ 0.54 (d, 6H), 2.18 (m, 2H), 2.85 (m, 4H), 7.05 (m, 2H), 7.20-7.45 (m, 2H),

LRMS (APCI) 224 [MH$^+$]

Preparation 42

(3R,5S)-1-(4-Methoxybenzyl)-3,5-dimethylpiperidin-4-one

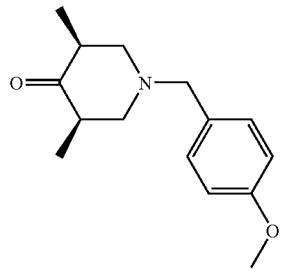

1M Hydrochloric acid solution (69 mL) was added to a solution of dimethyl 2,4-dimethyl-3-oxopentanedioate, from preparation 12 (69.6 g, 344 mmol) and 4-methoxybenzylamine (44.81 mL, 344 mmol) in methanol (1.8 L). Formaldehyde, 37% aqueous solution (56.8 mL, 760 mmol) was added. The solution was stirred for 72 hours at room temperature then evaporated to dryness.

The crude 1-(4-methoxybenzyl)-3,5-dimethyl-4-oxo-piperidine dicarboxylic acid, dimethyl ester (126.2 g) was added to 1M hydrochloric acid solution (1735 mL) and the mixture heated under reflux for 24 hours. The reaction mixture was cooled to 10° C. and 20 wt % aqueous sodium hydroxide solution (400 mL, 2.0 mol) added slowly. The mixture was extracted with dichloromethane (4×400 mL). The combined organic extracts were evaporated to dryness to give the crude product as a light brown oil, $^1$H NMR of the crude material indicated a 6:1 cis:trans mixture. A portion of the crude diastereomeric mixture (15 g) was purified using an automated chromatographic purification system employing a normal phase Redisep® silica cartridge column (330 g), solvent flow rate 100 mL/min, with elution of cyclohexane/ethyl acetate 2-3% ethyl acetate linear gradient over 35 minutes, 3-14% ethyl acetate linear gradient over 10 minutes, completing elution with 14% ethyl acetate. This produced pure cis-isomer as a pale yellow oil which solidified on standing (10.2 g, 99%+by LCMS).

$^1$H NMR (400 MHz, CD$_3$OD) δ 0.91 (d, 6H), 2.02 (m, 2H), 2.75 (m, 2H), 3.18 (m, 2H), 3.58 (s, 2H), 3.95 (s, 3H), 6.85 (d, 2H), 7.25 (d, 2H)

LRMS (APCI) 248 [MH$^+$]

Preparation 43

(3R,4s,5S)-4-(4-Chlorophenyl)-3,5-dimethylpiperidin-4-ol

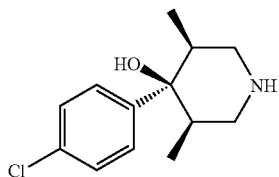

A solution of 4-chloroiodobenzene (4.6 g, 25 mmol) in anhydrous diethyl ether (200 mL) was cooled to −78° C. under nitrogen. n-Butyllithium (2.5M in hexanes) (15.2 mL, 20 mmol) was added dropwise maintaining the temperature below −65° C. The mixture was stirred at −78 IC for 2 hours and allowed to warm to room temperature. The solution of 4-chlorophenyl lithium was then added dropwise to a solution of (3R,5S)-1-(4-methoxybenzyl)-3,5-dimethylpiperidin-4-one, from preparation 42 (5.0 g, 20 mmol) in diethyl ether (25 mL) at −78° C. The mixture was stirred at −78° C. for a further 2 hours and then allowed to warm to room temperature. The mixture was quenched with saturated ammonium chloride (50 mL). The organic phase was separated, washed with water (3×50 mL), dried over sodium sulfate, filtered and then evaporated to dryness to give the crude intermediate. This crude was dissolved in dry dichloromethane (150 mL), triethylamine (4.0 mL, 29 mmol) was added and the solution was cooled to 0° C. under nitrogen. 1-Chloroethylchloroformate (3.21 mL, 30 mmol) was added dropwise to the stirred solution and on completion of addition the mixture was stirred for a further 3 hours at room temperature. The mixture was then washed with 10% aqueous potassium carbonate solution (3×25 mL), dried over sodium sulfate and evaporated to dryness. The crude residue was heated under reflux in methanol (150 mL) for 3 hours and the solvent was removed in vacuo. The residue was dissolved in dichloromethane (100 mL), solid potassium carbonate (5 g) was added and the heterogeneous mixture was stirred for 1 hour. The solid potassium carbonate was filtered off and the filtrate was evaporated to dryness. The crude product was then recrystallised from acetonitrile to give the desired product as fine white needles (3.90 g).

$^1$H NMR (400 MHz, CD$_3$OD) δ 0.60 (m, 6H), 2.25 (m, 2H), 3.10 (m, 4H) 7.38 (d, 2H), 7.55 (m, 4H)

LRMS (APCI) 240 [MH$^+$]

Preparation 44

(3R,4s,5S)-4-(2,6-Difluorophenyl)-3,5-dimethylpiperidin-4-ol

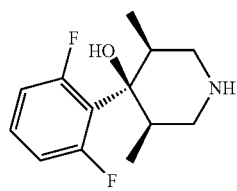

tert-Butyllithium (1.7M in pentane) (9.62 mL, 16.4 mmol) was added dropwise to a stirred solution of 2,6-difluorobromobenzene (3.0 g, 15.5 mmol) at −78° C. The solution was stirred for a further 3 hours at −78° C. A solution of (3R,5S)-1-benzyl-3,5-dimethylpiperidin-4-one, preparation 14 (2.16 g, 12 mmol) in diethylether (30 mL) was then added dropwise, maintaining the temperature below −65° C. The mixture was stirred at −78° C. for 1 hour, then allowed to warm to room temperature overnight. Saturated ammonium chloride solution (20 mL) was added and the mixture stirred for 30 minutes. The organic phase was washed with water (3×50 mL) and dried over sodium sulfate. The solvent was removed in vacuo, the residue was dissolved in methanol (100 mL) and the solution hydrogenated (50 psi and 50° C. over 20% palladium on carbon) for 18 hours. The mixture was filtered through Celite® and the filtrate was evaporated to dryness. The crude product was recrystallised from acetonitrile to afford the desired product (1.78 g) as fine white needles.

$^1$H NMR (400 MHz, CD$_3$OD) (Rotamers) δ 0.60 (d, 6H), 2.21 (m, 2H), 3.10 (m, 4H), 7.38 (d, 2H), 7.05-7.20 (m, 1H), 7.25 (m, 1H), 7.31-7.50 (m, 1.20H)

LRMS (APCI) 242 [MH$^+$]

Preparation 45

(3R,4s,5S)-4-(3-Fluorophenyl)-1-(4-methoxybenzyl)-3,5-dimethylpiperidin-4-ol

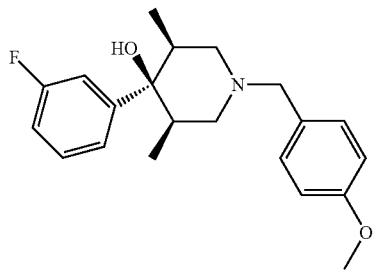

n-BuLi (2.5M in hexanes) (7.2 mL, 18 mmol) was added dropwise to a stirred solution of 3-fluoroiodobenzene (1.91 g, 8.0 mmol) in anhydrous diethylether (10 mL) at −78° C. The mixture was stirred at −78° C. for 3 hours and (3R,5S)-1-(4-methoxybenzyl)-3,5-dimethylpiperidin-4-one, from preparation 42 (1.85 g, 7.5 mmol) in diethyl ether (10 mL) was then added dropwise keeping the temperature below −60° C. The mixture was then allowed to warm to room temperature. Saturated ammonium chloride solution (25 mL) was added, the mixture stirred for 30 minutes and the organic phase separated. The organic phase was washed with water (3×50 mL) and dried over sodium sulfate, filtered and the solvent was removed in vacuo. Recrystallisation from ethyl acetate:cyclohexane afforded the desired product (2.88 g).

¹H NMR (400 MHz, CD₃OD) δ 0.51 (d, 6H), 2.18 (m, 2H), 2.35 (m, 2H), 2.71 (m, 2H), 3.58 (s, 2H), 3.65 (s, 3H), 7.12 (m, 3H), 7.35 (m, 5H)

LRMS (APCI) 344 [MH⁺]

Preparation 46

(3R,4s,5S)-4-(3-Fluorophenyl)-3,5-dimethylpiperidin-4-ol

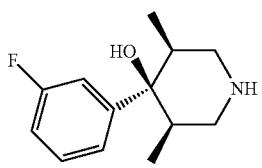

A solution of (3R,4s,5S)-4-(3-fluorophenyl)-1-(4-methoxybenzyl)-3,5-dimethylpiperidin-4-ol, from preparation 45 (2.5 g, 7.3 mmol) in methanol (25 mL) was hydrogenated (50 psi and 50° C. over 20% palladium on carbon) for 18 hours. The mixture was filtered through Celite® and the filtrate evaporated to dryness. Recrystallisation of the crude product from acetonitrile afforded the title compound (1.52 g).

¹H NMR (400 MHz, CD₃OD) δ 0.59 (d, 6H), 2.10 (m, 2H), 2.85 (m, 5H), 6.95 (m, 1H), 7.35 (m, 2H)

LRMS (APCI) 224 [MH⁺]

Preparation 47

(3R,4s,5S)-1-Benzyl-4-(4-methoxyphenyl)-3,5-dimethylpiperidin-4-ol

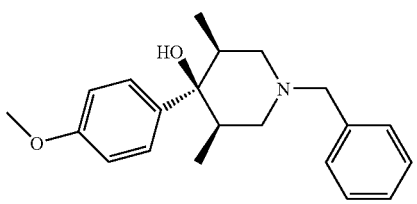

tert-Butyllithium (1.7M in pentane) (33.0 mL, 56 mmol) was added to anhydrous diethylether (20 mL) under nitrogen and cooled to −78° C. A solution of 4-methoxy-iodobenzene (6.89 g, 29 mmol) in anhydrous diethylether (25 mL) was added dropwise to the tert-butyllithium solution maintaining the temperature between −78° C. and −60° C. On completion of addition, the mixture was stirred for a further 30 minutes at −78° C. then allowed to warm to room temperature. The resultant 4-methoxyphenyllithium solution was then added dropwise to a solution of (3R,5S)-1-benzyl-3,5-dimethylpiperidin-4-one, from preparation 14 (4.0 g, 18 mmol) in anhydrous diethyl ether (70 mL) at −78° C. The mixture was stirred at −78° C. for 2 hours and then allowed to warm to room temperature. Saturated ammonium chloride (20 mL) was added dropwise and the mixture stirred for 30 minutes. The organic layer was separated, washed with water (3×100 mL), dried over sodium sulfate and evaporated to dryness to give the crude product, which was recrystallised from cyclohexane/ethyl acetate to give the pure product (7.1 g)

¹H NMR (400 MHz, CD₃OD) δ 0.51 (d, 6H), 2.12 (m, 2H), 2.25 (m, 2H), 2.61 (m, 2H), 3.58 (s, 2H), 3.78 (s, 3H), 6.85 (m, 3H), 7.25 (m, 6H)

LRMS (APCI) 326 [MH⁺]

Preparation 48

(3R,4s,5S)-4-(4-Methoxyphenyl)-3,5-dimethylpiperidin-4-ol

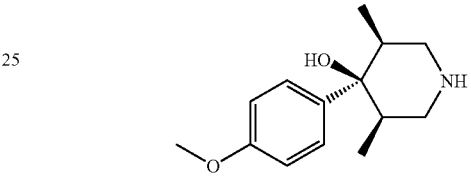

A solution of (3R,4s,5S)-1-benzyl-4-(4-methoxyphenyl)-3,5-dimethylpiperidin-4-ol (7.1 g, 21 mmol), from preparation 47 in methanol (100 mL) was hydrogenated over palladium on carbon (1.09) (50 psi and 50° C.) for 18 hours. The mixture was filtered through Celite® and the filtrate was evaporated to dryness to give the crude product. Recrystallisation from acetonitrile afforded the desired compound (3.1 g) which was used directly without further purification.

¹H NMR (400 MHz, CD₃OD) δ 0.52 (d, 6H), 2.00 (m, 2H), 2.68 (m, 4H), 3.78 (s, 3H), 6.82 (d, 2H), 7.20-7.60 (m, 2H).

LRMS (APCI) 235 [MH⁺]

Preparation 49

(3R,4s,5S)-4-(2,4-difluorophenyl)-3,5-dimethylpiperidin-4-ol

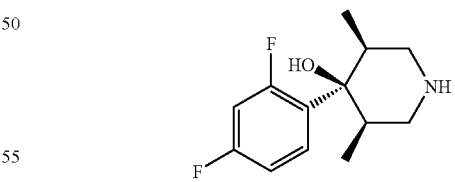

A solution of 2,4-difluorobromobenzene (4.51 g, 22 mmol) in diethylether (20 mL) was cooled to −78° C. under nitrogen. n-Butyllithium (2.5M in hexanes) (8.40 mL, 21 mmol) was added dropwise with stirring, maintaining the temperature below −65° C. The mixture was stirred at −78° C. for 4 hours. (3R,5S)-1-Benzyl-3,5-dimethylpiperidin-4-one, from preparation 14 (6.00 g, 19 mmol) in diethylether (25 mL) was then added dropwise, maintaining the temperature below −65° C. The mixture was stirred at −78° C. for 1 hour then allowed to warm to room temperature. Saturated ammonium chloride solution (40 mL) was added and the mixture stirred for 30 minutes. The ether layer was separated, washed with water (3×50 mL), dried over sodium sulfate, filtered and then evaporated to dryness. The product was dissolved in methanol (100 mL) and the solution hydrogenated (50 psi and 50° C. over 20% palladium on carbon) for 18 hours. The mixture was filtered through Celite® and the filtrate was evaporated to dryness.

Recrystallisation of the crude product from acetonitrile afforded the desired product (1.78 g) as fine white needles.

$^1$H NMR (400 MHz, CD$_3$OD) δ 0.60 (d, 6H), 2.21 (m, 2H), 3.10 (m, 4H), 7.38 (d, 2H), 7.05-7.20 (br, 1.00H), 7.25 (m, 1H), 7.31-7.50 (m, 1.20H)

LRMS (APCI) 242 [MH$^+$]

Preparation 50

(3R,4s,5S)-1-Benzyl-3,5-dimethyl-4-pyridin-3-ylpiperidin-4-ol

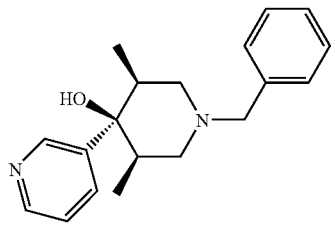

A cooled solution of 3-bromopyridine (2.4 mL, 25 mmol) in dry diethyl ether (2 mL) was added to a solution of n-butyllithium (2.5M in hexane) (10 mL, 25 mmol) at −78° C. The reaction mixture was stirred for 1 hour. A solution of (3R,5S)-1-benzyl-3,5-dimethylpiperidin-4-one, from preparation 14 (5.42 mg, 25 mmol) in tetrahydrofuran (2 mL) was added at −78° C. and the reaction mixture stirred for 1 hour. The reaction was allowed to warm to −20° C. and saturated ammonium chloride solution (10 mL) was added and the resulting mixture was stirred for 24 hours at room temperature. The suspension was filtered and the solid washed with diethyl ether (4×50 mL). The solid was redissolved in dichloromethane:methanol (90:10) and the solution was washed with brine. The phases were separated, the organic phase was dried over magnesium sulfate, filtered and concentrated in vacuo to afford the desired product, 4.35 g (61%).

$^1$H-NMR (400 MHz, CDCl$_3$): o=0.56 (d, 6H), 2.07-2.43 (br, 4H), 2.79 (br, 2H), 3.63 (br, 2H), 7.25-7.46 (m, 5H), 7.65 (br, 1H), 7.84 (br, 1H), 8.47 (d, 1H), 8.68 (br, 1H)

LRMS (APCI+)=297 [MH$^+$]

Preparation 51

(3R,4s,5S)-3,5-Dimethyl-4-pyridin-3-ylpiperidin-4-ol

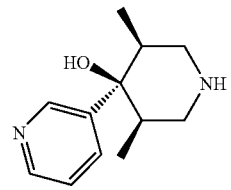

A mixture of (3R,4s,5S)-1-benzyl-3,5-dimethyl-4-pyridin-3-ylpiperidin-4-ol from preparation 50 (3.0 g, 10.12 mmol) and 20 wt % palladium hydroxide on carbon (0.45 g) in ethanol (50 mL) was hydrogenated at 40° C. and 40 psi for 14 hours. The reaction mixture was then filtered through Arbocel® and the filtrate was concentrated in vacuo to give the desired product as an off-white foam, 2.05 g.

$^1$H-NMR (400 MHz, CDCl$_3$): δ=0.57 (d, 6H), 2.12 (m, 2H), 2.81 (t, 2H), 2.94 (m, 2H), 7.27 (m, 1H), 7.51-7.99 (br, 1H), 8.48 (d, 1H), 8.67 (br, 1H)

LRMS (APCI+)=207 [MH$^+$]

Preparation 52

1-tert-Butyl 3-methyl (3S,4R)-4-(2,4-difluorophenyl)pyrrolidine-1,3-dicarboxylate

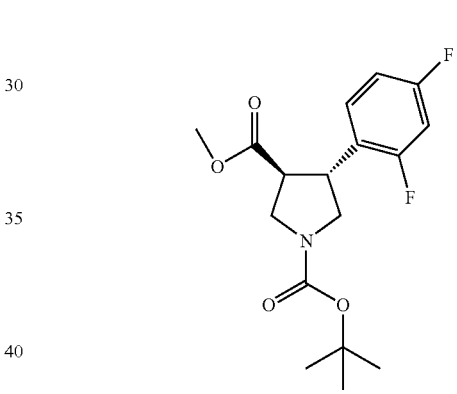

To a solution of methyl (3S,4R)-1-benzyl-4-(2,4-difluorophenyl)pyrrolidine-3-carboxylate, from preparation 30 (1.0 g, 3.01 mmol), 1-methylcyclohexa-1,4-diene (1.25 mL, 11.12 mmol) and di-tert-butyl dicarbonate (0.72 g, 3.31 mmol) in ethanol (10 mL) was added palladium hydroxide on carbon (0.1 g) at room temperature. The resulting mixture was heated under reflux for 4 hours, cooled to room temperature and filtered through Arbocel®. The filtrate was concentrated in vacuo to give the crude residue which was partitioned between ethyl acetate (80 mL) and 10% citric acid solution (5 mL). The phases were separated and the organic layer was washed with brine (60 mL), dried over magnesium sulfate, filtered and concentrated in vacuo to give the desired product as a colourless oil, 940 mg.

$^1$H NMR (400 MHz, CDCl$_3$) δ 1.40 (s, 9H), 3.14-3.25 (m, 1H), 3.25-3.40 (m, 1H), 3.48-3.59 (m, 4H), 3.68-3.89 (m, 3H), 6.71-6.82 (m, 2H), 7.15 (m, 1H)

LRMS (APCI) 242 [MH$^+$−BOC+1]

Preparation 53

(3S,4R)-1-(tert-Butoxycarbonyl)-4-(2,4-difluorophenyl)pyrrolidine-3-carboxylic acid

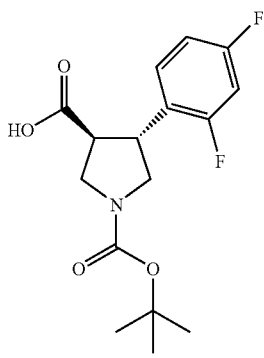

Lithium hydroxide (130 mg, 23.5 mmol) was added dropwise to a stirred solution of 1-tert-butyl 3-methyl (3S,4R)-4-(2,4-difluorophenyl)pyrrolidine-1,3-dicarboxylate, from preparation 52 (930 mg, 2.72 mmol) in tetrahydrofuran (10 mL) at room temperature. The reaction mixture was stirred for 48 hours, concentrated in vacuo and diluted with water (15 mL). The phases were separated and the aqueous phase was extracted with ethyl acetate (1×25 mL). The aqueous layer was acidified with 2M hydrochloric acid solution (2.7 mL) and further extracted with ethyl acetate (2×40 mL). The combined organic extracts were dried over magnesium sulfate, filtered, concentrated in vacuo and azeotroped with dichloromethane to give the desired product, 775 mg (87%).

$^1$H NMR (400 MHz, CDCl$_3$) δ 1.45 (s, 9H), 3.23-3.46 (m, 2H), 3.56-3.65 (m, 1H), 3.74-3.93 (m, 3H), 6.75-6.87 (m, 2H), 7.20 (m, 1H)

LRMS (APCI) 228 [MH$^+$−BOC+1]

LRMS (APCI-)=326 [M−1]

Preparation 54 tert-Butyl (3R,4S)-3-(2,4-difluorophenyl)-4-{[(3R,4R,5S)-4-hydroxy-3,5-dimethyl-4-pyridin-2-ylpiperidin-1-yl]carbonyl}pyrrolidine-1-carboxylate

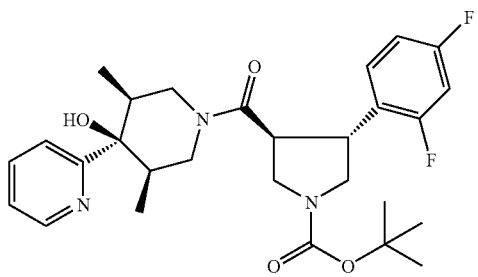

A solution of (3R,4s,5S)-3,5-dimethyl-4-pyridin-2-ylpiperidin-4-ol, from preparation 74 (835 mg, 4 mmol), (3S,4R)-1-(tert-butoxycarbonyl)-4-(2,4-difluorophenyl)pyrrolidine-3-carboxylic acid, from preparation 53 (1.32 g, 4 mmol), 1-(3-dimethylaminopropyl)-3-ethylcarbodiimide hydrochloride (776 mg, 4 mmol) and 1-hydroxybenzotriazole hydrate (62 mg, 0.4 mmol) in tetrahydrofuran (20 mL) was stirred at room temperature for 20 hours. The solvent was removed in vacuo and the crude residue was partitioned between water (15 mL) and ethyl acetate (15 mL). The phases were separated and the organic phase was washed with saturated sodium hydrogen carbonate solution (15 mL), dried over magnesium sulfate, filtered and concentrated in vacuo to give the crude residue. Purification of the residue by column chromatography using ethyl acetate:pentane (10:90-40:60) as eluent gave the desired product as a white foam, 380 mg (43%).

$^1$H NMR (400 MHz, CDCl$_3$) (Rotamers) δ 0.27-0.52 (m, 6H), 1.46 (s, 9H), 0.81-1.97 (m, 2H), 2.68 (m, 1H), 2.93-3.24 (m, 2H), 3.38-4.14 (m, 7H), 4.41 (m, 1H), 5.50 (m, 1H), 6.82 (m, 1H), 6.87-7.36 (m, 3H), 7.71 (m, 1H), 8.47 (m, 1H).

LRMS (APCI) 516 [MH$^+$].

Preparation 55 tert-Butyl (3R,4S)-3-(2,4-difluorophenyl)-4-{[(3R,4R,5S)-4-hydroxy-3,5-dimethyl-4-phenylpiperidin-1-yl]carbonyl}pyrrolidine-1-carboxylate

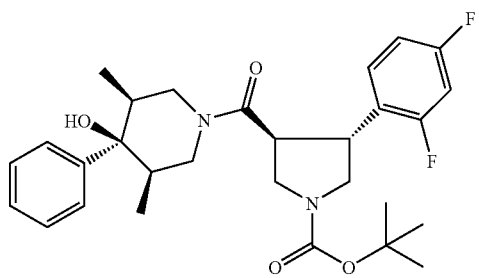

To a solution of (3S,4R)-1-(tert-butoxycarbonyl)-4-(2,4-difluorophenyl)pyrrolidine-3-carboxylic acid, from preparation 53 (1000 mg, 3 mmol), (3R,4s,5S)-3,5-dimethyl-4-phenylpiperidin-4-ol, from preparation 16 (522 mg, 2.54 mmol) and triethylamine (706 μL, 0.73 mmol) in ethyl acetate (10 mL) was added 1-propylphosphonic acid cyclic anhydride (50% in ethyl acetate) (1.5 mL, 2.54 mmol) at 0° C. and the resulting solution was stirred at room temperature for 24 hours. The reaction mixture was diluted with ethyl acetate (70 mL) and saturated potassium carbonate solution was added (2×50 mL) followed by 10% citric acid solution (1×50 mL). The phases were separated and the organic phase was washed with brine (1×50 mL), dried over magnesium sulfate, filtered and concentrated in vacuo to give the crude residue. Purification of the residue by column chromatography using ethyl acetate:pentane (10:90-40:60) as eluent afforded the desired product as a white foam, 560 mg (43%).

$^1$H NMR (400 MHz, CDCl$_3$) (Rotamers) δ 0.41-0.62 (m, 6H), 0.94-1.24 (m, 1H), 1.47 (s, 9H), 1.65-2.07 (m, 1H), 2.59-3.02 (m, 1H), 3.15 (m, 1H), 3.40-4.15 (m, 7H), 4.42 (d, 1H), 6.76-6.85 (m, 2H), 7.16-7.41 (m, 6H)

LRMS (APCI) 515 [MH$^+$].

Preparation 56

(3R,4s,5S)-1-Benzyl-4-isopropyl-3,5-dimethylpiperidin-4-ol

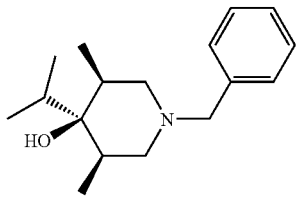

To a solution of (3R,5S)-1-benzyl-3,5-dimethylpiperidin-4-one from preparation 14 (500 mg, 2.3 mmol) was added isopropyl lithium (0.7M in pentane) (3.6 mL, 2.53 mmol) The reaction mixture was stirred at −78° C. for 1 hour then slowly warmed to 0° C. and stirred at this temperature for a further 30 minutes. Saturated ammonium chloride solution (6 mL) was then added at −10° C. The reaction mixture was partitioned between ethyl acetate (6 mL) and water (6 mL). The phases were separated and the aqueous phase was extracted with ethyl acetate (6 mL). The combined organic extracts were dried over magnesium sulfate, filtered and the solvent was removed in vacuo to give the crude residue. Purification of the residue by column chromatography using dichloromethane:methanol:0.88 ammonia (100:0-99:1-96:4:0.4) as eluent gave the desired product, 244 mg (41%).

$^1$H NMR (400 MHz, CDCl$_3$) δ 0.82 (d, 6H), 0.99 (d, 6H), 1.88-2.03 (m, 4H), 2.08 (m, 1H), 2.48 (m, 2H), 3.45 (m, 2H), 7.19-7.34 (m, 5H)

LRMS (APCI) 262 [MH$^+$], 244 [MH$^+$—H$_2$O]

Preparation 57

(3R,4s,5S)-4-isopropyl-3,5-dimethylpiperidin-4-ol

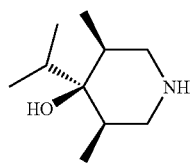

A solution of (3R,4s,5S)-1-benzyl-4-isopropyl-3,5-dimethylpiperidin-4-ol, from preparation 56 (1.42 g, 5.44 mmol) and palladium hydroxide on carbon (210 mg) in ethanol (25 mL) was hydrogenated for 40 IC and 40 psi for 24 hours. The reaction mixture was filtered through Arbocel® and washed with ethanol (25 mL). The filtrate was concentrated in vacuo to give the crude residue which was recrystallised from acetonitrile to afford the desired product as brown needles, 390 mg (42%)

$^1$H NMR (400 MHz, CDCl$_3$) δ 0.83 (d, 6H), 0.99 (d, 6H), 1.74 (m, 2H), 2.08 (m, 1H), 2.64 (m, 4H)

LRMS (APCI) 172 [MH$^+$].

Preparation 58

(3R,4s,5S)-1-Benzyl-3,5-dimethyl-4-propylpiperidin-4-ol

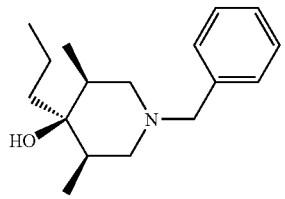

To a stirred solution of (3R,5S)-1-benzyl-3,5-dimethylpiperidin-4-one, from preparation 19 (1.0 g, 4.6 mmol) in tetrahydrofuran (7 mL) was added propylmagnesium chloride (2M in diethyl ether) (7.5 mL, 15 mmol) at −78° C. The reaction mixture was stirred for 1 hour and saturated ammonium chloride solution (20 mL) was added and the mixture was slowly warmed to room temperature. The reaction mixture was diluted with ethyl acetate (40 mL) and the phases were separated. The aqueous phase was extracted with ethyl acetate (1×40 mL) and the organic extracts were combined, dried over magnesium sulfate, filtered and concentrated in vacuo to give the crude residue. Purification of the residue by column chromatography using dichloromethane:methanol:0.88 ammonia (98:2:0-95:5:0.5) as eluent afforded the desired product, 790 mg (66%).

$^1$H NMR (400 MHz, CDCl$_3$) δ 0.80 (d, 6H), 0.90 (t, 3H), 1.20 (m, 2H), 1.51 (m, 2H), 1.87 (m, 2H), 2.04 (m, 2H), 2.54 (m, 2H), 3.47 (m, 2H), 7.19-7.36 (m, 5H).

LRMS (APCI) 262 [MH$^+$], 244 [MH$^+$—H$_2$O].

Preparation 59

(3R,4s,5S)-3,5-Dimethyl-4-propylpiperidin-4-ol

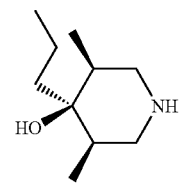

A solution of (3R,4s,5S)-1-benzyl-3,5-dimethyl-4-propylpiperidin-4-ol, from preparation 58 (780 mg, 3 mmol) and palladium hydroxide (20% on carbon, 130 mg) in ethanol (10 mL) was hydrogenated at IC and 40 psi for 24 hours. The reaction mixture was filtered through Arbocel® and washed with ethanol (10 mL). The filtrate was concentrated in vacuo to afford the desired product, 504 mg (98%).

$^1$H NMR (400 MHz, CDCl$_3$): δ 0.80 (d, 6H), 0.91 (t, 3H), 1.21 (m, 2H), 1.50 (m, 2H), 1.70 (m, 2H), 2.70 (m, 5H)

LRMS (APCI) 172 [MH$^+$].

131

Preparation 60

(3R,4s,5S)-1-Benzyl-4-cyclopropyl-3,5-dimethylpiperidin-4-ol

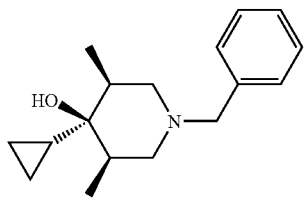

To a stirred solution of (3R,5S)-1-benzyl-3,5-dimethylpiperidin-4-one, from preparation 19 (1.0 g, 4.6 mmol) in tetrahydrofuran (8 mL) was added bromo(cyclopropyl)magnesium (0.5M in tetrahydrofuran) (28 mL, 14 mmol) at −78° C. The reaction mixture was stirred for 2 hours and saturated ammonium chloride solution (40 mL) was added and the mixture was slowly warmed to room temperature. The reaction mixture was diluted with water (40 mL) and the phases were separated. The aqueous phase was extracted with ethyl acetate (2×60 mL) and the organic extracts were combined, dried over magnesium sulfate, filtered and concentrated in vacuo to give the crude residue. Purification of the residue by column chromatography using dichloromethane:methanol (100:0-96:4) as eluent afforded the desired product as a colourless liquid, 780 mg (65%).

$^1$H NMR (400 MHz, CDCl$_3$) δ 0.35 (m, 4H), 0.52 (m, 1H), 0.90 (d, 6H), 1.95 (m, 4H), 2.56 (d, 2H), 3.50 (s, 2H), 7.20-7.37 (m, 5H)

LRMS (APCI+)=260 [MH$^+$], 242 [MH$^+$—H$_2$O]

Preparation 61

(3R,4s,5S)-4-Cyclopropyl-3,5-dimethylpiperidin-4-ol

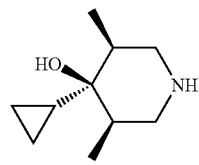

A solution of (3R,4s,5S)-1-benzyl-4-cyclopropyl-3,5-dimethylpiperidin-4-ol, from preparation 60 (780 mg, 3 mmol) and palladium hydroxide (20% on carbon) (140 mg) in ethanol (10 mL) was hydrogenated at 40 IC and 40 psi for 24 hours. The reaction mixture was filtered through Arbocel® and washed with ethanol (10 mL). The filtrate was concentrated in vacuo to afford the desired product, 480 mg (94%).

$^1$H NMR (400 MHz, CDCl$_3$) δ 0.35 (m, 4H), 0.55 (m, 1H), 0.92 (d, 6H), 1.72 (m, 2H), 1.84 (m, 1H), 2.65 (m, 4H)

LRMS (APCI+)=170 [MH$^+$], 152 [MH$^+$—H$_2$O]

132

Preparation 62

(3S,4R)-4-(2,4-difluorophenyl)-1-methylpyrrolidine-3-carboxylic acid

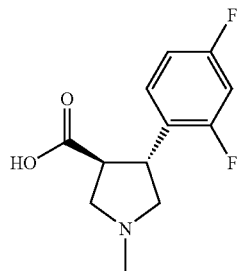

To a solution of methyl (3S,4R)-4-(2,4-difluorophenyl)-1-methylpyrrolidine-3-carboxylate, from preparation 37 (800 mg, 3.13 mmol) in tetrahydrofuran (10 mL) was added lithium hydroxide (150 mg, 6.27 mmol) at room temperature. The reaction mixture was stirred for 2 hours and the solvent concentrated in vacuo. The crude residue was dissolved in water (20 mL) and partitioned with ethyl acetate (2×20 mL). The phases were separated and the aqueous phase was acidified using 2M hydrochloric acid solution (3.13 mL). The aqueous phase was evaporated and the residue was azeotroped with toluene (6×20 mL) to afford an oily residue (1000 mg) which was used without further purification in the subsequent step.

$^1$H NMR (400 MHz, CD$_3$OD) δ 3.05 (s, 3H), 3.41 (m, 1H), 3.50-3.81 (m, 3H), 3.91 (m, 3H), 7.06 (m, 2H), 7.62 (m, 1H).

LRMS (APCI+): 242 [MH$^+$]

LRMS (APCI−): 240 (M−1)

Preparation 63 tert-Butyl (3R,4S)-3-(2,4-difluorophenyl)-4-{[(3R,4R,5S)-4-(3,4-difluorophenyl)-4-hydroxy-3,5-dimethylpiperidin-1-yl]carbonyl}pyrrolidine-1-carboxylate

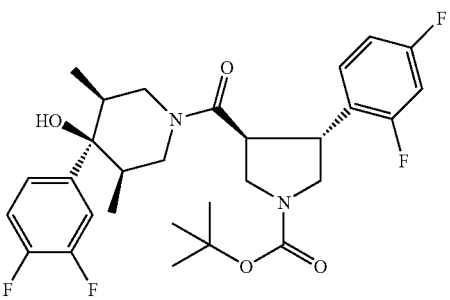

A solution of (3S,4R)-1-(tert-butoxycarbonyl)-4-(2,4-difluorophenyl)pyrrolidine-3-carboxylic acid, from preparation 53 (160 mg, 0.49 mmol) and (3R,4s,5S)-4-(3,4-difluorophenyl)-3,5-dimethylpiperidin-4-ol, from preparation 39 (100 mg, 0.42 mmol), 1-propylphosphonic acid cyclic anhydride (50% in ethyl acetate) (244 µL, 0.41 mmol) and triethylamine (120 µL, 0.82 mmol) in dichloromethane (2 mL) was stirred at room temperature for 16 hours. The reaction mixture was diluted with dichloromethane (20 mL) and saturated potassium carbonate solution (2×20 mL) was added. The phases were separated and the organic phase was washed with brine (20 mL), dried over magnesium sulfate, filtered and concentrated in vacuo to afford the desired product as a white foam, 257 mg (77%).

$^1$H NMR (400 MHz, CDCl$_3$) (Rotamers) □0.44-0.61 (4×d, 6H), 1.47 (s, 9H), 2.59 (t, 2H), 3.10 (m, 2H), 3.51-3.91 (m, 6H), 4.44 (d, 2H), 6.82 (m, 2H), 6.90 (m, 1H), 7.07-7.15 (m, 3H).

LRMS (APCI+): 551 (MH$^+$)

Preparation 64

(3R,4s,5S)-1-Benzyl-3,5-dimethyl-4-[4-(trifluoromethyl)phenyl]piperidin-4-ol

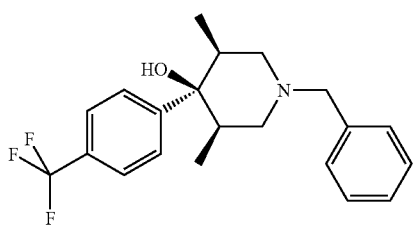

The title compound was prepared in 33% yield from (3R,5S)-1-benzyl-3,5-dimethylpiperidin-4-one, preparation 14 and 4-bromo-trifluoromethylbenzene following a similar procedure to that described in preparation 40, except the compound was additionally purified by column chromatography using pentane:ethyl acetate (4:1) as eluent.

$^1$H NMR (400 MHz, CDCl$_3$) □0.54 (d, 6H), 1.58 (s, 1H), 2.12 (t, 2H), 2.24 (m, 2H), 2.71 (dd, 2H), 3.55 (s, 2H), 7.27-7.36 (m, 7H), 7.59 (d, 2H).

LRMS (APCI) 364 [MH$^+$]

Preparation 65

(3R,4s,5S)-3,5-Dimethyl-4-[4-(trifluoromethyl)phenyl]piperidin-4-ol

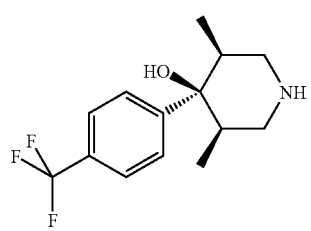

A mixture of (3R,4s,5S)-1-benzyl-3,5-dimethyl-4-[4-(trifluoromethyl)phenyl]piperidin-4-ol, from preparation 64 (527 mg, 1.45 mmol), 20% palladium on carbon (65 mg) and dihydrotoluene (570 μL, 5.4 mmol) in ethanol (10 mL) was heated under reflux for 3 hours. The reaction mixture was filtered through Arbocel® and washed with ethanol (100 mL). The solvent was removed in vacuo to afford the desired compound as a brown foam, 501 mg (87%).

$^1$H NMR (400 MHz, CDCl$_3$) □0.53 (d, 6H), 1.74 (s, 2H), 2.07 (m, 2H), 2.73 (t, 2H), 2.91 (dd, 2H), 7.26-7.70 (m, 4H).

LRMS (APCI) 274 [MH$^+$]

Preparation 66 tert-Butyl (3R,4S)-3-(2,4-difluorophenyl)-4-({(3R,4r,5S)-4-hydroxy-3,5-dimethyl-4-[4-(trifluoromethyl)phenyl]piperidin-1-yl}carbonyl)pyrrolidine-1-carboxylate

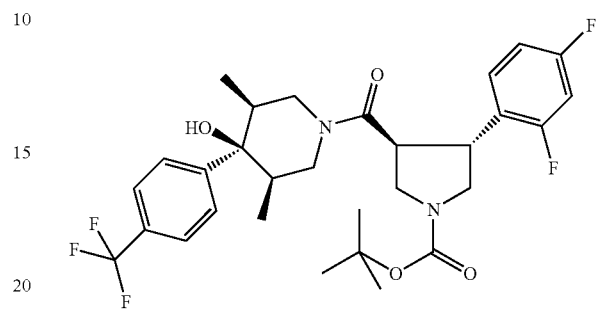

The title compound was prepared in 94% yield from (3S,4R)-1-(tert-butoxycarbonyl)-4-(2,4-difluorophenyl)pyrrolidine-3-carboxylic acid, from preparation 53 and (3R,4s,5S)-3,5-dimethyl-4-[4-(trifluoromethyl)phenyl]piperidin-4-ol, from preparation 65 following a similar procedure to that described in preparation 38.

$^1$H NMR (400 MHz, CDCl$_3$) (Rotamers) □0.43-0.60 (m, 6H), 1.46 (s, 9H), 2.63 (m, 2H), 3.14 (m, 2H), 3.45-3.90 (m, 6H), 4.44 (d, 2H), 6.82 (m, 2H), 6.86 (m, 1H), 7.16-7.32 (m, 2H), 7.58 (m, 2H).

LRMS (EI) 583 [MH$^+$]

Preparation 67

1-tert-Butyl 3-methyl (3S,4R)-4-(4-chlorophenyl)pyrrolidine-1,3-dicarboxylate

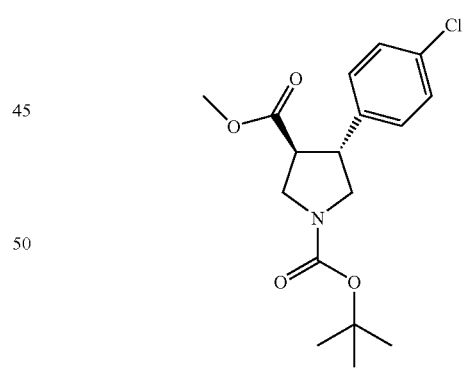

To a solution of methyl (3S,4R)-4-(4-chlorophenyl)pyrrolidine-3-carboxylate hydrochloride, from preparation 26 (870 mg, 2.8 mmol) and triethylamine (780 μL, 5.6 mmol) in dichloromethane (5 mL) was added di-tert-butyl dicarbonate (610 mg, 2.8 mmol) in dichloromethane (5 mL). The reaction mixture was stirred for 20 hours and diluted with ethyl acetate (50 mL). The phases were separated and the organic phase was washed with 5% citric acid solution (3×20 mL) and brine (1×20 mL). The organic phase was dried over magnesium sulfate, filtered and concentrated in vacuo to afford the desired product as a colourless oil in quantitative yield.

¹H NMR (400 MHz, CDCl₃) δ 1.45 (s, 9H), 3.07-3.25 (m, 2H), 3.36 (m, 1H), 3.58 (m, 1H), 3.63 (s, 3H), 3.85 (m, 2H), 7.17 (d, 2H), 7.29 (d, 1H)

LRMS (APCI) 340 [MH⁺], 240 [MH⁺−BOC+1]

Preparation 68

(3S,4R)-1-(tert-Butoxycarbonyl)-4-(4-chlorophenyl) pyrrolidine-3-carboxylic acid

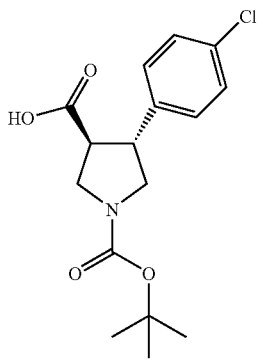

To a solution of 1-tert-butyl 3-methyl (3S,4R)-4-(4-chlorophenyl)pyrrolidine-1,3-dicarboxylate, from preparation 67 (0.98 g, 2.88 mmol) in tetrahydrofuran (8 mL) was added lithium hydroxide (0.21 g, 8.64 mmol) at room temperature. The reaction mixture was stirred for 24 hours and the solvent was removed in vacuo. The crude residue was dissolved in water (8 mL) and 1M hydrochloric acid solution (8.65 mL) was added. The suspension was extracted with dichloromethane (2×40 mL) and the organic phase was dried over magnesium sulfate, filtered and concentrated in vacuo to afforded the desired product as a white solid, 705 mg (75%).

¹H NMR (400 MHz, CDCl₃) δ 1.45 (s, 9H), 3.17 (m, 1H), 3.36 (m, 1H), 3.61 (m, 2H), 3.88 (m, 2H), 7.18 (d, 2H), 7.29 (d, 2H)

LRMS (APCI) 226 [MH⁺−BOC+1]
LRMS (APCI−)=324 [M−1]

Preparation 69 tert-Butyl (3R,4S)-3-(4-chlorophenyl)-4-{[(3R,4R,5S)-4-hydroxy-3,5-dimethyl-4-phenylpiperidin-1-yl]carbonyl}pyrrolidine-1-carboxylate

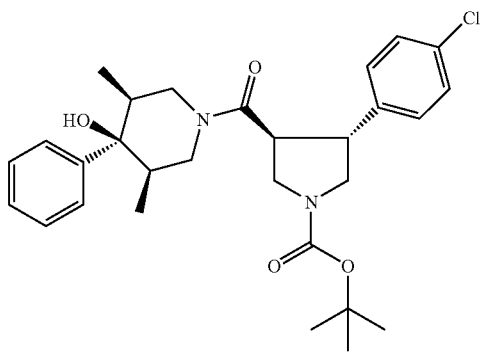

To a solution of (3S,4R)-1-(tert-butoxycarbonyl)-4-(4-chlorophenyl)pyrrolidine-3-carboxylic acid, from preparation 68 (250 mg, 0.76 mmol), (3R,4s,5S)-3,5-dimethyl-4-phenylpiperidin-4-ol, from preparation 16 (190 mg, 0.91 mmol) and triethylamine (320 μL, 2.28 mmol) in ethyl acetate (5 mL) was added 1-propylphosphonic acid cyclic anhydride (50% in ethyl acetate) (540 μL, 1.10 mmol) at room temperature. The reaction mixture was stirred for 24 hours, 1M hydrochloric acid solution (20 mL) was added and the solution was stirred 10 minutes. The phases were separated, the organic phase was diluted with ethyl acetate (3 mL) and 1M sodium hydroxide solution (6 mL) was added. The organic phase was separated, dried over magnesium sulfate, filtered, and the solvent was removed in vacuo. The crude residue was purified by column chromatography using pentane:ethyl acetate (90:10-50:50) as eluent to afford the desired product as a white foam, 370 mg (95%).

¹H NMR (400 MHz, CDCl₃) (Rotamers) δ 0.32-0.59 (m, 6H), 1.46 (s, 9H), 0.64-2.05 (m, 2H), 2.63 (m, 1H), 2.79-3.15 (2×q, 1H), 3.30-4.01 (m, 7H), 4.42 (m, 1H), 7.16-7.40 (m, 9H)

LRMS (APCI) 513 [MH⁺], 457 [MH⁺-t-Bu+1], 413 [MH⁺−BOC+1]

Preparation 70

(3R,4s,5S)-4-(4-Bromophenyl)-1-(4-methoxybenzyl)-3,5-dimethylpiperidin-4-ol

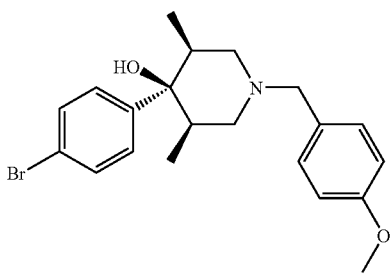

n-BuLi (2.5M in hexanes) (7.89 mL, 195 mmol) was added dropwise to a solution of 1,4-dibromobenzene (4.9 g, 20 mmol) in diethyl ether (150 mL) at −78° C. The mixture was stirred for 3 hours and allowed to warm to room temperature. 1-(4-Methoxy-benzyl)-trans-3,5-dimethyl-piperidin-4-one (5.0 g, 20 mmol) in diethyl ether (25 mL) was added dropwise and the reaction mixture was stirred for a further 2 hours. The mixture was quenched with saturated ammonium chloride (50 mL) and the phases separated. The organic phase was washed with water (3×50 mL), dried over sodium sulfate, filtered and the solvent was removed in vacuo to give the crude (3R,4s,5S)-4-(4-bromophenyl)-1-(4-methoxybenzyl)-3,5-dimethylpiperidin-4-ol (7.9 g), which was used directly without further purification.

¹H NMR (400 MHz, CD₃OD) δ 0.51 (d, 6H), 2.18 (m, 2H), 2.35 (m, 2H), 2.71 (m, 2H), 3.58 (s, 2H), 3.65 (s, 3H), 7.12 (m, 3H), 7.35 (m, 5H)

LRMS (APCI)=404 [MH⁺]

Preparation 71

4-[(3R,4s,5S)-4-hydroxy-1-(4-methoxybenzyl)-3,5-dimethylpiperidin-4-yl]benzonitrile

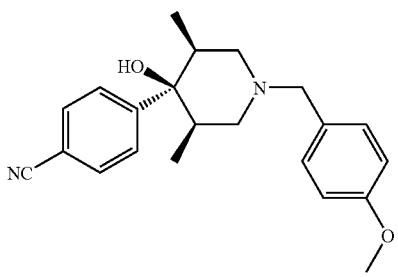

A solution of (3R,4s,5S)-4-(4-bromophenyl)-1-(4-methoxybenzyl)-3,5-dimethylpiperidin-4-ol, from preparation 70 (3.50 g, 8 mmol), potassium cyanide (1.05 g, 16 mmol), tris(triphenylphosphonio)palladate(1-) (0.462 g, 0.4 mmol) and copper iodide (1.52 g, 8 mmol) in acetonitrile (30 mL) was heated under reflux for 1 hour. The mixture was cooled to room temperature, diluted with ethyl acetate (30 mL) and filtered through Celite®. The filtrate was washed with water, brine, dried over sodium sulfate and filtered. Concentration in vacuo gave the crude residue which was purified by column chromatography on silica gel using ethyl acetate:hexane (3:97-15:85) as eluent to afford the title compound as a yellow solid (2.51 g).

$^1$H NMR (400 MHz, CD$_3$OD) δ 0.51 (d, 6H), 2.25 (m, 2H), 2.42 (m, 2H), 2.79 (m, 2H), 3.58 (s, 2H), 3.65 (s, 3H), 7.12 (m, 4H), 7.52 (d, 2H), 8.10 (m, 2H).

LRMS (APCI) 351 [MH$^+$]

Preparation 72

4-[(3R,4s,5S)-4-hydroxy-3,5-dimethylpiperidin-4-yl]benzonitrile

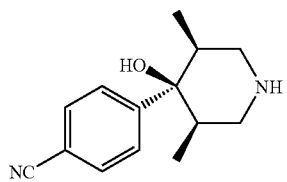

To a solution of (3R,4s,5S)-4-(4-isocyanophenyl)-1-(4-methoxybenzyl)-3,5-dimethylpiperidin-4-ol, from preparation 71 (2.50 g, 7.1 mmol) in dichloromethane (50 mL) was added triethylamine (2.0 mL, 14 mmol) at −15° C. 1-Chloroethylchloroformate (1.50 mL, 14 mmol) was added dropwise to the stirred solution, maintaining the temperature at −15° C. and the mixture was stirred for 30 minutes. The solvent was removed in vacuo to give a crude residue which was refluxed in methanol (150 mL) for 3 hours. After cooling the reaction mixture to room temperature, the solvent was removed in vacuo and the residue was dissolved in dichloromethane (100 mL). Potassium carbonate (5 g) was added and the mixture was stirred for 1 hour, then filtered, and the solvent was removed in vacuo. The crude residue was recrystallised from acetonitrile to afford the pure compound as fine white needles (1.23 g).

$^1$H NMR (400 MHz, CD$_3$OD) δ 0.60 (d, 6H), 2.25 (m, 2H), 3.1 (m, 4H), 7.62 (d, 2H), 8.15 (d, 2H)

LRMS (APCI)=232 [MH$^+$]

Preparation 73

(3R,4s,5S)-1-Benzyl-3,5-dimethyl-4-pyridin-2-ylpiperidin-4-ol

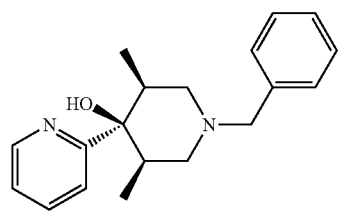

A solution of 2-bromopyridine (4.10 ml, 0.024 mol) in diethylether (50 mL) was cooled to −78° C. under nitrogen. n-BuLi (2.5M/hexanes) (10.10 mL, 25.3 mmol) was added dropwise with stirring, maintaining the temperature below −65° C. The mixture was stirred at −78° C. for 3 hours. A solution of (3R,5S)-1-benzyl-3,5-dimethylpiperidinone from preparation 14 (6.10 g, 28.0 mmol) in diethylether (50 mL) was then added dropwise maintaining the temperature below −65° C. The mixture was stirred at −78° C. for 1 hour and then allowed to warm to room temperature. Saturated ammonium chloride solution (40 ml) was added and the mixture stirred for 30 minutes. The ether layer was separated, washed with water (3×50 ml), dried over sodium sulfate, filtered and concentrated in vacuo. The residue was purified by column chromatography on silica gel to give the desired product as an orange oil 7.31 g $^1$H-NMR (400 MHz, CDCl$_3$): δ=0.43 (d, 6H), 2.09-2.30 (m, 4H), 2.71 (d, 2H), 3.59 (s, 2H), 5.48 (s, 1H), 7.19 (m, 1H), 7.22-7.42 (m, 6H), 7.71 (t, 1H), 8.48 (d, 1H)

LRMS (APCI$^+$)=297 [MH$^+$]

Preparation 74

(3R,4s,5S)-3,5-Dimethyl-4-pyridin-2-ylpiperidin-4-ol

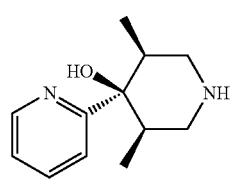

A mixture of (3R,4s,5S)-1-benzyl-3,5-dimethyl-4-pyridin-2-ylpiperidin-4-ol, from preparation 73 (3.0 g, 10.12 mmol) and palladium hydroxide (20% on carbon) (0.45 g) in ethanol (50 mL) was hydrogenated at 40° C. and 40 psi for 14 hours. The reaction mixture was allowed to cool to room temperature and stirred under 40 psi for 5 hours. The reaction mixture was filtered through Arbocel® and the filtrate concentrated in vacuo to give the crude residue. Purification by column chromatography on silica gel using dichloromethane:methanol:0.88 ammonia (97.5:2.5:0.25-90:10:1) as eluent afforded the desired product, 2.05 g (99%).

¹H NMR (400 MHz, CDCl₃) δ 0.43 (d, 6H), 2.00 (m, 2H), 2.84 (m, 4H), 5.50 (br, 1H), 7.20 (m, 1H), 7.33 (d, 1H), 7.72 (t, 1H), 8.49 (d, 1H)

LRMS (ESI+)=207 [MH⁺], 413 [2 MH⁺]

Preparation 75

(3S,4R)-4-(2,4-Difluorophenyl)-1-ethylpyrrolidine-3-carboxylic acid hydrochloride

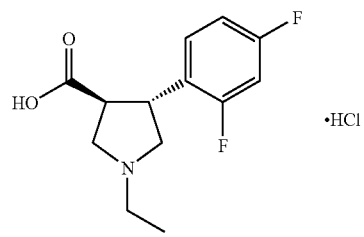

Concentrated aqueous hydrochloric acid (10 ml) was added to methyl (3S,4R)-4-(2,4-difluorophenyl)-1-ethylpyrrolidine-3-carboxylate from Preparation 76 (500 mg, 1.85 mmol) and the resulting solution was stirred at room temperature for 16 hours. The reaction mixture was then evaporated to dryness in vacuo and the resultant residue was azeotroped with toluene (2×50 ml). This gave the title compound as an off-white foam, 500 mg.

¹H-NMR (400 MHz, CD₃OD): □□ 1.10 (t, 3H), 2.51-2.62 (m, 2H), 2.69 (t, 1H), 2.86 (t, 1H), 3.05 (t, 1H), 3.10-3.13 (m, 2H), 3.92 (q, 1H), 6.80-6.86 (m, 2H), 7.45 (q, 1H).

LRMS (APCI)=256 [MH⁺]

Preparation 76

Methyl (3S,4R)-4-(2,4-difluorophenyl)-1-ethylpyrrolidine-3-carboxylate

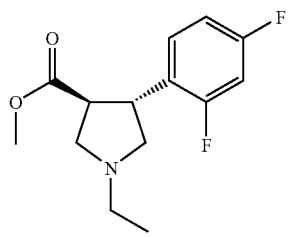

A mixture of methyl (3S,4R)-4-(2,4-difluorophenyl)pyrrolidine-3-carboxylate from Preparation 31 (500 mg, 2.07 mmol), ethyl tosylate (519 mg, 2.59 mmol) and potassium carbonate (573 mg, 4.15 mmol) were heated in acetonitrile at 70° C. for 16 hours under nitrogen. The reaction mixture was then cooled to room temperature and concentrated in vacuo. The residue was dissolved in dichloromethane (30 ml) and partitioned with saturated aqueous sodium bicarbonate (30 ml). The organic layer was then washed with brine (20 ml), dried over magnesium sulfate, filtered, and the solvent was removed in vacuo. The above procedure was performed in duplicate. The crude products from the two reactions were then combined and purified by column chromatography on silica eluting with dichloromethane:methanol (99:1) to give the title compound as a pale yellow oil, 968 mg.

¹H-NMR (400 MHz, CDCl₃): □□ 1.14 (t, 3H), 2.55-2.62 (m, 1H), 2.63-2.68 (m, 1H), 2.70-2.73 (m, 1H), 2.95-3.05 (m, 2H), 3.11 (t, 1H), 3.69 (s, 3H), 3.89 (q, 1H), 6.76 (t, 1H), 6.83 (t, 1H), 7.37 (q, 1H).

LRMS (EI)=270 [MH⁺]

According to a preferred embodiment compounds and intermediate compounds according to the present invention and especially the compounds and intermediates exemplified hereinbefore are made available in pure isolated form. As defined herein pure isolated form means that such compounds and/or intermediates are substantially free of compounds having alternative stereo-specific features. As defined herein substantially free means at least 90%, preferably at least 92%, more preferably at least 95%, more preferably still at least 98%, and especially at least 99% of the compound is present in the desired stereo-specific form.

Data

Compounds according to the present invention, including the compounds of Examples 12, 20, 16, 48, 1, 5, 6, 22, 13, 9, 10, 50, 14, 17, 19, 53, 40, 15, 52, 51, 8, 33, 31, 34, 35, 36, 42, 44 and 47, have been tested and found to demonstrate functional potencies of less than about 150 nM at the MC4 receptor when tested using the assay method described in Protocol E.

The MCR1, MCR3, MCR4 and MCR5 EC₅₀ data for compounds of the invention generated using the assay methods described in Protocols A, B, C and D as well as their relative selectivity for MCR4 versus MCR3, MCR1 and MCR5 is illustrated in Table 5.

TABLE 5

| Ex no. | MCR4 EC₅₀ (nM) | MCR3 EC₅₀ (nM) | MCR1 EC₅₀ (nM) | MCR5 EC₅₀ (nM) | Selectivity MCR3/MCR4 | Selectivity MCR1/MCR4 | Selectivity MCR5/MCR4 |
|---|---|---|---|---|---|---|---|
| 1 | 25 | 1389 | 8100 | 6710 | 56 | 324 | 268 |
| 2 | 68 | 8380 | — | — | 123 | — | — |
| 3 | 44 | 2620 | — | — | 60 | — | — |
| 4 | 45 | — | — | — | — | — | — |

The MCR1, MCR3, MCR4 and MCR5 EC₅₀ data for compounds of the invention generated using the assay methods described in Protocols A, B, D and E as well as their relative selectivity for MCR4 versus MCR3, MCR1 and MCR5 is illustrated in Table 6.

TABLE 6

| Ex no. | MCR4 EC₅₀ (nM) | MCR1 EC₅₀ (nM) | MCR5 EC₅₀ (nM) | Selectivity MCR1/MCR4 | Selectivity MCR5/MCR4 |
|---|---|---|---|---|---|
| 1 | 9.6 | 1197 | 2738 | 125 | 285 |
| 6 | 19 | 541 | 1586 | 28 | 83 |
| 22 | 23 | — | 17754 | — | 772 |
| 13 | 27 | 8403 | 16861 | 311 | 624 |
| 31 | 3.6 | 10687 | 956 | 2969 | 266 |
| 34 | 4 | — | — | — | — |
| 12 | 75 | 667 | 20000 | 9 | 267 |
| 35 | 1.5 | 1270 | 20000 | 847 | 13,333 |
| 15 | 6.3 | — | 3505 | — | 556 |
| 16 | 54 | — | — | — | — |
| 5 | 9.6 | 1197 | 2738 | 125 | 285 |

The invention claimed is:

1. A compound of formula (I)

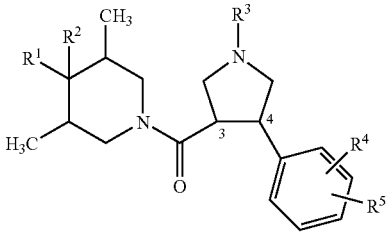

or a pharmaceutically acceptable salt thereof
wherein
$R^1$ is a —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_2$)alkyl($C_3$-$C_8$)cycloalkyl, aryl, —($C_1$-$C_2$)alkylaryl, heterocyclic, or —($C_1$-$C_2$)alkylheterocyclic group wherein each $R^1$ group is optionally substituted with one to four groups independently selected from: —($C_1$-$C_4$alkyl, —($CH_2$)$_m$($C_3$-$C_5$)cycloalkyl, halogen, —($CH_2$)$_m$OR$^6$, —CN, —C(O)OR$^6$, —($CH_2$)$_m$NR$^7$SO$_2$R$^8$, CF$_3$, CH$_2$CF$_3$, OCF$_3$ and OCH$_2$CF$_3$;
m at each occurrence is independently 0, 1 or 2;
$R^2$ is H, OH or OCH$_3$;
$R^3$ is a H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_1$-$C_2$)alkyl($C_3$-$C_8$)cycloalkyl, aryl, —($C_1$-$C_2$)alkylaryl, heterocyclic, or —($C_1$-$C_2$)alkylheterocyclic group each $R^3$ group other than H is optionally substituted with one to four groups independently selected from: —OH, —($C_1$-$C_4$)alkyl, —($CH_2$)$_n$($C_3$-$C_5$)cycloalkyl, halogen, —CN, —($CH_2$)$_n$OR$^6$ and —($CH_2$)$_n$NR$^7$R$^8$;
n at each occurrence is independently 0, 1 or 2;
$R^4$ is —H, —($C_1$-$C_4$alkyl, —($C_2$-$C_4$)alkenyl, —($C_2$-$C_4$)alkynyl, —($CH_2$)$_p$($C_3$-$C_5$)cycloalkyl, —($CH_2$)$_p$($C_5$)cyclo-alkenyl, halogen, —($CH_2$)$_p$OR$^6$, —($CH_2$)$_p$NR$^7$R$^8$, —CN, —O(O)R$^6$, —O(O)OR$^6$, —O(O)NR$^7$R$^8$, —($CH_2$)$_p$NR$^7$SO$_2$R$^8$, CF$_3$, CH$_2$CF$_3$, OCF$_3$ or OCH$_2$CF$_3$;
$R^5$ is —($C_1$-$C_4$)alkyl, —($C_2$-$C_4$)alkenyl, —($C_2$-$C_4$)alkynyl, —($CH_2$)$_p$($C_3$-$C_5$)cycloalkyl, —($CH_2$)$_p$($C_5$)cycloalkenyl, halogen, —($CH_2$)$_p$OR$^6$, —($CH_2$)$_p$NR$^7$R$^8$, —CN, —O(O)R$^6$, —O(O)OR$^6$, —C(O)NR$^7$R$^8$, —($CH_2$)$_p$NR$^7$SO$_2$R$^8$, CF$_3$, CH$_2$CF$_3$, OCF$_3$ or OCH$_2$CF$_3$;
or $R^4$ and $R^5$ are taken together with the carbons to which they are attached to form a fused 5- to 7-membered unsaturated or partially unsaturated ring;
p at each occurrence is independently 0, 1 or 2;
$R^6$, $R^7$ and $R^8$ are each independently H, CH$_3$ or CH$_2$CH$_3$;
provided that the heterocyclic groups within the definitions of $R^1$ and $R^3$ are independently selected from 4- to 10-membered ring systems containing one to four heteroatoms independently selected from O, N and S.

2. The compound according to claim 1, or a pharmaceutically acceptable salt thereof, wherein $R^1$ is a —($C_1$-$C_6$)alkyl, —($C_3$-$C_8$)cycloalkyl, —($C_1$-$C_2$)alkyl($C_3$-$C_8$)cycloalkyl, phenyl, —($C_1$-$C_2$)alkylaryl, heterocyclic, or —($C_1$-$C_2$)alkylheterocyclic group; $R^1$ is optionally substituted with one to four groups independently selected from —($C_1$-$C_4$)alkyl, —($CH_2$)$_m$OR$^6$, —($CH_2$)$_m$($C_3$-$C_5$)cycloalkyl, halogen, OCH$_3$, OCH$_2$CH$_3$, CN, CF$_3$, CH$_2$CF$_3$, OCF$_3$ and OCH$_2$CF$_3$; and provided that when $R^1$ is a heterocyclic, or a —($C_1$-$C_2$)alkylheterocyclic group said heterocyclic group is a mono-cyclic 5- to 6-membered ring containing one to three heteroatoms independently selected from O, N and S.

3. The compound according to claim 2, or a pharmaceutically acceptable salt thereof, wherein $R^1$ is a —($C_1$-$C_6$)alkyl, —($C_3$-$C_8$)cycloalkyl, —($C_1$-$C_2$)alkyl($C_3$-$C_8$)cycloalkyl, phenyl, —($C_1$-$C_2$)alkylaryl, heterocyclic, or —($C_1$-$C_2$)alkylheterocyclic group;
wherein the $R^1$ group is optionally substituted with one to four groups selected independently from: —($C_1$-$C_4$)alkyl, halogen, —($CH_2$)$_m$OR$^6$, CN, CF$_3$ or OCF$_3$;
m at each occurrence is independently 1 or 2;
$R^2$ is OH;
$R^3$ is a —H, —($C_1$-$C_6$)alkyl, —($C_3$-$C_8$)cycloalkyl, —($C_1$-$C_2$)alkyl($C_3$-$C_8$)cycloalkyl, aryl, —($C_1$-$C_2$)alkylaryl, heterocyclic, or —($C_1$-$C_2$)alkylheterocyclic group;
wherein each $R^3$ group other than —H is optionally substituted with one to four groups selected independently from: —OH, —($C_1$-$C_4$)alkyl, —($CH_2$)$_n$($C_3$-$C_5$)cycloalkyl, halogen, CN, —($CH_2$)$_n$OR$^6$ and —($CH_2$)$_n$NR$^7$R$^8$ wherein n at each occurrence is independently 0, 1 or 2;
$R^4$ is —H, —($C_1$-$C_4$)alkyl, —($CH_2$)$_p$($C_3$-$C_5$)cycloalkyl, halogen, —($CH_2$)$_p$OR$^6$, —($CH_2$)$_p$NR$^7$R$^8$, —CN, —O(O)R$^6$, —C(O)OR$^6$, —O(O)NR$^7$R$^8$, —($CH_2$)$_p$NR$^7$SO$_2$R$^8$, CF$_3$, CH$_2$CF$_3$, OCF$_3$ or OCH$_2$CF$_3$ wherein p is 0, 1 or 2;
$R^5$ is ($C_1$-$C_4$)alkyl, —($CH_2$)$_p$($O_3$-$O_5$)cycloalkyl, halogen, —($CH_2$)$_p$OR$^6$, ($CH_2$)$_p$NR$^7$R$^8$, CN, C(O)R$^6$, C(O)OR$^6$, CONR$^7$R$^8$, ($CH_2$)$_p$NR$^7$SO$_2$R$^8$, CF$_3$, CH$_2$CF$_3$, OCF$_3$ or OCH$_2$CF$_3$ wherein p is 0, 1 or 2;
provided that the heterocyclic group of $R^3$ is a mono-cyclic 5- to 6-membered ring containing one to two heteroatoms independently selected from O and N;
and the heterocyclic group of $R^1$ is a mono-cyclic 5- to 6-membered ring containing one heteroatom selected from O and N.

4. The compound according to claim 3, or a pharmaceutically acceptable salt thereof, wherein
$R^3$ is a —H, —($C_1$-$C_6$)alkyl, —($C_3$-$C_8$)cycloalkyl, —($C_1$-$C_2$)alkyl($C_3$-$C_8$)cycloalkyl, —($C_1$-$C_2$)alkylaryl or a heterocyclic group and wherein each $R^3$ group other than —H is optionally substituted with one to four groups independently selected from —OH, —($C_1$-$C_4$alkyl, —($CH_2$)$_n$($C_3$-$C_5$)cycloalkyl, halogen, —CN and —($CH_2$)$_n$OR$^6$; and
n at each occurrence is independently 0 or 1;
provided that when $R^3$ is a heterocyclic group said heterocyclic group is a mono-cyclic 5- to 6-membered ring containing one to 2 heteroatoms independently selected from O and N.

5. The compound according to claim 2, or a pharmaceutically acceptable salt thereof, wherein $R^1$ is a —($C_1$-$C_6$)alkyl, —($C_3$-$C_8$)cycloalkyl, phenyl or a heterocyclic group and wherein each $R^1$ group is optionally substituted with one to four groups independently selected from: —($C_1$-$C_4$)alkyl, halogen, —OR$^6$ and CN;

R² is —OH;

R³ is a —H, —(C₂-C₆)alkyl, —(C₃-C₈)cycloalkyl, —(C₁-C₂)alkyl(C₃-C₈)cycloalkyl or heterocyclic group; each R³ group other than —H is optionally substituted with one to four groups independently selected from: ⁻OH, —(C₁-C₄)alkyl, —(CH₂)ₙ(C₃-C₅)cycloalkyl, halogen, —CN, —OR⁶ and —(CH₂)ₙNR⁷R⁸;

n at each occurrence is independently 0, 1 or 2;

R⁴ is H, F or Cl;

R⁵ is F or Cl;

provided that the heterocyclic group of R³ is a mono-cyclic 6-membered ring containing one to two heteroatoms independently selected from O and N;

and the heterocyclic group of R¹ is a mono-cyclic 6-membered ring containing one heteroatom selected from O or N.

6. The compound according to claim 5, or a pharmaceutically acceptable salt thereof, wherein the heterocyclic group of R¹ is a monocyclic 6-membered ring containing one N heteroatom.

7. The compound according to claim 6, or a pharmaceutically acceptable salt thereof, wherein the heterocyclic group of R³ is a monocyclic 6-membered ring containing one to two N heteroatoms.

8. The compound according to claim 1, or a pharmaceutically acceptable salt thereof, of formula (1A)

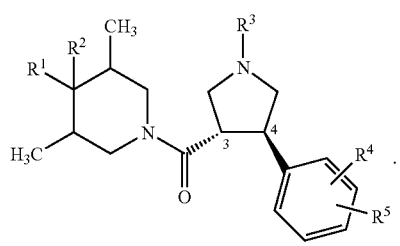

IA

9. The compound according to claim 1, or a pharmaceutically acceptable salt thereof, of formula (1B)

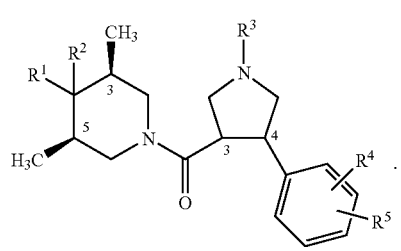

IB

10. The compound according to claim 9, or a pharmaceutically acceptable salt thereof, wherein the stereochemistry of the groups at the 3 and 4 positions of the pyrrolidine ring are trans relative to each other.

11. The compound according to claim 1, or a pharmaceutically acceptable salt thereof, of formula (1C)

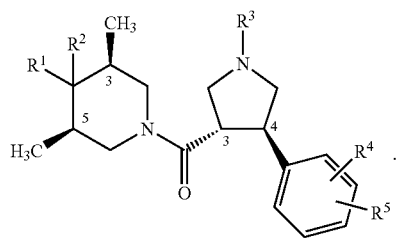

IC

12. The compound according to claim 1, or a pharmaceutically acceptable salt thereof, of formula (1D)

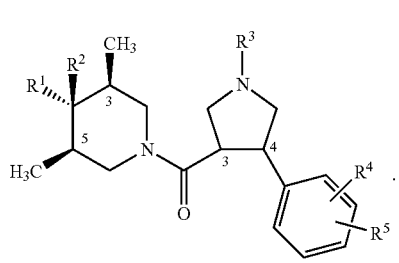

ID

13. The compound according to claim 12, or a pharmaceutically acceptable salt thereof, wherein the stereochemistry of the groups at the 3 and 4 positions of the pyrrolidine ring are trans relative to each other.

14. The compound according to claim 1, or a pharmaceutically acceptable salt thereof, of formula (1E)

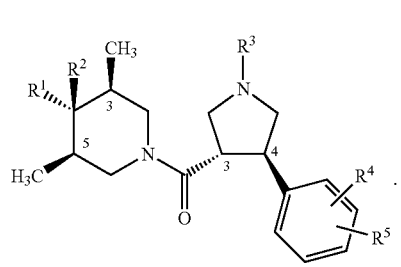

IE

15. The compound according to claim 1, or a pharmaceutically acceptable salt thereof, of formula (1F)

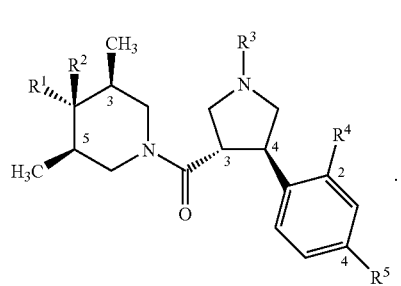

IF

16. The compound according to claim 15, or a pharmaceutically acceptable salt thereof, wherein R¹ is —(C₁-C₄)alkyl, —(C₃-C₆)cycloalkyl, phenyl or pyridyl and R¹ is optionally substituted by one to four groups independently selected from CH$_3$, CH$_2$CH$_3$, halogen, OCH$_3$, OCH$_2$CH$_3$, CN, CF$_3$ and OCF$_3$.

17. The compound according to claim 16, or a pharmaceutically acceptable salt thereof, wherein R$^1$ is n-propyl, i-propyl, n-butyl, methoxymethyl, cyclopropyl, cyclohexyl, phenyl, 3-fluorophenyl, 4-fluorophenyl, 4-chlorophenyl, 4-methylphenyl, 4-methoxyphenyl, 2,6-difluorophenyl, 2,4-difluorophenyl, 3,4-difluorophenyl, pyridin-2-yl or pyridin-3-yl.

18. The compound according to claim 17, or a pharmaceutically acceptable salt thereof, wherein R$^1$ is pyridin-2-yl, phenyl, 3-fluorophenyl, 4-fluorophenyl, 4-chlorophenyl, 4-methylphenyl, 4-methoxyphenyl, 2,6-difluorophenyl, 2,4-difluorophenyl or 3,4-difluorophenyl.

19. The compound according to claim 15, or a pharmaceutically acceptable salt thereof, wherein R$^3$ is —H, —(C$_2$-C$_6$) alkyl, —(C$_3$-C$_8$)cycloalkyl, —(C$_1$-C$_2$)alkyl(C$_3$-C$_8$)cycloalkyl or heterocyclic wherein each R$^3$ other than —H is optionally substituted by one to four groups independently selected from —(C$_1$-C$_4$)alkyl or —OR$^6$; provided that when R$^3$ is a heterocyclic group said heterocyclic group is a monocyclic 6-membered ring containing one to two N heteroatoms.

20. The compound according to claim 18, or a pharmaceutically acceptable salt thereof, wherein R$^3$ is hydrogen, ethyl, i-propyl, n-propyl, n-butyl, t-butyl, i-butyl, 2-methoxyethyl, cyclopentyl, cyclobutyl, cyclopentylmethyl, pyridin-2-yl, pyridin-3-yl, pyridazin-3-yl, pyrazinyl, pyrimidin-5-yl, pyrimidin-2-yl, pyrimidin-4-yl or tetrahydropyran-4-yl.

21. The compound according to claim 20, or a pharmaceutically acceptable salt thereof, wherein R$^4$ is H, F or Cl and R$^5$ is F or Cl.

22. The compound according to claim 21, or a pharmaceutically acceptable salt thereof, wherein the phenyl group substituted with the R$^4$ and R$^5$ substituents is: a 2, 4 di-substituted phenyl group wherein R$^4$ and R$^5$ are each independently F or Cl; or, a 4-mono-substituted phenyl group wherein R$^4$ is H and R$^5$ is F or Cl.

23. The compound according to claim 22, or a pharmaceutically acceptable salt thereof, wherein the phenyl group substituted with the R$^4$ and R$^5$ substituents is 4-chlorophenyl or 2,4-difluorophenyl.

24. The compound according to claim 11, or a pharmaceutically acceptable salt thereof, wherein:
R$^1$ is phenyl, 3-fluorophenyl, 4-fluorophenyl, 2,6-difluorophenyl, 2,4-difluorophenyl, 3,4-difluorophenyl or pyridin-2-yl;
R$^2$ is OH;
R$^3$ is H;
R$^4$ is H or F; and
R$^5$ is F or Cl.

25. The compound according to claim 24 selected from:
(3R,4R,5S)-1-{[(3S,4R)-4-(2,4-difluorophenyl)pyrrolidin-3-yl]carbonyl}-4-(4-fluorophenyl)-3,5-dimethylpiperidin-4-ol hydrochloride;
(3R,4R,5S)-4-(2,4-difluorophenyl)-1-{[(3S,4R)-4-(2,4-difluorophenyl)pyrrolidin-3-yl]carbonyl}-3,5-dimethylpiperidin-4-ol hydrochloride;
(3R,4R,5S)-1-{[(3S,4R)-4-(2,4-Difluorophenyl)pyrrolidin-3-yl]carbonyl}-3,5-dimethyl-4-phenylpiperidin-4-ol hydrochloride; and
(3R,4R,5S)-1-{[(3S,4R)-4-(4-Chlorophenyl)pyrrolidin-3-yl]carbonyl}-3,5-dimethyl-4-phenylpiperidin-4-ol hydrochloride.

26. The compound according to claim 11, or a pharmaceutically acceptable salt thereof, wherein:

R$^1$ is phenyl or pyridin-2-yl;
R$^2$ is OH;
R$^3$ is pyridin-2-yl, pyridin-3-yl, pyridazin-3-yl, pyrazinyl, pyrimidin-5-yl, pyrimidin-4-yl, pyrimidin-2-yl or tetrahydropyran-4-yl; and
R$^4$ and R$^5$ are each F.

27. The compound according to claim 26, selected from
(3R,4R,5S)-1-{[(3S,4R)-4-(2,4-Difluorophenyl)-1-pyridin-2-yl pyrrolidin-3-yl]carbonyl}-3,5-dimethyl-4-phenylpiperidin-4-ol hydrochloride;
(3R,4R,5S)-1-{[(3S,4R)-4-(2,4-Difluorophenyl)-1-pyridin-3-yl pyrrolidin-3-yl]carbonyl}-3,5-dimethyl-4-phenyl piperidin-4-ol hydrochloride;
(3R,4R,5S)-1-{[(3S,4R)-4-(2,4-Difluorophenyl)-1-pyridazin-3-ylpyrrolidin-3-yl]carbonyl}-3,5-dimethyl-4-phenylpiperidin-4-ol hydrochloride;
(3R,4R,5S)-1-{[(3S,4R)-4-(2,4-Difluorophenyl)-1-pyrimidin-4-ylpyrrolidin-3-yl]carbonyl}-3,5-dimethyl-4-phenylpiperidin-4-ol hydrochloride; and
(3R,4R,5S)-1-{[(3S,4R)-4-(2,4-Difluorophenyl)-1-pyridazin-3-ylpyrrolidin-3-yl]carbonyl}-3,5-dimethyl-4-pyridin-2-ylpiperidin-4-ol hydrochloride.

28. The compound according to claim 11, or a pharmaceutically acceptable salt thereof, wherein
R$^1$ is phenyl, 4-fluorophenyl, 4-chlorophenyl, 3-fluorophenyl, 2,4-difluorophenyl, 3,4-difluorophenyl, or pyridin-2-yl;
R$^2$ is OH;
R$^3$ is t-butyl, isopropyl or ethyl; and
R$^4$ and R$^5$ are each F.

29. The compound according to claim 28, selected from
(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol;
(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride;
(3R,4R,5S)-1-{[(3S,4R)-4-(2,4-Difluorophenyl)-1-isopropylpyrrolidin-3-yl]carbonyl}-3,5-dimethyl-4-phenylpiperidin-4-ol hydrochloride;
(3R,4R,5S)-1-{[(3S,4R)-1-tert-Butyl-4-(2,4-difluorophenyl)pyrrolidin-3-yl]carbonyl}-4-(3,4-difluorophenyl)-3,5-dimethylpiperidin-4-ol hydrochloride;
(3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol hydrochloride;
(3R,4R,5S)-1-{[(3S,4R)-4-(2,4-difluorophenyl)-1-isopropylpyrrolidin-3-yl]carbonyl}-4-(4-fluorophenyl)-3,5-dimethylpiperidin-4-ol hydrochloride;
(3R,4R,5S)-1-{[(3S,4R)-1-tert-butyl-4-(2,4-difluorophenyl)pyrrolidin-3-yl]carbonyl}-4-(4-chlorophenyl)-3,5-dimethylpiperidin-4-ol hydrochloride;
(3R,4R,5S)-1-{[(3S,4R)-1-tert-butyl-4-(2,4-difluorophenyl)pyrrolidin-3-yl]carbonyl}-4-(2,4-difluorophenyl)-3,5-dimethylpiperidin-4-ol hydrochloride;
(3R,4R,5S)-1-{[(3S,4R)-1-tert-Butyl-4-(2,4-difluorophenyl)pyrrolidin-3-yl]carbonyl}-3,5-dimethyl-4-pyridin-2-ylpiperidin-4-ol hydrochloride;
(3R,4R,5S)-1-{[(3S,4R)-1-tert-Butyl-4-(2,4-difluorophenyl)pyrrolidin-3-yl]carbonyl}-3,5-dimethyl-4-propylpiperidin-4-ol hydrochloride;
(3R,4R,5S)-4-(4-chlorophenyl)-1-{[(3S,4R)-4-(2,4-difluorophenyl)-1-isopropylpyrrolidin-3-yl]carbonyl}-3,5-dimethylpiperidin-4-ol hydrochloride;
(3R,4R,5S)-4-(3,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride;

(3R,4R,5S)-4-(2,4-difluorophenyl)-1-{[(3S,4R)-4-(2,4-difluorophenyl)-1-isopropylpyrrolidin-3-yl]carbonyl}-3,5-dimethyl piperidin-4-ol hydrochloride; and (3R,4R,5S)-1-{[(3S,4R)-4-(2,4-difluorophenyl)-1-ethylpyrrolidin-3-yl]carbonyl}-4-(3-fluorophenyl)-3,5-dimethyl piperidin-4-ol hydrochloride.

30. The compound according to claim 1, selected from:

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol;

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-isopropylpyrrolidin-3-yl]carbonyl}-3,5-dimethyl-4-phenylpiperidin-4-ol hydrochloride;

(3R,4R,5S)-1-{[(3S,4R)-1-tert-Butyl-4-(2,4-difluorophenyl)pyrrolidin-3-yl]carbonyl}-4-(3,4-difluorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-4-(2,4-difluorophenyl)-1-isopropylpyrrolidin-3-yl]carbonyl}-4-(4-fluorophenyl)-3,5-dimethylpiperidin-4-ol hydrochloride;

(3R,4R,5S)-1-{[(3S,4R)-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-chlorophenyl)-3,5-dimethylpiperidin-4-ol hydrochloride;

(3R,4R,5S)-1-{[(3S,4R)-1-tert-butyl-4-(2,4-difluorophenyl)pyrrolidin-3-yl]carbonyl}-4-(2,4-difluorophenyl)-3,5-dimethylpiperidin-4-ol hydrochloride;

(3R,4R,5S)-4-(2,4-difluorophenyl)-1-{[(3S,4R)-4-(2,4-difluorophenyl)pyrrolidin-3-yl]carbonyl}-3,5-dimethyl piperidin-4-ol hydrochloride;

(3R,4R,5S)-1-{[(3S,4R)-1-tert-Butyl-4-(2,4-difluorophenyl)pyrrolidin-3-yl]carbonyl}-3,5-dimethyl-4-pyridin-2-ylpiperidin-4-ol hydrochloride;

(3R,4R,5S)-1-{[(3S,4R)-4-(2,4-Difluorophenyl)pyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridin-2-ylpyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridin-3-ylpyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridazin-3-ylpyrrolidin-3-yl]carbonyl}-3,5-dimethyl-4-phenylpiperidin-4-ol hydrochloride;

(3R,4R,5S)-1-{[(3S,4R)-1-tert-Butyl-4-(2,4-difluorophenyl)pyrrolidin-3-yl]carbonyl}-3,5-dimethyl-4-propylpiperidin-4-ol hydrochloride;

(3R,4R,5S)-1-{[(3S,4R)-4-(2,4-Difluorophenyl)-1-pyrimidin-4-ylpyrrolidin-3-yl]carbonyl}-3,5-dimethyl-4-phenylpiperidin-4-ol hydrochloride;

(3R,4R,5S)-1-{[(3S,4R)-4-(2,4-Difluorophenyl)-1-pyridazin-3-ylpyrrolidin-3-yl]carbonyl}-3,5-dimethyl-4-pyridin-2-yl piperidin-4-ol hydrochloride;

(3R,4R,5S)-1-{[(3S,4R)-4-(4-Chlorophenyl)pyrrolidin-3-yl]carbonyl}-3,5-dimethyl-4-phenylpiperidin-4-ol hydrochloride;

(3R,4R,5S)-4-(4-chlorophenyl)-1-{[(3S,4R)-4-(2,4-difluorophenyl)-1-isopropylpyrrolidin-3-yl]carbonyl}-3,5-dimethylpiperidin-4-ol hydrochloride;

(3R,4R,5S)-4-(3,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride;

(3R,4R,5S)-4-(2,4-difluorophenyl)-1-{[(3S,4R)-4-(2,4-difluorophenyl)-1-isopropylpyrrolidin-3-yl]carbonyl}-3,5-dimethylpiperidin-4-ol hydrochloride; and (3R,4R,5S)-1-{[(3S,4R)-4-(2,4-difluorophenyl)-1-ethylpyrrolidin-3-yl]carbonyl}-4-(3-fluorophenyl)-3,5-dimethylpiperidin-4-ol hydrochloride.

31. A compound according to claim 30, selected from:

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol;

(3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride;

(3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol hydrochloride;

(3R,4R,5S)-1-{[(3S,4R)-4-(2,4-difluorophenyl)pyrrolidin-3-yl]carbonyl}-4-(4-fluorophenyl)-3,5-dimethylpiperidin-4-ol hydrochloride; and (3R,4R,5S)-1-{[(3S,4R)-1-tert-butyl-4-(2,4-difluorophenyl)pyrrolidin-3-yl]carbonyl}-4-(4-chlorophenyl)-3,5-dimethylpiperidin-4-ol hydrochloride.

32. (3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol or a pharmaceutically acceptable salt thereof.

33. (3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride.

34. The compound according to claim 15, or a pharmaceutically acceptable salt thereof, wherein $R^1$ is phenyl or pyridin-2-yl;

$R^2$ is OH;

$R^3$ is t-Butyl;

$R^4$ is F; and $R^5$ is F.

35. [1-tert-Butyl-4-(2,4-difluoro-phenyl)-pyrrolidin-3-yl]-(4-hydroxy-3,5-dimethyl-4-phenyl-piperidin-1-yl)-methanone or a pharmaceutically acceptable salt thereof.

36. The compound of claim 35 wherein said compound is [1-tert-Butyl-4-(2,4-difluoro-phenyl)-pyrrolidin-3-yl]-(4-hydroxy-3,5-dimethyl-4-phenyl-piperidin-1-yl)-methanone hydrochloride.

37. (3R,4R,5S)-1-{[(3S,4R)-1-tert-butyl-4-(2,4-difluorophenyl)pyrrolidin-3-yl]carbonyl}-4-(4-fluorophenyl)-3,5-dimethylpiperidin-4-ol or a pharmaceutically acceptable salt thereof.

38. The compound of claim 37 wherein the compound is in its hydrochloride salt form.

39. A pharmaceutical composition comprising a therapeutically effective amount of a compound of claim 1 or 32 or a pharmaceutically acceptable salt thereof together with a pharmaceutically acceptable excipient, diluent or carrier.

40. A method of treating male erectile dysfunction, the method comprising administering to a patient in need of treatment thereof an effective amount of a compound of claim 1 or a pharmaceutically acceptable salt thereof.

41. A method of treating male erectile dysfunction the method comprising administering to a patient in need of treatment thereof an effective amount of a compound of claim 32 a pharmaceutically acceptable salt thereof.

42. The method as recited in claim 41 wherein the compound is (3R,4R,5S)-1-{[(3S,4R)-1-tert-Butyl-4-(2,4-difluorophenyl)pyrrolidin-3-yl]carbonyl}-3,5-dimethyl-4-phenylpiperidin-4-ol hydrochloride.

* * * * *